(12) United States Patent
Ueno et al.

(10) Patent No.: US 8,557,741 B2
(45) Date of Patent: Oct. 15, 2013

(54) 3-AMINOCARBONYL-SUBSTITUTED BENZOYLCYCLOHEXANEDIONES AND THEIR USE AS HERBICIDES

(75) Inventors: Chieko Ueno, Frankfurt (DE); Simon Dörner-Rieping, Neu-Anspach (DE); Andreas Van Almsick, Karben (DE); Christopher Hugh Rosinger, Hofheim (DE); Jan Dittgen, Frankfurt (DE); Dieter Feucht, Eschborn (DE); Isolde Häuser-Hahn, Leverkusen (DE)

(73) Assignee: Bayer CropScience AG, Monheim (DE)

( * ) Notice: Subject to any disclaimer, the term of this patent is extended or adjusted under 35 U.S.C. 154(b) by 181 days.

(21) Appl. No.: 13/029,373

(22) Filed: Feb. 17, 2011

(65) Prior Publication Data

US 2011/0207605 A1    Aug. 25, 2011

(30) Foreign Application Priority Data

Feb. 19, 2010  (EP) .................................... 10001688

(51) Int. Cl.
| | |
|---|---|
| A01N 35/00 | (2006.01) |
| A01N 37/34 | (2006.01) |
| A01N 43/40 | (2006.01) |
| A01N 41/06 | (2006.01) |
| A01N 47/46 | (2006.01) |
| C07C 41/00 | (2006.01) |
| C07C 43/20 | (2006.01) |
| C07C 49/00 | (2006.01) |
| C07C 319/00 | (2006.01) |
| C07C 381/00 | (2006.01) |

(52) U.S. Cl.
USPC ........... 504/254; 504/288; 504/292; 504/306; 504/308; 504/309; 504/310; 504/333; 504/334; 504/348; 568/63; 568/64; 568/331; 568/337; 568/630; 568/633; 568/634

(58) Field of Classification Search
USPC ......... 504/254, 288, 292, 334, 306, 308, 309, 504/310, 333, 348; 568/331, 337, 630, 633, 568/634, 63, 64
See application file for complete search history.

(56) References Cited

U.S. PATENT DOCUMENTS

| | | | | |
|---|---|---|---|---|
| 4,780,127 A | * | 10/1988 | Michaely et al. | ............ 504/348 |
| 4,816,066 A | | 3/1989 | Michaely et al. | |
| 5,306,695 A | | 4/1994 | Stark et al. | |
| 6,768,025 B2 | | 7/2004 | Seitz et al. | |
| 6,774,086 B2 | * | 8/2004 | Seitz et al. | .................... 504/224 |
| 2003/0060651 A1 | * | 3/2003 | Seitz et al. | .................... 558/415 |
| 2003/0191027 A1 | | 10/2003 | Seitz et al. | |

FOREIGN PATENT DOCUMENTS

| | | |
|---|---|---|
| EP | 0502492 | 3/1992 |
| WO | 02081434 | 10/2002 |
| WO | 03022810 | 3/2003 |
| WO | 2004105482 | 12/2004 |

OTHER PUBLICATIONS

International Search Report Based on PCT/EP2011/052168 Dated May 9, 2011.

* cited by examiner

*Primary Examiner* — Jane C Oswecki

(74) *Attorney, Agent, or Firm* — Miles & Stockbridge PC

(57) ABSTRACT

What is described are 3-aminocarbonyl-substituted benzoyl-cyclohexanediones of the formula (I) as herbicides.

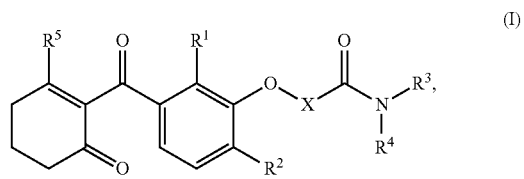

In this formula (I), $R^1$ to $R^5$ are radicals such as hydrogen, organic radicals such as alkyl, and other radicals such as halogen. X is alkylene.

19 Claims, No Drawings

3-AMINOCARBONYL-SUBSTITUTED BENZOYLCYCLOHEXANEDIONES AND THEIR USE AS HERBICIDES

CROSS REFERENCE TO RELATED APPLICATION

This application claims priority from to EP10001688.0 filed Feb. 19, 2010, the content of which is incorporated herein by reference in its entirety.

BACKGROUND OF THE INVENTION

1. Field of the Invention

The invention relates to the technical field of herbicides, in particular that of herbicides for the selective control of broad-leaved weeds and weed grasses in crops of useful plants.

2. Description of Related Art

It is already known from various publications that certain benzoylcyclohexanediones have herbicidal properties. Thus, WO 03/022810 describes benzoylcyclohexanediones whose phenyl ring is substituted in the 3-position by aminocarbonyl. WO 2004/105482 A2 describes benzoylcyclohexanediones whose phenyl ring carries a trifluoromethyl group in the 2-position and an alkoxyalkoxy group in the 3-position. EP 0 502 492 A2 describes benzoylcyclohexanediones whose phenyl ring carries a trifluoromethyl group in the 2-position and a haloalkoxy group in the 3-position. U.S. Pat. No. 4,816,066 A and WO 02/081434 A1 describe benzoylcyclohexanediones whose phenyl ring carries in each case a trifluoromethyl group in the 2-position and various radicals in the 3-position. However, frequently, the compounds known from this publication have insufficient herbicidal activity or an insufficient compatibility with crop plants.

SUMMARY OF THE INVENTION

It is therefore an object of the present invention to provide further herbicidally active compounds having properties which—relative to those of the compounds disclosed in the state of the art—are improved. It has now been found that 2-benzoylcyclohexanediones whose phenyl ring carries certain radicals from the aminocarbonylalkyl group—attached via an oxygen atom—in the 3-position are particularly suitable as herbicides.

The present invention provides 3-aminocarbonyl-substituted benzoylcyclohexanediones of the formula (I) or salts thereof

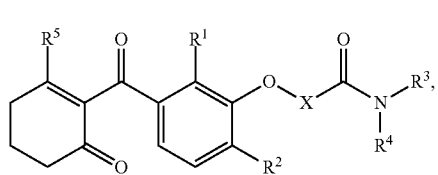

(I)

in which
X is a straight-chain or branched $(C_1-C_6)$-alkylene chain;
$R^1$ is halo-$(C_1-C_6)$-alkyl;
$R^2$ is halogen or $(C_1-C_6)$-alkyl-$S(O)_n$;
$R^3$ and $R^4$ independently of one another are hydrogen, $(C_1-C_6)$-alkyl or $(C_1-C_4)$-alkoxy;
$R^5$ is hydroxyl or (2-methoxy-2-oxoethyl)sulfanyl;
n is 0, 1 or 2.

DETAILED DESCRIPTION OF A PREFERRED EMBODIMENT

In formula (I) and all the formulae below, alkyl radicals having more than two carbon atoms can be straight-chain or branched. Alkyl radicals are, for example, methyl, ethyl, n- or isopropyl, n-, iso-, t- or 2-butyl, pentyls, hexyls, such as n-hexyl, isohexyl and 1,3-dimethylbutyl. In an analogous manner, this also applies to alkoxy radicals.

Where a group is substituted by a plurality of radicals, this means that this group is substituted by one or more identical or different representatives of the radicals mentioned.

Depending on the nature and the attachment of the substituents, the compounds of the formula (I) may be present as stereoisomers. If, for example, one or more asymmetrically substituted carbon atoms are present, there may be enantiomers and diastereomers. There may also be stereoisomers if n is 1 (sulfoxides). Stereoisomers may be obtained from the mixtures resulting from the preparation using customary separation methods, for example by chromatographic separation techniques. It is also possible to prepare stereoisomers selectively by using stereoselective reactions employing optically active starting materials and/or auxiliaries. The invention also relates to all stereoisomers and mixtures thereof embraced by the formula (I) but not specifically defined.

Preferred are compounds of the general formula (I) in which
X is methylene;
$R^1$ is trifluoromethyl;
$R^2$ is $(C_1-C_6)$-alkyl-$S(O)_n$;
$R^3$ and $R^4$ independently of one another are hydrogen, methyl, ethyl, methoxy or ethoxy;
$R^5$ is hydroxyl;
n is 0, 1 or 2.

In all of the formulae below, the substituents and symbols have the same definition as described under formula (I), unless otherwise defined.

Compounds according to the invention in which $R^5$ is hydroxyl may be prepared, for example, by the method indicated in Scheme 1, by base-catalyzed reaction of a compound of the formula (II) in which $L^a$ is a leaving group such as fluorine or chlorine with alcohols of the formula (III). Such methods are described inter alia in *Science of Synthesis* (2007), 31, p. 609 ff.

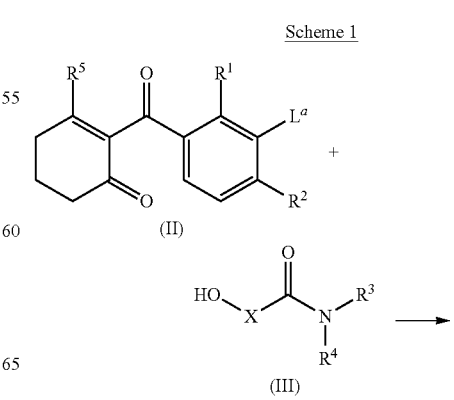

Scheme 1

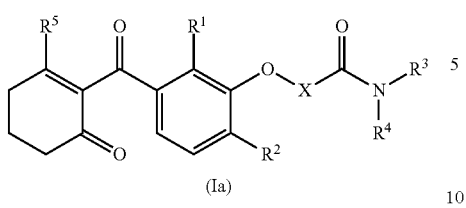

(Ia)

Compounds of the formula (II) can be prepared, for example, by the method shown in Scheme 2 by base-catalyzed reaction of a compound of the formula (V) in which T is halogen or hydroxyl with cyclohexanedione (IV) in the presence of a cyanide source. Such methods are described, for example, in EP0186117.

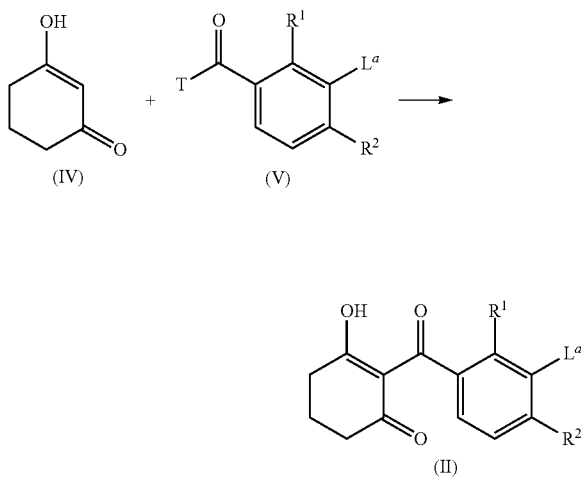

Compounds of the formula (III) can be prepared, for example, by the method shown in Scheme 3. The reaction described therein of activated carboxylic acid compounds of the formula (VI) in which $L^b$ is a leaving group such as chlorine and $G^1$ is a hydroxyl protective group such as, for example, benzyl with amines of the formula (VII) initially leads to amides of the formula (VIII) which, after subsequent removal of the hydroxyl protective group $G^1$ can be converted into alcohols of the formula (III). Such syntheses are known, for example, from *Organic Letters* (2003), Vol. 5, No. 14, pages 2539-2541.

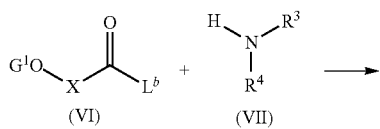

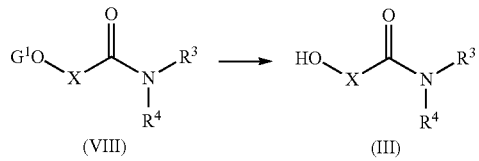

According to the methods given in Scheme 4, it is possible to prepare compounds of the formula (V) from compounds of the formula (Va) which are described, for example, in WO2008002853A2. If $R^2$ is $(C_1-C_6)$-alkyl-S(O)$_n$, initially an aniline of the formula (Va) may be diazotized, and the resulting diazonium salt can then be reacted with the appropriate sulfur compounds to give compounds of the formula (Vb). Such methods are described inter alia in *Science of Synthesis* (2007), 31, page 984ff. or in Synthetic Communications (2001), 31, 12, pages 1857-1861. If $R^2$ is chlorine, initially an aniline of the formula (Va) may be diazotized, and the resulting diazonium salt can then be reacted in a Sandmeyer reaction in the presence of copper chloride to give compounds of the formula (Vb), as described, for example, in *Science of Synthesis* (2007), 31, page 86ff. Via bromine-lithium exchange on compounds of the formula (Vb) by treatment with lithium compounds such as, for example, n-butyllithium and subsequent reaction with electrophiles such as carbon monoxide, compounds of the formula (V) according to the invention are obtained where in this case T is hydroxyl. Syntheses of this type are described, for example, in *Science of Synthesis* (2003), 17, page 42. Reaction with an oxidizing agent such as hydrogen peroxide, m-chloroperoxybenzoic acid, peroxyacetic acid and potassium peroxymonosulfate yields further compounds of the formula (V) according to the invention in which $R^2$ is $(C_1-C_6)$-alkyl-SO or $(C_1-C_6)$-alkyl-S(O)$_2$. Such reactions are described, for example, in *J. Org. Chem.* (1988), 53, 532 or *Tetrahedron Lett.* (1981), 21, page 1287.

Compounds of the formula (V) according to the invention in which $R^2$ is bromine or iodine can be obtained by initially protecting the amine functionality in anilines of the formula (Va) with a protective group $G^2$ such as, for example, the phthalimide protective group. Such methods are described inter alia in *Science of Synthesis* (2005), 21, page 282 or in *Protective Groups in Organic Synthesis, Third Edition*. T. W. Greene, P. G. M. Wuts, page 564. This affords compounds of the formula (Vc). Via methods such as the bromine-lithium exchange already described carried out on such compounds by treatment with lithium compounds such as, for example, n-butyllithium and subsequent reaction with electrophiles such as carbon dioxide, compounds of the formula (Vd) in which T is hydroxyl are obtained. The removal of the amine protective group in such compounds leads to compounds of the formula (Ve). Such methods are described, for example, in *Protective Groups in Organic Synthesis, Third Edition*. T. W. Greene, P. G. M. Wuts, page 565. Sandmeyer reactions in the presence of, for example, copper bromide or potassium iodide yield further compounds of the formula (V) according to the invention. Such methods are described, for example, in *Science of Synthesis* (2007), 31 page 132 or *Science of Synthesis* (2007), 31 page 260.

Scheme 4

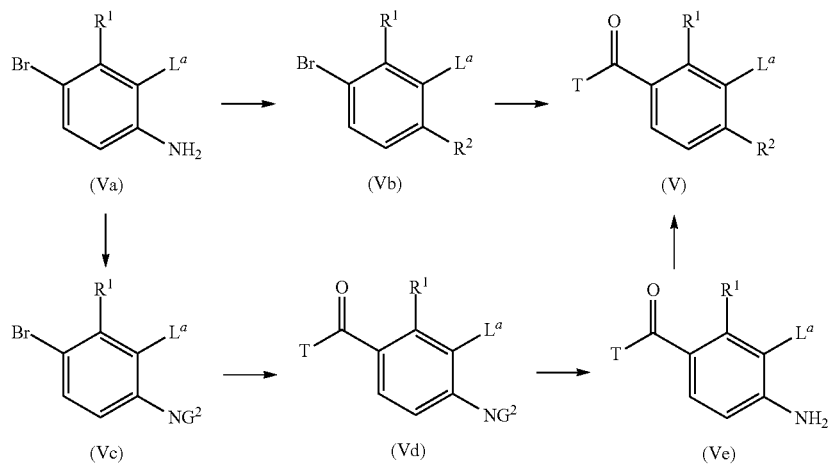

Compounds of the formula (V) in which T is halogen can be prepared by generally known methods from the analogous hydroxyl compounds by reaction with a halogenating agent such as, for example, oxalyl chloride.

Compounds of the formula (I) according to the invention in which $R^5$ is a radical different from hydroxyl can be prepared, for example, according to Scheme 5. The reaction shown therein of a compound of the formula (Ia) with a halogenating agent such as oxalyl chloride or oxalyl bromide leads to compounds of the formula (Ib) in which $L^c$ is chlorine or bromine. The subsequent reaction, if appropriate with base catalysis, of such compounds with nucleophiles such as, for example, thiols affords compounds of the formula (I) according to the invention. Such reactions are described, for example, in *Synthesis* (1992), pages 1287-1291.

Scheme 5

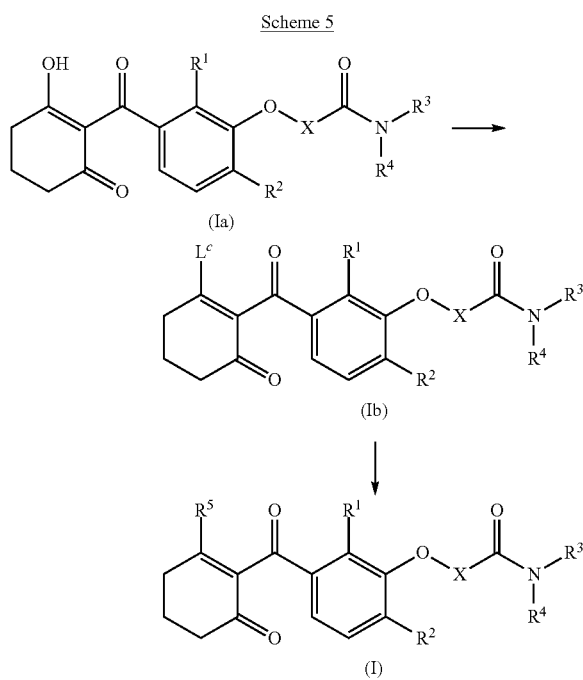

Collections of compounds of the formula (I) and/or salts thereof which can be synthesized by the aforementioned reactions can also be prepared in a parallel manner, it being possible for this to take place in a manual, partly automated or completely automated manner. In this connection, it is, for example, possible to automate the reaction procedure, the work-up or the purification of the products and/or intermediates. Overall, this is understood as meaning a procedure as described, for example, by D. Tiebes in Combinatorial Chemistry—Synthesis, Analysis, Screening (editor Günther Jung), Verlag Wiley 1999, on pages 1 to 34.

For the parallel reaction procedure and work-up, it is possible to use a series of commercially available instruments, for example Calpyso reaction blocks from Barnstead International, Dubuque, Iowa 52004-0797, USA or reaction stations from Radleys, Shirehill, Saffron Walden, Essex, CB 11 3AZ, England or MultiPROBE Automated Workstations from PerkinElmer, Waltham, Mass. 02451, USA. For the parallel purification of compounds of the formula (I) and salts thereof or of intermediates produced during the preparation, there are available, inter alia, chromatography apparatuses, for example from ISCO, Inc., 4700 Superior Street, Lincoln, Nebr. 68504, USA.

The apparatuses listed lead to a modular procedure in which the individual process steps are automated, but between the process steps manual operations have to be carried out. This can be circumvented by using partly or completely integrated automation systems in which the respective automation modules are operated, for example, by robots. Automation systems of this type can be acquired, for example, from Caliper, Hopkinton, Mass. 01748, USA.

The implementation of single or several synthesis steps can be supported through the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Besides the methods described here, the preparation of compounds of the formula (I) and salts thereof can take place completely or partially by solid-phase supported methods. For this purpose, individual intermediates or all intermediates in the synthesis or a synthesis adapted for the corresponding procedure are bonded to a synthesis resin. Solid-phase supported synthesis methods are sufficiently described in the specialist literature, e.g. Barry A. Bunin in "The Combinatorial Index", Verlag Academic Press, 1998 and Combinatorial Chemistry—Synthesis, Analysis, Screening (editor Günther Jung), Verlag Wiley, 1999. The use of solid-phase supported synthesis methods permits a series of protocols known in the literature, which again can be carried out manually or in an automated manner. The reactions can be carried out, for example, by means of IRORI technology in microreactors from Nexus Biosystems, 12140 Community Road, Poway, Calif. 92064, USA.

Both on a solid phase and in liquid phase can the procedure of individual or several synthesis steps be supported through the use of microwave technology. The specialist literature describes a series of experimental protocols, for example in Microwaves in Organic and Medicinal Chemistry (editor C. O. Kappe and A. Stadler), Verlag Wiley, 2005.

The preparation according to the process described here produces compounds of the formula (I) and their salts in the form of substance collections which are called libraries. The present invention also provides libraries which comprise at least two compounds of the formula (I) and their salts.

The compounds of the formula (I) according to the invention (and/or their salts), hereinbelow also referred to together as "compounds according to the invention", have excellent herbicidal efficacy against a broad spectrum of economically important monocotyledonous and dicotyledonous annual harmful plants. The active compounds act efficiently even on perennial harmful plants which produce shoots from rhizomes, root stocks and other perennial organs and which are difficult to control.

The present invention therefore also relates to a method for controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). In this context, the compounds according to the invention can be applied for example pre-sowing (if appropriate also by incorporation into the soil), pre-emergence or post-emergence. Specific examples may be mentioned of some representatives of the monocotyledonous and dicotyledonous weed flora which can be controlled by the compounds according to the invention, without the enumeration being restricted to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Erio-chloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds according to the invention are applied to the soil surface before germination, the weed seedlings are either prevented completely from emerging or else the weeds grow until they have reached the cotyledon stage, but then their growth stops, and, eventually, after three to four weeks have elapsed, they die completely.

If the active compounds are applied post-emergence to the green parts of the plants, growth stops after the treatment, and the harmful plants remain at the growth stage of the point of time of application, or they die completely after a certain time, so that in this manner competition by the weeds, which is harmful to the crop plants, is eliminated very early and in a sustained manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*, are damaged only to an insignificant extent, or not at all, depending on the structure of the respective compound according to the invention and its application rate. This is why the present compounds are highly suitable for the selective control of unwanted plant growth in plant crops such as agriculturally useful plants or ornamentals.

Moreover, the compounds according to the invention (depending on their respective structure and the application rate applied) have outstanding growth-regulatory properties in crop plants. They engage in the plant's metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops since for example lodging can be reduced, or prevented completely, hereby.

By virtue of their herbicidal and plant-growth-regulatory properties, the active compounds can also be employed for controlling harmful plants in crops of genetically modified plants or plants modified by conventional mutagenesis. In general, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other specific characteristics relate, for example, to the harvested material with regard to quantity, quality, storability, composition and specific constituents. Thus, transgenic plants are known whose starch content is increased, or whose starch quality is altered, or those where the harvested material has a different fatty acid composition.

It is preferred, with respect to transgenic crops, to use the compounds according to the invention in economically important transgenic crops of useful plants and ornamentals, for example of cereals such as wheat, barley, rye, oats, millet, rice and corn or else crops of sugar beet, cotton, soybean, oilseed rape, potato, tomato, peas and other vegetables. It is preferred to employ the compounds according to the invention as herbicides in crops of useful plants which are resistant, or have been made resistant by recombinant means, to the phytotoxic effects of the herbicides.

It is preferred to use the compounds according to the invention or their salts in economically important transgenic crops of useful plants and ornamentals, for example of cereals such as wheat, barley, rye, oats, millet, rice, cassava and corn or else crops of sugar beet, cotton, soybean, oilseed rape, potato, tomato, peas and other vegetables. It is preferred to employ the compounds according to the invention as herbicides in crops of useful plants which are resistant, or have been made resistant by recombinant means, to the phytotoxic effects of the herbicides.

Conventional methods of generating novel plants which have modified properties in comparison to plants occurring to date consist, for example, in traditional breeding methods and the generation of mutants. Alternatively, novel plants with altered properties can be generated with the aid of recombinant methods (see, for example, EP-A-0221044, EP-A-0131624). For example, the following have been described in several cases:
- the modification, by recombinant technology, of crop plants with the aim of modifying the starch synthesized in the plants (for example WO 92/11376, WO 92/14827, WO 91/19806),
- transgenic crop plants which are resistant to certain herbicides of the glufosinate type (cf., for example, EP 0242236 A, EP 0242246 A) or of the glyphosate type (WO 92/000377) or of the sulfonylurea type (EP 0257993 A, U.S. Pat. No. 5,013,659) or to combinations or mixtures of these herbicides through "gene stacking", such as transgenic crop plants e.g. corn or soybean with the tradename or the name Optimum™ GAT™ (glyphosate ALS tolerant),
- transgenic crop plants, for example cotton, with the capability of producing *Bacillus thuringiensis* toxins (Bt toxins), which make the plants resistant to certain pests (EP-A-0142924, EP-A-0193259),
- transgenic crop plants with a modified fatty acid composition (WO 91/13972),
- genetically modified crop plants with novel constituents or secondary metabolites, for example novel phytoalexins, which bring about an increased disease resistance (EPA 309862, EPA0464461),
- genetically modified plants with reduced photorespiration which feature higher yields and higher stress tolerance (EPA 0305398),
- transgenic crop plants which produce pharmaceutically or diagnostically important proteins ("molecular pharming"),
- transgenic crop plants which are distinguished by higher yields or better quality,
- transgenic crop plants which are distinguished by a combination, for example of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431.

To carry out such recombinant manipulations, nucleic acid molecules which allow mutagenesis or a sequence change by recombination of DNA sequences can be introduced into plasmids. For example, base substitutions can be carried out, part-sequences can be removed, or natural or synthetic sequences may be added with the aid of standard methods. To link the DNA fragments with one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone", VCH Weinheim 2nd ed., 1996.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product. To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or the expression of heterologous (=foreign) genes or gene sequences.

It is preferred to employ the compounds (I) according to the invention in transgenic crops which are resistant to growth regulators such as, for example, 2,4 D, dicamba, or against herbicides which inhibit essential plant enzymes, for example acetolactate synthases (ALS), EPSP synthases, glutamine synthases (GS) or hydroxyphenylpyruvate dioxygenases (HPPD), or against herbicides from the group of the sulfonylureas, glyphosate, glufosinate or benzoylisoxazoles and analogous active compounds, or against any combinations of these active compounds. Particularly preferably, the compounds according to the invention can be used in transgenic crop plants which are resistant to a combination of glyphosates and glufosinates, glyphosates and sulfonylureas or imidazolinones. Very particularly preferably, the compounds according to the invention can be used in transgenic crop plants such as e.g. corn or soybean with the tradename or the name Optimum™ GAT™ (glyphosate ALS tolerant).

When the active compounds according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds according to the invention as herbicides for controlling harmful plants in transgenic crop plants. The compounds according to the invention can be used in the form of wettable powders, emulsifiable concentrates, sprayable solutions, dusting products or granules in the customary formulations. The invention therefore also provides herbicidal and plant-growth-regulating compositions which comprise the compounds according to the invention.

The compounds according to the invention can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical technology], Volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell., Stuttgart 1976; Winnacker-Kuchler, "Chemische Technologie", Volume 7, C. Hanser Verlag Munich, 4th Ed. 1986.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix. Particularly suitable safeners are mefenpyr-diethyl, isoxadifen-ethyl and cyprosulfamide.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurinate. To prepare the wettable powders, the herbicidally active compounds are ground finely, for example in customary apparatuses such as hammer mills, blower mills and air-jet mills, and simultaneously or subsequently mixed with the formulation assistants.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusts are obtained by grinding the active compound with finely distributed solid substances, for example talc, natural clays, such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be prepared, for example, by means of stirrers, colloid mills and/or static mixers using aqueous organic solvents and optionally surfactants, as have, for example, already been listed above for the other formulation types.

Granules can be prepared either by spraying the active compound onto granulated inert material capable of adsorption or by applying active compound concentrates to the surface of carrier substances, such as sand, kaolinites or granulated inert material, by means of adhesives, for example polyvinyl alcohol, sodium polyacrylate or mineral oils. Suitable active compounds can also be granulated in the manner customary for the preparation of fertilizer granules—if desired as a mixture with fertilizers.

Water-dispersible granules are prepared generally by the customary processes such as spray-drying, fluidized bed granulation, pan granulation, mixing with high-speed mixers and extrusion without solid inert material.

For the preparation of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 if; "Perry's Chemical Engineer's Handbook", 5th Ed., McGraw-Hill, New York 1973, p. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally from 0.1 to 99% by weight, in particular from 0.1 to 95% by weight, of compounds according to the invention. In wettable powders, the active compound concentration is, for example, from about 10 to 90% by weight, the remainder to 100% by weight consisting of customary formulation components. In the case of emulsifiable concentrates, the active compound concentration can be from about 1 to 90, preferably from 5 to 80, % by weight. Formulations in the form of dusts comprise from 1 to 30% by weight of active compound, preferably usually from 5 to 20% by weight of active compound; sprayable solutions contain from about 0.05 to 80% by weight, preferably from 2 to 50% by weight of active compound. In the case of water-dispersible granules, the active compound content depends partially on whether the active compound is present in liquid or solid form and on which granulation auxiliaries, fillers, etc., are used. In the water-dispersible granules, the content of active compound is, for example, between 1 and 95% by weight, preferably between 10 and 80% by weight.

In addition, the active compound formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix.

Active compounds which can be employed in combination with the compounds according to the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoen desaturase, photosystem I, photosystem II, protoporphyrinogen oxidase, as are described in, for example, Weed Research 26 (1986) 441-445 or "The Pesticide Manual", 14th edition, The British Crop Protection Council and the Royal Soc. of Chemistry, 2003 and the literature cited therein. Known herbicides or plant growth regulators which can be combined with the compounds according to the invention are, for example, the following active compounds (the compounds are either designated by the common name according to the International Organization for Standardization (ISO) or by the chemical name, or by the code number) and always comprise all use forms such as acids, salts, esters and isomers such as stereoisomers and optical isomers. Here, by way of example, one and in some cases a plurality of use forms are mentioned:

acetochlor, acibenzolar, acibenzolar-S-methyl, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryn, BAH-043, BAS-140H, BAS-693H, BAS-714H, BAS-762H, BAS-776H, BAS-800H, beflubutamid, benazolin, benazolin-ethyl, bencarbazone, benfluralin, benfuresate, bensulide, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat dibromide, dithiopyr, diuron, DNOC, eglinazine-ethyl, endothal, EPTC, esprocarb, ethalfluralin, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, L-glufosinate, L-glufosinate-ammonium, glufosinate-ammonium, glyphosate, glyphosate-isopropylammonium, H-9201, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HNPC-9908, HOK-201, HW-02, imazamethabenz, imazamethabenz-methyl, imazamox, imazapic, imazapyr, imazaquin, imazethapyr, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, IDH-100, KUH-043, KUH-071, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat chloride, mesosulfuron, mesosulfuron-methyl, mesotrione, methabenzthiazuron, metam, metamifop, metamitron, metazachlor, metazosulfuron, methazole, methiozolin, methoxyphenone, methyldymron, 1-methylcyclopropene, methyl isothiocyanate, metobenzuron, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monuron, MT 128, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron-ethyl, pyrazoxyfen, pyribambenz, pyribambenz-isopropyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, sulcotrione, sulfallate (CDEC), sulfentrazone, sulfometuron, sulfometuron-methyl, sulfosate (glyphosate-trimesium), sulfosulfuron, SYN-523, SYP-249, SYP-298, SYP-300, tebutam, tebuthiuron, tecnazene, tefuryltrione, tembotrione, tepraloxydim, terbacil, terbucarb, terbuchlor, terbumeton, terbuthylazine, terbutryn, TH-547, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0166, ZJ-0270, ZJ-0543, ZJ-0862 and the following compounds

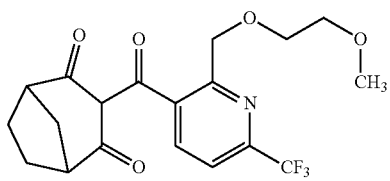

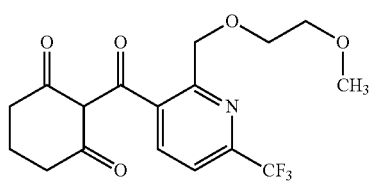

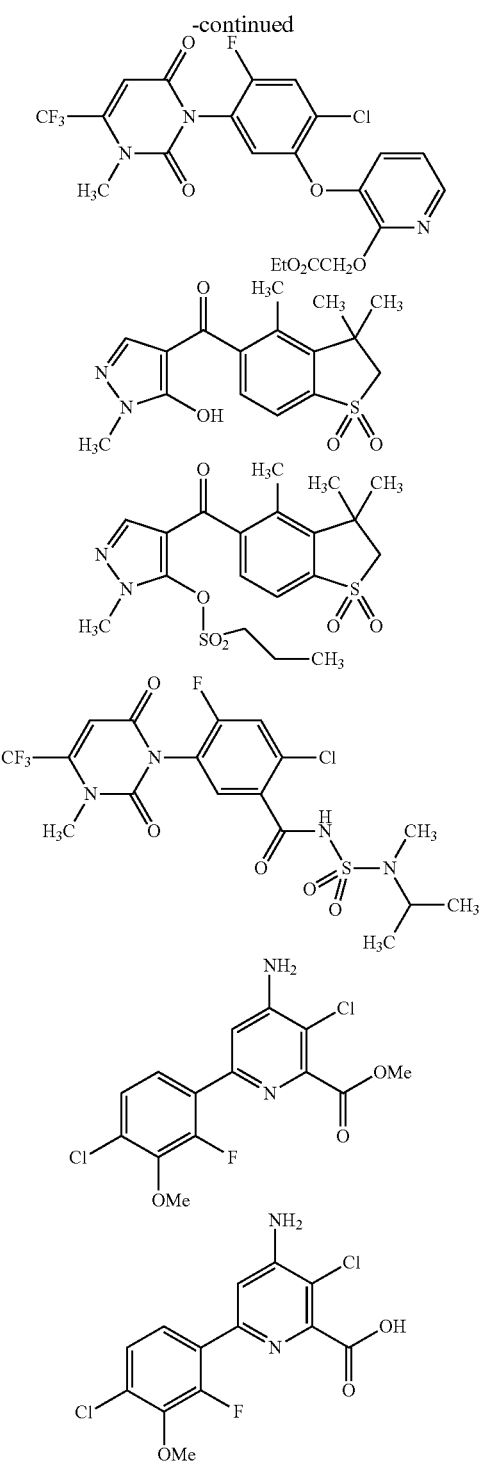

-continued

For application, the formulations present in commercial form are, if appropriate, diluted in a customary manner, for example in the case of wettable powders, emulsifiable concentrates, dispersions and water-dispersible granules with water. Preparations in the form of dusts, granules for soil application or granules for broadcasting and sprayable solutions are usually not diluted further with other inert substances prior to application.

The required application rate of the compounds of the formula (I) varies according to the external conditions such as, inter alia, temperature, humidity and the type of herbicide used. It may vary within wide limits, for example between 0.001 and 1.0 kg/ha or more of active substance; however, preferably it is between 0.005 and 750 g/ha.

The examples below illustrate the invention:

A. CHEMICAL EXAMPLES

Preparation of 2-{3-[(2,6-dioxocyclohexyl)carbonyl]-6-(methylsulfonyl)-2-(trifluoromethyl)phenoxy}-N,N-diethylacetamide (Table Example No. 1-1829)

Step 1: Synthesis of 2-(benzyloxy)-N,N-diethylacetamide

At 0° C., 1.54 ml (9.7 mmol) of benzyloxyacetyl chloride and 0.92 ml (8.9 mmol) of diethylamine were dissolved in 35 ml of $CH_2Cl_2$. The reaction mixture was stirred at room temperature (RT) for 2 hours and then washed with dilute HCl solution and saturated NaCl solution. The organic phase was dried over $Na_2SO_4$ and evaporated to dryness. 2-(Benzyloxy)-N,N-diethylacetamide was obtained as a colorless residue.

Yield: 2.26 g (99% of theory)
$^1$H-NMR ($CDCl_3$): 7.28-7.40 (m, 5H), 4.61 (s, 2H), 4.16 (s, 2H), 3.39 (q, 2H), 3.29 (q, 2H), 1.12 (t, 6H).

Step 2: Synthesis of N,N-Diethyl-2-hydroxyacetamide 2.20 g (9.9 mmol) of 2-(benzyloxy)-N,N-diethylacetamide were dissolved in 45 ml of ethyl acetate, and 200 mg of Pd/C (10%) were added. The reaction mixture was stirred under an atmosphere of hydrogen for 24 hours and then filtered through kieselguhr. The filtrate was evaporated to dryness, and N,N-diethyl-2-hydroxyacetamide was obtained as a colorless residue.

Yield: 1.22 g (82% of theory)
$^1$H-NMR ($CDCl_3$): 4.13 (s, 2H), 3.44 (q, 2H), 3.15 (q, 2H), 1.18 (t, 3H), 1.17 (t, 3H).

Step 3: Synthesis of 1-bromo-3-fluoro-4-(methylsulfanyl)-2-(trifluoromethyl)benzene With cooling, 1.12 g (16.3 mmol) of sodium nitrite were introduced carefully into 8.00 ml of concentrated sulfuric acid. At 10-15° C., 4.00 g (15.5 mmol) of 4-bromo-2-fluoro-3-(trifluoromethyl)aniline dissolved in 30 ml of glacial acetic acid were slowly added dropwise to the clear solution, and the mixture was stirred at this temperature for 1.5 hours. 20 mg (0.31 mmol) of copper powder and 1.82 ml (20.2 mmol) of dimethyl disulfide were initially charged in 12 ml of glacial acetic acid and warmed to 45° C. The solution of the diazonium salt prepared beforehand was slowly added dropwise to this solution. After the addition had ended, the reaction mixture was stirred at 70° C. for 4 hours. The solution was then added to about 500 ml of water and extracted with $CH_2Cl_2$. The organic phase was washed with water, dilute $NaHCO_3$ solution, dilute HCl solution and saturated NaCl solution. The organic phase was dried over $Na_2SO_4$ and evaporated to dryness. The crude product obtained was separated by column chromatography (silica gel, gradient heptane/ethyl acetate). 1-Bromo-3-fluoro-4-(methylsulfanyl)-2-(trifluoromethyl)benzene was obtained as a brown solid.

Yield: 4.16 g (93% of theory)
$^1$H-NMR ($CDCl_3$): 7.46 (d, 1H), 7.21 (t, 1H), 2.48 (s, 3H).

Step 4: Synthesis of 3-fluoro-4-(methylsulfanyl)-2-(trifluoromethyl)benzoic acid 21.0 g (72.98 mmol) of 1-bromo-3-fluoro-4-(methylsulfanyl)-2-(trifluoromethyl)benzene were dissolved in 275 ml of absolute diethyl ether and cooled to −78° C. 54.8 ml (87.59 mmol) of a 1.6M solution of n-butyllithium in hexane were slowly added dropwise, and the resulting solution was stirred at −78° C. for 60 minutes. The reaction mixture was then added to freshly ground dry ice and slowly warmed to RT. Water was added, and the reaction mixture was made alkaline using 2M NaOH solution and washed with diethyl ether. The aqueous phase was then acidified with 51M HCl solution, causing the product to precipitate. The precipitate was filtered off with suction and dried under reduced pressure.

Yield: 16.32 g (84% of theory)
$^1$H-NMR ($CDCl_3$): 7.35-7.42 (m, 2H), 2.50 (s, 3H).

Step 5: Synthesis of 3-fluoro-4-(methylsulfonyl)-2-(trifluoromethyl)benzoic acid 30.00 g (118.0 mmol) of 3-fluoro-4-(methylsulfanyl)-2-(trifluoromethyl)benzoic acid were dissolved in 350 ml of acetic acid, and 1.04 g (472.1 mmol) of sodium tungstate were added. The reaction mixture was warmed to 60° C., and 35% strength hydrogen peroxide solution was slowly added dropwise such that the temperature did not exceed 80° C. After the addition, stirring was continued at 60° C. for 60 minutes. The reaction mixture was then diluted with 500 ml of water. The aqueous phase was saturated with sodium chloride and extracted with ethyl acetate. The combined organic phases were washed with sodium bisulfate solution, dried over $Na_2SO_4$ and evaporated to dryness. 3-Fluoro-4-(methylsulfonyl)-2-(trifluoromethyl)benzoic acid was obtained as a beige solid.

Yield: 33.00 g (98% of theory)
$^1$H-NMR ($CDCl_3$): 8.26 (t, 1H), 7.63 (d, 1H), 3.30 (s, 3H).

Step 6: Synthesis of 2-[3-fluoro-4-(methylsulfonyl)-2-(trifluoromethyl)benzoyl]cyclo-hexane-1,3-dione 3.00 g (10.5 mmol) of 3-fluoro-4-(methylsulfonyl)-2-(trifluoromethyl)benzoic acid were dissolved in 30 ml of $CH_2Cl_2$, and 5 drops of dimethylformamide were added. 1.14 ml (13.1 mmol) of oxalyl chloride were added dropwise, and the solution was heated under reflux for 15 minutes. The reaction mixture was then concentrated, and the residue was briefly dried under reduced pressure. The residue was taken up in 30 ml of dichloromethane, and 1.29 g (11.5 mmol) of 1,3-cyclohexanedione and 2.92 ml (21.0 mmol) of triethylamine were added. The reaction mixture was stirred at RT for 60 minutes. The mixture was then washed with 1M HCl solution and the organic phase was dried over $Na_2SO_4$ and evaporated to dryness.

The enol ester obtained in this manner was dissolved in 30 ml of acetonitrile, and 2.19 ml (15.7 mmol) of triethylamine, 210 µl (1.6 mmol) of trimethylsilyl cyanide and 205 mg (3.1 mmol) of potassium cyanide were added. The reaction mixture was stirred at RT overnight, and the solvent was then removed under reduced pressure. 1N $H_2SO_4$ solution was added to the residue, and the mixture was extracted with diethyl ether. The organic phase was dried over $Na_2SO_4$ and evaporated to dryness. This gave 2-[3-fluoro-4-(methylsulfonyl)-2-(trifluoromethyl)benzoyl]cyclohexane-1,3-dione as a yellow solid.

Yield: 3.82 g (86% of theory)

$^1$H-NMR (CDCl$_3$): 16.2 (bs, 1H), 8.15 (dd, 1H), 7.08 (d, 1H), 3.38 (s, 3H), 2.82 (t, 2H), 2.42 (t, 2H), 2.07 (quin, 2H).

Step 7

Synthesis of 2-{3-[(2,6-dioxocyclohexyl)carbonyl]-6-(methylsulfonyl)-2-(trifluoromethyl)phenoxy}-N,N-diethylacetamide 150 mg (0.39 mmol) of 2-[3-fluoro-4-(methylsulfonyl)-2-(trifluoromethyl)benzoyl]cyclo-hexane-1,3-dione and 56.9 mg (0.43 mmol) of N,N-diethyl-2-hydroxyacetamide were dissolved in 5 ml of absolute dimethylformamide.

56.8 mg (1.42 mmol) of sodium hydride (60% suspension in mineral oil) were added, and the resulting reaction mixture was stirred at RT overnight. After careful addition of 10 ml of water, the mixture was washed with diethyl ether. The aqueous phase was then acidified with 2M HCl solution and extracted with dichloromethane. The organic phase was dried over Na$_2$SO$_4$ and evaporated to dryness. 2-{3-[(2,6-Dioxocyclohexyl)carbonyl]-6-(methylsulfonyl)-2-(trifluoromethyl)phenoxy}-N,N-diethylacetamide was obtained as a yellowish solid.

Yield: 210 mg (99% of theory)

$^1$H-NMR (CDCl$_3$): 8.01 (d, 1H), 7.07 (d, 1H), 4.90-5.00 (m, 2H), 3.49 (s, 3H), 3.44 (q, 2H), 3.12 (q, 2H), 2.82 (t, 2H), 2.42 (t, 2H), 2.08 (quin, 2H), 1.19 (t, 3H), 1.18 (t, 3H).

The examples listed in Table 1 below were prepared analogously to the methods mentioned above or can be obtained analogously to the methods mentioned above. These compounds are very particularly preferred.

The abbreviations used denote:

Et=ethyl Me=methyl Pr=propyl Ph=phenyl

TABLE 1

| No. | X$^1$ | R$^1$ | R$^2$ | —NR$^3$R$^4$ | R$^5$ | Physical data |
|---|---|---|---|---|---|---|
| 1-1 | —CH$_2$— | CF$_3$ | Cl | —NH$_2$ | OH | |
| 1-2 | —CH$_2$— | CF$_3$ | Cl | —NHMe | OH | |
| 1-3 | —CH$_2$— | CF$_3$ | Cl | —NMe$_2$ | OH | CDCl$_3$: 16.63 (bs, 1H), 7.58 (d, 1H), 6.83 (d, 1H), 4.75 (s, 2H), 3.08 (s, 3H), 3.01 (s, 3H), 2.78 (t, 2H), 2.40 (t, 3H), 2.03 (s, 3H) |
| 1-4 | —CH$_2$— | CF$_3$ | Cl | —NHEt | OH | |
| 1-5 | —CH$_2$— | CF$_3$ | Cl | —NEt$_2$ | OH | |
| 1-6 | —CH$_2$— | CF$_3$ | Cl | —NH(n-Pr) | OH | |
| 1-7 | —CH$_2$— | CF$_3$ | Cl | —N(n-Pr)$_2$ | OH | |
| 1-8 | —CH$_2$— | CF$_3$ | Cl | —NMeEt | OH | |
| 1-9 | —CH$_2$— | CF$_3$ | Cl | —NMe(n-Pr) | OH | |
| 1-10 | —CH$_2$— | CF$_3$ | Cl | —NEt(n-Pr) | OH | |
| 1-11 | —CH$_2$— | CF$_3$ | Cl | —NH(i-Pr) | OH | |
| 1-12 | —CH$_2$— | CF$_3$ | Cl | —NMe(i-Pr) | OH | |
| 1-13 | —CH$_2$— | CF$_3$ | Cl | —NEt(i-Pr) | OH | |
| 1-14 | —CH$_2$— | CF$_3$ | Cl | —N(Me)OMe | OH | |
| 1-15 | —CH$_2$— | CF$_3$ | Cl | —N(Me)OEt | OH | |
| 1-16 | —CH$_2$— | CF$_3$ | Cl | —N(Me)O(n-Pr) | OH | |
| 1-17 | —CH$_2$— | CF$_3$ | Cl | —N(Et)OMe | OH | |
| 1-18 | —CH$_2$— | CF$_3$ | Cl | —N(Et)OEt | OH | |
| 1-19 | —CH$_2$— | CF$_3$ | Cl | —N(Et)O(n-Pr) | OH | |
| 1-20 | —CH$_2$— | CCl$_3$ | Cl | —NH$_2$ | OH | |
| 1-21 | —CH$_2$— | CCl$_3$ | Cl | —NHMe | OH | |
| 1-22 | —CH$_2$— | CCl$_3$ | Cl | —NMe$_2$ | OH | |
| 1-23 | —CH$_2$— | CCl$_3$ | Cl | —NHEt | OH | |
| 1-24 | —CH$_2$— | CCl$_3$ | Cl | —NEt$_2$ | OH | |
| 1-25 | —CH$_2$— | CCl$_3$ | Cl | —NH(n-Pr) | OH | |
| 1-26 | —CH$_2$— | CCl$_3$ | Cl | —N(n-Pr)$_2$ | OH | |
| 1-27 | —CH$_2$— | CCl$_3$ | Cl | —NMeEt | OH | |
| 1-28 | —CH$_2$— | CCl$_3$ | Cl | —NMe(n-Pr) | OH | |
| 1-29 | —CH$_2$— | CCl$_3$ | Cl | —NEt(n-Pr) | OH | |
| 1-30 | —CH$_2$— | CCl$_3$ | Cl | —NH(i-Pr) | OH | |
| 1-31 | —CH$_2$— | CCl$_3$ | Cl | —NMe(i-Pr) | OH | |
| 1-32 | —CH$_2$— | CCl$_3$ | Cl | —NEt(i-Pr) | OH | |
| 1-33 | —CH$_2$— | CCl$_3$ | Cl | —N(Me)OMe | OH | |
| 1-34 | —CH$_2$— | CCl$_3$ | Cl | —N(Me)OEt | OH | |
| 1-35 | —CH$_2$— | CCl$_3$ | Cl | —N(Me)O(n-Pr) | OH | |
| 1-36 | —CH$_2$— | CCl$_3$ | Cl | —N(Et)OMe | OH | |
| 1-37 | —CH$_2$— | CCl$_3$ | Cl | —N(Et)OEt | OH | |
| 1-38 | —CH$_2$— | CCl$_3$ | Cl | —N(Et)O(n-Pr) | OH | |
| 1-39 | —CH$_2$— | C$_2$F$_5$ | Cl | —NH$_2$ | OH | |
| 1-40 | —CH$_2$— | C$_2$F$_5$ | Cl | —NHMe | OH | |
| 1-41 | —CH$_2$— | C$_2$F$_5$ | Cl | —NMe$_2$ | OH | |
| 1-42 | —CH$_2$— | C$_2$F$_5$ | Cl | —NHEt | OH | |
| 1-43 | —CH$_2$— | C$_2$F$_5$ | Cl | —NEt$_2$ | OH | |
| 1-44 | —CH$_2$— | C$_2$F$_5$ | Cl | —NH(n-Pr) | OH | |
| 1-45 | —CH$_2$— | C$_2$F$_5$ | Cl | —N(n-Pr)$_2$ | OH | |
| 1-46 | —CH$_2$— | C$_2$F$_5$ | Cl | —NMeEt | OH | |
| 1-47 | —CH$_2$— | C$_2$F$_5$ | Cl | —NMe(n-Pr) | OH | |
| 1-48 | —CH$_2$— | C$_2$F$_5$ | Cl | —NEt(n-Pr) | OH | |

TABLE 1-continued

| No. | X¹ | R¹ | R² | —NR³R⁴ | R⁵ | Physical data |
|---|---|---|---|---|---|---|
| 1-49 | —CH$_2$— | C$_2$F$_5$ | Cl | —NH(i-Pr) | OH | |
| 1-50 | —CH$_2$— | C$_2$F$_5$ | Cl | —NMe(i-Pr) | OH | |
| 1-51 | —CH$_2$— | C$_2$F$_5$ | Cl | —NEt(i-Pr) | OH | |
| 1-52 | —CH$_2$— | C$_2$F$_5$ | Cl | —N(Me)OMe | OH | |
| 1-53 | —CH$_2$— | C$_2$F$_5$ | Cl | —N(Me)OEt | OH | |
| 1-54 | —CH$_2$— | C$_2$F$_5$ | Cl | —N(Me)O(n-Pr) | OH | |
| 1-55 | —CH$_2$— | C$_2$F$_5$ | Cl | —N(Et)OMe | OH | |
| 1-56 | —CH$_2$— | C$_2$F$_5$ | Cl | —N(Et)OEt | OH | |
| 1-57 | —CH$_2$— | C$_2$F$_5$ | Cl | —N(Et)O(n-Pr) | OH | |
| 1-58 | —CH$_2$— | CHF$_2$ | Cl | —NH$_2$ | OH | |
| 1-59 | —CH$_2$— | CHF$_2$ | Cl | —NHMe | OH | |
| 1-60 | —CH$_2$— | CHF$_2$ | Cl | —NMe$_2$ | OH | |
| 1-61 | —CH$_2$— | CHF$_2$ | Cl | —NHEt | OH | |
| 1-62 | —CH$_2$— | CHF$_2$ | Cl | —NEt$_2$ | OH | |
| 1-63 | —CH$_2$— | CHF$_2$ | Cl | —NH(n-Pr) | OH | |
| 1-64 | —CH$_2$— | CHF$_2$ | Cl | —N(n-Pr)$_2$ | OH | |
| 1-65 | —CH$_2$— | CHF$_2$ | Cl | —NMeEt | OH | |
| 1-66 | —CH$_2$— | CHF$_2$ | Cl | —NMe(n-Pr) | OH | |
| 1-67 | —CH$_2$— | CHF$_2$ | Cl | —NEt(n-Pr) | OH | |
| 1-68 | —CH$_2$— | CHF$_2$ | Cl | —NH(i-Pr) | OH | |
| 1-69 | —CH$_2$— | CHF$_2$ | Cl | —NMe(i-Pr) | OH | |
| 1-70 | —CH$_2$— | CHF$_2$ | Cl | —NEt(i-Pr) | OH | |
| 1-71 | —CH$_2$— | CHF$_2$ | Cl | —N(Me)OMe | OH | |
| 1-72 | —CH$_2$— | CHF$_2$ | Cl | —N(Me)OEt | OH | |
| 1-73 | —CH$_2$— | CHF$_2$ | Cl | —N(Me)O(n-Pr) | OH | |
| 1-74 | —CH$_2$— | CHF$_2$ | Cl | —N(Et)OMe | OH | |
| 1-75 | —CH$_2$— | CHF$_2$ | Cl | —N(Et)OEt | OH | |
| 1-76 | —CH$_2$— | CHF$_2$ | Cl | —N(Et)O(n-Pr) | OH | |
| 1-77 | —CH$_2$— | CF$_3$ | Cl | —NH$_2$ | SCH$_2$C(O)OMe | |
| 1-78 | —CH$_2$— | CF$_3$ | Cl | —NHMe | SCH$_2$C(O)OMe | |
| 1-79 | —CH$_2$— | CF$_3$ | Cl | —NMe$_2$ | SCH$_2$C(O)OMe | |
| 1-80 | —CH$_2$— | CF$_3$ | Cl | —NHEt | SCH$_2$C(O)OMe | |
| 1-81 | —CH$_2$— | CF$_3$ | Cl | —NEt$_2$ | SCH$_2$C(O)OMe | |
| 1-82 | —CH$_2$— | CF$_3$ | Cl | —NH(n-Pr) | SCH$_2$C(O)OMe | |
| 1-83 | —CH$_2$— | CF$_3$ | Cl | —N(n-Pr)$_2$ | SCH$_2$C(O)OMe | |
| 1-84 | —CH$_2$— | CF$_3$ | Cl | —NMeEt | SCH$_2$C(O)OMe | |
| 1-85 | —CH$_2$— | CF$_3$ | Cl | —NMe(n-Pr) | SCH$_2$C(O)OMe | |
| 1-86 | —CH$_2$— | CF$_3$ | Cl | —NEt(n-Pr) | SCH$_2$C(O)OMe | |
| 1-87 | —CH$_2$— | CF$_3$ | Cl | —NH(i-Pr) | SCH$_2$C(O)OMe | |
| 1-88 | —CH$_2$— | CF$_3$ | Cl | —NMe(i-Pr) | SCH$_2$C(O)OMe | |
| 1-89 | —CH$_2$— | CF$_3$ | Cl | —NEt(i-Pr) | SCH$_2$C(O)OMe | |
| 1-90 | —CH$_2$— | CF$_3$ | Cl | —N(Me)OMe | SCH$_2$C(O)OMe | |
| 1-91 | —CH$_2$— | CF$_3$ | Cl | —N(Me)OEt | SCH$_2$C(O)OMe | |
| 1-92 | —CH$_2$— | CF$_3$ | Cl | —N(Me)O(n-Pr) | SCH$_2$C(O)OMe | |
| 1-93 | —CH$_2$— | CF$_3$ | Cl | —N(Et)OMe | SCH$_2$C(O)OMe | |
| 1-94 | —CH$_2$— | CF$_3$ | Cl | —N(Et)OEt | SCH$_2$C(O)OMe | |
| 1-95 | —CH$_2$— | CF$_3$ | Cl | —N(Et)O(n-Pr) | SCH$_2$C(O)OMe | |
| 1-96 | —CH$_2$— | CCl$_3$ | Cl | —NH$_2$ | SCH$_2$C(O)OMe | |
| 1-97 | —CH$_2$— | CCl$_3$ | Cl | —NHMe | SCH$_2$C(O)OMe | |
| 1-98 | —CH$_2$— | CCl$_3$ | Cl | —NMe$_2$ | SCH$_2$C(O)OMe | |
| 1-99 | —CH$_2$— | CCl$_3$ | Cl | —NHEt | SCH$_2$C(O)OMe | |
| 1-100 | —CH$_2$— | CCl$_3$ | Cl | —NEt$_2$ | SCH$_2$C(O)OMe | |
| 1-101 | —CH$_2$— | CCl$_3$ | Cl | —NH(n-Pr) | SCH$_2$C(O)OMe | |
| 1-102 | —CH$_2$— | CCl$_3$ | Cl | —N(n-Pr)$_2$ | SCH$_2$C(O)OMe | |
| 1-103 | —CH$_2$— | CCl$_3$ | Cl | —NMeEt | SCH$_2$C(O)OMe | |
| 1-104 | —CH$_2$— | CCl$_3$ | Cl | —NMe(n-Pr) | SCH$_2$C(O)OMe | |
| 1-105 | —CH$_2$— | CCl$_3$ | Cl | —NEt(n-Pr) | SCH$_2$C(O)OMe | |
| 1-106 | —CH$_2$— | CCl$_3$ | Cl | —NH(i-Pr) | SCH$_2$C(O)OMe | |
| 1-107 | —CH$_2$— | CCl$_3$ | Cl | —NMe(i-Pr) | SCH$_2$C(O)OMe | |
| 1-108 | —CH$_2$— | CCl$_3$ | Cl | —NEt(i-Pr) | SCH$_2$C(O)OMe | |
| 1-109 | —CH$_2$— | CCl$_3$ | Cl | —N(Me)OMe | SCH$_2$C(O)OMe | |
| 1-110 | —CH$_2$— | CCl$_3$ | Cl | —N(Me)OEt | SCH$_2$C(O)OMe | |
| 1-111 | —CH$_2$— | CCl$_3$ | Cl | —N(Me)O(n-Pr) | SCH$_2$C(O)OMe | |
| 1-112 | —CH$_2$— | CCl$_3$ | Cl | —N(Et)OMe | SCH$_2$C(O)OMe | |
| 1-113 | —CH$_2$— | CCl$_3$ | Cl | —N(Et)OEt | SCH$_2$C(O)OMe | |
| 1-114 | —CH$_2$— | CCl$_3$ | Cl | —N(Et)O(n-Pr) | SCH$_2$C(O)OMe | |
| 1-115 | —CH$_2$— | C$_2$F$_5$ | Cl | —NH$_2$ | SCH$_2$C(O)OMe | |
| 1-116 | —CH$_2$— | C$_2$F$_5$ | Cl | —NHMe | SCH$_2$C(O)OMe | |
| 1-117 | —CH$_2$— | C$_2$F$_5$ | Cl | —NMe$_2$ | SCH$_2$C(O)OMe | |
| 1-118 | —CH$_2$— | C$_2$F$_5$ | Cl | —NHEt | SCH$_2$C(O)OMe | |
| 1-119 | —CH$_2$— | C$_2$F$_5$ | Cl | —NEt$_2$ | SCH$_2$C(O)OMe | |
| 1-120 | —CH$_2$— | C$_2$F$_5$ | Cl | —NH(n-Pr) | SCH$_2$C(O)OMe | |
| 1-121 | —CH$_2$— | C$_2$F$_5$ | Cl | —N(n-Pr)$_2$ | SCH$_2$C(O)OMe | |
| 1-122 | —CH$_2$— | C$_2$F$_5$ | Cl | —NMeEt | SCH$_2$C(O)OMe | |
| 1-123 | —CH$_2$— | C$_2$F$_5$ | Cl | —NMe(n-Pr) | SCH$_2$C(O)OMe | |
| 1-124 | —CH$_2$— | C$_2$F$_5$ | Cl | —NEt(n-Pr) | SCH$_2$C(O)OMe | |
| 1-125 | —CH$_2$— | C$_2$F$_5$ | Cl | —NH(i-Pr) | SCH$_2$C(O)OMe | |

TABLE 1-continued

| No. | X$^1$ | R$^1$ | R$^2$ | —NR$^3$R$^4$ | R$^5$ | Physical data |
|---|---|---|---|---|---|---|
| 1-126 | —CH$_2$— | C$_2$F$_5$ | Cl | —NMe(i-Pr) | SCH$_2$C(O)OMe | |
| 1-127 | —CH$_2$— | C$_2$F$_5$ | Cl | —NEt(i-Pr) | SCH$_2$C(O)OMe | |
| 1-128 | —CH$_2$— | C$_2$F$_5$ | Cl | —N(Me)OMe | SCH$_2$C(O)OMe | |
| 1-129 | —CH$_2$— | C$_2$F$_5$ | Cl | —N(Me)OEt | SCH$_2$C(O)OMe | |
| 1-130 | —CH$_2$— | C$_2$F$_5$ | Cl | —N(Me)O(n-Pr) | SCH$_2$C(O)OMe | |
| 1-131 | —CH$_2$— | C$_2$F$_5$ | Cl | —N(Et)OMe | SCH$_2$C(O)OMe | |
| 1-132 | —CH$_2$— | C$_2$F$_5$ | Cl | —N(Et)OEt | SCH$_2$C(O)OMe | |
| 1-133 | —CH$_2$— | C$_2$F$_5$ | Cl | —N(Et)O(n-Pr) | SCH$_2$C(O)OMe | |
| 1-134 | —CH$_2$— | CHF$_2$ | Cl | —NH$_2$ | SCH$_2$C(O)OMe | |
| 1-135 | —CH$_2$— | CHF$_2$ | Cl | —NHMe | SCH$_2$C(O)OMe | |
| 1-136 | —CH$_2$— | CHF$_2$ | Cl | —NMe$_2$ | SCH$_2$C(O)OMe | |
| 1-137 | —CH$_2$— | CHF$_2$ | Cl | —NHEt | SCH$_2$C(O)OMe | |
| 1-138 | —CH$_2$— | CHF$_2$ | Cl | —NEt$_2$ | SCH$_2$C(O)OMe | |
| 1-139 | —CH$_2$— | CHF$_2$ | Cl | —NH(n-Pr) | SCH$_2$C(O)OMe | |
| 1-140 | —CH$_2$— | CHF$_2$ | Cl | —N(n-Pr)$_2$ | SCH$_2$C(O)OMe | |
| 1-141 | —CH$_2$— | CHF$_2$ | Cl | —NMeEt | SCH$_2$C(O)OMe | |
| 1-142 | —CH$_2$— | CHF$_2$ | Cl | —NMe(n-Pr) | SCH$_2$C(O)OMe | |
| 1-143 | —CH$_2$— | CHF$_2$ | Cl | —NEt(n-Pr) | SCH$_2$C(O)OMe | |
| 1-144 | —CH$_2$— | CHF$_2$ | Cl | —NH(i-Pr) | SCH$_2$C(O)OMe | |
| 1-145 | —CH$_2$— | CHF$_2$ | Cl | —NMe(i-Pr) | SCH$_2$C(O)OMe | |
| 1-146 | —CH$_2$— | CHF$_2$ | Cl | —NEt(i-Pr) | SCH$_2$C(O)OMe | |
| 1-147 | —CH$_2$— | CHF$_2$ | Cl | —N(Me)OMe | SCH$_2$C(O)OMe | |
| 1-148 | —CH$_2$— | CHF$_2$ | Cl | —N(Me)OEt | SCH$_2$C(O)OMe | |
| 1-149 | —CH$_2$— | CHF$_2$ | Cl | —N(Me)O(n-Pr) | SCH$_2$C(O)OMe | |
| 1-150 | —CH$_2$— | CHF$_2$ | Cl | —N(Et)OMe | SCH$_2$C(O)OMe | |
| 1-151 | —CH$_2$— | CHF$_2$ | Cl | —N(Et)OEt | SCH$_2$C(O)OMe | |
| 1-152 | —CH$_2$— | CHF$_2$ | Cl | —N(Et)O(n-Pr) | SCH$_2$C(O)OMe | |
| 1-153 | —(CH$_2$)$_2$— | CF$_3$ | Cl | —NH$_2$ | OH | |
| 1-154 | —(CH$_2$)$_2$— | CF$_3$ | Cl | —NHMe | OH | |
| 1-155 | —(CH$_2$)$_2$— | CF$_3$ | Cl | —NMe$_2$ | OH | |
| 1-156 | —(CH$_2$)$_2$— | CF$_3$ | Cl | —NHEt | OH | |
| 1-157 | —(CH$_2$)$_2$— | CF$_3$ | Cl | —NEt$_2$ | OH | |
| 1-158 | —(CH$_2$)$_2$— | CF$_3$ | Cl | —NH(n-Pr) | OH | |
| 1-159 | —(CH$_2$)$_2$— | CF$_3$ | Cl | —N(n-Pr)$_2$ | OH | |
| 1-160 | —(CH$_2$)$_2$— | CF$_3$ | Cl | —NMeEt | OH | |
| 1-161 | —(CH$_2$)$_2$— | CF$_3$ | Cl | —NMe(n-Pr) | OH | |
| 1-162 | —(CH$_2$)$_2$— | CF$_3$ | Cl | —NEt(n-Pr) | OH | |
| 1-163 | —(CH$_2$)$_2$— | CF$_3$ | Cl | —NH(i-Pr) | OH | |
| 1-164 | —(CH$_2$)$_2$— | CF$_3$ | Cl | —NMe(i-Pr) | OH | |
| 1-165 | —(CH$_2$)$_2$— | CF$_3$ | Cl | —NEt(i-Pr) | OH | |
| 1-166 | —(CH$_2$)$_2$— | CF$_3$ | Cl | —N(Me)OMe | OH | |
| 1-167 | —(CH$_2$)$_2$— | CF$_3$ | Cl | —N(Me)OEt | OH | |
| 1-168 | —(CH$_2$)$_2$— | CF$_3$ | Cl | —N(Me)O(n-Pr) | OH | |
| 1-169 | —(CH$_2$)$_2$— | CF$_3$ | Cl | —N(Et)OMe | OH | |
| 1-170 | —(CH$_2$)$_2$— | CF$_3$ | Cl | —N(Et)OEt | OH | |
| 1-171 | —(CH$_2$)$_2$— | CF$_3$ | Cl | —N(Et)O(n-Pr) | OH | |
| 1-172 | —(CH$_2$)$_2$— | CCl$_3$ | Cl | —NH$_2$ | OH | |
| 1-173 | —(CH$_2$)$_2$— | CCl$_3$ | Cl | —NHMe | OH | |
| 1-174 | —(CH$_2$)$_2$— | CCl$_3$ | Cl | —NMe$_2$ | OH | |
| 1-175 | —(CH$_2$)$_2$— | CCl$_3$ | Cl | —NHEt | OH | |
| 1-176 | —(CH$_2$)$_2$— | CCl$_3$ | Cl | —NEt$_2$ | OH | |
| 1-177 | —(CH$_2$)$_2$— | CCl$_3$ | Cl | —NH(n-Pr) | OH | |
| 1-178 | —(CH$_2$)$_2$— | CCl$_3$ | Cl | —N(n-Pr)$_2$ | OH | |
| 1-179 | —(CH$_2$)$_2$— | CCl$_3$ | Cl | —NMeEt | OH | |
| 1-180 | —(CH$_2$)$_2$— | CCl$_3$ | Cl | —NMe(n-Pr) | OH | |
| 1-181 | —(CH$_2$)$_2$— | CCl$_3$ | Cl | —NEt(n-Pr) | OH | |
| 1-182 | —(CH$_2$)$_2$— | CCl$_3$ | Cl | —NH(i-Pr) | OH | |
| 1-183 | —(CH$_2$)$_2$— | CCl$_3$ | Cl | —NMe(i-Pr) | OH | |
| 1-184 | —(CH$_2$)$_2$— | CCl$_3$ | Cl | —NEt(i-Pr) | OH | |
| 1-185 | —(CH$_2$)$_2$— | CCl$_3$ | Cl | —N(Me)OMe | OH | |
| 1-186 | —(CH$_2$)$_2$— | CCl$_3$ | Cl | —N(Me)OEt | OH | |
| 1-187 | —(CH$_2$)$_2$— | CCl$_3$ | Cl | —N(Me)O(n-Pr) | OH | |
| 1-188 | —(CH$_2$)$_2$— | CCl$_3$ | Cl | —N(Et)OMe | OH | |
| 1-189 | —(CH$_2$)$_2$— | CCl$_3$ | Cl | —N(Et)OEt | OH | |
| 1-190 | —(CH$_2$)$_2$— | CCl$_3$ | Cl | —N(Et)O(n-Pr) | OH | |
| 1-191 | —(CH$_2$)$_2$— | C$_2$F$_5$ | Cl | —NH$_2$ | OH | |
| 1-192 | —(CH$_2$)$_2$— | C$_2$F$_5$ | Cl | —NHMe | OH | |
| 1-193 | —(CH$_2$)$_2$— | C$_2$F$_5$ | Cl | —NMe$_2$ | OH | |
| 1-194 | —(CH$_2$)$_2$— | C$_2$F$_5$ | Cl | —NHEt | OH | |
| 1-195 | —(CH$_2$)$_2$— | C$_2$F$_5$ | Cl | —NEt$_2$ | OH | |
| 1-196 | —(CH$_2$)$_2$— | C$_2$F$_5$ | Cl | —NH(n-Pr) | OH | |
| 1-197 | —(CH$_2$)$_2$— | C$_2$F$_5$ | Cl | —N(n-Pr)$_2$ | OH | |
| 1-198 | —(CH$_2$)$_2$— | C$_2$F$_5$ | Cl | —NMeEt | OH | |
| 1-199 | —(CH$_2$)$_2$— | C$_2$F$_5$ | Cl | —NMe(n-Pr) | OH | |
| 1-200 | —(CH$_2$)$_2$— | C$_2$F$_5$ | Cl | —NEt(n-Pr) | OH | |
| 1-201 | —(CH$_2$)$_2$— | C$_2$F$_5$ | Cl | —NH(i-Pr) | OH | |
| 1-202 | —(CH$_2$)$_2$— | C$_2$F$_5$ | Cl | —NMe(i-Pr) | OH | |

TABLE 1-continued

| No. | X¹ | R¹ | R² | —NR³R⁴ | R⁵ | Physical data |
|---|---|---|---|---|---|---|
| 1-203 | —(CH$_2$)$_2$— | C$_2$F$_5$ | Cl | —NEt(i-Pr) | OH | |
| 1-204 | —(CH$_2$)$_2$— | C$_2$F$_5$ | Cl | —N(Me)OMe | OH | |
| 1-205 | —(CH$_2$)$_2$— | C$_2$F$_5$ | Cl | —N(Me)OEt | OH | |
| 1-206 | —(CH$_2$)$_2$— | C$_2$F$_5$ | Cl | —N(Me)O(n-Pr) | OH | |
| 1-207 | —(CH$_2$)$_2$— | C$_2$F$_5$ | Cl | —N(Et)OMe | OH | |
| 1-208 | —(CH$_2$)$_2$— | C$_2$F$_5$ | Cl | —N(Et)OEt | OH | |
| 1-209 | —(CH$_2$)$_2$— | C$_2$F$_5$ | Cl | —N(Et)O(n-Pr) | OH | |
| 1-210 | —(CH$_2$)$_2$— | CHF$_2$ | Cl | —NH$_2$ | OH | |
| 1-211 | —(CH$_2$)$_2$— | CHF$_2$ | Cl | —NHMe | OH | |
| 1-212 | —(CH$_2$)$_2$— | CHF$_2$ | Cl | —NMe$_2$ | OH | |
| 1-213 | —(CH$_2$)$_2$— | CHF$_2$ | Cl | —NHEt | OH | |
| 1-214 | —(CH$_2$)$_2$— | CHF$_2$ | Cl | —NEt$_2$ | OH | |
| 1-215 | —(CH$_2$)$_2$— | CHF$_2$ | Cl | —NH(n-Pr) | OH | |
| 1-216 | —(CH$_2$)$_2$— | CHF$_2$ | Cl | —N(n-Pr)$_2$ | OH | |
| 1-217 | —(CH$_2$)$_2$— | CHF$_2$ | Cl | —NMeEt | OH | |
| 1-218 | —(CH$_2$)$_2$— | CHF$_2$ | Cl | —NMe(n-Pr) | OH | |
| 1-219 | —(CH$_2$)$_2$— | CHF$_2$ | Cl | —NEt(n-Pr) | OH | |
| 1-220 | —(CH$_2$)$_2$— | CHF$_2$ | Cl | —NH(i-Pr) | OH | |
| 1-221 | —(CH$_2$)$_2$— | CHF$_2$ | Cl | —NMe(i-Pr) | OH | |
| 1-222 | —(CH$_2$)$_2$— | CHF$_2$ | Cl | —NEt(i-Pr) | OH | |
| 1-223 | —(CH$_2$)$_2$— | CHF$_2$ | Cl | —N(Me)OMe | OH | |
| 1-224 | —(CH$_2$)$_2$— | CHF$_2$ | Cl | —N(Me)OEt | OH | |
| 1-225 | —(CH$_2$)$_2$— | CHF$_2$ | Cl | —N(Me)O(n-Pr) | OH | |
| 1-226 | —(CH$_2$)$_2$— | CHF$_2$ | Cl | —N(Et)OMe | OH | |
| 1-227 | —(CH$_2$)$_2$— | CHF$_2$ | Cl | —N(Et)OEt | OH | |
| 1-228 | —(CH$_2$)$_2$— | CHF$_2$ | Cl | —N(Et)O(n-Pr) | OH | |
| 1-229 | —(CH$_2$)$_2$— | CF$_3$ | Cl | —NH$_2$ | SCH$_2$C(O)OMe | |
| 1-230 | —(CH$_2$)$_2$— | CF$_3$ | Cl | —NHMe | SCH$_2$C(O)OMe | |
| 1-231 | —(CH$_2$)$_2$— | CF$_3$ | Cl | —NMe$_2$ | SCH$_2$C(O)OMe | |
| 1-232 | —(CH$_2$)$_2$— | CF$_3$ | Cl | —NHEt | SCH$_2$C(O)OMe | |
| 1-233 | —(CH$_2$)$_2$— | CF$_3$ | Cl | —NEt$_2$ | SCH$_2$C(O)OMe | |
| 1-234 | —(CH$_2$)$_2$— | CF$_3$ | Cl | —NH(n-Pr) | SCH$_2$C(O)OMe | |
| 1-235 | —(CH$_2$)$_2$— | CF$_3$ | Cl | —N(n-Pr)$_2$ | SCH$_2$C(O)OMe | |
| 1-236 | —(CH$_2$)$_2$— | CF$_3$ | Cl | —NMeEt | SCH$_2$C(O)OMe | |
| 1-237 | —(CH$_2$)$_2$— | CF$_3$ | Cl | —NMe(n-Pr) | SCH$_2$C(O)OMe | |
| 1-238 | —(CH$_2$)$_2$— | CF$_3$ | Cl | —NEt(n-Pr) | SCH$_2$C(O)OMe | |
| 1-239 | —(CH$_2$)$_2$— | CF$_3$ | Cl | —NH(i-Pr) | SCH$_2$C(O)OMe | |
| 1-240 | —(CH$_2$)$_2$— | CF$_3$ | Cl | —NMe(i-Pr) | SCH$_2$C(O)OMe | |
| 1-241 | —(CH$_2$)$_2$— | CF$_3$ | Cl | —NEt(i-Pr) | SCH$_2$C(O)OMe | |
| 1-242 | —(CH$_2$)$_2$— | CF$_3$ | Cl | —N(Me)OMe | SCH$_2$C(O)OMe | |
| 1-243 | —(CH$_2$)$_2$— | CF$_3$ | Cl | —N(Me)OEt | SCH$_2$C(O)OMe | |
| 1-244 | —(CH$_2$)$_2$— | CF$_3$ | Cl | —N(Me)O(n-Pr) | SCH$_2$C(O)OMe | |
| 1-245 | —(CH$_2$)$_2$— | CF$_3$ | Cl | —N(Et)OMe | SCH$_2$C(O)OMe | |
| 1-246 | —(CH$_2$)$_2$— | CF$_3$ | Cl | —N(Et)OEt | SCH$_2$C(O)OMe | |
| 1-247 | —(CH$_2$)$_2$— | CF$_3$ | Cl | —N(Et)O(n-Pr) | SCH$_2$C(O)OMe | |
| 1-248 | —(CH$_2$)$_2$— | CCl$_3$ | Cl | —NH$_2$ | SCH$_2$C(O)OMe | |
| 1-249 | —(CH$_2$)$_2$— | CCl$_3$ | Cl | —NHMe | SCH$_2$C(O)OMe | |
| 1-250 | —(CH$_2$)$_2$— | CCl$_3$ | Cl | —NMe$_2$ | SCH$_2$C(O)OMe | |
| 1-251 | —(CH$_2$)$_2$— | CCl$_3$ | Cl | —NHEt | SCH$_2$C(O)OMe | |
| 1-252 | —(CH$_2$)$_2$— | CCl$_3$ | Cl | —NEt$_2$ | SCH$_2$C(O)OMe | |
| 1-253 | —(CH$_2$)$_2$— | CCl$_3$ | Cl | —NH(n-Pr) | SCH$_2$C(O)OMe | |
| 1-254 | —(CH$_2$)$_2$— | CCl$_3$ | Cl | —N(n-Pr)$_2$ | SCH$_2$C(O)OMe | |
| 1-255 | —(CH$_2$)$_2$— | CCl$_3$ | Cl | —NMeEt | SCH$_2$C(O)OMe | |
| 1-256 | —(CH$_2$)$_2$— | CCl$_3$ | Cl | —NMe(n-Pr) | SCH$_2$C(O)OMe | |
| 1-257 | —(CH$_2$)$_2$— | CCl$_3$ | Cl | —NEt(n-Pr) | SCH$_2$C(O)OMe | |
| 1-258 | —(CH$_2$)$_2$— | CCl$_3$ | Cl | —NH(i-Pr) | SCH$_2$C(O)OMe | |
| 1-259 | —(CH$_2$)$_2$— | CCl$_3$ | Cl | —NMe(i-Pr) | SCH$_2$C(O)OMe | |
| 1-260 | —(CH$_2$)$_2$— | CCl$_3$ | Cl | —NEt(i-Pr) | SCH$_2$C(O)OMe | |
| 1-261 | —(CH$_2$)$_2$— | CCl$_3$ | Cl | —N(Me)OMe | SCH$_2$C(O)OMe | |
| 1-262 | —(CH$_2$)$_2$— | CCl$_3$ | Cl | —N(Me)OEt | SCH$_2$C(O)OMe | |
| 1-263 | —(CH$_2$)$_2$— | CCl$_3$ | Cl | —N(Me)O(n-Pr) | SCH$_2$C(O)OMe | |
| 1-264 | —(CH$_2$)$_2$— | CCl$_3$ | Cl | —N(Et)OMe | SCH$_2$C(O)OMe | |
| 1-265 | —(CH$_2$)$_2$— | CCl$_3$ | Cl | —N(Et)OEt | SCH$_2$C(O)OMe | |
| 1-266 | —(CH$_2$)$_2$— | CCl$_3$ | Cl | —N(Et)O(n-Pr) | SCH$_2$C(O)OMe | |
| 1-267 | —(CH$_2$)$_2$— | C$_2$F$_5$ | Cl | —NH$_2$ | SCH$_2$C(O)OMe | |
| 1-268 | —(CH$_2$)$_2$— | C$_2$F$_5$ | Cl | —NHMe | SCH$_2$C(O)OMe | |
| 1-269 | —(CH$_2$)$_2$— | C$_2$F$_5$ | Cl | —NMe$_2$ | SCH$_2$C(O)OMe | |
| 1-270 | —(CH$_2$)$_2$— | C$_2$F$_5$ | Cl | —NHEt | SCH$_2$C(O)OMe | |
| 1-271 | —(CH$_2$)$_2$— | C$_2$F$_5$ | Cl | —NEt$_2$ | SCH$_2$C(O)OMe | |
| 1-272 | —(CH$_2$)$_2$— | C$_2$F$_5$ | Cl | —NH(n-Pr) | SCH$_2$C(O)OMe | |
| 1-273 | —(CH$_2$)$_2$— | C$_2$F$_5$ | Cl | —N(n-Pr)$_2$ | SCH$_2$C(O)OMe | |
| 1-274 | —(CH$_2$)$_2$— | C$_2$F$_5$ | Cl | —NMeEt | SCH$_2$C(O)OMe | |
| 1-275 | —(CH$_2$)$_2$— | C$_2$F$_5$ | Cl | —NMe(n-Pr) | SCH$_2$C(O)OMe | |
| 1-276 | —(CH$_2$)$_2$— | C$_2$F$_5$ | Cl | —NEt(n-Pr) | SCH$_2$C(O)OMe | |
| 1-277 | —(CH$_2$)$_2$— | C$_2$F$_5$ | Cl | —NH(i-Pr) | SCH$_2$C(O)OMe | |
| 1-278 | —(CH$_2$)$_2$— | C$_2$F$_5$ | Cl | —NMe(i-Pr) | SCH$_2$C(O)OMe | |
| 1-279 | —(CH$_2$)$_2$— | C$_2$F$_5$ | Cl | —NEt(i-Pr) | SCH$_2$C(O)OMe | |

TABLE 1-continued

| No. | X¹ | R¹ | R² | —NR³R⁴ | R⁵ | Physical data |
|---|---|---|---|---|---|---|
| 1-280 | —(CH$_2$)$_2$— | C$_2$F$_5$ | Cl | —N(Me)OMe | SCH$_2$C(O)OMe | |
| 1-281 | —(CH$_2$)$_2$— | C$_2$F$_5$ | Cl | —N(Me)OEt | SCH$_2$C(O)OMe | |
| 1-282 | —(CH$_2$)$_2$— | C$_2$F$_5$ | Cl | —N(Me)O(n-Pr) | SCH$_2$C(O)OMe | |
| 1-283 | —(CH$_2$)$_2$— | C$_2$F$_5$ | Cl | —N(Et)OMe | SCH$_2$C(O)OMe | |
| 1-284 | —(CH$_2$)$_2$— | C$_2$F$_5$ | Cl | —N(Et)OEt | SCH$_2$C(O)OMe | |
| 1-285 | —(CH$_2$)$_2$— | C$_2$F$_5$ | Cl | —N(Et)O(n-Pr) | SCH$_2$C(O)OMe | |
| 1-286 | —(CH$_2$)$_2$— | CHF$_2$ | Cl | —NH$_2$ | SCH$_2$C(O)OMe | |
| 1-287 | —(CH$_2$)$_2$— | CHF$_2$ | Cl | —NHMe | SCH$_2$C(O)OMe | |
| 1-288 | —(CH$_2$)$_2$— | CHF$_2$ | Cl | —NMe$_2$ | SCH$_2$C(O)OMe | |
| 1-289 | —(CH$_2$)$_2$— | CHF$_2$ | Cl | —NHEt | SCH$_2$C(O)OMe | |
| 1-290 | —(CH$_2$)$_2$— | CHF$_2$ | Cl | —NEt$_2$ | SCH$_2$C(O)OMe | |
| 1-291 | —(CH$_2$)$_2$— | CHF$_2$ | Cl | —NH(n-Pr) | SCH$_2$C(O)OMe | |
| 1-292 | —(CH$_2$)$_2$— | CHF$_2$ | Cl | —N(n-Pr)$_2$ | SCH$_2$C(O)OMe | |
| 1-293 | —(CH$_2$)$_2$— | CHF$_2$ | Cl | —NMeEt | SCH$_2$C(O)OMe | |
| 1-294 | —(CH$_2$)$_2$— | CHF$_2$ | Cl | —NMe(n-Pr) | SCH$_2$C(O)OMe | |
| 1-295 | —(CH$_2$)$_2$— | CHF$_2$ | Cl | —NEt(n-Pr) | SCH$_2$C(O)OMe | |
| 1-296 | —(CH$_2$)$_2$— | CHF$_2$ | Cl | —NH(i-Pr) | SCH$_2$C(O)OMe | |
| 1-297 | —(CH$_2$)$_2$— | CHF$_2$ | Cl | —NMe(i-Pr) | SCH$_2$C(O)OMe | |
| 1-298 | —(CH$_2$)$_2$— | CHF$_2$ | Cl | —NEt(i-Pr) | SCH$_2$C(O)OMe | |
| 1-299 | —(CH$_2$)$_2$— | CHF$_2$ | Cl | —N(Me)OMe | SCH$_2$C(O)OMe | |
| 1-300 | —(CH$_2$)$_2$— | CHF$_2$ | Cl | —N(Me)OEt | SCH$_2$C(O)OMe | |
| 1-301 | —(CH$_2$)$_2$— | CHF$_2$ | Cl | —N(Me)O(n-Pr) | SCH$_2$C(O)OMe | |
| 1-302 | —(CH$_2$)$_2$— | CHF$_2$ | Cl | —N(Et)OMe | SCH$_2$C(O)OMe | |
| 1-303 | —(CH$_2$)$_2$— | CHF$_2$ | Cl | —N(Et)OEt | SCH$_2$C(O)OMe | |
| 1-304 | —(CH$_2$)$_2$— | CHF$_2$ | Cl | —N(Et)O(n-Pr) | SCH$_2$C(O)OMe | |
| 1-305 | —CHMe— | CF$_3$ | Cl | —NH$_2$ | OH | |
| 1-306 | —CHMe— | CF$_3$ | Cl | —NHMe | OH | |
| 1-307 | —CHMe— | CF$_3$ | Cl | —NMe$_2$ | OH | |
| 1-308 | —CHMe— | CF$_3$ | Cl | —NHEt | OH | |
| 1-309 | —CHMe— | CF$_3$ | Cl | —NEt$_2$ | OH | |
| 1-310 | —CHMe— | CF$_3$ | Cl | —NH(n-Pr) | OH | |
| 1-311 | —CHMe— | CF$_3$ | Cl | —N(n-Pr)$_2$ | OH | |
| 1-312 | —CHMe— | CF$_3$ | Cl | —NMeEt | OH | |
| 1-313 | —CHMe— | CF$_3$ | Cl | —NMe(n-Pr) | OH | |
| 1-314 | —CHMe— | CF$_3$ | Cl | —NEt(n-Pr) | OH | |
| 1-315 | —CHMe— | CF$_3$ | Cl | —NH(i-Pr) | OH | |
| 1-316 | —CHMe— | CF$_3$ | Cl | —NMe(i-Pr) | OH | |
| 1-317 | —CHMe— | CF$_3$ | Cl | —NEt(i-Pr) | OH | |
| 1-318 | —CHMe— | CF$_3$ | Cl | —N(Me)OMe | OH | |
| 1-319 | —CHMe— | CF$_3$ | Cl | —N(Me)OEt | OH | |
| 1-320 | —CHMe— | CF$_3$ | Cl | —N(Me)O(n-Pr) | OH | |
| 1-321 | —CHMe— | CF$_3$ | Cl | —N(Et)OMe | OH | |
| 1-322 | —CHMe— | CF$_3$ | Cl | —N(Et)OEt | OH | |
| 1-323 | —CHMe— | CF$_3$ | Cl | —N(Et)O(n-Pr) | OH | |
| 1-324 | —CHMe— | CCl$_3$ | Cl | —NH$_2$ | OH | |
| 1-325 | —CHMe— | CCl$_3$ | Cl | —NHMe | OH | |
| 1-326 | —CHMe— | CCl$_3$ | Cl | —NMe$_2$ | OH | |
| 1-327 | —CHMe— | CCl$_3$ | Cl | —NHEt | OH | |
| 1-328 | —CHMe— | CCl$_3$ | Cl | —NEt$_2$ | OH | |
| 1-329 | —CHMe— | CCl$_3$ | Cl | —NH(n-Pr) | OH | |
| 1-330 | —CHMe— | CCl$_3$ | Cl | —N(n-Pr)$_2$ | OH | |
| 1-331 | —CHMe— | CCl$_3$ | Cl | —NMeEt | OH | |
| 1-332 | —CHMe— | CCl$_3$ | Cl | —NMe(n-Pr) | OH | |
| 1-333 | —CHMe— | CCl$_3$ | Cl | —NEt(n-Pr) | OH | |
| 1-334 | —CHMe— | CCl$_3$ | Cl | —NH(i-Pr) | OH | |
| 1-335 | —CHMe— | CCl$_3$ | Cl | —NMe(i-Pr) | OH | |
| 1-336 | —CHMe— | CCl$_3$ | Cl | —NEt(i-Pr) | OH | |
| 1-337 | —CHMe— | CCl$_3$ | Cl | —N(Me)OMe | OH | |
| 1-338 | —CHMe— | CCl$_3$ | Cl | —N(Me)OEt | OH | |
| 1-339 | —CHMe— | CCl$_3$ | Cl | —N(Me)O(n-Pr) | OH | |
| 1-340 | —CHMe— | CCl$_3$ | Cl | —N(Et)OMe | OH | |
| 1-341 | —CHMe— | CCl$_3$ | Cl | —N(Et)OEt | OH | |
| 1-342 | —CHMe— | CCl$_3$ | Cl | —N(Et)O(n-Pr) | OH | |
| 1-343 | —CHMe— | C$_2$F$_5$ | Cl | —NH$_2$ | OH | |
| 1-344 | —CHMe— | C$_2$F$_5$ | Cl | —NHMe | OH | |
| 1-345 | —CHMe— | C$_2$F$_5$ | Cl | —NMe$_2$ | OH | |
| 1-346 | —CHMe— | C$_2$F$_5$ | Cl | —NHEt | OH | |
| 1-347 | —CHMe— | C$_2$F$_5$ | Cl | —NEt$_2$ | OH | |
| 1-348 | —CHMe— | C$_2$F$_5$ | Cl | —NH(n-Pr) | OH | |
| 1-349 | —CHMe— | C$_2$F$_5$ | Cl | —N(n-Pr)$_2$ | OH | |
| 1-350 | —CHMe— | C$_2$F$_5$ | Cl | —NMeEt | OH | |
| 1-351 | —CHMe— | C$_2$F$_5$ | Cl | —NMe(n-Pr) | OH | |
| 1-352 | —CHMe— | C$_2$F$_5$ | Cl | —NEt(n-Pr) | OH | |
| 1-353 | —CHMe— | C$_2$F$_5$ | Cl | —NH(i-Pr) | OH | |
| 1-354 | —CHMe— | C$_2$F$_5$ | Cl | —NMe(i-Pr) | OH | |
| 1-355 | —CHMe— | C$_2$F$_5$ | Cl | —NEt(i-Pr) | OH | |
| 1-356 | —CHMe— | C$_2$F$_5$ | Cl | —N(Me)OMe | OH | |

TABLE 1-continued

| No. | X¹ | R¹ | R² | —NR³R⁴ | R⁵ | Physical data |
|---|---|---|---|---|---|---|
| 1-357 | —CHMe— | $C_2F_5$ | Cl | —N(Me)OEt | OH | |
| 1-358 | —CHMe— | $C_2F_5$ | Cl | —N(Me)O(n-Pr) | OH | |
| 1-359 | —CHMe— | $C_2F_5$ | Cl | —N(Et)OMe | OH | |
| 1-360 | —CHMe— | $C_2F_5$ | Cl | —N(Et)OEt | OH | |
| 1-361 | —CHMe— | $C_2F_5$ | Cl | —N(Et)O(n-Pr) | OH | |
| 1-362 | —CHMe— | $CHF_2$ | Cl | —$NH_2$ | OH | |
| 1-363 | —CHMe— | $CHF_2$ | Cl | —NHMe | OH | |
| 1-364 | —CHMe— | $CHF_2$ | Cl | —$NMe_2$ | OH | |
| 1-365 | —CHMe— | $CHF_2$ | Cl | —NHEt | OH | |
| 1-366 | —CHMe— | $CHF_2$ | Cl | —$NEt_2$ | OH | |
| 1-367 | —CHMe— | $CHF_2$ | Cl | —NH(n-Pr) | OH | |
| 1-368 | —CHMe— | $CHF_2$ | Cl | —N(n-Pr)$_2$ | OH | |
| 1-369 | —CHMe— | $CHF_2$ | Cl | —NMeEt | OH | |
| 1-370 | —CHMe— | $CHF_2$ | Cl | —NMe(n-Pr) | OH | |
| 1-371 | —CHMe— | $CHF_2$ | Cl | —NEt(n-Pr) | OH | |
| 1-372 | —CHMe— | $CHF_2$ | Cl | —NH(i-Pr) | OH | |
| 1-373 | —CHMe— | $CHF_2$ | Cl | —NMe(i-Pr) | OH | |
| 1-374 | —CHMe— | $CHF_2$ | Cl | —NEt(i-Pr) | OH | |
| 1-375 | —CHMe— | $CHF_2$ | Cl | —N(Me)OMe | OH | |
| 1-376 | —CHMe— | $CHF_2$ | Cl | —N(Me)OEt | OH | |
| 1-377 | —CHMe— | $CHF_2$ | Cl | —N(Me)O(n-Pr) | OH | |
| 1-378 | —CHMe— | $CHF_2$ | Cl | —N(Et)OMe | OH | |
| 1-379 | —CHMe— | $CHF_2$ | Cl | —N(Et)OEt | OH | |
| 1-380 | —CHMe— | $CHF_2$ | Cl | —N(Et)O(n-Pr) | OH | |
| 1-381 | —CHMe— | $CF_3$ | Cl | —$NH_2$ | $SCH_2C(O)OMe$ | |
| 1-382 | —CHMe— | $CF_3$ | Cl | —NHMe | $SCH_2C(O)OMe$ | |
| 1-383 | —CHMe— | $CF_3$ | Cl | —$NMe_2$ | $SCH_2C(O)OMe$ | |
| 1-384 | —CHMe— | $CF_3$ | Cl | —NHEt | $SCH_2C(O)OMe$ | |
| 1-385 | —CHMe— | $CF_3$ | Cl | —$NEt_2$ | $SCH_2C(O)OMe$ | |
| 1-386 | —CHMe— | $CF_3$ | Cl | —NH(n-Pr) | $SCH_2C(O)OMe$ | |
| 1-387 | —CHMe— | $CF_3$ | Cl | —N(n-Pr)$_2$ | $SCH_2C(O)OMe$ | |
| 1-388 | —CHMe— | $CF_3$ | Cl | —NMeEt | $SCH_2C(O)OMe$ | |
| 1-389 | —CHMe— | $CF_3$ | Cl | —NMe(n-Pr) | $SCH_2C(O)OMe$ | |
| 1-390 | —CHMe— | $CF_3$ | Cl | —NEt(n-Pr) | $SCH_2C(O)OMe$ | |
| 1-391 | —CHMe— | $CF_3$ | Cl | —NH(i-Pr) | $SCH_2C(O)OMe$ | |
| 1-392 | —CHMe— | $CF_3$ | Cl | —NMe(i-Pr) | $SCH_2C(O)OMe$ | |
| 1-393 | —CHMe— | $CF_3$ | Cl | —NEt(i-Pr) | $SCH_2C(O)OMe$ | |
| 1-394 | —CHMe— | $CF_3$ | Cl | —N(Me)OMe | $SCH_2C(O)OMe$ | |
| 1-395 | —CHMe— | $CF_3$ | Cl | —N(Me)OEt | $SCH_2C(O)OMe$ | |
| 1-396 | —CHMe— | $CF_3$ | Cl | —N(Me)O(n-Pr) | $SCH_2C(O)OMe$ | |
| 1-397 | —CHMe— | $CF_3$ | Cl | —N(Et)OMe | $SCH_2C(O)OMe$ | |
| 1-398 | —CHMe— | $CF_3$ | Cl | —N(Et)OEt | $SCH_2C(O)OMe$ | |
| 1-399 | —CHMe— | $CF_3$ | Cl | —N(Et)O(n-Pr) | $SCH_2C(O)OMe$ | |
| 1-400 | —CHMe— | $CCl_3$ | Cl | —$NH_2$ | $SCH_2C(O)OMe$ | |
| 1-401 | —CHMe— | $CCl_3$ | Cl | —NHMe | $SCH_2C(O)OMe$ | |
| 1-402 | —CHMe— | $CCl_3$ | Cl | —$NMe_2$ | $SCH_2C(O)OMe$ | |
| 1-403 | —CHMe— | $CCl_3$ | Cl | —NHEt | $SCH_2C(O)OMe$ | |
| 1-404 | —CHMe— | $CCl_3$ | Cl | —$NEt_2$ | $SCH_2C(O)OMe$ | |
| 1-405 | —CHMe— | $CCl_3$ | Cl | —NH(n-Pr) | $SCH_2C(O)OMe$ | |
| 1-406 | —CHMe— | $CCl_3$ | Cl | —N(n-Pr)$_2$ | $SCH_2C(O)OMe$ | |
| 1-407 | —CHMe— | $CCl_3$ | Cl | —NMeEt | $SCH_2C(O)OMe$ | |
| 1-408 | —CHMe— | $CCl_3$ | Cl | —NMe(n-Pr) | $SCH_2C(O)OMe$ | |
| 1-409 | —CHMe— | $CCl_3$ | Cl | —NEt(n-Pr) | $SCH_2C(O)OMe$ | |
| 1-410 | —CHMe— | $CCl_3$ | Cl | —NH(i-Pr) | $SCH_2C(O)OMe$ | |
| 1-411 | —CHMe— | $CCl_3$ | Cl | —NMe(i-Pr) | $SCH_2C(O)OMe$ | |
| 1-412 | —CHMe— | $CCl_3$ | Cl | —NEt(i-Pr) | $SCH_2C(O)OMe$ | |
| 1-413 | —CHMe— | $CCl_3$ | Cl | —N(Me)OMe | $SCH_2C(O)OMe$ | |
| 1-414 | —CHMe— | $CCl_3$ | Cl | —N(Me)OEt | $SCH_2C(O)OMe$ | |
| 1-415 | —CHMe— | $CCl_3$ | Cl | —N(Me)O(n-Pr) | $SCH_2C(O)OMe$ | |
| 1-416 | —CHMe— | $CCl_3$ | Cl | —N(Et)OMe | $SCH_2C(O)OMe$ | |
| 1-417 | —CHMe— | $CCl_3$ | Cl | —N(Et)OEt | $SCH_2C(O)OMe$ | |
| 1-418 | —CHMe— | $CCl_3$ | Cl | —N(Et)O(n-Pr) | $SCH_2C(O)OMe$ | |
| 1-419 | —CHMe— | $C_2F_5$ | Cl | —$NH_2$ | $SCH_2C(O)OMe$ | |
| 1-420 | —CHMe— | $C_2F_5$ | Cl | —NHMe | $SCH_2C(O)OMe$ | |
| 1-421 | —CHMe— | $C_2F_5$ | Cl | —$NMe_2$ | $SCH_2C(O)OMe$ | |
| 1-422 | —CHMe— | $C_2F_5$ | Cl | —NHEt | $SCH_2C(O)OMe$ | |
| 1-423 | —CHMe— | $C_2F_5$ | Cl | —$NEt_2$ | $SCH_2C(O)OMe$ | |
| 1-424 | —CHMe— | $C_2F_5$ | Cl | —NH(n-Pr) | $SCH_2C(O)OMe$ | |
| 1-425 | —CHMe— | $C_2F_5$ | Cl | —N(n-Pr)$_2$ | $SCH_2C(O)OMe$ | |
| 1-426 | —CHMe— | $C_2F_5$ | Cl | —NMeEt | $SCH_2C(O)OMe$ | |
| 1-427 | —CHMe— | $C_2F_5$ | Cl | —NMe(n-Pr) | $SCH_2C(O)OMe$ | |
| 1-428 | —CHMe— | $C_2F_5$ | Cl | —NEt(n-Pr) | $SCH_2C(O)OMe$ | |
| 1-429 | —CHMe— | $C_2F_5$ | Cl | —NH(i-Pr) | $SCH_2C(O)OMe$ | |
| 1-430 | —CHMe— | $C_2F_5$ | Cl | —NMe(i-Pr) | $SCH_2C(O)OMe$ | |
| 1-431 | —CHMe— | $C_2F_5$ | Cl | —NEt(i-Pr) | $SCH_2C(O)OMe$ | |
| 1-432 | —CHMe— | $C_2F_5$ | Cl | —N(Me)OMe | $SCH_2C(O)OMe$ | |
| 1-433 | —CHMe— | $C_2F_5$ | Cl | —N(Me)OEt | $SCH_2C(O)OMe$ | |

TABLE 1-continued

| No. | $X^1$ | $R^1$ | $R^2$ | $-NR^3R^4$ | $R^5$ | Physical data |
|---|---|---|---|---|---|---|
| 1-434 | —CHMe— | $C_2F_5$ | Cl | —N(Me)O(n-Pr) | $SCH_2C(O)OMe$ | |
| 1-435 | —CHMe— | $C_2F_5$ | Cl | —N(Et)OMe | $SCH_2C(O)OMe$ | |
| 1-436 | —CHMe— | $C_2F_5$ | Cl | —N(Et)OEt | $SCH_2C(O)OMe$ | |
| 1-437 | —CHMe— | $C_2F_5$ | Cl | —N(Et)O(n-Pr) | $SCH_2C(O)OMe$ | |
| 1-438 | —CHMe— | $CHF_2$ | Cl | —$NH_2$ | $SCH_2C(O)OMe$ | |
| 1-439 | —CHMe— | $CHF_2$ | Cl | —NHMe | $SCH_2C(O)OMe$ | |
| 1-440 | —CHMe— | $CHF_2$ | Cl | —$NMe_2$ | $SCH_2C(O)OMe$ | |
| 1-441 | —CHMe— | $CHF_2$ | Cl | —NHEt | $SCH_2C(O)OMe$ | |
| 1-442 | —CHMe— | $CHF_2$ | Cl | —$NEt_2$ | $SCH_2C(O)OMe$ | |
| 1-443 | —CHMe— | $CHF_2$ | Cl | —NH(n-Pr) | $SCH_2C(O)OMe$ | |
| 1-444 | —CHMe— | $CHF_2$ | Cl | —N(n-Pr)$_2$ | $SCH_2C(O)OMe$ | |
| 1-445 | —CHMe— | $CHF_2$ | Cl | —NMeEt | $SCH_2C(O)OMe$ | |
| 1-446 | —CHMe— | $CHF_2$ | Cl | —NMe(n-Pr) | $SCH_2C(O)OMe$ | |
| 1-447 | —CHMe— | $CHF_2$ | Cl | —NEt(n-Pr) | $SCH_2C(O)OMe$ | |
| 1-448 | —CHMe— | $CHF_2$ | Cl | —NH(i-Pr) | $SCH_2C(O)OMe$ | |
| 1-449 | —CHMe— | $CHF_2$ | Cl | —NMe(i-Pr) | $SCH_2C(O)OMe$ | |
| 1-450 | —CHMe— | $CHF_2$ | Cl | —NEt(i-Pr) | $SCH_2C(O)OMe$ | |
| 1-451 | —CHMe— | $CHF_2$ | Cl | —N(Me)OMe | $SCH_2C(O)OMe$ | |
| 1-452 | —CHMe— | $CHF_2$ | Cl | —N(Me)OEt | $SCH_2C(O)OMe$ | |
| 1-453 | —CHMe— | $CHF_2$ | Cl | —N(Me)O(n-Pr) | $SCH_2C(O)OMe$ | |
| 1-454 | —CHMe— | $CHF_2$ | Cl | —N(Et)OMe | $SCH_2C(O)OMe$ | |
| 1-455 | —CHMe— | $CHF_2$ | Cl | —N(Et)OEt | $SCH_2C(O)OMe$ | |
| 1-456 | —CHMe— | $CHF_2$ | Cl | —N(Et)O(n-Pr) | $SCH_2C(O)OMe$ | |
| 1-457 | —$CH_2$— | $CF_3$ | Br | —$NH_2$ | OH | |
| 1-458 | —$CH_2$— | $CF_3$ | Br | —NHMe | OH | |
| 1-459 | —$CH_2$— | $CF_3$ | Br | —$NMe_2$ | OH | |
| 1-460 | —$CH_2$— | $CF_3$ | Br | —NHEt | OH | |
| 1-461 | —$CH_2$— | $CF_3$ | Br | —$NEt_2$ | OH | |
| 1-462 | —$CH_2$— | $CF_3$ | Br | —NH(n-Pr) | OH | |
| 1-463 | —$CH_2$— | $CF_3$ | Br | —N(n-Pr)$_2$ | OH | |
| 1-464 | —$CH_2$— | $CF_3$ | Br | —NMeEt | OH | |
| 1-465 | —$CH_2$— | $CF_3$ | Br | —NMe(n-Pr) | OH | |
| 1-466 | —$CH_2$— | $CF_3$ | Br | —NEt(n-Pr) | OH | |
| 1-467 | —$CH_2$— | $CF_3$ | Br | —NH(i-Pr) | OH | |
| 1-468 | —$CH_2$— | $CF_3$ | Br | —NMe(i-Pr) | OH | |
| 1-469 | —$CH_2$— | $CF_3$ | Br | —NEt(i-Pr) | OH | |
| 1-470 | —$CH_2$— | $CF_3$ | Br | —N(Me)OMe | OH | |
| 1-471 | —$CH_2$— | $CF_3$ | Br | —N(Me)OEt | OH | |
| 1-472 | —$CH_2$— | $CF_3$ | Br | —N(Me)O(n-Pr) | OH | |
| 1-473 | —$CH_2$— | $CF_3$ | Br | —N(Et)OMe | OH | |
| 1-474 | —$CH_2$— | $CF_3$ | Br | —N(Et)OEt | OH | |
| 1-475 | —$CH_2$— | $CF_3$ | Br | —N(Et)O(n-Pr) | OH | |
| 1-476 | —$CH_2$— | $CCl_3$ | Br | —$NH_2$ | OH | |
| 1-477 | —$CH_2$— | $CCl_3$ | Br | —NHMe | OH | |
| 1-478 | —$CH_2$— | $CCl_3$ | Br | —$NMe_2$ | OH | |
| 1-479 | —$CH_2$— | $CCl_3$ | Br | —NHEt | OH | |
| 1-480 | —$CH_2$— | $CCl_3$ | Br | —$NEt_2$ | OH | |
| 1-481 | —$CH_2$— | $CCl_3$ | Br | —NH(n-Pr) | OH | |
| 1-482 | —$CH_2$— | $CCl_3$ | Br | —N(n-Pr)$_2$ | OH | |
| 1-483 | —$CH_2$— | $CCl_3$ | Br | —NMeEt | OH | |
| 1-484 | —$CH_2$— | $CCl_3$ | Br | —NMe(n-Pr) | OH | |
| 1-485 | —$CH_2$— | $CCl_3$ | Br | —NEt(n-Pr) | OH | |
| 1-486 | —$CH_2$— | $CCl_3$ | Br | —NH(i-Pr) | OH | |
| 1-487 | —$CH_2$— | $CCl_3$ | Br | —NMe(i-Pr) | OH | |
| 1-488 | —$CH_2$— | $CCl_3$ | Br | —NEt(i-Pr) | OH | |
| 1-489 | —$CH_2$— | $CCl_3$ | Br | —N(Me)OMe | OH | |
| 1-490 | —$CH_2$— | $CCl_3$ | Br | —N(Me)OEt | OH | |
| 1-491 | —$CH_2$— | $CCl_3$ | Br | —N(Me)O(n-Pr) | OH | |
| 1-492 | —$CH_2$— | $CCl_3$ | Br | —N(Et)OMe | OH | |
| 1-493 | —$CH_2$— | $CCl_3$ | Br | —N(Et)OEt | OH | |
| 1-494 | —$CH_2$— | $CCl_3$ | Br | —N(Et)O(n-Pr) | OH | |
| 1-495 | —$CH_2$— | $C_2F_5$ | Br | —$NH_2$ | OH | |
| 1-496 | —$CH_2$— | $C_2F_5$ | Br | —NHMe | OH | |
| 1-497 | —$CH_2$— | $C_2F_5$ | Br | —$NMe_2$ | OH | |
| 1-498 | —$CH_2$— | $C_2F_5$ | Br | —NHEt | OH | |
| 1-499 | —$CH_2$— | $C_2F_5$ | Br | —$NEt_2$ | OH | |
| 1-500 | —$CH_2$— | $C_2F_5$ | Br | —NH(n-Pr) | OH | |
| 1-501 | —$CH_2$— | $C_2F_5$ | Br | —N(n-Pr)$_2$ | OH | |
| 1-502 | —$CH_2$— | $C_2F_5$ | Br | —NMeEt | OH | |
| 1-503 | —$CH_2$— | $C_2F_5$ | Br | —NMe(n-Pr) | OH | |
| 1-504 | —$CH_2$— | $C_2F_5$ | Br | —NEt(n-Pr) | OH | |
| 1-505 | —$CH_2$— | $C_2F_5$ | Br | —NH(i-Pr) | OH | |
| 1-506 | —$CH_2$— | $C_2F_5$ | Br | —NMe(i-Pr) | OH | |
| 1-507 | —$CH_2$— | $C_2F_5$ | Br | —NEt(i-Pr) | OH | |
| 1-508 | —$CH_2$— | $C_2F_5$ | Br | —N(Me)OMe | OH | |
| 1-509 | —$CH_2$— | $C_2F_5$ | Br | —N(Me)OEt | OH | |
| 1-510 | —$CH_2$— | $C_2F_5$ | Br | —N(Me)O(n-Pr) | OH | |

TABLE 1-continued

| No. | $X^1$ | $R^1$ | $R^2$ | —$NR^3R^4$ | $R^5$ | Physical data |
|---|---|---|---|---|---|---|
| 1-511 | —$CH_2$— | $C_2F_5$ | Br | —N(Et)OMe | OH | |
| 1-512 | —$CH_2$— | $C_2F_5$ | Br | —N(Et)OEt | OH | |
| 1-513 | —$CH_2$— | $C_2F_5$ | Br | —N(Et)O(n-Pr) | OH | |
| 1-514 | —$CH_2$— | $CHF_2$ | Br | —$NH_2$ | OH | |
| 1-515 | —$CH_2$— | $CHF_2$ | Br | —NHMe | OH | |
| 1-516 | —$CH_2$— | $CHF_2$ | Br | —$NMe_2$ | OH | |
| 1-517 | —$CH_2$— | $CHF_2$ | Br | —NHEt | OH | |
| 1-518 | —$CH_2$— | $CHF_2$ | Br | —$NEt_2$ | OH | |
| 1-519 | —$CH_2$— | $CHF_2$ | Br | —NH(n-Pr) | OH | |
| 1-520 | —$CH_2$— | $CHF_2$ | Br | —N(n-Pr)$_2$ | OH | |
| 1-521 | —$CH_2$— | $CHF_2$ | Br | —NMeEt | OH | |
| 1-522 | —$CH_2$— | $CHF_2$ | Br | —NMe(n-Pr) | OH | |
| 1-523 | —$CH_2$— | $CHF_2$ | Br | —NEt(n-Pr) | OH | |
| 1-524 | —$CH_2$— | $CHF_2$ | Br | —NH(i-Pr) | OH | |
| 1-525 | —$CH_2$— | $CHF_2$ | Br | —NMe(i-Pr) | OH | |
| 1-526 | —$CH_2$— | $CHF_2$ | Br | —NEt(i-Pr) | OH | |
| 1-527 | —$CH_2$— | $CHF_2$ | Br | —N(Me)OMe | OH | |
| 1-528 | —$CH_2$— | $CHF_2$ | Br | —N(Me)OEt | OH | |
| 1-529 | —$CH_2$— | $CHF_2$ | Br | —N(Me)O(n-Pr) | OH | |
| 1-530 | —$CH_2$— | $CHF_2$ | Br | —N(Et)OMe | OH | |
| 1-531 | —$CH_2$— | $CHF_2$ | Br | —N(Et)OEt | OH | |
| 1-532 | —$CH_2$— | $CHF_2$ | Br | —N(Et)O(n-Pr) | OH | |
| 1-533 | —$CH_2$— | $CF_3$ | Br | —$NH_2$ | $SCH_2C(O)OMe$ | |
| 1-534 | —$CH_2$— | $CF_3$ | Br | —NHMe | $SCH_2C(O)OMe$ | |
| 1-535 | —$CH_2$— | $CF_3$ | Br | —$NMe_2$ | $SCH_2C(O)OMe$ | |
| 1-536 | —$CH_2$— | $CF_3$ | Br | —NHEt | $SCH_2C(O)OMe$ | |
| 1-537 | —$CH_2$— | $CF_3$ | Br | —$NEt_2$ | $SCH_2C(O)OMe$ | |
| 1-538 | —$CH_2$— | $CF_3$ | Br | —NH(n-Pr) | $SCH_2C(O)OMe$ | |
| 1-539 | —$CH_2$— | $CF_3$ | Br | —N(n-Pr)$_2$ | $SCH_2C(O)OMe$ | |
| 1-540 | —$CH_2$— | $CF_3$ | Br | —NMeEt | $SCH_2C(O)OMe$ | |
| 1-541 | —$CH_2$— | $CF_3$ | Br | —NMe(n-Pr) | $SCH_2C(O)OMe$ | |
| 1-542 | —$CH_2$— | $CF_3$ | Br | —NEt(n-Pr) | $SCH_2C(O)OMe$ | |
| 1-543 | —$CH_2$— | $CF_3$ | Br | —NH(i-Pr) | $SCH_2C(O)OMe$ | |
| 1-544 | —$CH_2$— | $CF_3$ | Br | —NMe(i-Pr) | $SCH_2C(O)OMe$ | |
| 1-545 | —$CH_2$— | $CF_3$ | Br | —NEt(i-Pr) | $SCH_2C(O)OMe$ | |
| 1-546 | —$CH_2$— | $CF_3$ | Br | —N(Me)OMe | $SCH_2C(O)OMe$ | |
| 1-547 | —$CH_2$— | $CF_3$ | Br | —N(Me)OEt | $SCH_2C(O)OMe$ | |
| 1-548 | —$CH_2$— | $CF_3$ | Br | —N(Me)O(n-Pr) | $SCH_2C(O)OMe$ | |
| 1-549 | —$CH_2$— | $CF_3$ | Br | —N(Et)OMe | $SCH_2C(O)OMe$ | |
| 1-550 | —$CH_2$— | $CF_3$ | Br | —N(Et)OEt | $SCH_2C(O)OMe$ | |
| 1-551 | —$CH_2$— | $CF_3$ | Br | —N(Et)O(n-Pr) | $SCH_2C(O)OMe$ | |
| 1-552 | —$CH_2$— | $CCl_3$ | Br | —$NH_2$ | $SCH_2C(O)OMe$ | |
| 1-553 | —$CH_2$— | $CCl_3$ | Br | —NHMe | $SCH_2C(O)OMe$ | |
| 1-554 | —$CH_2$— | $CCl_3$ | Br | —$NMe_2$ | $SCH_2C(O)OMe$ | |
| 1-555 | —$CH_2$— | $CCl_3$ | Br | —NHEt | $SCH_2C(O)OMe$ | |
| 1-556 | —$CH_2$— | $CCl_3$ | Br | —$NEt_2$ | $SCH_2C(O)OMe$ | |
| 1-557 | —$CH_2$— | $CCl_3$ | Br | —NH(n-Pr) | $SCH_2C(O)OMe$ | |
| 1-558 | —$CH_2$— | $CCl_3$ | Br | —N(n-Pr)$_2$ | $SCH_2C(O)OMe$ | |
| 1-559 | —$CH_2$— | $CCl_3$ | Br | —NMeEt | $SCH_2C(O)OMe$ | |
| 1-560 | —$CH_2$— | $CCl_3$ | Br | —NMe(n-Pr) | $SCH_2C(O)OMe$ | |
| 1-561 | —$CH_2$— | $CCl_3$ | Br | —NEt(n-Pr) | $SCH_2C(O)OMe$ | |
| 1-562 | —$CH_2$— | $CCl_3$ | Br | —NH(i-Pr) | $SCH_2C(O)OMe$ | |
| 1-563 | —$CH_2$— | $CCl_3$ | Br | —NMe(i-Pr) | $SCH_2C(O)OMe$ | |
| 1-564 | —$CH_2$— | $CCl_3$ | Br | —NEt(i-Pr) | $SCH_2C(O)OMe$ | |
| 1-565 | —$CH_2$— | $CCl_3$ | Br | —N(Me)OMe | $SCH_2C(O)OMe$ | |
| 1-566 | —$CH_2$— | $CCl_3$ | Br | —N(Me)OEt | $SCH_2C(O)OMe$ | |
| 1-567 | —$CH_2$— | $CCl_3$ | Br | —N(Me)O(n-Pr) | $SCH_2C(O)OMe$ | |
| 1-568 | —$CH_2$— | $CCl_3$ | Br | —N(Et)OMe | $SCH_2C(O)OMe$ | |
| 1-569 | —$CH_2$— | $CCl_3$ | Br | —N(Et)OEt | $SCH_2C(O)OMe$ | |
| 1-570 | —$CH_2$— | $CCl_3$ | Br | —N(Et)O(n-Pr) | $SCH_2C(O)OMe$ | |
| 1-571 | —$CH_2$— | $C_2F_5$ | Br | —$NH_2$ | $SCH_2C(O)OMe$ | |
| 1-572 | —$CH_2$— | $C_2F_5$ | Br | —NHMe | $SCH_2C(O)OMe$ | |
| 1-573 | —$CH_2$— | $C_2F_5$ | Br | —$NMe_2$ | $SCH_2C(O)OMe$ | |
| 1-574 | —$CH_2$— | $C_2F_5$ | Br | —NHEt | $SCH_2C(O)OMe$ | |
| 1-575 | —$CH_2$— | $C_2F_5$ | Br | —$NEt_2$ | $SCH_2C(O)OMe$ | |
| 1-576 | —$CH_2$— | $C_2F_5$ | Br | —NH(n-Pr) | $SCH_2C(O)OMe$ | |
| 1-577 | —$CH_2$— | $C_2F_5$ | Br | —N(n-Pr)$_2$ | $SCH_2C(O)OMe$ | |
| 1-578 | —$CH_2$— | $C_2F_5$ | Br | —NMeEt | $SCH_2C(O)OMe$ | |
| 1-579 | —$CH_2$— | $C_2F_5$ | Br | —NMe(n-Pr) | $SCH_2C(O)OMe$ | |
| 1-580 | —$CH_2$— | $C_2F_5$ | Br | —NEt(n-Pr) | $SCH_2C(O)OMe$ | |
| 1-581 | —$CH_2$— | $C_2F_5$ | Br | —NH(i-Pr) | $SCH_2C(O)OMe$ | |
| 1-582 | —$CH_2$— | $C_2F_5$ | Br | —NMe(i-Pr) | $SCH_2C(O)OMe$ | |
| 1-583 | —$CH_2$— | $C_2F_5$ | Br | —NEt(i-Pr) | $SCH_2C(O)OMe$ | |
| 1-584 | —$CH_2$— | $C_2F_5$ | Br | —N(Me)OMe | $SCH_2C(O)OMe$ | |
| 1-585 | —$CH_2$— | $C_2F_5$ | Br | —N(Me)OEt | $SCH_2C(O)OMe$ | |
| 1-586 | —$CH_2$— | $C_2F_5$ | Br | —N(Me)O(n-Pr) | $SCH_2C(O)OMe$ | |
| 1-587 | —$CH_2$— | $C_2F_5$ | Br | —N(Et)OMe | $SCH_2C(O)OMe$ | |

TABLE 1-continued

| No. | X¹ | R¹ | R² | —NR³R⁴ | R⁵ | Physical data |
|---|---|---|---|---|---|---|
| 1-588 | —CH₂— | C₂F₅ | Br | —N(Et)OEt | SCH₂C(O)OMe | |
| 1-589 | —CH₂— | C₂F₅ | Br | —N(Et)O(n-Pr) | SCH₂C(O)OMe | |
| 1-590 | —CH₂— | CHF₂ | Br | —NH₂ | SCH₂C(O)OMe | |
| 1-591 | —CH₂— | CHF₂ | Br | —NHMe | SCH₂C(O)OMe | |
| 1-592 | —CH₂— | CHF₂ | Br | —NMe₂ | SCH₂C(O)OMe | |
| 1-593 | —CH₂— | CHF₂ | Br | —NHEt | SCH₂C(O)OMe | |
| 1-594 | —CH₂— | CHF₂ | Br | —NEt₂ | SCH₂C(O)OMe | |
| 1-595 | —CH₂— | CHF₂ | Br | —NH(n-Pr) | SCH₂C(O)OMe | |
| 1-596 | —CH₂— | CHF₂ | Br | —N(n-Pr)₂ | SCH₂C(O)OMe | |
| 1-597 | —CH₂— | CHF₂ | Br | —NMeEt | SCH₂C(O)OMe | |
| 1-598 | —CH₂— | CHF₂ | Br | —NMe(n-Pr) | SCH₂C(O)OMe | |
| 1-599 | —CH₂— | CHF₂ | Br | —NEt(n-Pr) | SCH₂C(O)OMe | |
| 1-600 | —CH₂— | CHF₂ | Br | —NH(i-Pr) | SCH₂C(O)OMe | |
| 1-601 | —CH₂— | CHF₂ | Br | —NMe(i-Pr) | SCH₂C(O)OMe | |
| 1-602 | —CH₂— | CHF₂ | Br | —NEt(i-Pr) | SCH₂C(O)OMe | |
| 1-603 | —CH₂— | CHF₂ | Br | —N(Me)OMe | SCH₂C(O)OMe | |
| 1-604 | —CH₂— | CHF₂ | Br | —N(Me)OEt | SCH₂C(O)OMe | |
| 1-605 | —CH₂— | CHF₂ | Br | —N(Me)O(n-Pr) | SCH₂C(O)OMe | |
| 1-606 | —CH₂— | CHF₂ | Br | —N(Et)OMe | SCH₂C(O)OMe | |
| 1-607 | —CH₂— | CHF₂ | Br | —N(Et)OEt | SCH₂C(O)OMe | |
| 1-608 | —CH₂— | CHF₂ | Br | —N(Et)O(n-Pr) | SCH₂C(O)OMe | |
| 1-609 | —(CH₂)₂— | CF₃ | Br | —NH₂ | OH | |
| 1-610 | —(CH₂)₂— | CF₃ | Br | —NHMe | OH | |
| 1-611 | —(CH₂)₂— | CF₃ | Br | —NMe₂ | OH | |
| 1-612 | —(CH₂)₂— | CF₃ | Br | —NHEt | OH | |
| 1-613 | —(CH₂)₂— | CF₃ | Br | —NEt₂ | OH | |
| 1-614 | —(CH₂)₂— | CF₃ | Br | —NH(n-Pr) | OH | |
| 1-615 | —(CH₂)₂— | CF₃ | Br | —N(n-Pr)₂ | OH | |
| 1-616 | —(CH₂)₂— | CF₃ | Br | —NMeEt | OH | |
| 1-617 | —(CH₂)₂— | CF₃ | Br | —NMe(n-Pr) | OH | |
| 1-618 | —(CH₂)₂— | CF₃ | Br | —NEt(n-Pr) | OH | |
| 1-619 | —(CH₂)₂— | CF₃ | Br | —NH(i-Pr) | OH | |
| 1-620 | —(CH₂)₂— | CF₃ | Br | —NMe(i-Pr) | OH | |
| 1-621 | —(CH₂)₂— | CF₃ | Br | —NEt(i-Pr) | OH | |
| 1-622 | —(CH₂)₂— | CF₃ | Br | —N(Me)OMe | OH | |
| 1-623 | —(CH₂)₂— | CF₃ | Br | —N(Me)OEt | OH | |
| 1-624 | —(CH₂)₂— | CF₃ | Br | —N(Me)O(n-Pr) | OH | |
| 1-625 | —(CH₂)₂— | CF₃ | Br | —N(Et)OMe | OH | |
| 1-626 | —(CH₂)₂— | CF₃ | Br | —N(Et)OEt | OH | |
| 1-627 | —(CH₂)₂— | CF₃ | Br | —N(Et)O(n-Pr) | OH | |
| 1-628 | —(CH₂)₂— | CCl₃ | Br | —NH₂ | OH | |
| 1-629 | —(CH₂)₂— | CCl₃ | Br | —NHMe | OH | |
| 1-630 | —(CH₂)₂— | CCl₃ | Br | —NMe₂ | OH | |
| 1-631 | —(CH₂)₂— | CCl₃ | Br | —NHEt | OH | |
| 1-632 | —(CH₂)₂— | CCl₃ | Br | —NEt₂ | OH | |
| 1-633 | —(CH₂)₂— | CCl₃ | Br | —NH(n-Pr) | OH | |
| 1-634 | —(CH₂)₂— | CCl₃ | Br | —N(n-Pr)₂ | OH | |
| 1-635 | —(CH₂)₂— | CCl₃ | Br | —NMeEt | OH | |
| 1-636 | —(CH₂)₂— | CCl₃ | Br | —NMe(n-Pr) | OH | |
| 1-637 | —(CH₂)₂— | CCl₃ | Br | —NEt(n-Pr) | OH | |
| 1-638 | —(CH₂)₂— | CCl₃ | Br | —NH(i-Pr) | OH | |
| 1-639 | —(CH₂)₂— | CCl₃ | Br | —NMe(i-Pr) | OH | |
| 1-640 | —(CH₂)₂— | CCl₃ | Br | —NEt(i-Pr) | OH | |
| 1-641 | —(CH₂)₂— | CCl₃ | Br | —N(Me)OMe | OH | |
| 1-642 | —(CH₂)₂— | CCl₃ | Br | —N(Me)OEt | OH | |
| 1-643 | —(CH₂)₂— | CCl₃ | Br | —N(Me)O(n-Pr) | OH | |
| 1-644 | —(CH₂)₂— | CCl₃ | Br | —N(Et)OMe | OH | |
| 1-645 | —(CH₂)₂— | CCl₃ | Br | —N(Et)OEt | OH | |
| 1-646 | —(CH₂)₂— | CCl₃ | Br | —N(Et)O(n-Pr) | OH | |
| 1-647 | —(CH₂)₂— | C₂F₅ | Br | —NH₂ | OH | |
| 1-648 | —(CH₂)₂— | C₂F₅ | Br | —NHMe | OH | |
| 1-649 | —(CH₂)₂— | C₂F₅ | Br | —NMe₂ | OH | |
| 1-650 | —(CH₂)₂— | C₂F₅ | Br | —NHEt | OH | |
| 1-651 | —(CH₂)₂— | C₂F₅ | Br | —NEt₂ | OH | |
| 1-652 | —(CH₂)₂— | C₂F₅ | Br | —NH(n-Pr) | OH | |
| 1-653 | —(CH₂)₂— | C₂F₅ | Br | —N(n-Pr)₂ | OH | |
| 1-654 | —(CH₂)₂— | C₂F₅ | Br | —NMeEt | OH | |
| 1-655 | —(CH₂)₂— | C₂F₅ | Br | —NMe(n-Pr) | OH | |
| 1-656 | —(CH₂)₂— | C₂F₅ | Br | —NEt(n-Pr) | OH | |
| 1-657 | —(CH₂)₂— | C₂F₅ | Br | —NH(i-Pr) | OH | |
| 1-658 | —(CH₂)₂— | C₂F₅ | Br | —NMe(i-Pr) | OH | |
| 1-659 | —(CH₂)₂— | C₂F₅ | Br | —NEt(i-Pr) | OH | |
| 1-660 | —(CH₂)₂— | C₂F₅ | Br | —N(Me)OMe | OH | |
| 1-661 | —(CH₂)₂— | C₂F₅ | Br | —N(Me)OEt | OH | |
| 1-662 | —(CH₂)₂— | C₂F₅ | Br | —N(Me)O(n-Pr) | OH | |
| 1-663 | —(CH₂)₂— | C₂F₅ | Br | —N(Et)OMe | OH | |
| 1-664 | —(CH₂)₂— | C₂F₅ | Br | —N(Et)OEt | OH | |

TABLE 1-continued

| No. | X¹ | R¹ | R² | —NR³R⁴ | R⁵ | Physical data |
|---|---|---|---|---|---|---|
| 1-665 | —(CH$_2$)$_2$— | C$_2$F$_5$ | Br | —N(Et)O(n-Pr) | OH | |
| 1-666 | —(CH$_2$)$_2$— | CHF$_2$ | Br | —NH$_2$ | OH | |
| 1-667 | —(CH$_2$)$_2$— | CHF$_2$ | Br | —NHMe | OH | |
| 1-668 | —(CH$_2$)$_2$— | CHF$_2$ | Br | —NMe$_2$ | OH | |
| 1-669 | —(CH$_2$)$_2$— | CHF$_2$ | Br | —NHEt | OH | |
| 1-670 | —(CH$_2$)$_2$— | CHF$_2$ | Br | —NEt$_2$ | OH | |
| 1-671 | —(CH$_2$)$_2$— | CHF$_2$ | Br | —NH(n-Pr) | OH | |
| 1-672 | —(CH$_2$)$_2$— | CHF$_2$ | Br | —N(n-Pr)$_2$ | OH | |
| 1-673 | —(CH$_2$)$_2$— | CHF$_2$ | Br | —NMeEt | OH | |
| 1-674 | —(CH$_2$)$_2$— | CHF$_2$ | Br | —NMe(n-Pr) | OH | |
| 1-675 | —(CH$_2$)$_2$— | CHF$_2$ | Br | —NEt(n-Pr) | OH | |
| 1-676 | —(CH$_2$)$_2$— | CHF$_2$ | Br | —NH(i-Pr) | OH | |
| 1-677 | —(CH$_2$)$_2$— | CHF$_2$ | Br | —NMe(i-Pr) | OH | |
| 1-678 | —(CH$_2$)$_2$— | CHF$_2$ | Br | —NEt(i-Pr) | OH | |
| 1-679 | —(CH$_2$)$_2$— | CHF$_2$ | Br | —N(Me)OMe | OH | |
| 1-680 | —(CH$_2$)$_2$— | CHF$_2$ | Br | —N(Me)OEt | OH | |
| 1-681 | —(CH$_2$)$_2$— | CHF$_2$ | Br | —N(Me)O(n-Pr) | OH | |
| 1-682 | —(CH$_2$)$_2$— | CHF$_2$ | Br | —N(Et)OMe | OH | |
| 1-683 | —(CH$_2$)$_2$— | CHF$_2$ | Br | —N(Et)OEt | OH | |
| 1-684 | —(CH$_2$)$_2$— | CHF$_2$ | Br | —N(Et)O(n-Pr) | OH | |
| 1-685 | —(CH$_2$)$_2$— | CF$_3$ | Br | —NH$_2$ | SCH$_2$C(O)OMe | |
| 1-686 | —(CH$_2$)$_2$— | CF$_3$ | Br | —NHMe | SCH$_2$C(O)OMe | |
| 1-687 | —(CH$_2$)$_2$— | CF$_3$ | Br | —NMe$_2$ | SCH$_2$C(O)OMe | |
| 1-688 | —(CH$_2$)$_2$— | CF$_3$ | Br | —NHEt | SCH$_2$C(O)OMe | |
| 1-689 | —(CH$_2$)$_2$— | CF$_3$ | Br | —NEt$_2$ | SCH$_2$C(O)OMe | |
| 1-690 | —(CH$_2$)$_2$— | CF$_3$ | Br | —NH(n-Pr) | SCH$_2$C(O)OMe | |
| 1-691 | —(CH$_2$)$_2$— | CF$_3$ | Br | —N(n-Pr)$_2$ | SCH$_2$C(O)OMe | |
| 1-692 | —(CH$_2$)$_2$— | CF$_3$ | Br | —NMeEt | SCH$_2$C(O)OMe | |
| 1-693 | —(CH$_2$)$_2$— | CF$_3$ | Br | —NMe(n-Pr) | SCH$_2$C(O)OMe | |
| 1-694 | —(CH$_2$)$_2$— | CF$_3$ | Br | —NEt(n-Pr) | SCH$_2$C(O)OMe | |
| 1-695 | —(CH$_2$)$_2$— | CF$_3$ | Br | —NH(i-Pr) | SCH$_2$C(O)OMe | |
| 1-696 | —(CH$_2$)$_2$— | CF$_3$ | Br | —NMe(i-Pr) | SCH$_2$C(O)OMe | |
| 1-697 | —(CH$_2$)$_2$— | CF$_3$ | Br | —NEt(i-Pr) | SCH$_2$C(O)OMe | |
| 1-698 | —(CH$_2$)$_2$— | CF$_3$ | Br | —N(Me)OMe | SCH$_2$C(O)OMe | |
| 1-699 | —(CH$_2$)$_2$— | CF$_3$ | Br | —N(Me)OEt | SCH$_2$C(O)OMe | |
| 1-700 | —(CH$_2$)$_2$— | CF$_3$ | Br | —N(Me)O(n-Pr) | SCH$_2$C(O)OMe | |
| 1-701 | —(CH$_2$)$_2$— | CF$_3$ | Br | —N(Et)OMe | SCH$_2$C(O)OMe | |
| 1-702 | —(CH$_2$)$_2$— | CF$_3$ | Br | —N(Et)OEt | SCH$_2$C(O)OMe | |
| 1-703 | —(CH$_2$)$_2$— | CF$_3$ | Br | —N(Et)O(n-Pr) | SCH$_2$C(O)OMe | |
| 1-704 | —(CH$_2$)$_2$— | CCl$_3$ | Br | —NH$_2$ | SCH$_2$C(O)OMe | |
| 1-705 | —(CH$_2$)$_2$— | CCl$_3$ | Br | —NHMe | SCH$_2$C(O)OMe | |
| 1-706 | —(CH$_2$)$_2$— | CCl$_3$ | Br | —NMe$_2$ | SCH$_2$C(O)OMe | |
| 1-707 | —(CH$_2$)$_2$— | CCl$_3$ | Br | —NHEt | SCH$_2$C(O)OMe | |
| 1-708 | —(CH$_2$)$_2$— | CCl$_3$ | Br | —NEt$_2$ | SCH$_2$C(O)OMe | |
| 1-709 | —(CH$_2$)$_2$— | CCl$_3$ | Br | —NH(n-Pr) | SCH$_2$C(O)OMe | |
| 1-710 | —(CH$_2$)$_2$— | CCl$_3$ | Br | —N(n-Pr)$_2$ | SCH$_2$C(O)OMe | |
| 1-711 | —(CH$_2$)$_2$— | CCl$_3$ | Br | —NMeEt | SCH$_2$C(O)OMe | |
| 1-712 | —(CH$_2$)$_2$— | CCl$_3$ | Br | —NMe(n-Pr) | SCH$_2$C(O)OMe | |
| 1-713 | —(CH$_2$)$_2$— | CCl$_3$ | Br | —NEt(n-Pr) | SCH$_2$C(O)OMe | |
| 1-714 | —(CH$_2$)$_2$— | CCl$_3$ | Br | —NH(i-Pr) | SCH$_2$C(O)OMe | |
| 1-715 | —(CH$_2$)$_2$— | CCl$_3$ | Br | —NMe(i-Pr) | SCH$_2$C(O)OMe | |
| 1-716 | —(CH$_2$)$_2$— | CCl$_3$ | Br | —NEt(i-Pr) | SCH$_2$C(O)OMe | |
| 1-717 | —(CH$_2$)$_2$— | CCl$_3$ | Br | —N(Me)OMe | SCH$_2$C(O)OMe | |
| 1-718 | —(CH$_2$)$_2$— | CCl$_3$ | Br | —N(Me)OEt | SCH$_2$C(O)OMe | |
| 1-719 | —(CH$_2$)$_2$— | CCl$_3$ | Br | —N(Me)O(n-Pr) | SCH$_2$C(O)OMe | |
| 1-720 | —(CH$_2$)$_2$— | CCl$_3$ | Br | —N(Et)OMe | SCH$_2$C(O)OMe | |
| 1-721 | —(CH$_2$)$_2$— | CCl$_3$ | Br | —N(Et)OEt | SCH$_2$C(O)OMe | |
| 1-722 | —(CH$_2$)$_2$— | CCl$_3$ | Br | —N(Et)O(n-Pr) | SCH$_2$C(O)OMe | |
| 1-723 | —(CH$_2$)$_2$— | C$_2$F$_5$ | Br | —NH$_2$ | SCH$_2$C(O)OMe | |
| 1-724 | —(CH$_2$)$_2$— | C$_2$F$_5$ | Br | —NHMe | SCH$_2$C(O)OMe | |
| 1-725 | —(CH$_2$)$_2$— | C$_2$F$_5$ | Br | —NMe$_2$ | SCH$_2$C(O)OMe | |
| 1-726 | —(CH$_2$)$_2$— | C$_2$F$_5$ | Br | —NHEt | SCH$_2$C(O)OMe | |
| 1-727 | —(CH$_2$)$_2$— | C$_2$F$_5$ | Br | —NEt$_2$ | SCH$_2$C(O)OMe | |
| 1-728 | —(CH$_2$)$_2$— | C$_2$F$_5$ | Br | —NH(n-Pr) | SCH$_2$C(O)OMe | |
| 1-729 | —(CH$_2$)$_2$— | C$_2$F$_5$ | Br | —N(n-Pr)$_2$ | SCH$_2$C(O)OMe | |
| 1-730 | —(CH$_2$)$_2$— | C$_2$F$_5$ | Br | —NMeEt | SCH$_2$C(O)OMe | |
| 1-731 | —(CH$_2$)$_2$— | C$_2$F$_5$ | Br | —NMe(n-Pr) | SCH$_2$C(O)OMe | |
| 1-732 | —(CH$_2$)$_2$— | C$_2$F$_5$ | Br | —NEt(n-Pr) | SCH$_2$C(O)OMe | |
| 1-733 | —(CH$_2$)$_2$— | C$_2$F$_5$ | Br | —NH(i-Pr) | SCH$_2$C(O)OMe | |
| 1-734 | —(CH$_2$)$_2$— | C$_2$F$_5$ | Br | —NMe(i-Pr) | SCH$_2$C(O)OMe | |
| 1-735 | —(CH$_2$)$_2$— | C$_2$F$_5$ | Br | —NEt(i-Pr) | SCH$_2$C(O)OMe | |
| 1-736 | —(CH$_2$)$_2$— | C$_2$F$_5$ | Br | —N(Me)OMe | SCH$_2$C(O)OMe | |
| 1-737 | —(CH$_2$)$_2$— | C$_2$F$_5$ | Br | —N(Me)OEt | SCH$_2$C(O)OMe | |
| 1-738 | —(CH$_2$)$_2$— | C$_2$F$_5$ | Br | —N(Me)O(n-Pr) | SCH$_2$C(O)OMe | |
| 1-739 | —(CH$_2$)$_2$— | C$_2$F$_5$ | Br | —N(Et)OMe | SCH$_2$C(O)OMe | |
| 1-740 | —(CH$_2$)$_2$— | C$_2$F$_5$ | Br | —N(Et)OEt | SCH$_2$C(O)OMe | |
| 1-741 | —(CH$_2$)$_2$— | C$_2$F$_5$ | Br | —N(Et)O(n-Pr) | SCH$_2$C(O)OMe | |

TABLE 1-continued

| No. | $X^1$ | $R^1$ | $R^2$ | $-NR^3R^4$ | $R^5$ | Physical data |
|---|---|---|---|---|---|---|
| 1-742 | —(CH$_2$)$_2$— | CHF$_2$ | Br | —NH$_2$ | SCH$_2$C(O)OMe | |
| 1-743 | —(CH$_2$)$_2$— | CHF$_2$ | Br | —NHMe | SCH$_2$C(O)OMe | |
| 1-744 | —(CH$_2$)$_2$— | CHF$_2$ | Br | —NMe$_2$ | SCH$_2$C(O)OMe | |
| 1-745 | —(CH$_2$)$_2$— | CHF$_2$ | Br | —NHEt | SCH$_2$C(O)OMe | |
| 1-746 | —(CH$_2$)$_2$— | CHF$_2$ | Br | —NEt$_2$ | SCH$_2$C(O)OMe | |
| 1-747 | —(CH$_2$)$_2$— | CHF$_2$ | Br | —NH(n-Pr) | SCH$_2$C(O)OMe | |
| 1-748 | —(CH$_2$)$_2$— | CHF$_2$ | Br | —N(n-Pr)$_2$ | SCH$_2$C(O)OMe | |
| 1-749 | —(CH$_2$)$_2$— | CHF$_2$ | Br | —NMeEt | SCH$_2$C(O)OMe | |
| 1-750 | —(CH$_2$)$_2$— | CHF$_2$ | Br | —NMe(n-Pr) | SCH$_2$C(O)OMe | |
| 1-751 | —(CH$_2$)$_2$— | CHF$_2$ | Br | —NEt(n-Pr) | SCH$_2$C(O)OMe | |
| 1-752 | —(CH$_2$)$_2$— | CHF$_2$ | Br | —NH(i-Pr) | SCH$_2$C(O)OMe | |
| 1-753 | —(CH$_2$)$_2$— | CHF$_2$ | Br | —NMe(i-Pr) | SCH$_2$C(O)OMe | |
| 1-754 | —(CH$_2$)$_2$— | CHF$_2$ | Br | —NEt(i-Pr) | SCH$_2$C(O)OMe | |
| 1-755 | —(CH$_2$)$_2$— | CHF$_2$ | Br | —N(Me)OMe | SCH$_2$C(O)OMe | |
| 1-756 | —(CH$_2$)$_2$— | CHF$_2$ | Br | —N(Me)OEt | SCH$_2$C(O)OMe | |
| 1-757 | —(CH$_2$)$_2$— | CHF$_2$ | Br | —N(Me)O(n-Pr) | SCH$_2$C(O)OMe | |
| 1-758 | —(CH$_2$)$_2$— | CHF$_2$ | Br | —N(Et)OMe | SCH$_2$C(O)OMe | |
| 1-759 | —(CH$_2$)$_2$— | CHF$_2$ | Br | —N(Et)OEt | SCH$_2$C(O)OMe | |
| 1-760 | —(CH$_2$)$_2$— | CHF$_2$ | Br | —N(Et)O(n-Pr) | SCH$_2$C(O)OMe | |
| 1-761 | —CHMe— | CF$_3$ | Br | —NH$_2$ | OH | |
| 1-762 | —CHMe— | CF$_3$ | Br | —NHMe | OH | |
| 1-763 | —CHMe— | CF$_3$ | Br | —NMe$_2$ | OH | |
| 1-764 | —CHMe— | CF$_3$ | Br | —NHEt | OH | |
| 1-765 | —CHMe— | CF$_3$ | Br | —NEt$_2$ | OH | |
| 1-766 | —CHMe— | CF$_3$ | Br | —NH(n-Pr) | OH | |
| 1-767 | —CHMe— | CF$_3$ | Br | —N(n-Pr)$_2$ | OH | |
| 1-768 | —CHMe— | CF$_3$ | Br | —NMeEt | OH | |
| 1-769 | —CHMe— | CF$_3$ | Br | —NMe(n-Pr) | OH | |
| 1-770 | —CHMe— | CF$_3$ | Br | —NEt(n-Pr) | OH | |
| 1-771 | —CHMe— | CF$_3$ | Br | —NH(i-Pr) | OH | |
| 1-772 | —CHMe— | CF$_3$ | Br | —NMe(i-Pr) | OH | |
| 1-773 | —CHMe— | CF$_3$ | Br | —NEt(i-Pr) | OH | |
| 1-774 | —CHMe— | CF$_3$ | Br | —N(Me)OMe | OH | |
| 1-775 | —CHMe— | CF$_3$ | Br | —N(Me)OEt | OH | |
| 1-776 | —CHMe— | CF$_3$ | Br | —N(Me)O(n-Pr) | OH | |
| 1-777 | —CHMe— | CF$_3$ | Br | —N(Et)OMe | OH | |
| 1-778 | —CHMe— | CF$_3$ | Br | —N(Et)OEt | OH | |
| 1-779 | —CHMe— | CF$_3$ | Br | —N(Et)O(n-Pr) | OH | |
| 1-780 | —CHMe— | CCl$_3$ | Br | —NH$_2$ | OH | |
| 1-781 | —CHMe— | CCl$_3$ | Br | —NHMe | OH | |
| 1-782 | —CHMe— | CCl$_3$ | Br | —NMe$_2$ | OH | |
| 1-783 | —CHMe— | CCl$_3$ | Br | —NHEt | OH | |
| 1-784 | —CHMe— | CCl$_3$ | Br | —NEt$_2$ | OH | |
| 1-785 | —CHMe— | CCl$_3$ | Br | —NH(n-Pr) | OH | |
| 1-786 | —CHMe— | CCl$_3$ | Br | —N(n-Pr)$_2$ | OH | |
| 1-787 | —CHMe— | CCl$_3$ | Br | —NMeEt | OH | |
| 1-788 | —CHMe— | CCl$_3$ | Br | —NMe(n-Pr) | OH | |
| 1-789 | —CHMe— | CCl$_3$ | Br | —NEt(n-Pr) | OH | |
| 1-790 | —CHMe— | CCl$_3$ | Br | —NH(i-Pr) | OH | |
| 1-791 | —CHMe— | CCl$_3$ | Br | —NMe(i-Pr) | OH | |
| 1-792 | —CHMe— | CCl$_3$ | Br | —NEt(i-Pr) | OH | |
| 1-793 | —CHMe— | CCl$_3$ | Br | —N(Me)OMe | OH | |
| 1-794 | —CHMe— | CCl$_3$ | Br | —N(Me)OEt | OH | |
| 1-795 | —CHMe— | CCl$_3$ | Br | —N(Me)O(n-Pr) | OH | |
| 1-796 | —CHMe— | CCl$_3$ | Br | —N(Et)OMe | OH | |
| 1-797 | —CHMe— | CCl$_3$ | Br | —N(Et)OEt | OH | |
| 1-798 | —CHMe— | CCl$_3$ | Br | —N(Et)O(n-Pr) | OH | |
| 1-799 | —CHMe— | C$_2$F$_5$ | Br | —NH$_2$ | OH | |
| 1-800 | —CHMe— | C$_2$F$_5$ | Br | —NHMe | OH | |
| 1-801 | —CHMe— | C$_2$F$_5$ | Br | —NMe$_2$ | OH | |
| 1-802 | —CHMe— | C$_2$F$_5$ | Br | —NHEt | OH | |
| 1-803 | —CHMe— | C$_2$F$_5$ | Br | —NEt$_2$ | OH | |
| 1-804 | —CHMe— | C$_2$F$_5$ | Br | —NH(n-Pr) | OH | |
| 1-805 | —CHMe— | C$_2$F$_5$ | Br | —N(n-Pr)$_2$ | OH | |
| 1-806 | —CHMe— | C$_2$F$_5$ | Br | —NMeEt | OH | |
| 1-807 | —CHMe— | C$_2$F$_5$ | Br | —NMe(n-Pr) | OH | |
| 1-808 | —CHMe— | C$_2$F$_5$ | Br | —NEt(n-Pr) | OH | |
| 1-809 | —CHMe— | C$_2$F$_5$ | Br | —NH(i-Pr) | OH | |
| 1-810 | —CHMe— | C$_2$F$_5$ | Br | —NMe(i-Pr) | OH | |
| 1-811 | —CHMe— | C$_2$F$_5$ | Br | —NEt(i-Pr) | OH | |
| 1-812 | —CHMe— | C$_2$F$_5$ | Br | —N(Me)OMe | OH | |
| 1-813 | —CHMe— | C$_2$F$_5$ | Br | —N(Me)OEt | OH | |
| 1-814 | —CHMe— | C$_2$F$_5$ | Br | —N(Me)O(n-Pr) | OH | |
| 1-815 | —CHMe— | C$_2$F$_5$ | Br | —N(Et)OMe | OH | |
| 1-816 | —CHMe— | C$_2$F$_5$ | Br | —N(Et)OEt | OH | |
| 1-817 | —CHMe— | C$_2$F$_5$ | Br | —N(Et)O(n-Pr) | OH | |
| 1-818 | —CHMe— | CHF$_2$ | Br | —NH$_2$ | OH | |

TABLE 1-continued

| No. | $X^1$ | $R^1$ | $R^2$ | $-NR^3R^4$ | $R^5$ | Physical data |
|---|---|---|---|---|---|---|
| 1-819 | —CHMe— | $CHF_2$ | Br | —NHMe | OH | |
| 1-820 | —CHMe— | $CHF_2$ | Br | —$NMe_2$ | OH | |
| 1-821 | —CHMe— | $CHF_2$ | Br | —NHEt | OH | |
| 1-822 | —CHMe— | $CHF_2$ | Br | —$NEt_2$ | OH | |
| 1-823 | —CHMe— | $CHF_2$ | Br | —NH(n-Pr) | OH | |
| 1-824 | —CHMe— | $CHF_2$ | Br | —N(n-Pr)$_2$ | OH | |
| 1-825 | —CHMe— | $CHF_2$ | Br | —NMeEt | OH | |
| 1-826 | —CHMe— | $CHF_2$ | Br | —NMe(n-Pr) | OH | |
| 1-827 | —CHMe— | $CHF_2$ | Br | —NEt(n-Pr) | OH | |
| 1-828 | —CHMe— | $CHF_2$ | Br | —NH(i-Pr) | OH | |
| 1-829 | —CHMe— | $CHF_2$ | Br | —NMe(i-Pr) | OH | |
| 1-830 | —CHMe— | $CHF_2$ | Br | —NEt(i-Pr) | OH | |
| 1-831 | —CHMe— | $CHF_2$ | Br | —N(Me)OMe | OH | |
| 1-832 | —CHMe— | $CHF_2$ | Br | —N(Me)OEt | OH | |
| 1-833 | —CHMe— | $CHF_2$ | Br | —N(Me)O(n-Pr) | OH | |
| 1-834 | —CHMe— | $CHF_2$ | Br | —N(Et)OMe | OH | |
| 1-835 | —CHMe— | $CHF_2$ | Br | —N(Et)OEt | OH | |
| 1-836 | —CHMe— | $CHF_2$ | Br | —N(Et)O(n-Pr) | OH | |
| 1-837 | —CHMe— | $CF_3$ | Br | —$NH_2$ | $SCH_2C(O)OMe$ | |
| 1-838 | —CHMe— | $CF_3$ | Br | —NHMe | $SCH_2C(O)OMe$ | |
| 1-839 | —CHMe— | $CF_3$ | Br | —$NMe_2$ | $SCH_2C(O)OMe$ | |
| 1-840 | —CHMe— | $CF_3$ | Br | —NHEt | $SCH_2C(O)OMe$ | |
| 1-841 | —CHMe— | $CF_3$ | Br | —$NEt_2$ | $SCH_2C(O)OMe$ | |
| 1-842 | —CHMe— | $CF_3$ | Br | —NH(n-Pr) | $SCH_2C(O)OMe$ | |
| 1-843 | —CHMe— | $CF_3$ | Br | —N(n-Pr)$_2$ | $SCH_2C(O)OMe$ | |
| 1-844 | —CHMe— | $CF_3$ | Br | —NMeEt | $SCH_2C(O)OMe$ | |
| 1-845 | —CHMe— | $CF_3$ | Br | —NMe(n-Pr) | $SCH_2C(O)OMe$ | |
| 1-846 | —CHMe— | $CF_3$ | Br | —NEt(n-Pr) | $SCH_2C(O)OMe$ | |
| 1-847 | —CHMe— | $CF_3$ | Br | —NH(i-Pr) | $SCH_2C(O)OMe$ | |
| 1-848 | —CHMe— | $CF_3$ | Br | —NMe(i-Pr) | $SCH_2C(O)OMe$ | |
| 1-849 | —CHMe— | $CF_3$ | Br | —NEt(i-Pr) | $SCH_2C(O)OMe$ | |
| 1-850 | —CHMe— | $CF_3$ | Br | —N(Me)OMe | $SCH_2C(O)OMe$ | |
| 1-851 | —CHMe— | $CF_3$ | Br | —N(Me)OEt | $SCH_2C(O)OMe$ | |
| 1-852 | —CHMe— | $CF_3$ | Br | —N(Me)O(n-Pr) | $SCH_2C(O)OMe$ | |
| 1-853 | —CHMe— | $CF_3$ | Br | —N(Et)OMe | $SCH_2C(O)OMe$ | |
| 1-854 | —CHMe— | $CF_3$ | Br | —N(Et)OEt | $SCH_2C(O)OMe$ | |
| 1-855 | —CHMe— | $CF_3$ | Br | —N(Et)O(n-Pr) | $SCH_2C(O)OMe$ | |
| 1-856 | —CHMe— | $CCl_3$ | Br | —$NH_2$ | $SCH_2C(O)OMe$ | |
| 1-857 | —CHMe— | $CCl_3$ | Br | —NHMe | $SCH_2C(O)OMe$ | |
| 1-858 | —CHMe— | $CCl_3$ | Br | —$NMe_2$ | $SCH_2C(O)OMe$ | |
| 1-859 | —CHMe— | $CCl_3$ | Br | —NHEt | $SCH_2C(O)OMe$ | |
| 1-860 | —CHMe— | $CCl_3$ | Br | —$NEt_2$ | $SCH_2C(O)OMe$ | |
| 1-861 | —CHMe— | $CCl_3$ | Br | —NH(n-Pr) | $SCH_2C(O)OMe$ | |
| 1-862 | —CHMe— | $CCl_3$ | Br | —N(n-Pr)$_2$ | $SCH_2C(O)OMe$ | |
| 1-863 | —CHMe— | $CCl_3$ | Br | —NMeEt | $SCH_2C(O)OMe$ | |
| 1-864 | —CHMe— | $CCl_3$ | Br | —NMe(n-Pr) | $SCH_2C(O)OMe$ | |
| 1-865 | —CHMe— | $CCl_3$ | Br | —NEt(n-Pr) | $SCH_2C(O)OMe$ | |
| 1-866 | —CHMe— | $CCl_3$ | Br | —NH(i-Pr) | $SCH_2C(O)OMe$ | |
| 1-867 | —CHMe— | $CCl_3$ | Br | —NMe(i-Pr) | $SCH_2C(O)OMe$ | |
| 1-868 | —CHMe— | $CCl_3$ | Br | —NEt(i-Pr) | $SCH_2C(O)OMe$ | |
| 1-869 | —CHMe— | $CCl_3$ | Br | —N(Me)OMe | $SCH_2C(O)OMe$ | |
| 1-870 | —CHMe— | $CCl_3$ | Br | —N(Me)OEt | $SCH_2C(O)OMe$ | |
| 1-871 | —CHMe— | $CCl_3$ | Br | —N(Me)O(n-Pr) | $SCH_2C(O)OMe$ | |
| 1-872 | —CHMe— | $CCl_3$ | Br | —N(Et)OMe | $SCH_2C(O)OMe$ | |
| 1-873 | —CHMe— | $CCl_3$ | Br | —N(Et)OEt | $SCH_2C(O)OMe$ | |
| 1-874 | —CHMe— | $CCl_3$ | Br | —N(Et)O(n-Pr) | $SCH_2C(O)OMe$ | |
| 1-875 | —CHMe— | $C_2F_5$ | Br | —$NH_2$ | $SCH_2C(O)OMe$ | |
| 1-876 | —CHMe— | $C_2F_5$ | Br | —NHMe | $SCH_2C(O)OMe$ | |
| 1-877 | —CHMe— | $C_2F_5$ | Br | —$NMe_2$ | $SCH_2C(O)OMe$ | |
| 1-878 | —CHMe— | $C_2F_5$ | Br | —NHEt | $SCH_2C(O)OMe$ | |
| 1-879 | —CHMe— | $C_2F_5$ | Br | —$NEt_2$ | $SCH_2C(O)OMe$ | |
| 1-880 | —CHMe— | $C_2F_5$ | Br | —NH(n-Pr) | $SCH_2C(O)OMe$ | |
| 1-881 | —CHMe— | $C_2F_5$ | Br | —N(n-Pr)$_2$ | $SCH_2C(O)OMe$ | |
| 1-882 | —CHMe— | $C_2F_5$ | Br | —NMeEt | $SCH_2C(O)OMe$ | |
| 1-883 | —CHMe— | $C_2F_5$ | Br | —NMe(n-Pr) | $SCH_2C(O)OMe$ | |
| 1-884 | —CHMe— | $C_2F_5$ | Br | —NEt(n-Pr) | $SCH_2C(O)OMe$ | |
| 1-885 | —CHMe— | $C_2F_5$ | Br | —NH(i-Pr) | $SCH_2C(O)OMe$ | |
| 1-886 | —CHMe— | $C_2F_5$ | Br | —NMe(i-Pr) | $SCH_2C(O)OMe$ | |
| 1-887 | —CHMe— | $C_2F_5$ | Br | —NEt(i-Pr) | $SCH_2C(O)OMe$ | |
| 1-888 | —CHMe— | $C_2F_5$ | Br | —N(Me)OMe | $SCH_2C(O)OMe$ | |
| 1-889 | —CHMe— | $C_2F_5$ | Br | —N(Me)OEt | $SCH_2C(O)OMe$ | |
| 1-890 | —CHMe— | $C_2F_5$ | Br | —N(Me)O(n-Pr) | $SCH_2C(O)OMe$ | |
| 1-891 | —CHMe— | $C_2F_5$ | Br | —N(Et)OMe | $SCH_2C(O)OMe$ | |
| 1-892 | —CHMe— | $C_2F_5$ | Br | —N(Et)OEt | $SCH_2C(O)OMe$ | |
| 1-893 | —CHMe— | $C_2F_5$ | Br | —N(Et)O(n-Pr) | $SCH_2C(O)OMe$ | |
| 1-894 | —CHMe— | $CHF_2$ | Br | —$NH_2$ | $SCH_2C(O)OMe$ | |
| 1-895 | —CHMe— | $CHF_2$ | Br | —NHMe | $SCH_2C(O)OMe$ | |

TABLE 1-continued

| No. | X$^1$ | R$^1$ | R$^2$ | —NR$^3$R$^4$ | R$^5$ | Physical data |
|---|---|---|---|---|---|---|
| 1-896 | —CHMe— | CHF$_2$ | Br | —NMe$_2$ | SCH$_2$C(O)OMe | |
| 1-897 | —CHMe— | CHF$_2$ | Br | —NHEt | SCH$_2$C(O)OMe | |
| 1-898 | —CHMe— | CHF$_2$ | Br | —NEt$_2$ | SCH$_2$C(O)OMe | |
| 1-899 | —CHMe— | CHF$_2$ | Br | —NH(n-Pr) | SCH$_2$C(O)OMe | |
| 1-900 | —CHMe— | CHF$_2$ | Br | —N(n-Pr)$_2$ | SCH$_2$C(O)OMe | |
| 1-901 | —CHMe— | CHF$_2$ | Br | —NMeEt | SCH$_2$C(O)OMe | |
| 1-902 | —CHMe— | CHF$_2$ | Br | —NMe(n-Pr) | SCH$_2$C(O)OMe | |
| 1-903 | —CHMe— | CHF$_2$ | Br | —NEt(n-Pr) | SCH$_2$C(O)OMe | |
| 1-904 | —CHMe— | CHF$_2$ | Br | —NH(i-Pr) | SCH$_2$C(O)OMe | |
| 1-905 | —CHMe— | CHF$_2$ | Br | —NMe(i-Pr) | SCH$_2$C(O)OMe | |
| 1-906 | —CHMe— | CHF$_2$ | Br | —NEt(i-Pr) | SCH$_2$C(O)OMe | |
| 1-907 | —CHMe— | CHF$_2$ | Br | —N(Me)OMe | SCH$_2$C(O)OMe | |
| 1-908 | —CHMe— | CHF$_2$ | Br | —N(Me)OEt | SCH$_2$C(O)OMe | |
| 1-909 | —CHMe— | CHF$_2$ | Br | —N(Me)O(n-Pr) | SCH$_2$C(O)OMe | |
| 1-910 | —CHMe— | CHF$_2$ | Br | —N(Et)OMe | SCH$_2$C(O)OMe | |
| 1-911 | —CHMe— | CHF$_2$ | Br | —N(Et)OEt | SCH$_2$C(O)OMe | |
| 1-912 | —CHMe— | CHF$_2$ | Br | —N(Et)O(n-Pr) | SCH$_2$C(O)OMe | |
| 1-913 | —CH$_2$— | CF$_3$ | I | —NH$_2$ | OH | |
| 1-914 | —CH$_2$— | CF$_3$ | I | —NHMe | OH | |
| 1-915 | —CH$_2$— | CF$_3$ | I | —NMe$_2$ | OH | |
| 1-916 | —CH$_2$— | CF$_3$ | I | —NHEt | OH | |
| 1-917 | —CH$_2$— | CF$_3$ | I | —NEt$_2$ | OH | |
| 1-918 | —CH$_2$— | CF$_3$ | I | —NH(n-Pr) | OH | |
| 1-919 | —CH$_2$— | CF$_3$ | I | —N(n-Pr)$_2$ | OH | |
| 1-920 | —CH$_2$— | CF$_3$ | I | —NMeEt | OH | |
| 1-921 | —CH$_2$— | CF$_3$ | I | —NMe(n-Pr) | OH | |
| 1-922 | —CH$_2$— | CF$_3$ | I | —NEt(n-Pr) | OH | |
| 1-923 | —CH$_2$— | CF$_3$ | I | —NH(i-Pr) | OH | |
| 1-924 | —CH$_2$— | CF$_3$ | I | —NMe(i-Pr) | OH | |
| 1-925 | —CH$_2$— | CF$_3$ | I | —NEt(i-Pr) | OH | |
| 1-926 | —CH$_2$— | CF$_3$ | I | —N(Me)OMe | OH | |
| 1-927 | —CH$_2$— | CF$_3$ | I | —N(Me)OEt | OH | |
| 1-928 | —CH$_2$— | CF$_3$ | I | —N(Me)O(n-Pr) | OH | |
| 1-929 | —CH$_2$— | CF$_3$ | I | —N(Et)OMe | OH | |
| 1-930 | —CH$_2$— | CF$_3$ | I | —N(Et)OEt | OH | |
| 1-931 | —CH$_2$— | CF$_3$ | I | —N(Et)O(n-Pr) | OH | |
| 1-932 | —CH$_2$— | CCl$_3$ | I | —NH$_2$ | OH | |
| 1-933 | —CH$_2$— | CCl$_3$ | I | —NHMe | OH | |
| 1-934 | —CH$_2$— | CCl$_3$ | I | —NMe$_2$ | OH | |
| 1-935 | —CH$_2$— | CCl$_3$ | I | —NHEt | OH | |
| 1-936 | —CH$_2$— | CCl$_3$ | I | —NEt$_2$ | OH | |
| 1-937 | —CH$_2$— | CCl$_3$ | I | —NH(n-Pr) | OH | |
| 1-938 | —CH$_2$— | CCl$_3$ | I | —N(n-Pr)$_2$ | OH | |
| 1-939 | —CH$_2$— | CCl$_3$ | I | —NMeEt | OH | |
| 1-940 | —CH$_2$— | CCl$_3$ | I | —NMe(n-Pr) | OH | |
| 1-941 | —CH$_2$— | CCl$_3$ | I | —NEt(n-Pr) | OH | |
| 1-942 | —CH$_2$— | CCl$_3$ | I | —NH(i-Pr) | OH | |
| 1-943 | —CH$_2$— | CCl$_3$ | I | —NMe(i-Pr) | OH | |
| 1-944 | —CH$_2$— | CCl$_3$ | I | —NEt(i-Pr) | OH | |
| 1-945 | —CH$_2$— | CCl$_3$ | I | —N(Me)OMe | OH | |
| 1-946 | —CH$_2$— | CCl$_3$ | I | —N(Me)OEt | OH | |
| 1-947 | —CH$_2$— | CCl$_3$ | I | —N(Me)O(n-Pr) | OH | |
| 1-948 | —CH$_2$— | CCl$_3$ | I | —N(Et)OMe | OH | |
| 1-949 | —CH$_2$— | CCl$_3$ | I | —N(Et)OEt | OH | |
| 1-950 | —CH$_2$— | CCl$_3$ | I | —N(Et)O(n-Pr) | OH | |
| 1-951 | —CH$_2$— | C$_2$F$_5$ | I | —NH$_2$ | OH | |
| 1-952 | —CH$_2$— | C$_2$F$_5$ | I | —NHMe | OH | |
| 1-953 | —CH$_2$— | C$_2$F$_5$ | I | —NMe$_2$ | OH | |
| 1-954 | —CH$_2$— | C$_2$F$_5$ | I | —NHEt | OH | |
| 1-955 | —CH$_2$— | C$_2$F$_5$ | I | —NEt$_2$ | OH | |
| 1-956 | —CH$_2$— | C$_2$F$_5$ | I | —NH(n-Pr) | OH | |
| 1-957 | —CH$_2$— | C$_2$F$_5$ | I | —N(n-Pr)$_2$ | OH | |
| 1-958 | —CH$_2$— | C$_2$F$_5$ | I | —NMeEt | OH | |
| 1-959 | —CH$_2$— | C$_2$F$_5$ | I | —NMe(n-Pr) | OH | |
| 1-960 | —CH$_2$— | C$_2$F$_5$ | I | —NEt(n-Pr) | OH | |
| 1-961 | —CH$_2$— | C$_2$F$_5$ | I | —NH(i-Pr) | OH | |
| 1-962 | —CH$_2$— | C$_2$F$_5$ | I | —NMe(i-Pr) | OH | |
| 1-963 | —CH$_2$— | C$_2$F$_5$ | I | —NEt(i-Pr) | OH | |
| 1-964 | —CH$_2$— | C$_2$F$_5$ | I | —N(Me)OMe | OH | |
| 1-965 | —CH$_2$— | C$_2$F$_5$ | I | —N(Me)OEt | OH | |
| 1-966 | —CH$_2$— | C$_2$F$_5$ | I | —N(Me)O(n-Pr) | OH | |
| 1-967 | —CH$_2$— | C$_2$F$_5$ | I | —N(Et)OMe | OH | |
| 1-968 | —CH$_2$— | C$_2$F$_5$ | I | —N(Et)OEt | OH | |
| 1-969 | —CH$_2$— | C$_2$F$_5$ | I | —N(Et)O(n-Pr) | OH | |
| 1-970 | —CH$_2$— | CHF$_2$ | I | —NH$_2$ | OH | |
| 1-971 | —CH$_2$— | CHF$_2$ | I | —NHMe | OH | |
| 1-972 | —CH$_2$— | CHF$_2$ | I | —NMe$_2$ | OH | |

TABLE 1-continued

| No. | X¹ | R¹ | R² | —NR³R⁴ | R⁵ | Physical data |
|---|---|---|---|---|---|---|
| 1-973 | —CH$_2$— | CHF$_2$ | I | —NHEt | OH | |
| 1-974 | —CH$_2$— | CHF$_2$ | I | —NEt$_2$ | OH | |
| 1-975 | —CH$_2$— | CHF$_2$ | I | —NH(n-Pr) | OH | |
| 1-976 | —CH$_2$— | CHF$_2$ | I | —N(n-Pr)$_2$ | OH | |
| 1-977 | —CH$_2$— | CHF$_2$ | I | —NMeEt | OH | |
| 1-978 | —CH$_2$— | CHF$_2$ | I | —NMe(n-Pr) | OH | |
| 1-979 | —CH$_2$— | CHF$_2$ | I | —NEt(n-Pr) | OH | |
| 1-980 | —CH$_2$— | CHF$_2$ | I | —NH(i-Pr) | OH | |
| 1-981 | —CH$_2$— | CHF$_2$ | I | —NMe(i-Pr) | OH | |
| 1-982 | —CH$_2$— | CHF$_2$ | I | —NEt(i-Pr) | OH | |
| 1-983 | —CH$_2$— | CHF$_2$ | I | —N(Me)OMe | OH | |
| 1-984 | —CH$_2$— | CHF$_2$ | I | —N(Me)OEt | OH | |
| 1-985 | —CH$_2$— | CHF$_2$ | I | —N(Me)O(n-Pr) | OH | |
| 1-986 | —CH$_2$— | CHF$_2$ | I | —N(Et)OMe | OH | |
| 1-987 | —CH$_2$— | CHF$_2$ | I | —N(Et)OEt | OH | |
| 1-988 | —CH$_2$— | CHF$_2$ | I | —N(Et)O(n-Pr) | OH | |
| 1-989 | —CH$_2$— | CF$_3$ | I | —NH$_2$ | SCH$_2$C(O)OMe | |
| 1-990 | —CH$_2$— | CF$_3$ | I | —NHMe | SCH$_2$C(O)OMe | |
| 1-991 | —CH$_2$— | CF$_3$ | I | —NMe$_2$ | SCH$_2$C(O)OMe | |
| 1-992 | —CH$_2$— | CF$_3$ | I | —NHEt | SCH$_2$C(O)OMe | |
| 1-993 | —CH$_2$— | CF$_3$ | I | —NEt$_2$ | SCH$_2$C(O)OMe | |
| 1-994 | —CH$_2$— | CF$_3$ | I | —NH(n-Pr) | SCH$_2$C(O)OMe | |
| 1-995 | —CH$_2$— | CF$_3$ | I | —N(n-Pr)$_2$ | SCH$_2$C(O)OMe | |
| 1-996 | —CH$_2$— | CF$_3$ | I | —NMeEt | SCH$_2$C(O)OMe | |
| 1-997 | —CH$_2$— | CF$_3$ | I | —NMe(n-Pr) | SCH$_2$C(O)OMe | |
| 1-998 | —CH$_2$— | CF$_3$ | I | —NEt(n-Pr) | SCH$_2$C(O)OMe | |
| 1-999 | —CH$_2$— | CF$_3$ | I | —NH(i-Pr) | SCH$_2$C(O)OMe | |
| 1-1000 | —CH$_2$— | CF$_3$ | I | —NMe(i-Pr) | SCH$_2$C(O)OMe | |
| 1-1001 | —CH$_2$— | CF$_3$ | I | —NEt(i-Pr) | SCH$_2$C(O)OMe | |
| 1-1002 | —CH$_2$— | CF$_3$ | I | —N(Me)OMe | SCH$_2$C(O)OMe | |
| 1-1003 | —CH$_2$— | CF$_3$ | I | —N(Me)OEt | SCH$_2$C(O)OMe | |
| 1-1004 | —CH$_2$— | CF$_3$ | I | —N(Me)O(n-Pr) | SCH$_2$C(O)OMe | |
| 1-1005 | —CH$_2$— | CF$_3$ | I | —N(Et)OMe | SCH$_2$C(O)OMe | |
| 1-1006 | —CH$_2$— | CF$_3$ | I | —N(Et)OEt | SCH$_2$C(O)OMe | |
| 1-1007 | —CH$_2$— | CF$_3$ | I | —N(Et)O(n-Pr) | SCH$_2$C(O)OMe | |
| 1-1008 | —CH$_2$— | CCl$_3$ | I | —NH$_2$ | SCH$_2$C(O)OMe | |
| 1-1009 | —CH$_2$— | CCl$_3$ | I | —NHMe | SCH$_2$C(O)OMe | |
| 1-1010 | —CH$_2$— | CCl$_3$ | I | —NMe$_2$ | SCH$_2$C(O)OMe | |
| 1-1011 | —CH$_2$— | CCl$_3$ | I | —NHEt | SCH$_2$C(O)OMe | |
| 1-1012 | —CH$_2$— | CCl$_3$ | I | —NEt$_2$ | SCH$_2$C(O)OMe | |
| 1-1013 | —CH$_2$— | CCl$_3$ | I | —NH(n-Pr) | SCH$_2$C(O)OMe | |
| 1-1014 | —CH$_2$— | CCl$_3$ | I | —N(n-Pr)$_2$ | SCH$_2$C(O)OMe | |
| 1-1015 | —CH$_2$— | CCl$_3$ | I | —NMeEt | SCH$_2$C(O)OMe | |
| 1-1016 | —CH$_2$— | CCl$_3$ | I | —NMe(n-Pr) | SCH$_2$C(O)OMe | |
| 1-1017 | —CH$_2$— | CCl$_3$ | I | —NEt(n-Pr) | SCH$_2$C(O)OMe | |
| 1-1018 | —CH$_2$— | CCl$_3$ | I | —NH(i-Pr) | SCH$_2$C(O)OMe | |
| 1-1019 | —CH$_2$— | CCl$_3$ | I | —NMe(i-Pr) | SCH$_2$C(O)OMe | |
| 1-1020 | —CH$_2$— | CCl$_3$ | I | —NEt(i-Pr) | SCH$_2$C(O)OMe | |
| 1-1021 | —CH$_2$— | CCl$_3$ | I | —N(Me)OMe | SCH$_2$C(O)OMe | |
| 1-1022 | —CH$_2$— | CCl$_3$ | I | —N(Me)OEt | SCH$_2$C(O)OMe | |
| 1-1023 | —CH$_2$— | CCl$_3$ | I | —N(Me)O(n-Pr) | SCH$_2$C(O)OMe | |
| 1-1024 | —CH$_2$— | CCl$_3$ | I | —N(Et)OMe | SCH$_2$C(O)OMe | |
| 1-1025 | —CH$_2$— | CCl$_3$ | I | —N(Et)OEt | SCH$_2$C(O)OMe | |
| 1-1026 | —CH$_2$— | CCl$_3$ | I | —N(Et)O(n-Pr) | SCH$_2$C(O)OMe | |
| 1-1027 | —CH$_2$— | C$_2$F$_5$ | I | —NH$_2$ | SCH$_2$C(O)OMe | |
| 1-1028 | —CH$_2$— | C$_2$F$_5$ | I | —NHMe | SCH$_2$C(O)OMe | |
| 1-1029 | —CH$_2$— | C$_2$F$_5$ | I | —NMe$_2$ | SCH$_2$C(O)OMe | |
| 1-1030 | —CH$_2$— | C$_2$F$_5$ | I | —NHEt | SCH$_2$C(O)OMe | |
| 1-1031 | —CH$_2$— | C$_2$F$_5$ | I | —NEt$_2$ | SCH$_2$C(O)OMe | |
| 1-1032 | —CH$_2$— | C$_2$F$_5$ | I | —NH(n-Pr) | SCH$_2$C(O)OMe | |
| 1-1033 | —CH$_2$— | C$_2$F$_5$ | I | —N(n-Pr)$_2$ | SCH$_2$C(O)OMe | |
| 1-1034 | —CH$_2$— | C$_2$F$_5$ | I | —NMeEt | SCH$_2$C(O)OMe | |
| 1-1035 | —CH$_2$— | C$_2$F$_5$ | I | —NMe(n-Pr) | SCH$_2$C(O)OMe | |
| 1-1036 | —CH$_2$— | C$_2$F$_5$ | I | —NEt(n-Pr) | SCH$_2$C(O)OMe | |
| 1-1037 | —CH$_2$— | C$_2$F$_5$ | I | —NH(i-Pr) | SCH$_2$C(O)OMe | |
| 1-1038 | —CH$_2$— | C$_2$F$_5$ | I | —NMe(i-Pr) | SCH$_2$C(O)OMe | |
| 1-1039 | —CH$_2$— | C$_2$F$_5$ | I | —NEt(i-Pr) | SCH$_2$C(O)OMe | |
| 1-1040 | —CH$_2$— | C$_2$F$_5$ | I | —N(Me)OMe | SCH$_2$C(O)OMe | |
| 1-1041 | —CH$_2$— | C$_2$F$_5$ | I | —N(Me)OEt | SCH$_2$C(O)OMe | |
| 1-1042 | —CH$_2$— | C$_2$F$_5$ | I | —N(Me)O(n-Pr) | SCH$_2$C(O)OMe | |
| 1-1043 | —CH$_2$— | C$_2$F$_5$ | I | —N(Et)OMe | SCH$_2$C(O)OMe | |
| 1-1044 | —CH$_2$— | C$_2$F$_5$ | I | —N(Et)OEt | SCH$_2$C(O)OMe | |
| 1-1045 | —CH$_2$— | C$_2$F$_5$ | I | —N(Et)O(n-Pr) | SCH$_2$C(O)OMe | |
| 1-1046 | —CH$_2$— | CHF$_2$ | I | —NH$_2$ | SCH$_2$C(O)OMe | |
| 1-1047 | —CH$_2$— | CHF$_2$ | I | —NHMe | SCH$_2$C(O)OMe | |
| 1-1048 | —CH$_2$— | CHF$_2$ | I | —NMe$_2$ | SCH$_2$C(O)OMe | |
| 1-1049 | —CH$_2$— | CHF$_2$ | I | —NHEt | SCH$_2$C(O)OMe | |

TABLE 1-continued

| No. | X$^1$ | R$^1$ | R$^2$ | —NR$^3$R$^4$ | R$^5$ | Physical data |
|---|---|---|---|---|---|---|
| 1-1050 | —CH$_2$— | CHF$_2$ | I | —NEt$_2$ | SCH$_2$C(O)OMe | |
| 1-1051 | —CH$_2$— | CHF$_2$ | I | —NH(n-Pr) | SCH$_2$C(O)OMe | |
| 1-1052 | —CH$_2$— | CHF$_2$ | I | —N(n-Pr)$_2$ | SCH$_2$C(O)OMe | |
| 1-1053 | —CH$_2$— | CHF$_2$ | I | —NMeEt | SCH$_2$C(O)OMe | |
| 1-1054 | —CH$_2$— | CHF$_2$ | I | —NMe(n-Pr) | SCH$_2$C(O)OMe | |
| 1-1055 | —CH$_2$— | CHF$_2$ | I | —NEt(n-Pr) | SCH$_2$C(O)OMe | |
| 1-1056 | —CH$_2$— | CHF$_2$ | I | —NH(i-Pr) | SCH$_2$C(O)OMe | |
| 1-1057 | —CH$_2$— | CHF$_2$ | I | —NMe(i-Pr) | SCH$_2$C(O)OMe | |
| 1-1058 | —CH$_2$— | CHF$_2$ | I | —NEt(i-Pr) | SCH$_2$C(O)OMe | |
| 1-1059 | —CH$_2$— | CHF$_2$ | I | —N(Me)OMe | SCH$_2$C(O)OMe | |
| 1-1060 | —CH$_2$— | CHF$_2$ | I | —N(Me)OEt | SCH$_2$C(O)OMe | |
| 1-1061 | —CH$_2$— | CHF$_2$ | I | —N(Me)O(n-Pr) | SCH$_2$C(O)OMe | |
| 1-1062 | —CH$_2$— | CHF$_2$ | I | —N(Et)OMe | SCH$_2$C(O)OMe | |
| 1-1063 | —CH$_2$— | CHF$_2$ | I | —N(Et)OEt | SCH$_2$C(O)OMe | |
| 1-1064 | —CH$_2$— | CHF$_2$ | I | —N(Et)O(n-Pr) | SCH$_2$C(O)OMe | |
| 1-1065 | —(CH$_2$)$_2$— | CF$_3$ | I | —NH$_2$ | OH | |
| 1-1066 | —(CH$_2$)$_2$— | CF$_3$ | I | —NHMe | OH | |
| 1-1067 | —(CH$_2$)$_2$— | CF$_3$ | I | —NMe$_2$ | OH | |
| 1-1068 | —(CH$_2$)$_2$— | CF$_3$ | I | —NHEt | OH | |
| 1-1069 | —(CH$_2$)$_2$— | CF$_3$ | I | —NEt$_2$ | OH | |
| 1-1070 | —(CH$_2$)$_2$— | CF$_3$ | I | —NH(n-Pr) | OH | |
| 1-1071 | —(CH$_2$)$_2$— | CF$_3$ | I | —N(n-Pr)$_2$ | OH | |
| 1-1072 | —(CH$_2$)$_2$— | CF$_3$ | I | —NMeEt | OH | |
| 1-1073 | —(CH$_2$)$_2$— | CF$_3$ | I | —NMe(n-Pr) | OH | |
| 1-1074 | —(CH$_2$)$_2$— | CF$_3$ | I | —NEt(n-Pr) | OH | |
| 1-1075 | —(CH$_2$)$_2$— | CF$_3$ | I | —NH(i-Pr) | OH | |
| 1-1076 | —(CH$_2$)$_2$— | CF$_3$ | I | —NMe(i-Pr) | OH | |
| 1-1077 | —(CH$_2$)$_2$— | CF$_3$ | I | —NEt(i-Pr) | OH | |
| 1-1078 | —(CH$_2$)$_2$— | CF$_3$ | I | —N(Me)OMe | OH | |
| 1-1079 | —(CH$_2$)$_2$— | CF$_3$ | I | —N(Me)OEt | OH | |
| 1-1080 | —(CH$_2$)$_2$— | CF$_3$ | I | —N(Me)O(n-Pr) | OH | |
| 1-1081 | —(CH$_2$)$_2$— | CF$_3$ | I | —N(Et)OMe | OH | |
| 1-1082 | —(CH$_2$)$_2$— | CF$_3$ | I | —N(Et)OEt | OH | |
| 1-1083 | —(CH$_2$)$_2$— | CF$_3$ | I | —N(Et)O(n-Pr) | OH | |
| 1-1084 | —(CH$_2$)$_2$— | CCl$_3$ | I | —NH$_2$ | OH | |
| 1-1085 | —(CH$_2$)$_2$— | CCl$_3$ | I | —NHMe | OH | |
| 1-1086 | —(CH$_2$)$_2$— | CCl$_3$ | I | —NMe$_2$ | OH | |
| 1-1087 | —(CH$_2$)$_2$— | CCl$_3$ | I | —NHEt | OH | |
| 1-1088 | —(CH$_2$)$_2$— | CCl$_3$ | I | —NEt$_2$ | OH | |
| 1-1089 | —(CH$_2$)$_2$— | CCl$_3$ | I | —NH(n-Pr) | OH | |
| 1-1090 | —(CH$_2$)$_2$— | CCl$_3$ | I | —N(n-Pr)$_2$ | OH | |
| 1-1091 | —(CH$_2$)$_2$— | CCl$_3$ | I | —NMeEt | OH | |
| 1-1092 | —(CH$_2$)$_2$— | CCl$_3$ | I | —NMe(n-Pr) | OH | |
| 1-1093 | —(CH$_2$)$_2$— | CCl$_3$ | I | —NEt(n-Pr) | OH | |
| 1-1094 | —(CH$_2$)$_2$— | CCl$_3$ | I | —NH(i-Pr) | OH | |
| 1-1095 | —(CH$_2$)$_2$— | CCl$_3$ | I | —NMe(i-Pr) | OH | |
| 1-1096 | —(CH$_2$)$_2$— | CCl$_3$ | I | —NEt(i-Pr) | OH | |
| 1-1097 | —(CH$_2$)$_2$— | CCl$_3$ | I | —N(Me)OMe | OH | |
| 1-1098 | —(CH$_2$)$_2$— | CCl$_3$ | I | —N(Me)OEt | OH | |
| 1-1099 | —(CH$_2$)$_2$— | CCl$_3$ | I | —N(Me)O(n-Pr) | OH | |
| 1-1100 | —(CH$_2$)$_2$— | CCl$_3$ | I | —N(Et)OMe | OH | |
| 1-1101 | —(CH$_2$)$_2$— | CCl$_3$ | I | —N(Et)OEt | OH | |
| 1-1102 | —(CH$_2$)$_2$— | CCl$_3$ | I | —N(Et)O(n-Pr) | OH | |
| 1-1103 | —(CH$_2$)$_2$— | C$_2$F$_5$ | I | —NH$_2$ | OH | |
| 1-1104 | —(CH$_2$)$_2$— | C$_2$F$_5$ | I | —NHMe | OH | |
| 1-1105 | —(CH$_2$)$_2$— | C$_2$F$_5$ | I | —NMe$_2$ | OH | |
| 1-1106 | —(CH$_2$)$_2$— | C$_2$F$_5$ | I | —NHEt | OH | |
| 1-1107 | —(CH$_2$)$_2$— | C$_2$F$_5$ | I | —NEt$_2$ | OH | |
| 1-1108 | —(CH$_2$)$_2$— | C$_2$F$_5$ | I | —NH(n-Pr) | OH | |
| 1-1109 | —(CH$_2$)$_2$— | C$_2$F$_5$ | I | —N(n-Pr)$_2$ | OH | |
| 1-1110 | —(CH$_2$)$_2$— | C$_2$F$_5$ | I | —NMeEt | OH | |
| 1-1111 | —(CH$_2$)$_2$— | C$_2$F$_5$ | I | —NMe(n-Pr) | OH | |
| 1-1112 | —(CH$_2$)$_2$— | C$_2$F$_5$ | I | —NEt(n-Pr) | OH | |
| 1-1113 | —(CH$_2$)$_2$— | C$_2$F$_5$ | I | —NH(i-Pr) | OH | |
| 1-1114 | —(CH$_2$)$_2$— | C$_2$F$_5$ | I | —NMe(i-Pr) | OH | |
| 1-1115 | —(CH$_2$)$_2$— | C$_2$F$_5$ | I | —NEt(i-Pr) | OH | |
| 1-1116 | —(CH$_2$)$_2$— | C$_2$F$_5$ | I | —N(Me)OMe | OH | |
| 1-1117 | —(CH$_2$)$_2$— | C$_2$F$_5$ | I | —N(Me)OEt | OH | |
| 1-1118 | —(CH$_2$)$_2$— | C$_2$F$_5$ | I | —N(Me)O(n-Pr) | OH | |
| 1-1119 | —(CH$_2$)$_2$— | C$_2$F$_5$ | I | —N(Et)OMe | OH | |
| 1-1120 | —(CH$_2$)$_2$— | C$_2$F$_5$ | I | —N(Et)OEt | OH | |
| 1-1121 | —(CH$_2$)$_2$— | C$_2$F$_5$ | I | —N(Et)O(n-Pr) | OH | |
| 1-1122 | —(CH$_2$)$_2$— | CHF$_2$ | I | —NH$_2$ | OH | |
| 1-1123 | —(CH$_2$)$_2$— | CHF$_2$ | I | —NHMe | OH | |
| 1-1124 | —(CH$_2$)$_2$— | CHF$_2$ | I | —NMe$_2$ | OH | |
| 1-1125 | —(CH$_2$)$_2$— | CHF$_2$ | I | —NHEt | OH | |
| 1-1126 | —(CH$_2$)$_2$— | CHF$_2$ | I | —NEt$_2$ | OH | |

TABLE 1-continued

| No. | X¹ | R¹ | R² | —NR³R⁴ | R⁵ | Physical data |
|---|---|---|---|---|---|---|
| 1-1127 | —(CH$_2$)$_2$— | CHF$_2$ | I | —NH(n-Pr) | OH | |
| 1-1128 | —(CH$_2$)$_2$— | CHF$_2$ | I | —N(n-Pr)$_2$ | OH | |
| 1-1129 | —(CH$_2$)$_2$— | CHF$_2$ | I | —NMeEt | OH | |
| 1-1130 | —(CH$_2$)$_2$— | CHF$_2$ | I | —NMe(n-Pr) | OH | |
| 1-1131 | —(CH$_2$)$_2$— | CHF$_2$ | I | —NEt(n-Pr) | OH | |
| 1-1132 | —(CH$_2$)$_2$— | CHF$_2$ | I | —NH(i-Pr) | OH | |
| 1-1133 | —(CH$_2$)$_2$— | CHF$_2$ | I | —NMe(i-Pr) | OH | |
| 1-1134 | —(CH$_2$)$_2$— | CHF$_2$ | I | —NEt(i-Pr) | OH | |
| 1-1135 | —(CH$_2$)$_2$— | CHF$_2$ | I | —N(Me)OMe | OH | |
| 1-1136 | —(CH$_2$)$_2$— | CHF$_2$ | I | —N(Me)OEt | OH | |
| 1-1137 | —(CH$_2$)$_2$— | CHF$_2$ | I | —N(Me)O(n-Pr) | OH | |
| 1-1138 | —(CH$_2$)$_2$— | CHF$_2$ | I | —N(Et)OMe | OH | |
| 1-1139 | —(CH$_2$)$_2$— | CHF$_2$ | I | —N(Et)OEt | OH | |
| 1-1140 | —(CH$_2$)$_2$— | CHF$_2$ | I | —N(Et)O(n-Pr) | OH | |
| 1-1141 | —(CH$_2$)$_2$— | CF$_3$ | I | —NH$_2$ | SCH$_2$C(O)OMe | |
| 1-1142 | —(CH$_2$)$_2$— | CF$_3$ | I | —NHMe | SCH$_2$C(O)OMe | |
| 1-1143 | —(CH$_2$)$_2$— | CF$_3$ | I | —NMe$_2$ | SCH$_2$C(O)OMe | |
| 1-1144 | —(CH$_2$)$_2$— | CF$_3$ | I | —NHEt | SCH$_2$C(O)OMe | |
| 1-1145 | —(CH$_2$)$_2$— | CF$_3$ | I | —NEt$_2$ | SCH$_2$C(O)OMe | |
| 1-1146 | —(CH$_2$)$_2$— | CF$_3$ | I | —NH(n-Pr) | SCH$_2$C(O)OMe | |
| 1-1147 | —(CH$_2$)$_2$— | CF$_3$ | I | —N(n-Pr)$_2$ | SCH$_2$C(O)OMe | |
| 1-1148 | —(CH$_2$)$_2$— | CF$_3$ | I | —NMeEt | SCH$_2$C(O)OMe | |
| 1-1149 | —(CH$_2$)$_2$— | CF$_3$ | I | —NMe(n-Pr) | SCH$_2$C(O)OMe | |
| 1-1150 | —(CH$_2$)$_2$— | CF$_3$ | I | —NEt(n-Pr) | SCH$_2$C(O)OMe | |
| 1-1151 | —(CH$_2$)$_2$— | CF$_3$ | I | —NH(i-Pr) | SCH$_2$C(O)OMe | |
| 1-1152 | —(CH$_2$)$_2$— | CF$_3$ | I | —NMe(i-Pr) | SCH$_2$C(O)OMe | |
| 1-1153 | —(CH$_2$)$_2$— | CF$_3$ | I | —NEt(i-Pr) | SCH$_2$C(O)OMe | |
| 1-1154 | —(CH$_2$)$_2$— | CF$_3$ | I | —N(Me)OMe | SCH$_2$C(O)OMe | |
| 1-1155 | —(CH$_2$)$_2$— | CF$_3$ | I | —N(Me)OEt | SCH$_2$C(O)OMe | |
| 1-1156 | —(CH$_2$)$_2$— | CF$_3$ | I | —N(Me)O(n-Pr) | SCH$_2$C(O)OMe | |
| 1-1157 | —(CH$_2$)$_2$— | CF$_3$ | I | —N(Et)OMe | SCH$_2$C(O)OMe | |
| 1-1158 | —(CH$_2$)$_2$— | CF$_3$ | I | —N(Et)OEt | SCH$_2$C(O)OMe | |
| 1-1159 | —(CH$_2$)$_2$— | CF$_3$ | I | —N(Et)O(n-Pr) | SCH$_2$C(O)OMe | |
| 1-1160 | —(CH$_2$)$_2$— | CCl$_3$ | I | —NH$_2$ | SCH$_2$C(O)OMe | |
| 1-1161 | —(CH$_2$)$_2$— | CCl$_3$ | I | —NHMe | SCH$_2$C(O)OMe | |
| 1-1162 | —(CH$_2$)$_2$— | CCl$_3$ | I | —NMe$_2$ | SCH$_2$C(O)OMe | |
| 1-1163 | —(CH$_2$)$_2$— | CCl$_3$ | I | —NHEt | SCH$_2$C(O)OMe | |
| 1-1164 | —(CH$_2$)$_2$— | CCl$_3$ | I | —NEt$_2$ | SCH$_2$C(O)OMe | |
| 1-1165 | —(CH$_2$)$_2$— | CCl$_3$ | I | —NH(n-Pr) | SCH$_2$C(O)OMe | |
| 1-1166 | —(CH$_2$)$_2$— | CCl$_3$ | I | —N(n-Pr)$_2$ | SCH$_2$C(O)OMe | |
| 1-1167 | —(CH$_2$)$_2$— | CCl$_3$ | I | —NMeEt | SCH$_2$C(O)OMe | |
| 1-1168 | —(CH$_2$)$_2$— | CCl$_3$ | I | —NMe(n-Pr) | SCH$_2$C(O)OMe | |
| 1-1169 | —(CH$_2$)$_2$— | CCl$_3$ | I | —NEt(n-Pr) | SCH$_2$C(O)OMe | |
| 1-1170 | —(CH$_2$)$_2$— | CCl$_3$ | I | —NH(i-Pr) | SCH$_2$C(O)OMe | |
| 1-1171 | —(CH$_2$)$_2$— | CCl$_3$ | I | —NMe(i-Pr) | SCH$_2$C(O)OMe | |
| 1-1172 | —(CH$_2$)$_2$— | CCl$_3$ | I | —NEt(i-Pr) | SCH$_2$C(O)OMe | |
| 1-1173 | —(CH$_2$)$_2$— | CCl$_3$ | I | —N(Me)OMe | SCH$_2$C(O)OMe | |
| 1-1174 | —(CH$_2$)$_2$— | CCl$_3$ | I | —N(Me)OEt | SCH$_2$C(O)OMe | |
| 1-1175 | —(CH$_2$)$_2$— | CCl$_3$ | I | —N(Me)O(n-Pr) | SCH$_2$C(O)OMe | |
| 1-1176 | —(CH$_2$)$_2$— | CCl$_3$ | I | —N(Et)OMe | SCH$_2$C(O)OMe | |
| 1-1177 | —(CH$_2$)$_2$— | CCl$_3$ | I | —N(Et)OEt | SCH$_2$C(O)OMe | |
| 1-1178 | —(CH$_2$)$_2$— | CCl$_3$ | I | —N(Et)O(n-Pr) | SCH$_2$C(O)OMe | |
| 1-1179 | —(CH$_2$)$_2$— | C$_2$F$_5$ | I | —NH$_2$ | SCH$_2$C(O)OMe | |
| 1-1180 | —(CH$_2$)$_2$— | C$_2$F$_5$ | I | —NHMe | SCH$_2$C(O)OMe | |
| 1-1181 | —(CH$_2$)$_2$— | C$_2$F$_5$ | I | —NMe$_2$ | SCH$_2$C(O)OMe | |
| 1-1182 | —(CH$_2$)$_2$— | C$_2$F$_5$ | I | —NHEt | SCH$_2$C(O)OMe | |
| 1-1183 | —(CH$_2$)$_2$— | C$_2$F$_5$ | I | —NEt$_2$ | SCH$_2$C(O)OMe | |
| 1-1184 | —(CH$_2$)$_2$— | C$_2$F$_5$ | I | —NH(n-Pr) | SCH$_2$C(O)OMe | |
| 1-1185 | —(CH$_2$)$_2$— | C$_2$F$_5$ | I | —N(n-Pr)$_2$ | SCH$_2$C(O)OMe | |
| 1-1186 | —(CH$_2$)$_2$— | C$_2$F$_5$ | I | —NMeEt | SCH$_2$C(O)OMe | |
| 1-1187 | —(CH$_2$)$_2$— | C$_2$F$_5$ | I | —NMe(n-Pr) | SCH$_2$C(O)OMe | |
| 1-1188 | —(CH$_2$)$_2$— | C$_2$F$_5$ | I | —NEt(n-Pr) | SCH$_2$C(O)OMe | |
| 1-1189 | —(CH$_2$)$_2$— | C$_2$F$_5$ | I | —NH(i-Pr) | SCH$_2$C(O)OMe | |
| 1-1190 | —(CH$_2$)$_2$— | C$_2$F$_5$ | I | —NMe(i-Pr) | SCH$_2$C(O)OMe | |
| 1-1191 | —(CH$_2$)$_2$— | C$_2$F$_5$ | I | —NEt(i-Pr) | SCH$_2$C(O)OMe | |
| 1-1192 | —(CH$_2$)$_2$— | C$_2$F$_5$ | I | —N(Me)OMe | SCH$_2$C(O)OMe | |
| 1-1193 | —(CH$_2$)$_2$— | C$_2$F$_5$ | I | —N(Me)OEt | SCH$_2$C(O)OMe | |
| 1-1194 | —(CH$_2$)$_2$— | C$_2$F$_5$ | I | —N(Me)O(n-Pr) | SCH$_2$C(O)OMe | |
| 1-1195 | —(CH$_2$)$_2$— | C$_2$F$_5$ | I | —N(Et)OMe | SCH$_2$C(O)OMe | |
| 1-1196 | —(CH$_2$)$_2$— | C$_2$F$_5$ | I | —N(Et)OEt | SCH$_2$C(O)OMe | |
| 1-1197 | —(CH$_2$)$_2$— | C$_2$F$_5$ | I | —N(Et)O(n-Pr) | SCH$_2$C(O)OMe | |
| 1-1198 | —(CH$_2$)$_2$— | CHF$_2$ | I | —NH$_2$ | SCH$_2$C(O)OMe | |
| 1-1199 | —(CH$_2$)$_2$— | CHF$_2$ | I | —NHMe | SCH$_2$C(O)OMe | |
| 1-1200 | —(CH$_2$)$_2$— | CHF$_2$ | I | —NMe$_2$ | SCH$_2$C(O)OMe | |
| 1-1201 | —(CH$_2$)$_2$— | CHF$_2$ | I | —NHEt | SCH$_2$C(O)OMe | |
| 1-1202 | —(CH$_2$)$_2$— | CHF$_2$ | I | —NEt$_2$ | SCH$_2$C(O)OMe | |
| 1-1203 | —(CH$_2$)$_2$— | CHF$_2$ | I | —NH(n-Pr) | SCH$_2$C(O)OMe | |

TABLE 1-continued

| No. | X$^1$ | R$^1$ | R$^2$ | —NR$^3$R$^4$ | R$^5$ | Physical data |
|---|---|---|---|---|---|---|
| 1-1204 | —(CH$_2$)$_2$— | CHF$_2$ | I | —N(n-Pr)$_2$ | SCH$_2$C(O)OMe | |
| 1-1205 | —(CH$_2$)$_2$— | CHF$_2$ | I | —NMeEt | SCH$_2$C(O)OMe | |
| 1-1206 | —(CH$_2$)$_2$— | CHF$_2$ | I | —NMe(n-Pr) | SCH$_2$C(O)OMe | |
| 1-1207 | —(CH$_2$)$_2$— | CHF$_2$ | I | —NEt(n-Pr) | SCH$_2$C(O)OMe | |
| 1-1208 | —(CH$_2$)$_2$— | CHF$_2$ | I | —NH(i-Pr) | SCH$_2$C(O)OMe | |
| 1-1209 | —(CH$_2$)$_2$— | CHF$_2$ | I | —NMe(i-Pr) | SCH$_2$C(O)OMe | |
| 1-1210 | —(CH$_2$)$_2$— | CHF$_2$ | I | —NEt(i-Pr) | SCH$_2$C(O)OMe | |
| 1-1211 | —(CH$_2$)$_2$— | CHF$_2$ | I | —N(Me)OMe | SCH$_2$C(O)OMe | |
| 1-1212 | —(CH$_2$)$_2$— | CHF$_2$ | I | —N(Me)OEt | SCH$_2$C(O)OMe | |
| 1-1213 | —(CH$_2$)$_2$— | CHF$_2$ | I | —N(Me)O(n-Pr) | SCH$_2$C(O)OMe | |
| 1-1214 | —(CH$_2$)$_2$— | CHF$_2$ | I | —N(Et)OMe | SCH$_2$C(O)OMe | |
| 1-1215 | —(CH$_2$)$_2$— | CHF$_2$ | I | —N(Et)OEt | SCH$_2$C(O)OMe | |
| 1-1216 | —(CH$_2$)$_2$— | CHF$_2$ | I | —N(Et)O(n-Pr) | SCH$_2$C(O)OMe | |
| 1-1217 | —CHMe— | CF$_3$ | I | —NH$_2$ | OH | |
| 1-1218 | —CHMe— | CF$_3$ | I | —NHMe | OH | |
| 1-1219 | —CHMe— | CF$_3$ | I | —NMe$_2$ | OH | |
| 1-1220 | —CHMe— | CF$_3$ | I | —NHEt | OH | |
| 1-1221 | —CHMe— | CF$_3$ | I | —NEt$_2$ | OH | |
| 1-1222 | —CHMe— | CF$_3$ | I | —NH(n-Pr) | OH | |
| 1-1223 | —CHMe— | CF$_3$ | I | —N(n-Pr)$_2$ | OH | |
| 1-1224 | —CHMe— | CF$_3$ | I | —NMeEt | OH | |
| 1-1225 | —CHMe— | CF$_3$ | I | —NMe(n-Pr) | OH | |
| 1-1226 | —CHMe— | CF$_3$ | I | —NEt(n-Pr) | OH | |
| 1-1227 | —CHMe— | CF$_3$ | I | —NH(i-Pr) | OH | |
| 1-1228 | —CHMe— | CF$_3$ | I | —NMe(i-Pr) | OH | |
| 1-1229 | —CHMe— | CF$_3$ | I | —NEt(i-Pr) | OH | |
| 1-1230 | —CHMe— | CF$_3$ | I | —N(Me)OMe | OH | |
| 1-1231 | —CHMe— | CF$_3$ | I | —N(Me)OEt | OH | |
| 1-1232 | —CHMe— | CF$_3$ | I | —N(Me)O(n-Pr) | OH | |
| 1-1233 | —CHMe— | CF$_3$ | I | —N(Et)OMe | OH | |
| 1-1234 | —CHMe— | CF$_3$ | I | —N(Et)OEt | OH | |
| 1-1235 | —CHMe— | CF$_3$ | I | —N(Et)O(n-Pr) | OH | |
| 1-1236 | —CHMe— | CCl$_3$ | I | —NH$_2$ | OH | |
| 1-1237 | —CHMe— | CCl$_3$ | I | —NHMe | OH | |
| 1-1238 | —CHMe— | CCl$_3$ | I | —NMe$_2$ | OH | |
| 1-1239 | —CHMe— | CCl$_3$ | I | —NHEt | OH | |
| 1-1240 | —CHMe— | CCl$_3$ | I | —NEt$_2$ | OH | |
| 1-1241 | —CHMe— | CCl$_3$ | I | —NH(n-Pr) | OH | |
| 1-1242 | —CHMe— | CCl$_3$ | I | —N(n-Pr)$_2$ | OH | |
| 1-1243 | —CHMe— | CCl$_3$ | I | —NMeEt | OH | |
| 1-1244 | —CHMe— | CCl$_3$ | I | —NMe(n-Pr) | OH | |
| 1-1245 | —CHMe— | CCl$_3$ | I | —NEt(n-Pr) | OH | |
| 1-1246 | —CHMe— | CCl$_3$ | I | —NH(i-Pr) | OH | |
| 1-1247 | —CHMe— | CCl$_3$ | I | —NMe(i-Pr) | OH | |
| 1-1248 | —CHMe— | CCl$_3$ | I | —NEt(i-Pr) | OH | |
| 1-1249 | —CHMe— | CCl$_3$ | I | —N(Me)OMe | OH | |
| 1-1250 | —CHMe— | CCl$_3$ | I | —N(Me)OEt | OH | |
| 1-1251 | —CHMe— | CCl$_3$ | I | —N(Me)O(n-Pr) | OH | |
| 1-1252 | —CHMe— | CCl$_3$ | I | —N(Et)OMe | OH | |
| 1-1253 | —CHMe— | CCl$_3$ | I | —N(Et)OEt | OH | |
| 1-1254 | —CHMe— | CCl$_3$ | I | —N(Et)O(n-Pr) | OH | |
| 1-1255 | —CHMe— | C$_2$F$_5$ | I | —NH$_2$ | OH | |
| 1-1256 | —CHMe— | C$_2$F$_5$ | I | —NHMe | OH | |
| 1-1257 | —CHMe— | C$_2$F$_5$ | I | —NMe$_2$ | OH | |
| 1-1258 | —CHMe— | C$_2$F$_5$ | I | —NHEt | OH | |
| 1-1259 | —CHMe— | C$_2$F$_5$ | I | —NEt$_2$ | OH | |
| 1-1260 | —CHMe— | C$_2$F$_5$ | I | —NH(n-Pr) | OH | |
| 1-1261 | —CHMe— | C$_2$F$_5$ | I | —N(n-Pr)$_2$ | OH | |
| 1-1262 | —CHMe— | C$_2$F$_5$ | I | —NMeEt | OH | |
| 1-1263 | —CHMe— | C$_2$F$_5$ | I | —NMe(n-Pr) | OH | |
| 1-1264 | —CHMe— | C$_2$F$_5$ | I | —NEt(n-Pr) | OH | |
| 1-1265 | —CHMe— | C$_2$F$_5$ | I | —NH(i-Pr) | OH | |
| 1-1266 | —CHMe— | C$_2$F$_5$ | I | —NMe(i-Pr) | OH | |
| 1-1267 | —CHMe— | C$_2$F$_5$ | I | —NEt(i-Pr) | OH | |
| 1-1268 | —CHMe— | C$_2$F$_5$ | I | —N(Me)OMe | OH | |
| 1-1269 | —CHMe— | C$_2$F$_5$ | I | —N(Me)OEt | OH | |
| 1-1270 | —CHMe— | C$_2$F$_5$ | I | —N(Me)O(n-Pr) | OH | |
| 1-1271 | —CHMe— | C$_2$F$_5$ | I | —N(Et)OMe | OH | |
| 1-1272 | —CHMe— | C$_2$F$_5$ | I | —N(Et)OEt | OH | |
| 1-1273 | —CHMe— | C$_2$F$_5$ | I | —N(Et)O(n-Pr) | OH | |
| 1-1274 | —CHMe— | CHF$_2$ | I | —NH$_2$ | OH | |
| 1-1275 | —CHMe— | CHF$_2$ | I | —NHMe | OH | |
| 1-1276 | —CHMe— | CHF$_2$ | I | —NMe$_2$ | OH | |
| 1-1277 | —CHMe— | CHF$_2$ | I | —NHEt | OH | |
| 1-1278 | —CHMe— | CHF$_2$ | I | —NEt$_2$ | OH | |
| 1-1279 | —CHMe— | CHF$_2$ | I | —NH(n-Pr) | OH | |
| 1-1280 | —CHMe— | CHF$_2$ | I | —N(n-Pr)$_2$ | OH | |

TABLE 1-continued

| No. | X$^1$ | R$^1$ | R$^2$ | —NR$^3$R$^4$ | R$^5$ | Physical data |
|---|---|---|---|---|---|---|
| 1-1281 | —CHMe— | CHF$_2$ | I | —NMeEt | OH | |
| 1-1282 | —CHMe— | CHF$_2$ | I | —NMe(n-Pr) | OH | |
| 1-1283 | —CHMe— | CHF$_2$ | I | —NEt(n-Pr) | OH | |
| 1-1284 | —CHMe— | CHF$_2$ | I | —NH(i-Pr) | OH | |
| 1-1285 | —CHMe— | CHF$_2$ | I | —NMe(i-Pr) | OH | |
| 1-1286 | —CHMe— | CHF$_2$ | I | —NEt(i-Pr) | OH | |
| 1-1287 | —CHMe— | CHF$_2$ | I | —N(Me)OMe | OH | |
| 1-1288 | —CHMe— | CHF$_2$ | I | —N(Me)OEt | OH | |
| 1-1289 | —CHMe— | CHF$_2$ | I | —N(Me)O(n-Pr) | OH | |
| 1-1290 | —CHMe— | CHF$_2$ | I | —N(Et)OMe | OH | |
| 1-1291 | —CHMe— | CHF$_2$ | I | —N(Et)OEt | OH | |
| 1-1292 | —CHMe— | CHF$_2$ | I | —N(Et)O(n-Pr) | OH | |
| 1-1293 | —CHMe— | CF$_3$ | I | —NH$_2$ | SCH$_2$C(O)OMe | |
| 1-1294 | —CHMe— | CF$_3$ | I | —NHMe | SCH$_2$C(O)OMe | |
| 1-1295 | —CHMe— | CF$_3$ | I | —NMe$_2$ | SCH$_2$C(O)OMe | |
| 1-1296 | —CHMe— | CF$_3$ | I | —NHEt | SCH$_2$C(O)OMe | |
| 1-1297 | —CHMe— | CF$_3$ | I | —NEt$_2$ | SCH$_2$C(O)OMe | |
| 1-1298 | —CHMe— | CF$_3$ | I | —NH(n-Pr) | SCH$_2$C(O)OMe | |
| 1-1299 | —CHMe— | CF$_3$ | I | —N(n-Pr)$_2$ | SCH$_2$C(O)OMe | |
| 1-1300 | —CHMe— | CF$_3$ | I | —NMeEt | SCH$_2$C(O)OMe | |
| 1-1301 | —CHMe— | CF$_3$ | I | —NMe(n-Pr) | SCH$_2$C(O)OMe | |
| 1-1302 | —CHMe— | CF$_3$ | I | —NEt(n-Pr) | SCH$_2$C(O)OMe | |
| 1-1303 | —CHMe— | CF$_3$ | I | —NH(i-Pr) | SCH$_2$C(O)OMe | |
| 1-1304 | —CHMe— | CF$_3$ | I | —NMe(i-Pr) | SCH$_2$C(O)OMe | |
| 1-1305 | —CHMe— | CF$_3$ | I | —NEt(i-Pr) | SCH$_2$C(O)OMe | |
| 1-1306 | —CHMe— | CF$_3$ | I | —N(Me)OMe | SCH$_2$C(O)OMe | |
| 1-1307 | —CHMe— | CF$_3$ | I | —N(Me)OEt | SCH$_2$C(O)OMe | |
| 1-1308 | —CHMe— | CF$_3$ | I | —N(Me)O(n-Pr) | SCH$_2$C(O)OMe | |
| 1-1309 | —CHMe— | CF$_3$ | I | —N(Et)OMe | SCH$_2$C(O)OMe | |
| 1-1310 | —CHMe— | CF$_3$ | I | —N(Et)OEt | SCH$_2$C(O)OMe | |
| 1-1311 | —CHMe— | CF$_3$ | I | —N(Et)O(n-Pr) | SCH$_2$C(O)OMe | |
| 1-1312 | —CHMe— | CCl$_3$ | I | —NH$_2$ | SCH$_2$C(O)OMe | |
| 1-1313 | —CHMe— | CCl$_3$ | I | —NHMe | SCH$_2$C(O)OMe | |
| 1-1314 | —CHMe— | CCl$_3$ | I | —NMe$_2$ | SCH$_2$C(O)OMe | |
| 1-1315 | —CHMe— | CCl$_3$ | I | —NHEt | SCH$_2$C(O)OMe | |
| 1-1316 | —CHMe— | CCl$_3$ | I | —NEt$_2$ | SCH$_2$C(O)OMe | |
| 1-1317 | —CHMe— | CCl$_3$ | I | —NH(n-Pr) | SCH$_2$C(O)OMe | |
| 1-1318 | —CHMe— | CCl$_3$ | I | —N(n-Pr)$_2$ | SCH$_2$C(O)OMe | |
| 1-1319 | —CHMe— | CCl$_3$ | I | —NMeEt | SCH$_2$C(O)OMe | |
| 1-1320 | —CHMe— | CCl$_3$ | I | —NMe(n-Pr) | SCH$_2$C(O)OMe | |
| 1-1321 | —CHMe— | CCl$_3$ | I | —NEt(n-Pr) | SCH$_2$C(O)OMe | |
| 1-1322 | —CHMe— | CCl$_3$ | I | —NH(i-Pr) | SCH$_2$C(O)OMe | |
| 1-1323 | —CHMe— | CCl$_3$ | I | —NMe(i-Pr) | SCH$_2$C(O)OMe | |
| 1-1324 | —CHMe— | CCl$_3$ | I | —NEt(i-Pr) | SCH$_2$C(O)OMe | |
| 1-1325 | —CHMe— | CCl$_3$ | I | —N(Me)OMe | SCH$_2$C(O)OMe | |
| 1-1326 | —CHMe— | CCl$_3$ | I | —N(Me)OEt | SCH$_2$C(O)OMe | |
| 1-1327 | —CHMe— | CCl$_3$ | I | —N(Me)O(n-Pr) | SCH$_2$C(O)OMe | |
| 1-1328 | —CHMe— | CCl$_3$ | I | —N(Et)OMe | SCH$_2$C(O)OMe | |
| 1-1329 | —CHMe— | CCl$_3$ | I | —N(Et)OEt | SCH$_2$C(O)OMe | |
| 1-1330 | —CHMe— | CCl$_3$ | I | —N(Et)O(n-Pr) | SCH$_2$C(O)OMe | |
| 1-1331 | —CHMe— | C$_2$F$_5$ | I | —NH$_2$ | SCH$_2$C(O)OMe | |
| 1-1332 | —CHMe— | C$_2$F$_5$ | I | —NHMe | SCH$_2$C(O)OMe | |
| 1-1333 | —CHMe— | C$_2$F$_5$ | I | —NMe$_2$ | SCH$_2$C(O)OMe | |
| 1-1334 | —CHMe— | C$_2$F$_5$ | I | —NHEt | SCH$_2$C(O)OMe | |
| 1-1335 | —CHMe— | C$_2$F$_5$ | I | —NEt$_2$ | SCH$_2$C(O)OMe | |
| 1-1336 | —CHMe— | C$_2$F$_5$ | I | —NH(n-Pr) | SCH$_2$C(O)OMe | |
| 1-1337 | —CHMe— | C$_2$F$_5$ | I | —N(n-Pr)$_2$ | SCH$_2$C(O)OMe | |
| 1-1338 | —CHMe— | C$_2$F$_5$ | I | —NMeEt | SCH$_2$C(O)OMe | |
| 1-1339 | —CHMe— | C$_2$F$_5$ | I | —NMe(n-Pr) | SCH$_2$C(O)OMe | |
| 1-1340 | —CHMe— | C$_2$F$_5$ | I | —NEt(n-Pr) | SCH$_2$C(O)OMe | |
| 1-1341 | —CHMe— | C$_2$F$_5$ | I | —NH(i-Pr) | SCH$_2$C(O)OMe | |
| 1-1342 | —CHMe— | C$_2$F$_5$ | I | —NMe(i-Pr) | SCH$_2$C(O)OMe | |
| 1-1343 | —CHMe— | C$_2$F$_5$ | I | —NEt(i-Pr) | SCH$_2$C(O)OMe | |
| 1-1344 | —CHMe— | C$_2$F$_5$ | I | —N(Me)OMe | SCH$_2$C(O)OMe | |
| 1-1345 | —CHMe— | C$_2$F$_5$ | I | —N(Me)OEt | SCH$_2$C(O)OMe | |
| 1-1346 | —CHMe— | C$_2$F$_5$ | I | —N(Me)O(n-Pr) | SCH$_2$C(O)OMe | |
| 1-1347 | —CHMe— | C$_2$F$_5$ | I | —N(Et)OMe | SCH$_2$C(O)OMe | |
| 1-1348 | —CHMe— | C$_2$F$_5$ | I | —N(Et)OEt | SCH$_2$C(O)OMe | |
| 1-1349 | —CHMe— | C$_2$F$_5$ | I | —N(Et)O(n-Pr) | SCH$_2$C(O)OMe | |
| 1-1350 | —CHMe— | CHF$_2$ | I | —NH$_2$ | SCH$_2$C(O)OMe | |
| 1-1351 | —CHMe— | CHF$_2$ | I | —NHMe | SCH$_2$C(O)OMe | |
| 1-1352 | —CHMe— | CHF$_2$ | I | —NMe$_2$ | SCH$_2$C(O)OMe | |
| 1-1353 | —CHMe— | CHF$_2$ | I | —NHEt | SCH$_2$C(O)OMe | |
| 1-1354 | —CHMe— | CHF$_2$ | I | —NEt$_2$ | SCH$_2$C(O)OMe | |
| 1-1355 | —CHMe— | CHF$_2$ | I | —NH(n-Pr) | SCH$_2$C(O)OMe | |
| 1-1356 | —CHMe— | CHF$_2$ | I | —N(n-Pr)$_2$ | SCH$_2$C(O)OMe | |
| 1-1357 | —CHMe— | CHF$_2$ | I | —NMeEt | SCH$_2$C(O)OMe | |

TABLE 1-continued

| No. | X¹ | R¹ | R² | —NR³R⁴ | R⁵ | Physical data |
|---|---|---|---|---|---|---|
| 1-1358 | —CHMe— | CHF₂ | I | —NMe(n-Pr) | SCH₂C(O)OMe | |
| 1-1359 | —CHMe— | CHF₂ | I | —NEt(n-Pr) | SCH₂C(O)OMe | |
| 1-1360 | —CHMe— | CHF₂ | I | —NH(i-Pr) | SCH₂C(O)OMe | |
| 1-1361 | —CHMe— | CHF₂ | I | —NMe(i-Pr) | SCH₂C(O)OMe | |
| 1-1362 | —CHMe— | CHF₂ | I | —NEt(i-Pr) | SCH₂C(O)OMe | |
| 1-1363 | —CHMe— | CHF₂ | I | —N(Me)OMe | SCH₂C(O)OMe | |
| 1-1364 | —CHMe— | CHF₂ | I | —N(Me)OEt | SCH₂C(O)OMe | |
| 1-1365 | —CHMe— | CHF₂ | I | —N(Me)O(n-Pr) | SCH₂C(O)OMe | |
| 1-1366 | —CHMe— | CHF₂ | I | —N(Et)OMe | SCH₂C(O)OMe | |
| 1-1367 | —CHMe— | CHF₂ | I | —N(Et)OEt | SCH₂C(O)OMe | |
| 1-1368 | —CHMe— | CHF₂ | I | —N(Et)O(n-Pr) | SCH₂C(O)OMe | |
| 1-1369 | —CH₂— | CF₃ | F | —NH₂ | OH | |
| 1-1370 | —CH₂— | CF₃ | F | —NHMe | OH | |
| 1-1371 | —CH₂— | CF₃ | F | —NMe₂ | OH | |
| 1-1372 | —CH₂— | CF₃ | F | —NHEt | OH | |
| 1-1373 | —CH₂— | CF₃ | F | —NEt₂ | OH | |
| 1-1374 | —CH₂— | CF₃ | F | —NH(n-Pr) | OH | |
| 1-1375 | —CH₂— | CF₃ | F | —N(n-Pr)₂ | OH | |
| 1-1376 | —CH₂— | CF₃ | F | —NMeEt | OH | |
| 1-1377 | —CH₂— | CF₃ | F | —NMe(n-Pr) | OH | |
| 1-1378 | —CH₂— | CF₃ | F | —NEt(n-Pr) | OH | |
| 1-1379 | —CH₂— | CF₃ | F | —NH(i-Pr) | OH | |
| 1-1380 | —CH₂— | CF₃ | F | —NMe(i-Pr) | OH | |
| 1-1381 | —CH₂— | CF₃ | F | —NEt(i-Pr) | OH | |
| 1-1382 | —CH₂— | CF₃ | F | —N(Me)OMe | OH | |
| 1-1383 | —CH₂— | CF₃ | F | —N(Me)OEt | OH | |
| 1-1384 | —CH₂— | CF₃ | F | —N(Me)O(n-Pr) | OH | |
| 1-1385 | —CH₂— | CF₃ | F | —N(Et)OMe | OH | |
| 1-1386 | —CH₂— | CF₃ | F | —N(Et)OEt | OH | |
| 1-1387 | —CH₂— | CF₃ | F | —N(Et)O(n-Pr) | OH | |
| 1-1388 | —CH₂— | CCl₃ | F | —NH₂ | OH | |
| 1-1389 | —CH₂— | CCl₃ | F | —NHMe | OH | |
| 1-1390 | —CH₂— | CCl₃ | F | —NMe₂ | OH | |
| 1-1391 | —CH₂— | CCl₃ | F | —NHEt | OH | |
| 1-1392 | —CH₂— | CCl₃ | F | —NEt₂ | OH | |
| 1-1393 | —CH₂— | CCl₃ | F | —NH(n-Pr) | OH | |
| 1-1394 | —CH₂— | CCl₃ | F | —N(n-Pr)₂ | OH | |
| 1-1395 | —CH₂— | CCl₃ | F | —NMeEt | OH | |
| 1-1396 | —CH₂— | CCl₃ | F | —NMe(n-Pr) | OH | |
| 1-1397 | —CH₂— | CCl₃ | F | —NEt(n-Pr) | OH | |
| 1-1398 | —CH₂— | CCl₃ | F | —NH(i-Pr) | OH | |
| 1-1399 | —CH₂— | CCl₃ | F | —NMe(i-Pr) | OH | |
| 1-1400 | —CH₂— | CCl₃ | F | —NEt(i-Pr) | OH | |
| 1-1401 | —CH₂— | CCl₃ | F | —N(Me)OMe | OH | |
| 1-1402 | —CH₂— | CCl₃ | F | —N(Me)OEt | OH | |
| 1-1403 | —CH₂— | CCl₃ | F | —N(Me)O(n-Pr) | OH | |
| 1-1404 | —CH₂— | CCl₃ | F | —N(Et)OMe | OH | |
| 1-1405 | —CH₂— | CCl₃ | F | —N(Et)OEt | OH | |
| 1-1406 | —CH₂— | CCl₃ | F | —N(Et)O(n-Pr) | OH | |
| 1-1407 | —CH₂— | C₂F₅ | F | —NH₂ | OH | |
| 1-1408 | —CH₂— | C₂F₅ | F | —NHMe | OH | |
| 1-1409 | —CH₂— | C₂F₅ | F | —NMe₂ | OH | |
| 1-1410 | —CH₂— | C₂F₅ | F | —NHEt | OH | |
| 1-1411 | —CH₂— | C₂F₅ | F | —NEt₂ | OH | |
| 1-1412 | —CH₂— | C₂F₅ | F | —NH(n-Pr) | OH | |
| 1-1413 | —CH₂— | C₂F₅ | F | —N(n-Pr)₂ | OH | |
| 1-1414 | —CH₂— | C₂F₅ | F | —NMeEt | OH | |
| 1-1415 | —CH₂— | C₂F₅ | F | —NMe(n-Pr) | OH | |
| 1-1416 | —CH₂— | C₂F₅ | F | —NEt(n-Pr) | OH | |
| 1-1417 | —CH₂— | C₂F₅ | F | —NH(i-Pr) | OH | |
| 1-1418 | —CH₂— | C₂F₅ | F | —NMe(i-Pr) | OH | |
| 1-1419 | —CH₂— | C₂F₅ | F | —NEt(i-Pr) | OH | |
| 1-1420 | —CH₂— | C₂F₅ | F | —N(Me)OMe | OH | |
| 1-1421 | —CH₂— | C₂F₅ | F | —N(Me)OEt | OH | |
| 1-1422 | —CH₂— | C₂F₅ | F | —N(Me)O(n-Pr) | OH | |
| 1-1423 | —CH₂— | C₂F₅ | F | —N(Et)OMe | OH | |
| 1-1424 | —CH₂— | C₂F₅ | F | —N(Et)OEt | OH | |
| 1-1425 | —CH₂— | C₂F₅ | F | —N(Et)O(n-Pr) | OH | |
| 1-1426 | —CH₂— | CHF₂ | F | —NH₂ | OH | |
| 1-1427 | —CH₂— | CHF₂ | F | —NHMe | OH | |
| 1-1428 | —CH₂— | CHF₂ | F | —NMe₂ | OH | |
| 1-1429 | —CH₂— | CHF₂ | F | —NHEt | OH | |
| 1-1430 | —CH₂— | CHF₂ | F | —NEt₂ | OH | |
| 1-1431 | —CH₂— | CHF₂ | F | —NH(n-Pr) | OH | |
| 1-1432 | —CH₂— | CHF₂ | F | —N(n-Pr)₂ | OH | |
| 1-1433 | —CH₂— | CHF₂ | F | —NMeEt | OH | |
| 1-1434 | —CH₂— | CHF₂ | F | —NMe(n-Pr) | OH | |

TABLE 1-continued

| No. | $X^1$ | $R^1$ | $R^2$ | —NR$^3$R$^4$ | $R^5$ | Physical data |
|---|---|---|---|---|---|---|
| 1-1435 | —CH$_2$— | CHF$_2$ | F | —NEt(n-Pr) | OH | |
| 1-1436 | —CH$_2$— | CHF$_2$ | F | —NH(i-Pr) | OH | |
| 1-1437 | —CH$_2$— | CHF$_2$ | F | —NMe(i-Pr) | OH | |
| 1-1438 | —CH$_2$— | CHF$_2$ | F | —NEt(i-Pr) | OH | |
| 1-1439 | —CH$_2$— | CHF$_2$ | F | —N(Me)OMe | OH | |
| 1-1440 | —CH$_2$— | CHF$_2$ | F | —N(Me)OEt | OH | |
| 1-1441 | —CH$_2$— | CHF$_2$ | F | —N(Me)O(n-Pr) | OH | |
| 1-1442 | —CH$_2$— | CHF$_2$ | F | —N(Et)OMe | OH | |
| 1-1443 | —CH$_2$— | CHF$_2$ | F | —N(Et)OEt | OH | |
| 1-1444 | —CH$_2$— | CHF$_2$ | F | —N(Et)O(n-Pr) | OH | |
| 1-1445 | —CH$_2$— | CF$_3$ | F | —NH$_2$ | SCH$_2$C(O)OMe | |
| 1-1446 | —CH$_2$— | CF$_3$ | F | —NHMe | SCH$_2$C(O)OMe | |
| 1-1447 | —CH$_2$— | CF$_3$ | F | —NMe$_2$ | SCH$_2$C(O)OMe | |
| 1-1448 | —CH$_2$— | CF$_3$ | F | —NHEt | SCH$_2$C(O)OMe | |
| 1-1449 | —CH$_2$— | CF$_3$ | F | —NEt$_2$ | SCH$_2$C(O)OMe | |
| 1-1450 | —CH$_2$— | CF$_3$ | F | —NH(n-Pr) | SCH$_2$C(O)OMe | |
| 1-1451 | —CH$_2$— | CF$_3$ | F | —N(n-Pr)$_2$ | SCH$_2$C(O)OMe | |
| 1-1452 | —CH$_2$— | CF$_3$ | F | —NMeEt | SCH$_2$C(O)OMe | |
| 1-1453 | —CH$_2$— | CF$_3$ | F | —NMe(n-Pr) | SCH$_2$C(O)OMe | |
| 1-1454 | —CH$_2$— | CF$_3$ | F | —NEt(n-Pr) | SCH$_2$C(O)OMe | |
| 1-1455 | —CH$_2$— | CF$_3$ | F | —NH(i-Pr) | SCH$_2$C(O)OMe | |
| 1-1456 | —CH$_2$— | CF$_3$ | F | —NMe(i-Pr) | SCH$_2$C(O)OMe | |
| 1-1457 | —CH$_2$— | CF$_3$ | F | —NEt(i-Pr) | SCH$_2$C(O)OMe | |
| 1-1458 | —CH$_2$— | CF$_3$ | F | —N(Me)OMe | SCH$_2$C(O)OMe | |
| 1-1459 | —CH$_2$— | CF$_3$ | F | —N(Me)OEt | SCH$_2$C(O)OMe | |
| 1-1460 | —CH$_2$— | CF$_3$ | F | —N(Me)O(n-Pr) | SCH$_2$C(O)OMe | |
| 1-1461 | —CH$_2$— | CF$_3$ | F | —N(Et)OMe | SCH$_2$C(O)OMe | |
| 1-1462 | —CH$_2$— | CF$_3$ | F | —N(Et)OEt | SCH$_2$C(O)OMe | |
| 1-1463 | —CH$_2$— | CF$_3$ | F | —N(Et)O(n-Pr) | SCH$_2$C(O)OMe | |
| 1-1464 | —CH$_2$— | CCl$_3$ | F | —NH$_2$ | SCH$_2$C(O)OMe | |
| 1-1465 | —CH$_2$— | CCl$_3$ | F | —NHMe | SCH$_2$C(O)OMe | |
| 1-1466 | —CH$_2$— | CCl$_3$ | F | —NMe$_2$ | SCH$_2$C(O)OMe | |
| 1-1467 | —CH$_2$— | CCl$_3$ | F | —NHEt | SCH$_2$C(O)OMe | |
| 1-1468 | —CH$_2$— | CCl$_3$ | F | —NEt$_2$ | SCH$_2$C(O)OMe | |
| 1-1469 | —CH$_2$— | CCl$_3$ | F | —NH(n-Pr) | SCH$_2$C(O)OMe | |
| 1-1470 | —CH$_2$— | CCl$_3$ | F | —N(n-Pr)$_2$ | SCH$_2$C(O)OMe | |
| 1-1471 | —CH$_2$— | CCl$_3$ | F | —NMeEt | SCH$_2$C(O)OMe | |
| 1-1472 | —CH$_2$— | CCl$_3$ | F | —NMe(n-Pr) | SCH$_2$C(O)OMe | |
| 1-1473 | —CH$_2$— | CCl$_3$ | F | —NEt(n-Pr) | SCH$_2$C(O)OMe | |
| 1-1474 | —CH$_2$— | CCl$_3$ | F | —NH(i-Pr) | SCH$_2$C(O)OMe | |
| 1-1475 | —CH$_2$— | CCl$_3$ | F | —NMe(i-Pr) | SCH$_2$C(O)OMe | |
| 1-1476 | —CH$_2$— | CCl$_3$ | F | —NEt(i-Pr) | SCH$_2$C(O)OMe | |
| 1-1477 | —CH$_2$— | CCl$_3$ | F | —N(Me)OMe | SCH$_2$C(O)OMe | |
| 1-1478 | —CH$_2$— | CCl$_3$ | F | —N(Me)OEt | SCH$_2$C(O)OMe | |
| 1-1479 | —CH$_2$— | CCl$_3$ | F | —N(Me)O(n-Pr) | SCH$_2$C(O)OMe | |
| 1-1480 | —CH$_2$— | CCl$_3$ | F | —N(Et)OMe | SCH$_2$C(O)OMe | |
| 1-1481 | —CH$_2$— | CCl$_3$ | F | —N(Et)OEt | SCH$_2$C(O)OMe | |
| 1-1482 | —CH$_2$— | CCl$_3$ | F | —N(Et)O(n-Pr) | SCH$_2$C(O)OMe | |
| 1-1483 | —CH$_2$— | C$_2$F$_5$ | F | —NH$_2$ | SCH$_2$C(O)OMe | |
| 1-1484 | —CH$_2$— | C$_2$F$_5$ | F | —NHMe | SCH$_2$C(O)OMe | |
| 1-1485 | —CH$_2$— | C$_2$F$_5$ | F | —NMe$_2$ | SCH$_2$C(O)OMe | |
| 1-1486 | —CH$_2$— | C$_2$F$_5$ | F | —NHEt | SCH$_2$C(O)OMe | |
| 1-1487 | —CH$_2$— | C$_2$F$_5$ | F | —NEt$_2$ | SCH$_2$C(O)OMe | |
| 1-1488 | —CH$_2$— | C$_2$F$_5$ | F | —NH(n-Pr) | SCH$_2$C(O)OMe | |
| 1-1489 | —CH$_2$— | C$_2$F$_5$ | F | —N(n-Pr)$_2$ | SCH$_2$C(O)OMe | |
| 1-1490 | —CH$_2$— | C$_2$F$_5$ | F | —NMeEt | SCH$_2$C(O)OMe | |
| 1-1491 | —CH$_2$— | C$_2$F$_5$ | F | —NMe(n-Pr) | SCH$_2$C(O)OMe | |
| 1-1492 | —CH$_2$— | C$_2$F$_5$ | F | —NEt(n-Pr) | SCH$_2$C(O)OMe | |
| 1-1493 | —CH$_2$— | C$_2$F$_5$ | F | —NH(i-Pr) | SCH$_2$C(O)OMe | |
| 1-1494 | —CH$_2$— | C$_2$F$_5$ | F | —NMe(i-Pr) | SCH$_2$C(O)OMe | |
| 1-1495 | —CH$_2$— | C$_2$F$_5$ | F | —NEt(i-Pr) | SCH$_2$C(O)OMe | |
| 1-1496 | —CH$_2$— | C$_2$F$_5$ | F | —N(Me)OMe | SCH$_2$C(O)OMe | |
| 1-1497 | —CH$_2$— | C$_2$F$_5$ | F | —N(Me)OEt | SCH$_2$C(O)OMe | |
| 1-1498 | —CH$_2$— | C$_2$F$_5$ | F | —N(Me)O(n-Pr) | SCH$_2$C(O)OMe | |
| 1-1499 | —CH$_2$— | C$_2$F$_5$ | F | —N(Et)OMe | SCH$_2$C(O)OMe | |
| 1-1500 | —CH$_2$— | C$_2$F$_5$ | F | —N(Et)OEt | SCH$_2$C(O)OMe | |
| 1-1501 | —CH$_2$— | C$_2$F$_5$ | F | —N(Et)O(n-Pr) | SCH$_2$C(O)OMe | |
| 1-1502 | —CH$_2$— | CHF$_2$ | F | —NH$_2$ | SCH$_2$C(O)OMe | |
| 1-1503 | —CH$_2$— | CHF$_2$ | F | —NHMe | SCH$_2$C(O)OMe | |
| 1-1504 | —CH$_2$— | CHF$_2$ | F | —NMe$_2$ | SCH$_2$C(O)OMe | |
| 1-1505 | —CH$_2$— | CHF$_2$ | F | —NHEt | SCH$_2$C(O)OMe | |
| 1-1506 | —CH$_2$— | CHF$_2$ | F | —NEt$_2$ | SCH$_2$C(O)OMe | |
| 1-1507 | —CH$_2$— | CHF$_2$ | F | —NH(n-Pr) | SCH$_2$C(O)OMe | |
| 1-1508 | —CH$_2$— | CHF$_2$ | F | —N(n-Pr)$_2$ | SCH$_2$C(O)OMe | |
| 1-1509 | —CH$_2$— | CHF$_2$ | F | —NMeEt | SCH$_2$C(O)OMe | |
| 1-1510 | —CH$_2$— | CHF$_2$ | F | —NMe(n-Pr) | SCH$_2$C(O)OMe | |
| 1-1511 | —CH$_2$— | CHF$_2$ | F | —NEt(n-Pr) | SCH$_2$C(O)OMe | |

TABLE 1-continued

| No. | X¹ | R¹ | R² | —NR³R⁴ | R⁵ | Physical data |
|---|---|---|---|---|---|---|
| 1-1512 | —CH₂— | CHF₂ | F | —NH(i-Pr) | SCH₂C(O)OMe | |
| 1-1513 | —CH₂— | CHF₂ | F | —NMe(i-Pr) | SCH₂C(O)OMe | |
| 1-1514 | —CH₂— | CHF₂ | F | —NEt(i-Pr) | SCH₂C(O)OMe | |
| 1-1515 | —CH₂— | CHF₂ | F | —N(Me)OMe | SCH₂C(O)OMe | |
| 1-1516 | —CH₂— | CHF₂ | F | —N(Me)OEt | SCH₂C(O)OMe | |
| 1-1517 | —CH₂— | CHF₂ | F | —N(Me)O(n-Pr) | SCH₂C(O)OMe | |
| 1-1518 | —CH₂— | CHF₂ | F | —N(Et)OMe | SCH₂C(O)OMe | |
| 1-1519 | —CH₂— | CHF₂ | F | —N(Et)OEt | SCH₂C(O)OMe | |
| 1-1520 | —CH₂— | CHF₂ | F | —N(Et)O(n-Pr) | SCH₂C(O)OMe | |
| 1-1521 | —(CH₂)₂— | CF₃ | F | —NH₂ | OH | |
| 1-1522 | —(CH₂)₂— | CF₃ | F | —NHMe | OH | |
| 1-1523 | —(CH₂)₂— | CF₃ | F | —NMe₂ | OH | |
| 1-1524 | —(CH₂)₂— | CF₃ | F | —NHEt | OH | |
| 1-1525 | —(CH₂)₂— | CF₃ | F | —NEt₂ | OH | |
| 1-1526 | —(CH₂)₂— | CF₃ | F | —NH(n-Pr) | OH | |
| 1-1527 | —(CH₂)₂— | CF₃ | F | —N(n-Pr)₂ | OH | |
| 1-1528 | —(CH₂)₂— | CF₃ | F | —NMeEt | OH | |
| 1-1529 | —(CH₂)₂— | CF₃ | F | —NMe(n-Pr) | OH | |
| 1-1530 | —(CH₂)₂— | CF₃ | F | —NEt(n-Pr) | OH | |
| 1-1531 | —(CH₂)₂— | CF₃ | F | —NH(i-Pr) | OH | |
| 1-1532 | —(CH₂)₂— | CF₃ | F | —NMe(i-Pr) | OH | |
| 1-1533 | —(CH₂)₂— | CF₃ | F | —NEt(i-Pr) | OH | |
| 1-1534 | —(CH₂)₂— | CF₃ | F | —N(Me)OMe | OH | |
| 1-1535 | —(CH₂)₂— | CF₃ | F | —N(Me)OEt | OH | |
| 1-1536 | —(CH₂)₂— | CF₃ | F | —N(Me)O(n-Pr) | OH | |
| 1-1537 | —(CH₂)₂— | CF₃ | F | —N(Et)OMe | OH | |
| 1-1538 | —(CH₂)₂— | CF₃ | F | —N(Et)OEt | OH | |
| 1-1539 | —(CH₂)₂— | CF₃ | F | —N(Et)O(n-Pr) | OH | |
| 1-1540 | —(CH₂)₂— | CCl₃ | F | —NH₂ | OH | |
| 1-1541 | —(CH₂)₂— | CCl₃ | F | —NHMe | OH | |
| 1-1542 | —(CH₂)₂— | CCl₃ | F | —NMe₂ | OH | |
| 1-1543 | —(CH₂)₂— | CCl₃ | F | —NHEt | OH | |
| 1-1544 | —(CH₂)₂— | CCl₃ | F | —NEt₂ | OH | |
| 1-1545 | —(CH₂)₂— | CCl₃ | F | —NH(n-Pr) | OH | |
| 1-1546 | —(CH₂)₂— | CCl₃ | F | —N(n-Pr)₂ | OH | |
| 1-1547 | —(CH₂)₂— | CCl₃ | F | —NMeEt | OH | |
| 1-1548 | —(CH₂)₂— | CCl₃ | F | —NMe(n-Pr) | OH | |
| 1-1549 | —(CH₂)₂— | CCl₃ | F | —NEt(n-Pr) | OH | |
| 1-1550 | —(CH₂)₂— | CCl₃ | F | —NH(i-Pr) | OH | |
| 1-1551 | —(CH₂)₂— | CCl₃ | F | —NMe(i-Pr) | OH | |
| 1-1552 | —(CH₂)₂— | CCl₃ | F | —NEt(i-Pr) | OH | |
| 1-1553 | —(CH₂)₂— | CCl₃ | F | —N(Me)OMe | OH | |
| 1-1554 | —(CH₂)₂— | CCl₃ | F | —N(Me)OEt | OH | |
| 1-1555 | —(CH₂)₂— | CCl₃ | F | —N(Me)O(n-Pr) | OH | |
| 1-1556 | —(CH₂)₂— | CCl₃ | F | —N(Et)OMe | OH | |
| 1-1557 | —(CH₂)₂— | CCl₃ | F | —N(Et)OEt | OH | |
| 1-1558 | —(CH₂)₂— | CCl₃ | F | —N(Et)O(n-Pr) | OH | |
| 1-1559 | —(CH₂)₂— | C₂F₅ | F | —NH₂ | OH | |
| 1-1560 | —(CH₂)₂— | C₂F₅ | F | —NHMe | OH | |
| 1-1561 | —(CH₂)₂— | C₂F₅ | F | —NMe₂ | OH | |
| 1-1562 | —(CH₂)₂— | C₂F₅ | F | —NHEt | OH | |
| 1-1563 | —(CH₂)₂— | C₂F₅ | F | —NEt₂ | OH | |
| 1-1564 | —(CH₂)₂— | C₂F₅ | F | —NH(n-Pr) | OH | |
| 1-1565 | —(CH₂)₂— | C₂F₅ | F | —N(n-Pr)₂ | OH | |
| 1-1566 | —(CH₂)₂— | C₂F₅ | F | —NMeEt | OH | |
| 1-1567 | —(CH₂)₂— | C₂F₅ | F | —NMe(n-Pr) | OH | |
| 1-1568 | —(CH₂)₂— | C₂F₅ | F | —NEt(n-Pr) | OH | |
| 1-1569 | —(CH₂)₂— | C₂F₅ | F | —NH(i-Pr) | OH | |
| 1-1570 | —(CH₂)₂— | C₂F₅ | F | —NMe(i-Pr) | OH | |
| 1-1571 | —(CH₂)₂— | C₂F₅ | F | —NEt(i-Pr) | OH | |
| 1-1572 | —(CH₂)₂— | C₂F₅ | F | —N(Me)OMe | OH | |
| 1-1573 | —(CH₂)₂— | C₂F₅ | F | —N(Me)OEt | OH | |
| 1-1574 | —(CH₂)₂— | C₂F₅ | F | —N(Me)O(n-Pr) | OH | |
| 1-1575 | —(CH₂)₂— | C₂F₅ | F | —N(Et)OMe | OH | |
| 1-1576 | —(CH₂)₂— | C₂F₅ | F | —N(Et)OEt | OH | |
| 1-1577 | —(CH₂)₂— | C₂F₅ | F | —N(Et)O(n-Pr) | OH | |
| 1-1578 | —(CH₂)₂— | CHF₂ | F | —NH₂ | OH | |
| 1-1579 | —(CH₂)₂— | CHF₂ | F | —NHMe | OH | |
| 1-1580 | —(CH₂)₂— | CHF₂ | F | —NMe₂ | OH | |
| 1-1581 | —(CH₂)₂— | CHF₂ | F | —NHEt | OH | |
| 1-1582 | —(CH₂)₂— | CHF₂ | F | —NEt₂ | OH | |
| 1-1583 | —(CH₂)₂— | CHF₂ | F | —NH(n-Pr) | OH | |
| 1-1584 | —(CH₂)₂— | CHF₂ | F | —N(n-Pr)₂ | OH | |
| 1-1585 | —(CH₂)₂— | CHF₂ | F | —NMeEt | OH | |
| 1-1586 | —(CH₂)₂— | CHF₂ | F | —NMe(n-Pr) | OH | |
| 1-1587 | —(CH₂)₂— | CHF₂ | F | —NEt(n-Pr) | OH | |
| 1-1588 | —(CH₂)₂— | CHF₂ | F | —NH(i-Pr) | OH | |

TABLE 1-continued

| No. | $X^1$ | $R^1$ | $R^2$ | —$NR^3R^4$ | $R^5$ | Physical data |
|---|---|---|---|---|---|---|
| 1-1589 | —(CH$_2$)$_2$— | CHF$_2$ | F | —NMe(i-Pr) | OH | |
| 1-1590 | —(CH$_2$)$_2$— | CHF$_2$ | F | —NEt(i-Pr) | OH | |
| 1-1591 | —(CH$_2$)$_2$— | CHF$_2$ | F | —N(Me)OMe | OH | |
| 1-1592 | —(CH$_2$)$_2$— | CHF$_2$ | F | —N(Me)OEt | OH | |
| 1-1593 | —(CH$_2$)$_2$— | CHF$_2$ | F | —N(Me)O(n-Pr) | OH | |
| 1-1594 | —(CH$_2$)$_2$— | CHF$_2$ | F | —N(Et)OMe | OH | |
| 1-1595 | —(CH$_2$)$_2$— | CHF$_2$ | F | —N(Et)OEt | OH | |
| 1-1596 | —(CH$_2$)$_2$— | CHF$_2$ | F | —N(Et)O(n-Pr) | OH | |
| 1-1597 | —(CH$_2$)$_2$— | CF$_3$ | F | —NH$_2$ | SCH$_2$C(O)OMe | |
| 1-1598 | —(CH$_2$)$_2$— | CF$_3$ | F | —NHMe | SCH$_2$C(O)OMe | |
| 1-1599 | —(CH$_2$)$_2$— | CF$_3$ | F | —NMe$_2$ | SCH$_2$C(O)OMe | |
| 1-1600 | —(CH$_2$)$_2$— | CF$_3$ | F | —NHEt | SCH$_2$C(O)OMe | |
| 1-1601 | —(CH$_2$)$_2$— | CF$_3$ | F | —NEt$_2$ | SCH$_2$C(O)OMe | |
| 1-1602 | —(CH$_2$)$_2$— | CF$_3$ | F | —NH(n-Pr) | SCH$_2$C(O)OMe | |
| 1-1603 | —(CH$_2$)$_2$— | CF$_3$ | F | —N(n-Pr)$_2$ | SCH$_2$C(O)OMe | |
| 1-1604 | —(CH$_2$)$_2$— | CF$_3$ | F | —NMeEt | SCH$_2$C(O)OMe | |
| 1-1605 | —(CH$_2$)$_2$— | CF$_3$ | F | —NMe(n-Pr) | SCH$_2$C(O)OMe | |
| 1-1606 | —(CH$_2$)$_2$— | CF$_3$ | F | —NEt(n-Pr) | SCH$_2$C(O)OMe | |
| 1-1607 | —(CH$_2$)$_2$— | CF$_3$ | F | —NH(i-Pr) | SCH$_2$C(O)OMe | |
| 1-1608 | —(CH$_2$)$_2$— | CF$_3$ | F | —NMe(i-Pr) | SCH$_2$C(O)OMe | |
| 1-1609 | —(CH$_2$)$_2$— | CF$_3$ | F | —NEt(i-Pr) | SCH$_2$C(O)OMe | |
| 1-1610 | —(CH$_2$)$_2$— | CF$_3$ | F | —N(Me)OMe | SCH$_2$C(O)OMe | |
| 1-1611 | —(CH$_2$)$_2$— | CF$_3$ | F | —N(Me)OEt | SCH$_2$C(O)OMe | |
| 1-1612 | —(CH$_2$)$_2$— | CF$_3$ | F | —N(Me)O(n-Pr) | SCH$_2$C(O)OMe | |
| 1-1613 | —(CH$_2$)$_2$— | CF$_3$ | F | —N(Et)OMe | SCH$_2$C(O)OMe | |
| 1-1614 | —(CH$_2$)$_2$— | CF$_3$ | F | —N(Et)OEt | SCH$_2$C(O)OMe | |
| 1-1615 | —(CH$_2$)$_2$— | CF$_3$ | F | —N(Et)O(n-Pr) | SCH$_2$C(O)OMe | |
| 1-1616 | —(CH$_2$)$_2$— | CCl$_3$ | F | —NH$_2$ | SCH$_2$C(O)OMe | |
| 1-1617 | —(CH$_2$)$_2$— | CCl$_3$ | F | —NHMe | SCH$_2$C(O)OMe | |
| 1-1618 | —(CH$_2$)$_2$— | CCl$_3$ | F | —NMe$_2$ | SCH$_2$C(O)OMe | |
| 1-1619 | —(CH$_2$)$_2$— | CCl$_3$ | F | —NHEt | SCH$_2$C(O)OMe | |
| 1-1620 | —(CH$_2$)$_2$— | CCl$_3$ | F | —NEt$_2$ | SCH$_2$C(O)OMe | |
| 1-1621 | —(CH$_2$)$_2$— | CCl$_3$ | F | —NH(n-Pr) | SCH$_2$C(O)OMe | |
| 1-1622 | —(CH$_2$)$_2$— | CCl$_3$ | F | —N(n-Pr)$_2$ | SCH$_2$C(O)OMe | |
| 1-1623 | —(CH$_2$)$_2$— | CCl$_3$ | F | —NMeEt | SCH$_2$C(O)OMe | |
| 1-1624 | —(CH$_2$)$_2$— | CCl$_3$ | F | —NMe(n-Pr) | SCH$_2$C(O)OMe | |
| 1-1625 | —(CH$_2$)$_2$— | CCl$_3$ | F | —NEt(n-Pr) | SCH$_2$C(O)OMe | |
| 1-1626 | —(CH$_2$)$_2$— | CCl$_3$ | F | —NH(i-Pr) | SCH$_2$C(O)OMe | |
| 1-1627 | —(CH$_2$)$_2$— | CCl$_3$ | F | —NMe(i-Pr) | SCH$_2$C(O)OMe | |
| 1-1628 | —(CH$_2$)$_2$— | CCl$_3$ | F | —NEt(i-Pr) | SCH$_2$C(O)OMe | |
| 1-1629 | —(CH$_2$)$_2$— | CCl$_3$ | F | —N(Me)OMe | SCH$_2$C(O)OMe | |
| 1-1630 | —(CH$_2$)$_2$— | CCl$_3$ | F | —N(Me)OEt | SCH$_2$C(O)OMe | |
| 1-1631 | —(CH$_2$)$_2$— | CCl$_3$ | F | —N(Me)O(n-Pr) | SCH$_2$C(O)OMe | |
| 1-1632 | —(CH$_2$)$_2$— | CCl$_3$ | F | —N(Et)OMe | SCH$_2$C(O)OMe | |
| 1-1633 | —(CH$_2$)$_2$— | CCl$_3$ | F | —N(Et)OEt | SCH$_2$C(O)OMe | |
| 1-1634 | —(CH$_2$)$_2$— | CCl$_3$ | F | —N(Et)O(n-Pr) | SCH$_2$C(O)OMe | |
| 1-1635 | —(CH$_2$)$_2$— | C$_2$F$_5$ | F | —NH$_2$ | SCH$_2$C(O)OMe | |
| 1-1636 | —(CH$_2$)$_2$— | C$_2$F$_5$ | F | —NHMe | SCH$_2$C(O)OMe | |
| 1-1637 | —(CH$_2$)$_2$— | C$_2$F$_5$ | F | —NMe$_2$ | SCH$_2$C(O)OMe | |
| 1-1638 | —(CH$_2$)$_2$— | C$_2$F$_5$ | F | —NHEt | SCH$_2$C(O)OMe | |
| 1-1639 | —(CH$_2$)$_2$— | C$_2$F$_5$ | F | —NEt$_2$ | SCH$_2$C(O)OMe | |
| 1-1640 | —(CH$_2$)$_2$— | C$_2$F$_5$ | F | —NH(n-Pr) | SCH$_2$C(O)OMe | |
| 1-1641 | —(CH$_2$)$_2$— | C$_2$F$_5$ | F | —N(n-Pr)$_2$ | SCH$_2$C(O)OMe | |
| 1-1642 | —(CH$_2$)$_2$— | C$_2$F$_5$ | F | —NMeEt | SCH$_2$C(O)OMe | |
| 1-1643 | —(CH$_2$)$_2$— | C$_2$F$_5$ | F | —NMe(n-Pr) | SCH$_2$C(O)OMe | |
| 1-1644 | —(CH$_2$)$_2$— | C$_2$F$_5$ | F | —NEt(n-Pr) | SCH$_2$C(O)OMe | |
| 1-1645 | —(CH$_2$)$_2$— | C$_2$F$_5$ | F | —NH(i-Pr) | SCH$_2$C(O)OMe | |
| 1-1646 | —(CH$_2$)$_2$— | C$_2$F$_5$ | F | —NMe(i-Pr) | SCH$_2$C(O)OMe | |
| 1-1647 | —(CH$_2$)$_2$— | C$_2$F$_5$ | F | —NEt(i-Pr) | SCH$_2$C(O)OMe | |
| 1-1648 | —(CH$_2$)$_2$— | C$_2$F$_5$ | F | —N(Me)OMe | SCH$_2$C(O)OMe | |
| 1-1649 | —(CH$_2$)$_2$— | C$_2$F$_5$ | F | —N(Me)OEt | SCH$_2$C(O)OMe | |
| 1-1650 | —(CH$_2$)$_2$— | C$_2$F$_5$ | F | —N(Me)O(n-Pr) | SCH$_2$C(O)OMe | |
| 1-1651 | —(CH$_2$)$_2$— | C$_2$F$_5$ | F | —N(Et)OMe | SCH$_2$C(O)OMe | |
| 1-1652 | —(CH$_2$)$_2$— | C$_2$F$_5$ | F | —N(Et)OEt | SCH$_2$C(O)OMe | |
| 1-1653 | —(CH$_2$)$_2$— | C$_2$F$_5$ | F | —N(Et)O(n-Pr) | SCH$_2$C(O)OMe | |
| 1-1654 | —(CH$_2$)$_2$— | CHF$_2$ | F | —NH$_2$ | SCH$_2$C(O)OMe | |
| 1-1655 | —(CH$_2$)$_2$— | CHF$_2$ | F | —NHMe | SCH$_2$C(O)OMe | |
| 1-1656 | —(CH$_2$)$_2$— | CHF$_2$ | F | —NMe$_2$ | SCH$_2$C(O)OMe | |
| 1-1657 | —(CH$_2$)$_2$— | CHF$_2$ | F | —NHEt | SCH$_2$C(O)OMe | |
| 1-1658 | —(CH$_2$)$_2$— | CHF$_2$ | F | —NEt$_2$ | SCH$_2$C(O)OMe | |
| 1-1659 | —(CH$_2$)$_2$— | CHF$_2$ | F | —NH(n-Pr) | SCH$_2$C(O)OMe | |
| 1-1660 | —(CH$_2$)$_2$— | CHF$_2$ | F | —N(n-Pr)$_2$ | SCH$_2$C(O)OMe | |
| 1-1661 | —(CH$_2$)$_2$— | CHF$_2$ | F | —NMeEt | SCH$_2$C(O)OMe | |
| 1-1662 | —(CH$_2$)$_2$— | CHF$_2$ | F | —NMe(n-Pr) | SCH$_2$C(O)OMe | |
| 1-1663 | —(CH$_2$)$_2$— | CHF$_2$ | F | —NEt(n-Pr) | SCH$_2$C(O)OMe | |
| 1-1664 | —(CH$_2$)$_2$— | CHF$_2$ | F | —NH(i-Pr) | SCH$_2$C(O)OMe | |
| 1-1665 | —(CH$_2$)$_2$— | CHF$_2$ | F | —NMe(i-Pr) | SCH$_2$C(O)OMe | |

TABLE 1-continued

| No. | X¹ | R¹ | R² | —NR³R⁴ | R⁵ | Physical data |
|---|---|---|---|---|---|---|
| 1-1666 | —(CH$_2$)$_2$— | CHF$_2$ | F | —NEt(i-Pr) | SCH$_2$C(O)OMe | |
| 1-1667 | —(CH$_2$)$_2$— | CHF$_2$ | F | —N(Me)OMe | SCH$_2$C(O)OMe | |
| 1-1668 | —(CH$_2$)$_2$— | CHF$_2$ | F | —N(Me)OEt | SCH$_2$C(O)OMe | |
| 1-1669 | —(CH$_2$)$_2$— | CHF$_2$ | F | —N(Me)O(n-Pr) | SCH$_2$C(O)OMe | |
| 1-1670 | —(CH$_2$)$_2$— | CHF$_2$ | F | —N(Et)OMe | SCH$_2$C(O)OMe | |
| 1-1671 | —(CH$_2$)$_2$— | CHF$_2$ | F | —N(Et)OEt | SCH$_2$C(O)OMe | |
| 1-1672 | —(CH$_2$)$_2$— | CHF$_2$ | F | —N(Et)O(n-Pr) | SCH$_2$C(O)OMe | |
| 1-1673 | —CHMe— | CF$_3$ | F | —NH$_2$ | OH | |
| 1-1674 | —CHMe— | CF$_3$ | F | —NHMe | OH | |
| 1-1675 | —CHMe— | CF$_3$ | F | —NMe$_2$ | OH | |
| 1-1676 | —CHMe— | CF$_3$ | F | —NHEt | OH | |
| 1-1677 | —CHMe— | CF$_3$ | F | —NEt$_2$ | OH | |
| 1-1678 | —CHMe— | CF$_3$ | F | —NH(n-Pr) | OH | |
| 1-1679 | —CHMe— | CF$_3$ | F | —N(n-Pr)$_2$ | OH | |
| 1-1680 | —CHMe— | CF$_3$ | F | —NMeEt | OH | |
| 1-1681 | —CHMe— | CF$_3$ | F | —NMe(n-Pr) | OH | |
| 1-1682 | —CHMe— | CF$_3$ | F | —NEt(n-Pr) | OH | |
| 1-1683 | —CHMe— | CF$_3$ | F | —NH(i-Pr) | OH | |
| 1-1684 | —CHMe— | CF$_3$ | F | —NMe(i-Pr) | OH | |
| 1-1685 | —CHMe— | CF$_3$ | F | —NEt(i-Pr) | OH | |
| 1-1686 | —CHMe— | CF$_3$ | F | —N(Me)OMe | OH | |
| 1-1687 | —CHMe— | CF$_3$ | F | —N(Me)OEt | OH | |
| 1-1688 | —CHMe— | CF$_3$ | F | —N(Me)O(n-Pr) | OH | |
| 1-1689 | —CHMe— | CF$_3$ | F | —N(Et)OMe | OH | |
| 1-1690 | —CHMe— | CF$_3$ | F | —N(Et)OEt | OH | |
| 1-1691 | —CHMe— | CF$_3$ | F | —N(Et)O(n-Pr) | OH | |
| 1-1692 | —CHMe— | CCl$_3$ | F | —NH$_2$ | OH | |
| 1-1693 | —CHMe— | CCl$_3$ | F | —NHMe | OH | |
| 1-1694 | —CHMe— | CCl$_3$ | F | —NMe$_2$ | OH | |
| 1-1695 | —CHMe— | CCl$_3$ | F | —NHEt | OH | |
| 1-1696 | —CHMe— | CCl$_3$ | F | —NEt$_2$ | OH | |
| 1-1697 | —CHMe— | CCl$_3$ | F | —NH(n-Pr) | OH | |
| 1-1698 | —CHMe— | CCl$_3$ | F | —N(n-Pr)$_2$ | OH | |
| 1-1699 | —CHMe— | CCl$_3$ | F | —NMeEt | OH | |
| 1-1700 | —CHMe— | CCl$_3$ | F | —NMe(n-Pr) | OH | |
| 1-1701 | —CHMe— | CCl$_3$ | F | —NEt(n-Pr) | OH | |
| 1-1702 | —CHMe— | CCl$_3$ | F | —NH(i-Pr) | OH | |
| 1-1703 | —CHMe— | CCl$_3$ | F | —NMe(i-Pr) | OH | |
| 1-1704 | —CHMe— | CCl$_3$ | F | —NEt(i-Pr) | OH | |
| 1-1705 | —CHMe— | CCl$_3$ | F | —N(Me)OMe | OH | |
| 1-1706 | —CHMe— | CCl$_3$ | F | —N(Me)OEt | OH | |
| 1-1707 | —CHMe— | CCl$_3$ | F | —N(Me)O(n-Pr) | OH | |
| 1-1708 | —CHMe— | CCl$_3$ | F | —N(Et)OMe | OH | |
| 1-1709 | —CHMe— | CCl$_3$ | F | —N(Et)OEt | OH | |
| 1-1710 | —CHMe— | CCl$_3$ | F | —N(Et)O(n-Pr) | OH | |
| 1-1711 | —CHMe— | C$_2$F$_5$ | F | —NH$_2$ | OH | |
| 1-1712 | —CHMe— | C$_2$F$_5$ | F | —NHMe | OH | |
| 1-1713 | —CHMe— | C$_2$F$_5$ | F | —NMe$_2$ | OH | |
| 1-1714 | —CHMe— | C$_2$F$_5$ | F | —NHEt | OH | |
| 1-1715 | —CHMe— | C$_2$F$_5$ | F | —NEt$_2$ | OH | |
| 1-1716 | —CHMe— | C$_2$F$_5$ | F | —NH(n-Pr) | OH | |
| 1-1717 | —CHMe— | C$_2$F$_5$ | F | —N(n-Pr)$_2$ | OH | |
| 1-1718 | —CHMe— | C$_2$F$_5$ | F | —NMeEt | OH | |
| 1-1719 | —CHMe— | C$_2$F$_5$ | F | —NMe(n-Pr) | OH | |
| 1-1720 | —CHMe— | C$_2$F$_5$ | F | —NEt(n-Pr) | OH | |
| 1-1721 | —CHMe— | C$_2$F$_5$ | F | —NH(i-Pr) | OH | |
| 1-1722 | —CHMe— | C$_2$F$_5$ | F | —NMe(i-Pr) | OH | |
| 1-1723 | —CHMe— | C$_2$F$_5$ | F | —NEt(i-Pr) | OH | |
| 1-1724 | —CHMe— | C$_2$F$_5$ | F | —N(Me)OMe | OH | |
| 1-1725 | —CHMe— | C$_2$F$_5$ | F | —N(Me)OEt | OH | |
| 1-1726 | —CHMe— | C$_2$F$_5$ | F | —N(Me)O(n-Pr) | OH | |
| 1-1727 | —CHMe— | C$_2$F$_5$ | F | —N(Et)OMe | OH | |
| 1-1728 | —CHMe— | C$_2$F$_5$ | F | —N(Et)OEt | OH | |
| 1-1729 | —CHMe— | C$_2$F$_5$ | F | —N(Et)O(n-Pr) | OH | |
| 1-1730 | —CHMe— | CHF$_2$ | F | —NH$_2$ | OH | |
| 1-1731 | —CHMe— | CHF$_2$ | F | —NHMe | OH | |
| 1-1732 | —CHMe— | CHF$_2$ | F | —NMe$_2$ | OH | |
| 1-1733 | —CHMe— | CHF$_2$ | F | —NHEt | OH | |
| 1-1734 | —CHMe— | CHF$_2$ | F | —NEt$_2$ | OH | |
| 1-1735 | —CHMe— | CHF$_2$ | F | —NH(n-Pr) | OH | |
| 1-1736 | —CHMe— | CHF$_2$ | F | —N(n-Pr)$_2$ | OH | |
| 1-1737 | —CHMe— | CHF$_2$ | F | —NMeEt | OH | |
| 1-1738 | —CHMe— | CHF$_2$ | F | —NMe(n-Pr) | OH | |
| 1-1739 | —CHMe— | CHF$_2$ | F | —NEt(n-Pr) | OH | |
| 1-1740 | —CHMe— | CHF$_2$ | F | —NH(i-Pr) | OH | |
| 1-1741 | —CHMe— | CHF$_2$ | F | —NMe(i-Pr) | OH | |
| 1-1742 | —CHMe— | CHF$_2$ | F | —NEt(i-Pr) | OH | |

TABLE 1-continued

| No. | X$^1$ | R$^1$ | R$^2$ | —NR$^3$R$^4$ | R$^5$ | Physical data |
|---|---|---|---|---|---|---|
| 1-1743 | —CHMe— | CHF$_2$ | F | —N(Me)OMe | OH | |
| 1-1744 | —CHMe— | CHF$_2$ | F | —N(Me)OEt | OH | |
| 1-1745 | —CHMe— | CHF$_2$ | F | —N(Me)O(n-Pr) | OH | |
| 1-1746 | —CHMe— | CHF$_2$ | F | —N(Et)OMe | OH | |
| 1-1747 | —CHMe— | CHF$_2$ | F | —N(Et)OEt | OH | |
| 1-1748 | —CHMe— | CHF$_2$ | F | —N(Et)O(n-Pr) | OH | |
| 1-1749 | —CHMe— | CF$_3$ | F | —NH$_2$ | SCH$_2$C(O)OMe | |
| 1-1750 | —CHMe— | CF$_3$ | F | —NHMe | SCH$_2$C(O)OMe | |
| 1-1751 | —CHMe— | CF$_3$ | F | —NMe$_2$ | SCH$_2$C(O)OMe | |
| 1-1752 | —CHMe— | CF$_3$ | F | —NHEt | SCH$_2$C(O)OMe | |
| 1-1753 | —CHMe— | CF$_3$ | F | —NEt$_2$ | SCH$_2$C(O)OMe | |
| 1-1754 | —CHMe— | CF$_3$ | F | —NH(n-Pr) | SCH$_2$C(O)OMe | |
| 1-1755 | —CHMe— | CF$_3$ | F | —N(n-Pr)$_2$ | SCH$_2$C(O)OMe | |
| 1-1756 | —CHMe— | CF$_3$ | F | —NMeEt | SCH$_2$C(O)OMe | |
| 1-1757 | —CHMe— | CF$_3$ | F | —NMe(n-Pr) | SCH$_2$C(O)OMe | |
| 1-1758 | —CHMe— | CF$_3$ | F | —NEt(n-Pr) | SCH$_2$C(O)OMe | |
| 1-1759 | —CHMe— | CF$_3$ | F | —NH(i-Pr) | SCH$_2$C(O)OMe | |
| 1-1760 | —CHMe— | CF$_3$ | F | —NMe(i-Pr) | SCH$_2$C(O)OMe | |
| 1-1761 | —CHMe— | CF$_3$ | F | —NEt(i-Pr) | SCH$_2$C(O)OMe | |
| 1-1762 | —CHMe— | CF$_3$ | F | —N(Me)OMe | SCH$_2$C(O)OMe | |
| 1-1763 | —CHMe— | CF$_3$ | F | —N(Me)OEt | SCH$_2$C(O)OMe | |
| 1-1764 | —CHMe— | CF$_3$ | F | —N(Me)O(n-Pr) | SCH$_2$C(O)OMe | |
| 1-1765 | —CHMe— | CF$_3$ | F | —N(Et)OMe | SCH$_2$C(O)OMe | |
| 1-1766 | —CHMe— | CF$_3$ | F | —N(Et)OEt | SCH$_2$C(O)OMe | |
| 1-1767 | —CHMe— | CF$_3$ | F | —N(Et)O(n-Pr) | SCH$_2$C(O)OMe | |
| 1-1768 | —CHMe— | CCl$_3$ | F | —NH$_2$ | SCH$_2$C(O)OMe | |
| 1-1769 | —CHMe— | CCl$_3$ | F | —NHMe | SCH$_2$C(O)OMe | |
| 1-1770 | —CHMe— | CCl$_3$ | F | —NMe$_2$ | SCH$_2$C(O)OMe | |
| 1-1771 | —CHMe— | CCl$_3$ | F | —NHEt | SCH$_2$C(O)OMe | |
| 1-1772 | —CHMe— | CCl$_3$ | F | —NEt$_2$ | SCH$_2$C(O)OMe | |
| 1-1773 | —CHMe— | CCl$_3$ | F | —NH(n-Pr) | SCH$_2$C(O)OMe | |
| 1-1774 | —CHMe— | CCl$_3$ | F | —N(n-Pr)$_2$ | SCH$_2$C(O)OMe | |
| 1-1775 | —CHMe— | CCl$_3$ | F | —NMeEt | SCH$_2$C(O)OMe | |
| 1-1776 | —CHMe— | CCl$_3$ | F | —NMe(n-Pr) | SCH$_2$C(O)OMe | |
| 1-1777 | —CHMe— | CCl$_3$ | F | —NEt(n-Pr) | SCH$_2$C(O)OMe | |
| 1-1778 | —CHMe— | CCl$_3$ | F | —NH(i-Pr) | SCH$_2$C(O)OMe | |
| 1-1779 | —CHMe— | CCl$_3$ | F | —NMe(i-Pr) | SCH$_2$C(O)OMe | |
| 1-1780 | —CHMe— | CCl$_3$ | F | —NEt(i-Pr) | SCH$_2$C(O)OMe | |
| 1-1781 | —CHMe— | CCl$_3$ | F | —N(Me)OMe | SCH$_2$C(O)OMe | |
| 1-1782 | —CHMe— | CCl$_3$ | F | —N(Me)OEt | SCH$_2$C(O)OMe | |
| 1-1783 | —CHMe— | CCl$_3$ | F | —N(Me)O(n-Pr) | SCH$_2$C(O)OMe | |
| 1-1784 | —CHMe— | CCl$_3$ | F | —N(Et)OMe | SCH$_2$C(O)OMe | |
| 1-1785 | —CHMe— | CCl$_3$ | F | —N(Et)OEt | SCH$_2$C(O)OMe | |
| 1-1786 | —CHMe— | CCl$_3$ | F | —N(Et)O(n-Pr) | SCH$_2$C(O)OMe | |
| 1-1787 | —CHMe— | C$_2$F$_5$ | F | —NH$_2$ | SCH$_2$C(O)OMe | |
| 1-1788 | —CHMe— | C$_2$F$_5$ | F | —NHMe | SCH$_2$C(O)OMe | |
| 1-1789 | —CHMe— | C$_2$F$_5$ | F | —NMe$_2$ | SCH$_2$C(O)OMe | |
| 1-1790 | —CHMe— | C$_2$F$_5$ | F | —NHEt | SCH$_2$C(O)OMe | |
| 1-1791 | —CHMe— | C$_2$F$_5$ | F | —NEt$_2$ | SCH$_2$C(O)OMe | |
| 1-1792 | —CHMe— | C$_2$F$_5$ | F | —NH(n-Pr) | SCH$_2$C(O)OMe | |
| 1-1793 | —CHMe— | C$_2$F$_5$ | F | —N(n-Pr)$_2$ | SCH$_2$C(O)OMe | |
| 1-1794 | —CHMe— | C$_2$F$_5$ | F | —NMeEt | SCH$_2$C(O)OMe | |
| 1-1795 | —CHMe— | C$_2$F$_5$ | F | —NMe(n-Pr) | SCH$_2$C(O)OMe | |
| 1-1796 | —CHMe— | C$_2$F$_5$ | F | —NEt(n-Pr) | SCH$_2$C(O)OMe | |
| 1-1797 | —CHMe— | C$_2$F$_5$ | F | —NH(i-Pr) | SCH$_2$C(O)OMe | |
| 1-1798 | —CHMe— | C$_2$F$_5$ | F | —NMe(i-Pr) | SCH$_2$C(O)OMe | |
| 1-1799 | —CHMe— | C$_2$F$_5$ | F | —NEt(i-Pr) | SCH$_2$C(O)OMe | |
| 1-1800 | —CHMe— | C$_2$F$_5$ | F | —N(Me)OMe | SCH$_2$C(O)OMe | |
| 1-1801 | —CHMe— | C$_2$F$_5$ | F | —N(Me)OEt | SCH$_2$C(O)OMe | |
| 1-1802 | —CHMe— | C$_2$F$_5$ | F | —N(Me)O(n-Pr) | SCH$_2$C(O)OMe | |
| 1-1803 | —CHMe— | C$_2$F$_5$ | F | —N(Et)OMe | SCH$_2$C(O)OMe | |
| 1-1804 | —CHMe— | C$_2$F$_5$ | F | —N(Et)OEt | SCH$_2$C(O)OMe | |
| 1-1805 | —CHMe— | C$_2$F$_5$ | F | —N(Et)O(n-Pr) | SCH$_2$C(O)OMe | |
| 1-1806 | —CHMe— | CHF$_2$ | F | —NH$_2$ | SCH$_2$C(O)OMe | |
| 1-1807 | —CHMe— | CHF$_2$ | F | —NHMe | SCH$_2$C(O)OMe | |
| 1-1808 | —CHMe— | CHF$_2$ | F | —NMe$_2$ | SCH$_2$C(O)OMe | |
| 1-1809 | —CHMe— | CHF$_2$ | F | —NHEt | SCH$_2$C(O)OMe | |
| 1-1810 | —CHMe— | CHF$_2$ | F | —NEt$_2$ | SCH$_2$C(O)OMe | |
| 1-1811 | —CHMe— | CHF$_2$ | F | —NH(n-Pr) | SCH$_2$C(O)OMe | |
| 1-1812 | —CHMe— | CHF$_2$ | F | —N(n-Pr)$_2$ | SCH$_2$C(O)OMe | |
| 1-1813 | —CHMe— | CHF$_2$ | F | —NMeEt | SCH$_2$C(O)OMe | |
| 1-1814 | —CHMe— | CHF$_2$ | F | —NMe(n-Pr) | SCH$_2$C(O)OMe | |
| 1-1815 | —CHMe— | CHF$_2$ | F | —NEt(n-Pr) | SCH$_2$C(O)OMe | |
| 1-1816 | —CHMe— | CHF$_2$ | F | —NH(i-Pr) | SCH$_2$C(O)OMe | |
| 1-1817 | —CHMe— | CHF$_2$ | F | —NMe(i-Pr) | SCH$_2$C(O)OMe | |
| 1-1818 | —CHMe— | CHF$_2$ | F | —NEt(i-Pr) | SCH$_2$C(O)OMe | |
| 1-1819 | —CHMe— | CHF$_2$ | F | —N(Me)OMe | SCH$_2$C(O)OMe | |

TABLE 1-continued

| No. | X¹ | R¹ | R² | —NR³R⁴ | R⁵ | Physical data |
|---|---|---|---|---|---|---|
| 1-1820 | —CHMe— | CHF₂ | F | —N(Me)OEt | SCH₂C(O)OMe | |
| 1-1821 | —CHMe— | CHF₂ | F | —N(Me)O(n-Pr) | SCH₂C(O)OMe | |
| 1-1822 | —CHMe— | CHF₂ | F | —N(Et)OMe | SCH₂C(O)OMe | |
| 1-1823 | —CHMe— | CHF₂ | F | —N(Et)OEt | SCH₂C(O)OMe | |
| 1-1824 | —CHMe— | CHF₂ | F | —N(Et)O(n-Pr) | SCH₂C(O)OMe | |
| 1-1825 | —CH₂— | CF₃ | SO₂Me | —NH₂ | OH | |
| 1-1826 | —CH₂— | CF₃ | SO₂Me | —NHMe | OH | |
| 1-1827 | —CH₂— | CF₃ | SO₂Me | —NMe₂ | OH | CDCl₃: 16.32 (bs, 1H), 8.21 (d, 1H), 7.07 (d, 1H), 4.90-5.00 (m, 2H), 3.50 (s, 3H), 3.01 (s, 3H), 2.90 (s, 3H), 2.82 (t, 2H), 2.42 (t, 2H), 2.07 (quin, 2H) |
| 1-1828 | —CH₂— | CF₃ | SO₂Me | —NHEt | OH | |
| 1-1829 | —CH₂— | CF₃ | SO₂Me | —NEt₂ | OH | CDCl₃: 8.21 (d, 1H), 7.07 (d, 1H), 4.90-4.98 (m, 2H), 3.50 (s, 3H), 3.43 (q, 2H), 3.12 (q, 2H), 2.81 (t, 2H), 2.41 (t, 2H), 2.06 (quin, 2H), 1.17 (t, 3H), 1.16 (t, 3H) |
| 1-1830 | —CH₂— | CF₃ | SO₂Me | —NH(n-Pr) | OH | |
| 1-1831 | —CH₂— | CF₃ | SO₂Me | —N(n-Pr)₂ | OH | |
| 1-1832 | —CH₂— | CF₃ | SO₂Me | —NMeEt | OH | CDCl₃: 16.31 (bs, 1H), 8.20 (d, 1H), 7.07 (d, 1H), 4.86-5.00 (m, 2H), 3.49 (s, 3H), 3.15 (q, 1H), 2.98 (s, 1H), 2.78-2.85 (m, 5H) 2.42 (t, 2H), 2.08 (quin, 2H), 1.12-1.20 (m, 3H) |
| 1-1833 | —CH₂— | CF₃ | SO₂Me | —NMe(n-Pr) | OH | |
| 1-1834 | —CH₂— | CF₃ | SO₂Me | —NEt(n-Pr) | OH | |
| 1-1835 | —CH₂— | CF₃ | SO₂Me | —NH(i-Pr) | OH | |
| 1-1836 | —CH₂— | CF₃ | SO₂Me | —NMe(i-Pr) | OH | |
| 1-1837 | —CH₂— | CF₃ | SO₂Me | —NEt(i-Pr) | OH | |
| 1-1838 | —CH₂— | CF₃ | SO₂Me | —N(Me)OMe | OH | CDCl₃: 16.32 (bs, 1H), 8.22 (d, 1H), 7.08 (d, 1H), 5.00-5.10 (m, 2H), 3.67 (s, 3H), 3.48 (s, 3H); 3.25 (s, 3H), 2.81 (t, 2H), 2.42 (t, 2H), 2.08 (quin, 2H) |
| 1-1839 | —CH₂— | CF₃ | SO₂Me | —N(Me)OEt | OH | |
| 1-1840 | —CH₂— | CF₃ | SO₂Me | —N(Me)O(n-Pr) | OH | |
| 1-1841 | —CH₂— | CF₃ | SO₂Me | —N(Et)OMe | OH | |
| 1-1842 | —CH₂— | CF₃ | SO₂Me | —N(Et)OEt | OH | |
| 1-1843 | —CH₂— | CF₃ | SO₂Me | —N(Et)O(n-Pr) | OH | |
| 1-1844 | —CH₂— | CCl₃ | SO₂Me | —NH₂ | OH | |
| 1-1845 | —CH₂— | CCl₃ | SO₂Me | —NHMe | OH | |
| 1-1846 | —CH₂— | CCl₃ | SO₂Me | —NMe₂ | OH | |
| 1-1847 | —CH₂— | CCl₃ | SO₂Me | —NHEt | OH | |
| 1-1848 | —CH₂— | CCl₃ | SO₂Me | —NEt₂ | OH | |
| 1-1849 | —CH₂— | CCl₃ | SO₂Me | —NH(n-Pr) | OH | |
| 1-1850 | —CH₂— | CCl₃ | SO₂Me | —N(n-Pr)₂ | OH | |
| 1-1851 | —CH₂— | CCl₃ | SO₂Me | —NMeEt | OH | |
| 1-1852 | —CH₂— | CCl₃ | SO₂Me | —NMe(n-Pr) | OH | |
| 1-1853 | —CH₂— | CCl₃ | SO₂Me | —NEt(n-Pr) | OH | |
| 1-1854 | —CH₂— | CCl₃ | SO₂Me | —NH(i-Pr) | OH | |
| 1-1855 | —CH₂— | CCl₃ | SO₂Me | —NMe(i-Pr) | OH | |
| 1-1856 | —CH₂— | CCl₃ | SO₂Me | —NEt(i-Pr) | OH | |
| 1-1857 | —CH₂— | CCl₃ | SO₂Me | —N(Me)OMe | OH | |
| 1-1858 | —CH₂— | CCl₃ | SO₂Me | —N(Me)OEt | OH | |
| 1-1859 | —CH₂— | CCl₃ | SO₂Me | —N(Me)O(n-Pr) | OH | |
| 1-1860 | —CH₂— | CCl₃ | SO₂Me | —N(Et)OMe | OH | |
| 1-1861 | —CH₂— | CCl₃ | SO₂Me | —N(Et)OEt | OH | |
| 1-1862 | —CH₂— | CCl₃ | SO₂Me | —N(Et)O(n-Pr) | OH | |
| 1-1863 | —CH₂— | C₂F₅ | SO₂Me | —NH₂ | OH | |

TABLE 1-continued

| No. | $X^1$ | $R^1$ | $R^2$ | $-NR^3R^4$ | $R^5$ | Physical data |
|---|---|---|---|---|---|---|
| 1-1864 | —CH$_2$— | C$_2$F$_5$ | SO$_2$Me | —NHMe | OH | |
| 1-1865 | —CH$_2$— | C$_2$F$_5$ | SO$_2$Me | —NMe$_2$ | OH | |
| 1-1866 | —CH$_2$— | C$_2$F$_5$ | SO$_2$Me | —NHEt | OH | |
| 1-1867 | —CH$_2$— | C$_2$F$_5$ | SO$_2$Me | —NEt$_2$ | OH | |
| 1-1868 | —CH$_2$— | C$_2$F$_5$ | SO$_2$Me | —NH(n-Pr) | OH | |
| 1-1869 | —CH$_2$— | C$_2$F$_5$ | SO$_2$Me | —N(n-Pr)$_2$ | OH | |
| 1-1870 | —CH$_2$— | C$_2$F$_5$ | SO$_2$Me | —NMeEt | OH | |
| 1-1871 | —CH$_2$— | C$_2$F$_5$ | SO$_2$Me | —NMe(n-Pr) | OH | |
| 1-1872 | —CH$_2$— | C$_2$F$_5$ | SO$_2$Me | —NEt(n-Pr) | OH | |
| 1-1873 | —CH$_2$— | C$_2$F$_5$ | SO$_2$Me | —NH(i-Pr) | OH | |
| 1-1874 | —CH$_2$— | C$_2$F$_5$ | SO$_2$Me | —NMe(i-Pr) | OH | |
| 1-1875 | —CH$_2$— | C$_2$F$_5$ | SO$_2$Me | —NEt(i-Pr) | OH | |
| 1-1876 | —CH$_2$— | C$_2$F$_5$ | SO$_2$Me | —N(Me)OMe | OH | |
| 1-1877 | —CH$_2$— | C$_2$F$_5$ | SO$_2$Me | —N(Me)OEt | OH | |
| 1-1878 | —CH$_2$— | C$_2$F$_5$ | SO$_2$Me | —N(Me)O(n-Pr) | OH | |
| 1-1879 | —CH$_2$— | C$_2$F$_5$ | SO$_2$Me | —N(Et)OMe | OH | |
| 1-1880 | —CH$_2$— | C$_2$F$_5$ | SO$_2$Me | —N(Et)OEt | OH | |
| 1-1881 | —CH$_2$— | C$_2$F$_5$ | SO$_2$Me | —N(Et)O(n-Pr) | OH | |
| 1-1882 | —CH$_2$— | CHF$_2$ | SO$_2$Me | —NH$_2$ | OH | |
| 1-1883 | —CH$_2$— | CHF$_2$ | SO$_2$Me | —NHMe | OH | |
| 1-1884 | —CH$_2$— | CHF$_2$ | SO$_2$Me | —NMe$_2$ | OH | |
| 1-1885 | —CH$_2$— | CHF$_2$ | SO$_2$Me | —NHEt | OH | |
| 1-1886 | —CH$_2$— | CHF$_2$ | SO$_2$Me | —NEt$_2$ | OH | |
| 1-1887 | —CH$_2$— | CHF$_2$ | SO$_2$Me | —NH(n-Pr) | OH | |
| 1-1888 | —CH$_2$— | CHF$_2$ | SO$_2$Me | —N(n-Pr)$_2$ | OH | |
| 1-1889 | —CH$_2$— | CHF$_2$ | SO$_2$Me | —NMeEt | OH | |
| 1-1890 | —CH$_2$— | CHF$_2$ | SO$_2$Me | —NMe(n-Pr) | OH | |
| 1-1891 | —CH$_2$— | CHF$_2$ | SO$_2$Me | —NEt(n-Pr) | OH | |
| 1-1892 | —CH$_2$— | CHF$_2$ | SO$_2$Me | —NH(i-Pr) | OH | |
| 1-1893 | —CH$_2$— | CHF$_2$ | SO$_2$Me | —NMe(i-Pr) | OH | |
| 1-1894 | —CH$_2$— | CHF$_2$ | SO$_2$Me | —NEt(i-Pr) | OH | |
| 1-1895 | —CH$_2$— | CHF$_2$ | SO$_2$Me | —N(Me)OMe | OH | |
| 1-1896 | —CH$_2$— | CHF$_2$ | SO$_2$Me | —N(Me)OEt | OH | |
| 1-1897 | —CH$_2$— | CHF$_2$ | SO$_2$Me | —N(Me)O(n-Pr) | OH | |
| 1-1898 | —CH$_2$— | CHF$_2$ | SO$_2$Me | —N(Et)OMe | OH | |
| 1-1899 | —CH$_2$— | CHF$_2$ | SO$_2$Me | —N(Et)OEt | OH | |
| 1-1900 | —CH$_2$— | CHF$_2$ | SO$_2$Me | —N(Et)O(n-Pr) | OH | |
| 1-1901 | —CH$_2$— | CF$_3$ | SO$_2$Me | —NH$_2$ | SCH$_2$C(O)OMe | |
| 1-1902 | —CH$_2$— | CF$_3$ | SO$_2$Me | —NHMe | SCH$_2$C(O)OMe | |
| 1-1903 | —CH$_2$— | CF$_3$ | SO$_2$Me | —NMe$_2$ | SCH$_2$C(O)OMe | |
| 1-1904 | —CH$_2$— | CF$_3$ | SO$_2$Me | —NHEt | SCH$_2$C(O)OMe | |
| 1-1905 | —CH$_2$— | CF$_3$ | SO$_2$Me | —NEt$_2$ | SCH$_2$C(O)OMe | |
| 1-1906 | —CH$_2$— | CF$_3$ | SO$_2$Me | —NH(n-Pr) | SCH$_2$C(O)OMe | |
| 1-1907 | —CH$_2$— | CF$_3$ | SO$_2$Me | —N(n-Pr)$_2$ | SCH$_2$C(O)OMe | |
| 1-1908 | —CH$_2$— | CF$_3$ | SO$_2$Me | —NMeEt | SCH$_2$C(O)OMe | |
| 1-1909 | —CH$_2$— | CF$_3$ | SO$_2$Me | —NMe(n-Pr) | SCH$_2$C(O)OMe | |
| 1-1910 | —CH$_2$— | CF$_3$ | SO$_2$Me | —NEt(n-Pr) | SCH$_2$C(O)OMe | |
| 1-1911 | —CH$_2$— | CF$_3$ | SO$_2$Me | —NH(i-Pr) | SCH$_2$C(O)OMe | |
| 1-1912 | —CH$_2$— | CF$_3$ | SO$_2$Me | —NMe(i-Pr) | SCH$_2$C(O)OMe | |
| 1-1913 | —CH$_2$— | CF$_3$ | SO$_2$Me | —NEt(i-Pr) | SCH$_2$C(O)OMe | |
| 1-1914 | —CH$_2$— | CF$_3$ | SO$_2$Me | —N(Me)OMe | SCH$_2$C(O)OMe | |
| 1-1915 | —CH$_2$— | CF$_3$ | SO$_2$Me | —N(Me)OEt | SCH$_2$C(O)OMe | |
| 1-1916 | —CH$_2$— | CF$_3$ | SO$_2$Me | —N(Me)O(n-Pr) | SCH$_2$C(O)OMe | |
| 1-1917 | —CH$_2$— | CF$_3$ | SO$_2$Me | —N(Et)OMe | SCH$_2$C(O)OMe | |
| 1-1918 | —CH$_2$— | CF$_3$ | SO$_2$Me | —N(Et)OEt | SCH$_2$C(O)OMe | |
| 1-1919 | —CH$_2$— | CF$_3$ | SO$_2$Me | —N(Et)O(n-Pr) | SCH$_2$C(O)OMe | |
| 1-1920 | —CH$_2$— | CCl$_3$ | SO$_2$Me | —NH$_2$ | SCH$_2$C(O)OMe | |
| 1-1921 | —CH$_2$— | CCl$_3$ | SO$_2$Me | —NHMe | SCH$_2$C(O)OMe | |
| 1-1922 | —CH$_2$— | CCl$_3$ | SO$_2$Me | —NMe$_2$ | SCH$_2$C(O)OMe | |
| 1-1923 | —CH$_2$— | CCl$_3$ | SO$_2$Me | —NHEt | SCH$_2$C(O)OMe | |
| 1-1924 | —CH$_2$— | CCl$_3$ | SO$_2$Me | —NEt$_2$ | SCH$_2$C(O)OMe | |
| 1-1925 | —CH$_2$— | CCl$_3$ | SO$_2$Me | —NH(n-Pr) | SCH$_2$C(O)OMe | |
| 1-1926 | —CH$_2$— | CCl$_3$ | SO$_2$Me | —N(n-Pr)$_2$ | SCH$_2$C(O)OMe | |
| 1-1927 | —CH$_2$— | CCl$_3$ | SO$_2$Me | —NMeEt | SCH$_2$C(O)OMe | |
| 1-1928 | —CH$_2$— | CCl$_3$ | SO$_2$Me | —NMe(n-Pr) | SCH$_2$C(O)OMe | |
| 1-1929 | —CH$_2$— | CCl$_3$ | SO$_2$Me | —NEt(n-Pr) | SCH$_2$C(O)OMe | |
| 1-1930 | —CH$_2$— | CCl$_3$ | SO$_2$Me | —NH(i-Pr) | SCH$_2$C(O)OMe | |
| 1-1931 | —CH$_2$— | CCl$_3$ | SO$_2$Me | —NMe(i-Pr) | SCH$_2$C(O)OMe | |
| 1-1932 | —CH$_2$— | CCl$_3$ | SO$_2$Me | —NEt(i-Pr) | SCH$_2$C(O)OMe | |
| 1-1933 | —CH$_2$— | CCl$_3$ | SO$_2$Me | —N(Me)OMe | SCH$_2$C(O)OMe | |
| 1-1934 | —CH$_2$— | CCl$_3$ | SO$_2$Me | —N(Me)OEt | SCH$_2$C(O)OMe | |
| 1-1935 | —CH$_2$— | CCl$_3$ | SO$_2$Me | —N(Me)O(n-Pr) | SCH$_2$C(O)OMe | |
| 1-1936 | —CH$_2$— | CCl$_3$ | SO$_2$Me | —N(Et)OMe | SCH$_2$C(O)OMe | |
| 1-1937 | —CH$_2$— | CCl$_3$ | SO$_2$Me | —N(Et)OEt | SCH$_2$C(O)OMe | |
| 1-1938 | —CH$_2$— | CCl$_3$ | SO$_2$Me | —N(Et)O(n-Pr) | SCH$_2$C(O)OMe | |
| 1-1939 | —CH$_2$— | C$_2$F$_5$ | SO$_2$Me | —NH$_2$ | SCH$_2$C(O)OMe | |
| 1-1940 | —CH$_2$— | C$_2$F$_5$ | SO$_2$Me | —NHMe | SCH$_2$C(O)OMe | |

TABLE 1-continued

| No. | X¹ | R¹ | R² | —NR³R⁴ | R⁵ | Physical data |
|---|---|---|---|---|---|---|
| 1-1941 | —CH₂— | C₂F₅ | SO₂Me | —NMe₂ | SCH₂C(O)OMe | |
| 1-1942 | —CH₂— | C₂F₅ | SO₂Me | —NHEt | SCH₂C(O)OMe | |
| 1-1943 | —CH₂— | C₂F₅ | SO₂Me | —NEt₂ | SCH₂C(O)OMe | |
| 1-1944 | —CH₂— | C₂F₅ | SO₂Me | —NH(n-Pr) | SCH₂C(O)OMe | |
| 1-1945 | —CH₂— | C₂F₅ | SO₂Me | —N(n-Pr)₂ | SCH₂C(O)OMe | |
| 1-1946 | —CH₂— | C₂F₅ | SO₂Me | —NMeEt | SCH₂C(O)OMe | |
| 1-1947 | —CH₂— | C₂F₅ | SO₂Me | —NMe(n-Pr) | SCH₂C(O)OMe | |
| 1-1948 | —CH₂— | C₂F₅ | SO₂Me | —NEt(n-Pr) | SCH₂C(O)OMe | |
| 1-1949 | —CH₂— | C₂F₅ | SO₂Me | —NH(i-Pr) | SCH₂C(O)OMe | |
| 1-1950 | —CH₂— | C₂F₅ | SO₂Me | —NMe(i-Pr) | SCH₂C(O)OMe | |
| 1-1951 | —CH₂— | C₂F₅ | SO₂Me | —NEt(i-Pr) | SCH₂C(O)OMe | |
| 1-1952 | —CH₂— | C₂F₅ | SO₂Me | —N(Me)OMe | SCH₂C(O)OMe | |
| 1-1953 | —CH₂— | C₂F₅ | SO₂Me | —N(Me)OEt | SCH₂C(O)OMe | |
| 1-1954 | —CH₂— | C₂F₅ | SO₂Me | —N(Me)O(n-Pr) | SCH₂C(O)OMe | |
| 1-1955 | —CH₂— | C₂F₅ | SO₂Me | —N(Et)OMe | SCH₂C(O)OMe | |
| 1-1956 | —CH₂— | C₂F₅ | SO₂Me | —N(Et)OEt | SCH₂C(O)OMe | |
| 1-1957 | —CH₂— | C₂F₅ | SO₂Me | —N(Et)O(n-Pr) | SCH₂C(O)OMe | |
| 1-1958 | —CH₂— | CHF₂ | SO₂Me | —NH₂ | SCH₂C(O)OMe | |
| 1-1959 | —CH₂— | CHF₂ | SO₂Me | —NHMe | SCH₂C(O)OMe | |
| 1-1960 | —CH₂— | CHF₂ | SO₂Me | —NMe₂ | SCH₂C(O)OMe | |
| 1-1961 | —CH₂— | CHF₂ | SO₂Me | —NHEt | SCH₂C(O)OMe | |
| 1-1962 | —CH₂— | CHF₂ | SO₂Me | —NEt₂ | SCH₂C(O)OMe | |
| 1-1963 | —CH₂— | CHF₂ | SO₂Me | —NH(n-Pr) | SCH₂C(O)OMe | |
| 1-1964 | —CH₂— | CHF₂ | SO₂Me | —N(n-Pr)₂ | SCH₂C(O)OMe | |
| 1-1965 | —CH₂— | CHF₂ | SO₂Me | —NMeEt | SCH₂C(O)OMe | |
| 1-1966 | —CH₂— | CHF₂ | SO₂Me | —NMe(n-Pr) | SCH₂C(O)OMe | |
| 1-1967 | —CH₂— | CHF₂ | SO₂Me | —NEt(n-Pr) | SCH₂C(O)OMe | |
| 1-1968 | —CH₂— | CHF₂ | SO₂Me | —NH(i-Pr) | SCH₂C(O)OMe | |
| 1-1969 | —CH₂— | CHF₂ | SO₂Me | —NMe(i-Pr) | SCH₂C(O)OMe | |
| 1-1970 | —CH₂— | CHF₂ | SO₂Me | —NEt(i-Pr) | SCH₂C(O)OMe | |
| 1-1971 | —CH₂— | CHF₂ | SO₂Me | —N(Me)OMe | SCH₂C(O)OMe | |
| 1-1972 | —CH₂— | CHF₂ | SO₂Me | —N(Me)OEt | SCH₂C(O)OMe | |
| 1-1973 | —CH₂— | CHF₂ | SO₂Me | —N(Me)O(n-Pr) | SCH₂C(O)OMe | |
| 1-1974 | —CH₂— | CHF₂ | SO₂Me | —N(Et)OMe | SCH₂C(O)OMe | |
| 1-1975 | —CH₂— | CHF₂ | SO₂Me | —N(Et)OEt | SCH₂C(O)OMe | |
| 1-1976 | —CH₂— | CHF₂ | SO₂Me | —N(Et)O(n-Pr) | SCH₂C(O)OMe | |
| 1-1977 | —(CH₂)₂— | CF₃ | SO₂Me | —NH₂ | OH | |
| 1-1978 | —(CH₂)₂— | CF₃ | SO₂Me | —NHMe | OH | |
| 1-1979 | —(CH₂)₂— | CF₃ | SO₂Me | —NMe₂ | OH | |
| 1-1980 | —(CH₂)₂— | CF₃ | SO₂Me | —NHEt | OH | |
| 1-1981 | —(CH₂)₂— | CF₃ | SO₂Me | —NEt₂ | OH | |
| 1-1982 | —(CH₂)₂— | CF₃ | SO₂Me | —NH(n-Pr) | OH | |
| 1-1983 | —(CH₂)₂— | CF₃ | SO₂Me | —N(n-Pr)₂ | OH | |
| 1-1984 | —(CH₂)₂— | CF₃ | SO₂Me | —NMeEt | OH | |
| 1-1985 | —(CH₂)₂— | CF₃ | SO₂Me | —NMe(n-Pr) | OH | |
| 1-1986 | —(CH₂)₂— | CF₃ | SO₂Me | —NEt(n-Pr) | OH | |
| 1-1987 | —(CH₂)₂— | CF₃ | SO₂Me | —NH(i-Pr) | OH | |
| 1-1988 | —(CH₂)₂— | CF₃ | SO₂Me | —NMe(i-Pr) | OH | |
| 1-1989 | —(CH₂)₂— | CF₃ | SO₂Me | —NEt(i-Pr) | OH | |
| 1-1990 | —(CH₂)₂— | CF₃ | SO₂Me | —N(Me)OMe | OH | |
| 1-1991 | —(CH₂)₂— | CF₃ | SO₂Me | —N(Me)OEt | OH | |
| 1-1992 | —(CH₂)₂— | CF₃ | SO₂Me | —N(Me)O(n-Pr) | OH | |
| 1-1993 | —(CH₂)₂— | CF₃ | SO₂Me | —N(Et)OMe | OH | |
| 1-1994 | —(CH₂)₂— | CF₃ | SO₂Me | —N(Et)OEt | OH | |
| 1-1995 | —(CH₂)₂— | CF₃ | SO₂Me | —N(Et)O(n-Pr) | OH | |
| 1-1996 | —(CH₂)₂— | CCl₃ | SO₂Me | —NH₂ | OH | |
| 1-1997 | —(CH₂)₂— | CCl₃ | SO₂Me | —NHMe | OH | |
| 1-1998 | —(CH₂)₂— | CCl₃ | SO₂Me | —NMe₂ | OH | |
| 1-1999 | —(CH₂)₂— | CCl₃ | SO₂Me | —NHEt | OH | |
| 1-2000 | —(CH₂)₂— | CCl₃ | SO₂Me | —NEt₂ | OH | |
| 1-2001 | —(CH₂)₂— | CCl₃ | SO₂Me | —NH(n-Pr) | OH | |
| 1-2002 | —(CH₂)₂— | CCl₃ | SO₂Me | —N(n-Pr)₂ | OH | |
| 1-2003 | —(CH₂)₂— | CCl₃ | SO₂Me | —NMeEt | OH | |
| 1-2004 | —(CH₂)₂— | CCl₃ | SO₂Me | —NMe(n-Pr) | OH | |
| 1-2005 | —(CH₂)₂— | CCl₃ | SO₂Me | —NEt(n-Pr) | OH | |
| 1-2006 | —(CH₂)₂— | CCl₃ | SO₂Me | —NH(i-Pr) | OH | |
| 1-2007 | —(CH₂)₂— | CCl₃ | SO₂Me | —NMe(i-Pr) | OH | |
| 1-2008 | —(CH₂)₂— | CCl₃ | SO₂Me | —NEt(i-Pr) | OH | |
| 1-2009 | —(CH₂)₂— | CCl₃ | SO₂Me | —N(Me)OMe | OH | |
| 1-2010 | —(CH₂)₂— | CCl₃ | SO₂Me | —N(Me)OEt | OH | |
| 1-2011 | —(CH₂)₂— | CCl₃ | SO₂Me | —N(Me)O(n-Pr) | OH | |
| 1-2012 | —(CH₂)₂— | CCl₃ | SO₂Me | —N(Et)OMe | OH | |
| 1-2013 | —(CH₂)₂— | CCl₃ | SO₂Me | —N(Et)OEt | OH | |
| 1-2014 | —(CH₂)₂— | CCl₃ | SO₂Me | —N(Et)O(n-Pr) | OH | |
| 1-2015 | —(CH₂)₂— | C₂F₅ | SO₂Me | —NH₂ | OH | |
| 1-2016 | —(CH₂)₂— | C₂F₅ | SO₂Me | —NHMe | OH | |
| 1-2017 | —(CH₂)₂— | C₂F₅ | SO₂Me | —NMe₂ | OH | |

TABLE 1-continued

| No. | X¹ | R¹ | R² | —NR³R⁴ | R⁵ | Physical data |
|---|---|---|---|---|---|---|
| 1-2018 | —(CH₂)₂— | C₂F₅ | SO₂Me | —NHEt | OH | |
| 1-2019 | —(CH₂)₂— | C₂F₅ | SO₂Me | —NEt₂ | OH | |
| 1-2020 | —(CH₂)₂— | C₂F₅ | SO₂Me | —NH(n-Pr) | OH | |
| 1-2021 | —(CH₂)₂— | C₂F₅ | SO₂Me | —N(n-Pr)₂ | OH | |
| 1-2022 | —(CH₂)₂— | C₂F₅ | SO₂Me | —NMeEt | OH | |
| 1-2023 | —(CH₂)₂— | C₂F₅ | SO₂Me | —NMe(n-Pr) | OH | |
| 1-2024 | —(CH₂)₂— | C₂F₅ | SO₂Me | —NEt(n-Pr) | OH | |
| 1-2025 | —(CH₂)₂— | C₂F₅ | SO₂Me | —NH(i-Pr) | OH | |
| 1-2026 | —(CH₂)₂— | C₂F₅ | SO₂Me | —NMe(i-Pr) | OH | |
| 1-2027 | —(CH₂)₂— | C₂F₅ | SO₂Me | —NEt(i-Pr) | OH | |
| 1-2028 | —(CH₂)₂— | C₂F₅ | SO₂Me | —N(Me)OMe | OH | |
| 1-2029 | —(CH₂)₂— | C₂F₅ | SO₂Me | —N(Me)OEt | OH | |
| 1-2030 | —(CH₂)₂— | C₂F₅ | SO₂Me | —N(Me)O(n-Pr) | OH | |
| 1-2031 | —(CH₂)₂— | C₂F₅ | SO₂Me | —N(Et)OMe | OH | |
| 1-2032 | —(CH₂)₂— | C₂F₅ | SO₂Me | —N(Et)OEt | OH | |
| 1-2033 | —(CH₂)₂— | C₂F₅ | SO₂Me | —N(Et)O(n-Pr) | OH | |
| 1-2034 | —(CH₂)₂— | CHF₂ | SO₂Me | —NH₂ | OH | |
| 1-2035 | —(CH₂)₂— | CHF₂ | SO₂Me | —NHMe | OH | |
| 1-2036 | —(CH₂)₂— | CHF₂ | SO₂Me | —NMe₂ | OH | |
| 1-2037 | —(CH₂)₂— | CHF₂ | SO₂Me | —NHEt | OH | |
| 1-2038 | —(CH₂)₂— | CHF₂ | SO₂Me | —NEt₂ | OH | |
| 1-2039 | —(CH₂)₂— | CHF₂ | SO₂Me | —NH(n-Pr) | OH | |
| 1-2040 | —(CH₂)₂— | CHF₂ | SO₂Me | —N(n-Pr)₂ | OH | |
| 1-2041 | —(CH₂)₂— | CHF₂ | SO₂Me | —NMeEt | OH | |
| 1-2042 | —(CH₂)₂— | CHF₂ | SO₂Me | —NMe(n-Pr) | OH | |
| 1-2043 | —(CH₂)₂— | CHF₂ | SO₂Me | —NEt(n-Pr) | OH | |
| 1-2044 | —(CH₂)₂— | CHF₂ | SO₂Me | —NH(i-Pr) | OH | |
| 1-2045 | —(CH₂)₂— | CHF₂ | SO₂Me | —NMe(i-Pr) | OH | |
| 1-2046 | —(CH₂)₂— | CHF₂ | SO₂Me | —NEt(i-Pr) | OH | |
| 1-2047 | —(CH₂)₂— | CHF₂ | SO₂Me | —N(Me)OMe | OH | |
| 1-2048 | —(CH₂)₂— | CHF₂ | SO₂Me | —N(Me)OEt | OH | |
| 1-2049 | —(CH₂)₂— | CHF₂ | SO₂Me | —N(Me)O(n-Pr) | OH | |
| 1-2050 | —(CH₂)₂— | CHF₂ | SO₂Me | —N(Et)OMe | OH | |
| 1-2051 | —(CH₂)₂— | CHF₂ | SO₂Me | —N(Et)OEt | OH | |
| 1-2052 | —(CH₂)₂— | CHF₂ | SO₂Me | —N(Et)O(n-Pr) | OH | |
| 1-2053 | —(CH₂)₂— | CF₃ | SO₂Me | —NH₂ | SCH₂C(O)OMe | |
| 1-2054 | —(CH₂)₂— | CF₃ | SO₂Me | —NHMe | SCH₂C(O)OMe | |
| 1-2055 | —(CH₂)₂— | CF₃ | SO₂Me | —NMe₂ | SCH₂C(O)OMe | |
| 1-2056 | —(CH₂)₂— | CF₃ | SO₂Me | —NHEt | SCH₂C(O)OMe | |
| 1-2057 | —(CH₂)₂— | CF₃ | SO₂Me | —NEt₂ | SCH₂C(O)OMe | |
| 1-2058 | —(CH₂)₂— | CF₃ | SO₂Me | —NH(n-Pr) | SCH₂C(O)OMe | |
| 1-2059 | —(CH₂)₂— | CF₃ | SO₂Me | —N(n-Pr)₂ | SCH₂C(O)OMe | |
| 1-2060 | —(CH₂)₂— | CF₃ | SO₂Me | —NMeEt | SCH₂C(O)OMe | |
| 1-2061 | —(CH₂)₂— | CF₃ | SO₂Me | —NMe(n-Pr) | SCH₂C(O)OMe | |
| 1-2062 | —(CH₂)₂— | CF₃ | SO₂Me | —NEt(n-Pr) | SCH₂C(O)OMe | |
| 1-2063 | —(CH₂)₂— | CF₃ | SO₂Me | —NH(i-Pr) | SCH₂C(O)OMe | |
| 1-2064 | —(CH₂)₂— | CF₃ | SO₂Me | —NMe(i-Pr) | SCH₂C(O)OMe | |
| 1-2065 | —(CH₂)₂— | CF₃ | SO₂Me | —NEt(i-Pr) | SCH₂C(O)OMe | |
| 1-2066 | —(CH₂)₂— | CF₃ | SO₂Me | —N(Me)OMe | SCH₂C(O)OMe | |
| 1-2067 | —(CH₂)₂— | CF₃ | SO₂Me | —N(Me)OEt | SCH₂C(O)OMe | |
| 1-2068 | —(CH₂)₂— | CF₃ | SO₂Me | —N(Me)O(n-Pr) | SCH₂C(O)OMe | |
| 1-2069 | —(CH₂)₂— | CF₃ | SO₂Me | —N(Et)OMe | SCH₂C(O)OMe | |
| 1-2070 | —(CH₂)₂— | CF₃ | SO₂Me | —N(Et)OEt | SCH₂C(O)OMe | |
| 1-2071 | —(CH₂)₂— | CF₃ | SO₂Me | —N(Et)O(n-Pr) | SCH₂C(O)OMe | |
| 1-2072 | —(CH₂)₂— | CCl₃ | SO₂Me | —NH₂ | SCH₂C(O)OMe | |
| 1-2073 | —(CH₂)₂— | CCl₃ | SO₂Me | —NHMe | SCH₂C(O)OMe | |
| 1-2074 | —(CH₂)₂— | CCl₃ | SO₂Me | —NMe₂ | SCH₂C(O)OMe | |
| 1-2075 | —(CH₂)₂— | CCl₃ | SO₂Me | —NHEt | SCH₂C(O)OMe | |
| 1-2076 | —(CH₂)₂— | CCl₃ | SO₂Me | —NEt₂ | SCH₂C(O)OMe | |
| 1-2077 | —(CH₂)₂— | CCl₃ | SO₂Me | —NH(n-Pr) | SCH₂C(O)OMe | |
| 1-2078 | —(CH₂)₂— | CCl₃ | SO₂Me | —N(n-Pr)₂ | SCH₂C(O)OMe | |
| 1-2079 | —(CH₂)₂— | CCl₃ | SO₂Me | —NMeEt | SCH₂C(O)OMe | |
| 1-2080 | —(CH₂)₂— | CCl₃ | SO₂Me | —NMe(n-Pr) | SCH₂C(O)OMe | |
| 1-2081 | —(CH₂)₂— | CCl₃ | SO₂Me | —NEt(n-Pr) | SCH₂C(O)OMe | |
| 1-2082 | —(CH₂)₂— | CCl₃ | SO₂Me | —NH(i-Pr) | SCH₂C(O)OMe | |
| 1-2083 | —(CH₂)₂— | CCl₃ | SO₂Me | —NMe(i-Pr) | SCH₂C(O)OMe | |
| 1-2084 | —(CH₂)₂— | CCl₃ | SO₂Me | —NEt(i-Pr) | SCH₂C(O)OMe | |
| 1-2085 | —(CH₂)₂— | CCl₃ | SO₂Me | —N(Me)OMe | SCH₂C(O)OMe | |
| 1-2086 | —(CH₂)₂— | CCl₃ | SO₂Me | —N(Me)OEt | SCH₂C(O)OMe | |
| 1-2087 | —(CH₂)₂— | CCl₃ | SO₂Me | —N(Me)O(n-Pr) | SCH₂C(O)OMe | |
| 1-2088 | —(CH₂)₂— | CCl₃ | SO₂Me | —N(Et)OMe | SCH₂C(O)OMe | |
| 1-2089 | —(CH₂)₂— | CCl₃ | SO₂Me | —N(Et)OEt | SCH₂C(O)OMe | |
| 1-2090 | —(CH₂)₂— | CCl₃ | SO₂Me | —N(Et)O(n-Pr) | SCH₂C(O)OMe | |
| 1-2091 | —(CH₂)₂— | C₂F₅ | SO₂Me | —NH₂ | SCH₂C(O)OMe | |
| 1-2092 | —(CH₂)₂— | C₂F₅ | SO₂Me | —NHMe | SCH₂C(O)OMe | |
| 1-2093 | —(CH₂)₂— | C₂F₅ | SO₂Me | —NMe₂ | SCH₂C(O)OMe | |
| 1-2094 | —(CH₂)₂— | C₂F₅ | SO₂Me | —NHEt | SCH₂C(O)OMe | |

TABLE 1-continued

| No. | X$^1$ | R$^1$ | R$^2$ | —NR$^3$R$^4$ | R$^5$ | Physical data |
|---|---|---|---|---|---|---|
| 1-2095 | —(CH$_2$)$_2$— | C$_2$F$_5$ | SO$_2$Me | —NEt$_2$ | SCH$_2$C(O)OMe | |
| 1-2096 | —(CH$_2$)$_2$— | C$_2$F$_5$ | SO$_2$Me | —NH(n-Pr) | SCH$_2$C(O)OMe | |
| 1-2097 | —(CH$_2$)$_2$— | C$_2$F$_5$ | SO$_2$Me | —N(n-Pr)$_2$ | SCH$_2$C(O)OMe | |
| 1-2098 | —(CH$_2$)$_2$— | C$_2$F$_5$ | SO$_2$Me | —NMeEt | SCH$_2$C(O)OMe | |
| 1-2099 | —(CH$_2$)$_2$— | C$_2$F$_5$ | SO$_2$Me | —NMe(n-Pr) | SCH$_2$C(O)OMe | |
| 1-2100 | —(CH$_2$)$_2$— | C$_2$F$_5$ | SO$_2$Me | —NEt(n-Pr) | SCH$_2$C(O)OMe | |
| 1-2101 | —(CH$_2$)$_2$— | C$_2$F$_5$ | SO$_2$Me | —NH(i-Pr) | SCH$_2$C(O)OMe | |
| 1-2102 | —(CH$_2$)$_2$— | C$_2$F$_5$ | SO$_2$Me | —NMe(i-Pr) | SCH$_2$C(O)OMe | |
| 1-2103 | —(CH$_2$)$_2$— | C$_2$F$_5$ | SO$_2$Me | —NEt(i-Pr) | SCH$_2$C(O)OMe | |
| 1-2104 | —(CH$_2$)$_2$— | C$_2$F$_5$ | SO$_2$Me | —N(Me)OMe | SCH$_2$C(O)OMe | |
| 1-2105 | —(CH$_2$)$_2$— | C$_2$F$_5$ | SO$_2$Me | —N(Me)OEt | SCH$_2$C(O)OMe | |
| 1-2106 | —(CH$_2$)$_2$— | C$_2$F$_5$ | SO$_2$Me | —N(Me)O(n-Pr) | SCH$_2$C(O)OMe | |
| 1-2107 | —(CH$_2$)$_2$— | C$_2$F$_5$ | SO$_2$Me | —N(Et)OMe | SCH$_2$C(O)OMe | |
| 1-2108 | —(CH$_2$)$_2$— | C$_2$F$_5$ | SO$_2$Me | —N(Et)OEt | SCH$_2$C(O)OMe | |
| 1-2109 | —(CH$_2$)$_2$— | C$_2$F$_5$ | SO$_2$Me | —N(Et)O(n-Pr) | SCH$_2$C(O)OMe | |
| 1-2110 | —(CH$_2$)$_2$— | CHF$_2$ | SO$_2$Me | —NH$_2$ | SCH$_2$C(O)OMe | |
| 1-2111 | —(CH$_2$)$_2$— | CHF$_2$ | SO$_2$Me | —NHMe | SCH$_2$C(O)OMe | |
| 1-2112 | —(CH$_2$)$_2$— | CHF$_2$ | SO$_2$Me | —NMe$_2$ | SCH$_2$C(O)OMe | |
| 1-2113 | —(CH$_2$)$_2$— | CHF$_2$ | SO$_2$Me | —NHEt | SCH$_2$C(O)OMe | |
| 1-2114 | —(CH$_2$)$_2$— | CHF$_2$ | SO$_2$Me | —NEt$_2$ | SCH$_2$C(O)OMe | |
| 1-2115 | —(CH$_2$)$_2$— | CHF$_2$ | SO$_2$Me | —NH(n-Pr) | SCH$_2$C(O)OMe | |
| 1-2116 | —(CH$_2$)$_2$— | CHF$_2$ | SO$_2$Me | —N(n-Pr)$_2$ | SCH$_2$C(O)OMe | |
| 1-2117 | —(CH$_2$)$_2$— | CHF$_2$ | SO$_2$Me | —NMeEt | SCH$_2$C(O)OMe | |
| 1-2118 | —(CH$_2$)$_2$— | CHF$_2$ | SO$_2$Me | —NMe(n-Pr) | SCH$_2$C(O)OMe | |
| 1-2119 | —(CH$_2$)$_2$— | CHF$_2$ | SO$_2$Me | —NEt(n-Pr) | SCH$_2$C(O)OMe | |
| 1-2120 | —(CH$_2$)$_2$— | CHF$_2$ | SO$_2$Me | —NH(i-Pr) | SCH$_2$C(O)OMe | |
| 1-2121 | —(CH$_2$)$_2$— | CHF$_2$ | SO$_2$Me | —NMe(i-Pr) | SCH$_2$C(O)OMe | |
| 1-2122 | —(CH$_2$)$_2$— | CHF$_2$ | SO$_2$Me | —NEt(i-Pr) | SCH$_2$C(O)OMe | |
| 1-2123 | —(CH$_2$)$_2$— | CHF$_2$ | SO$_2$Me | —N(Me)OMe | SCH$_2$C(O)OMe | |
| 1-2124 | —(CH$_2$)$_2$— | CHF$_2$ | SO$_2$Me | —N(Me)OEt | SCH$_2$C(O)OMe | |
| 1-2125 | —(CH$_2$)$_2$— | CHF$_2$ | SO$_2$Me | —N(Me)O(n-Pr) | SCH$_2$C(O)OMe | |
| 1-2126 | —(CH$_2$)$_2$— | CHF$_2$ | SO$_2$Me | —N(Et)OMe | SCH$_2$C(O)OMe | |
| 1-2127 | —(CH$_2$)$_2$— | CHF$_2$ | SO$_2$Me | —N(Et)OEt | SCH$_2$C(O)OMe | |
| 1-2128 | —(CH$_2$)$_2$— | CHF$_2$ | SO$_2$Me | —N(Et)O(n-Pr) | SCH$_2$C(O)OMe | |
| 1-2129 | —CHMe— | CF$_3$ | SO$_2$Me | —NH$_2$ | OH | |
| 1-2130 | —CHMe— | CF$_3$ | SO$_2$Me | —NHMe | OH | |
| 1-2131 | —CHMe— | CF$_3$ | SO$_2$Me | —NMe$_2$ | OH | |
| 1-2132 | —CHMe— | CF$_3$ | SO$_2$Me | —NHEt | OH | |
| 1-2133 | —CHMe— | CF$_3$ | SO$_2$Me | —NEt$_2$ | OH | |
| 1-2134 | —CHMe— | CF$_3$ | SO$_2$Me | —NH(n-Pr) | OH | |
| 1-2135 | —CHMe— | CF$_3$ | SO$_2$Me | —N(n-Pr)$_2$ | OH | |
| 1-2136 | —CHMe— | CF$_3$ | SO$_2$Me | —NMeEt | OH | |
| 1-2137 | —CHMe— | CF$_3$ | SO$_2$Me | —NMe(n-Pr) | OH | |
| 1-2138 | —CHMe— | CF$_3$ | SO$_2$Me | —NEt(n-Pr) | OH | |
| 1-2139 | —CHMe— | CF$_3$ | SO$_2$Me | —NH(i-Pr) | OH | |
| 1-2140 | —CHMe— | CF$_3$ | SO$_2$Me | —NMe(i-Pr) | OH | |
| 1-2141 | —CHMe— | CF$_3$ | SO$_2$Me | —NEt(i-Pr) | OH | |
| 1-2142 | —CHMe— | CF$_3$ | SO$_2$Me | —N(Me)OMe | OH | |
| 1-2143 | —CHMe— | CF$_3$ | SO$_2$Me | —N(Me)OEt | OH | |
| 1-2144 | —CHMe— | CF$_3$ | SO$_2$Me | —N(Me)O(n-Pr) | OH | |
| 1-2145 | —CHMe— | CF$_3$ | SO$_2$Me | —N(Et)OMe | OH | |
| 1-2146 | —CHMe— | CF$_3$ | SO$_2$Me | —N(Et)OEt | OH | |
| 1-2147 | —CHMe— | CF$_3$ | SO$_2$Me | —N(Et)O(n-Pr) | OH | |
| 1-2148 | —CHMe— | CCl$_3$ | SO$_2$Me | —NH$_2$ | OH | |
| 1-2149 | —CHMe— | CCl$_3$ | SO$_2$Me | —NHMe | OH | |
| 1-2150 | —CHMe— | CCl$_3$ | SO$_2$Me | —NMe$_2$ | OH | |
| 1-2151 | —CHMe— | CCl$_3$ | SO$_2$Me | —NHEt | OH | |
| 1-2152 | —CHMe— | CCl$_3$ | SO$_2$Me | —NEt$_2$ | OH | |
| 1-2153 | —CHMe— | CCl$_3$ | SO$_2$Me | —NH(n-Pr) | OH | |
| 1-2154 | —CHMe— | CCl$_3$ | SO$_2$Me | —N(n-Pr)$_2$ | OH | |
| 1-2155 | —CHMe— | CCl$_3$ | SO$_2$Me | —NMeEt | OH | |
| 1-2156 | —CHMe— | CCl$_3$ | SO$_2$Me | —NMe(n-Pr) | OH | |
| 1-2157 | —CHMe— | CCl$_3$ | SO$_2$Me | —NEt(n-Pr) | OH | |
| 1-2158 | —CHMe— | CCl$_3$ | SO$_2$Me | —NH(i-Pr) | OH | |
| 1-2159 | —CHMe— | CCl$_3$ | SO$_2$Me | —NMe(i-Pr) | OH | |
| 1-2160 | —CHMe— | CCl$_3$ | SO$_2$Me | —NEt(i-Pr) | OH | |
| 1-2161 | —CHMe— | CCl$_3$ | SO$_2$Me | —N(Me)OMe | OH | |
| 1-2162 | —CHMe— | CCl$_3$ | SO$_2$Me | —N(Me)OEt | OH | |
| 1-2163 | —CHMe— | CCl$_3$ | SO$_2$Me | —N(Me)O(n-Pr) | OH | |
| 1-2164 | —CHMe— | CCl$_3$ | SO$_2$Me | —N(Et)OMe | OH | |
| 1-2165 | —CHMe— | CCl$_3$ | SO$_2$Me | —N(Et)OEt | OH | |
| 1-2166 | —CHMe— | CCl$_3$ | SO$_2$Me | —N(Et)O(n-Pr) | OH | |
| 1-2167 | —CHMe— | C$_2$F$_5$ | SO$_2$Me | —NH$_2$ | OH | |
| 1-2168 | —CHMe— | C$_2$F$_5$ | SO$_2$Me | —NHMe | OH | |
| 1-2169 | —CHMe— | C$_2$F$_5$ | SO$_2$Me | —NMe$_2$ | OH | |
| 1-2170 | —CHMe— | C$_2$F$_5$ | SO$_2$Me | —NHEt | OH | |
| 1-2171 | —CHMe— | C$_2$F$_5$ | SO$_2$Me | —NEt$_2$ | OH | |

TABLE 1-continued

| No. | X¹ | R¹ | R² | —NR³R⁴ | R⁵ | Physical data |
|---|---|---|---|---|---|---|
| 1-2172 | —CHMe— | C₂F₅ | SO₂Me | —NH(n-Pr) | OH | |
| 1-2173 | —CHMe— | C₂F₅ | SO₂Me | —N(n-Pr)₂ | OH | |
| 1-2174 | —CHMe— | C₂F₅ | SO₂Me | —NMeEt | OH | |
| 1-2175 | —CHMe— | C₂F₅ | SO₂Me | —NMe(n-Pr) | OH | |
| 1-2176 | —CHMe— | C₂F₅ | SO₂Me | —NEt(n-Pr) | OH | |
| 1-2177 | —CHMe— | C₂F₅ | SO₂Me | —NH(i-Pr) | OH | |
| 1-2178 | —CHMe— | C₂F₅ | SO₂Me | —NMe(i-Pr) | OH | |
| 1-2179 | —CHMe— | C₂F₅ | SO₂Me | —NEt(i-Pr) | OH | |
| 1-2180 | —CHMe— | C₂F₅ | SO₂Me | —N(Me)OMe | OH | |
| 1-2181 | —CHMe— | C₂F₅ | SO₂Me | —N(Me)OEt | OH | |
| 1-2182 | —CHMe— | C₂F₅ | SO₂Me | —N(Me)O(n-Pr) | OH | |
| 1-2183 | —CHMe— | C₂F₅ | SO₂Me | —N(Et)OMe | OH | |
| 1-2184 | —CHMe— | C₂F₅ | SO₂Me | —N(Et)OEt | OH | |
| 1-2185 | —CHMe— | C₂F₅ | SO₂Me | —N(Et)O(n-Pr) | OH | |
| 1-2186 | —CHMe— | CHF₂ | SO₂Me | —NH₂ | OH | |
| 1-2187 | —CHMe— | CHF₂ | SO₂Me | —NHMe | OH | |
| 1-2188 | —CHMe— | CHF₂ | SO₂Me | —NMe₂ | OH | |
| 1-2189 | —CHMe— | CHF₂ | SO₂Me | —NHEt | OH | |
| 1-2190 | —CHMe— | CHF₂ | SO₂Me | —NEt₂ | OH | |
| 1-2191 | —CHMe— | CHF₂ | SO₂Me | —NH(n-Pr) | OH | |
| 1-2192 | —CHMe— | CHF₂ | SO₂Me | —N(n-Pr)₂ | OH | |
| 1-2193 | —CHMe— | CHF₂ | SO₂Me | —NMeEt | OH | |
| 1-2194 | —CHMe— | CHF₂ | SO₂Me | —NMe(n-Pr) | OH | |
| 1-2195 | —CHMe— | CHF₂ | SO₂Me | —NEt(n-Pr) | OH | |
| 1-2196 | —CHMe— | CHF₂ | SO₂Me | —NH(i-Pr) | OH | |
| 1-2197 | —CHMe— | CHF₂ | SO₂Me | —NMe(i-Pr) | OH | |
| 1-2198 | —CHMe— | CHF₂ | SO₂Me | —NEt(i-Pr) | OH | |
| 1-2199 | —CHMe— | CHF₂ | SO₂Me | —N(Me)OMe | OH | |
| 1-2200 | —CHMe— | CHF₂ | SO₂Me | —N(Me)OEt | OH | |
| 1-2201 | —CHMe— | CHF₂ | SO₂Me | —N(Me)O(n-Pr) | OH | |
| 1-2202 | —CHMe— | CHF₂ | SO₂Me | —N(Et)OMe | OH | |
| 1-2203 | —CHMe— | CHF₂ | SO₂Me | —N(Et)OEt | OH | |
| 1-2204 | —CHMe— | CHF₂ | SO₂Me | —N(Et)O(n-Pr) | OH | |
| 1-2205 | —CHMe— | CF₃ | SO₂Me | —NH₂ | SCH₂C(O)OMe | |
| 1-2206 | —CHMe— | CF₃ | SO₂Me | —NHMe | SCH₂C(O)OMe | |
| 1-2207 | —CHMe— | CF₃ | SO₂Me | —NMe₂ | SCH₂C(O)OMe | |
| 1-2208 | —CHMe— | CF₃ | SO₂Me | —NHEt | SCH₂C(O)OMe | |
| 1-2209 | —CHMe— | CF₃ | SO₂Me | —NEt₂ | SCH₂C(O)OMe | |
| 1-2210 | —CHMe— | CF₃ | SO₂Me | —NH(n-Pr) | SCH₂C(O)OMe | |
| 1-2211 | —CHMe— | CF₃ | SO₂Me | —N(n-Pr)₂ | SCH₂C(O)OMe | |
| 1-2212 | —CHMe— | CF₃ | SO₂Me | —NMeEt | SCH₂C(O)OMe | |
| 1-2213 | —CHMe— | CF₃ | SO₂Me | —NMe(n-Pr) | SCH₂C(O)OMe | |
| 1-2214 | —CHMe— | CF₃ | SO₂Me | —NEt(n-Pr) | SCH₂C(O)OMe | |
| 1-2215 | —CHMe— | CF₃ | SO₂Me | —NH(i-Pr) | SCH₂C(O)OMe | |
| 1-2216 | —CHMe— | CF₃ | SO₂Me | —NMe(i-Pr) | SCH₂C(O)OMe | |
| 1-2217 | —CHMe— | CF₃ | SO₂Me | —NEt(i-Pr) | SCH₂C(O)OMe | |
| 1-2218 | —CHMe— | CF₃ | SO₂Me | —N(Me)OMe | SCH₂C(O)OMe | |
| 1-2219 | —CHMe— | CF₃ | SO₂Me | —N(Me)OEt | SCH₂C(O)OMe | |
| 1-2220 | —CHMe— | CF₃ | SO₂Me | —N(Me)O(n-Pr) | SCH₂C(O)OMe | |
| 1-2221 | —CHMe— | CF₃ | SO₂Me | —N(Et)OMe | SCH₂C(O)OMe | |
| 1-2222 | —CHMe— | CF₃ | SO₂Me | —N(Et)OEt | SCH₂C(O)OMe | |
| 1-2223 | —CHMe— | CF₃ | SO₂Me | —N(Et)O(n-Pr) | SCH₂C(O)OMe | |
| 1-2224 | —CHMe— | CCl₃ | SO₂Me | —NH₂ | SCH₂C(O)OMe | |
| 1-2225 | —CHMe— | CCl₃ | SO₂Me | —NHMe | SCH₂C(O)OMe | |
| 1-2226 | —CHMe— | CCl₃ | SO₂Me | —NMe₂ | SCH₂C(O)OMe | |
| 1-2227 | —CHMe— | CCl₃ | SO₂Me | —NHEt | SCH₂C(O)OMe | |
| 1-2228 | —CHMe— | CCl₃ | SO₂Me | —NEt₂ | SCH₂C(O)OMe | |
| 1-2229 | —CHMe— | CCl₃ | SO₂Me | —NH(n-Pr) | SCH₂C(O)OMe | |
| 1-2230 | —CHMe— | CCl₃ | SO₂Me | —N(n-Pr)₂ | SCH₂C(O)OMe | |
| 1-2231 | —CHMe— | CCl₃ | SO₂Me | —NMeEt | SCH₂C(O)OMe | |
| 1-2232 | —CHMe— | CCl₃ | SO₂Me | —NMe(n-Pr) | SCH₂C(O)OMe | |
| 1-2233 | —CHMe— | CCl₃ | SO₂Me | —NEt(n-Pr) | SCH₂C(O)OMe | |
| 1-2234 | —CHMe— | CCl₃ | SO₂Me | —NH(i-Pr) | SCH₂C(O)OMe | |
| 1-2235 | —CHMe— | CCl₃ | SO₂Me | —NMe(i-Pr) | SCH₂C(O)OMe | |
| 1-2236 | —CHMe— | CCl₃ | SO₂Me | —NEt(i-Pr) | SCH₂C(O)OMe | |
| 1-2237 | —CHMe— | CCl₃ | SO₂Me | —N(Me)OMe | SCH₂C(O)OMe | |
| 1-2238 | —CHMe— | CCl₃ | SO₂Me | —N(Me)OEt | SCH₂C(O)OMe | |
| 1-2239 | —CHMe— | CCl₃ | SO₂Me | —N(Me)O(n-Pr) | SCH₂C(O)OMe | |
| 1-2240 | —CHMe— | CCl₃ | SO₂Me | —N(Et)OMe | SCH₂C(O)OMe | |
| 1-2241 | —CHMe— | CCl₃ | SO₂Me | —N(Et)OEt | SCH₂C(O)OMe | |
| 1-2242 | —CHMe— | CCl₃ | SO₂Me | —N(Et)O(n-Pr) | SCH₂C(O)OMe | |
| 1-2243 | —CHMe— | C₂F₅ | SO₂Me | —NH₂ | SCH₂C(O)OMe | |
| 1-2244 | —CHMe— | C₂F₅ | SO₂Me | —NHMe | SCH₂C(O)OMe | |
| 1-2245 | —CHMe— | C₂F₅ | SO₂Me | —NMe₂ | SCH₂C(O)OMe | |
| 1-2246 | —CHMe— | C₂F₅ | SO₂Me | —NHEt | SCH₂C(O)OMe | |
| 1-2247 | —CHMe— | C₂F₅ | SO₂Me | —NEt₂ | SCH₂C(O)OMe | |
| 1-2248 | —CHMe— | C₂F₅ | SO₂Me | —NH(n-Pr) | SCH₂C(O)OMe | |

TABLE 1-continued

| No. | X¹ | R¹ | R² | —NR³R⁴ | R⁵ | Physical data |
|---|---|---|---|---|---|---|
| 1-2249 | —CHMe— | C₂F₅ | SO₂Me | —N(n-Pr)₂ | SCH₂C(O)OMe | |
| 1-2250 | —CHMe— | C₂F₅ | SO₂Me | —NMeEt | SCH₂C(O)OMe | |
| 1-2251 | —CHMe— | C₂F₅ | SO₂Me | —NMe(n-Pr) | SCH₂C(O)OMe | |
| 1-2252 | —CHMe— | C₂F₅ | SO₂Me | —NEt(n-Pr) | SCH₂C(O)OMe | |
| 1-2253 | —CHMe— | C₂F₅ | SO₂Me | —NH(i-Pr) | SCH₂C(O)OMe | |
| 1-2254 | —CHMe— | C₂F₅ | SO₂Me | —NMe(i-Pr) | SCH₂C(O)OMe | |
| 1-2255 | —CHMe— | C₂F₅ | SO₂Me | —NEt(i-Pr) | SCH₂C(O)OMe | |
| 1-2256 | —CHMe— | C₂F₅ | SO₂Me | —N(Me)OMe | SCH₂C(O)OMe | |
| 1-2257 | —CHMe— | C₂F₅ | SO₂Me | —N(Me)OEt | SCH₂C(O)OMe | |
| 1-2258 | —CHMe— | C₂F₅ | SO₂Me | —N(Me)O(n-Pr) | SCH₂C(O)OMe | |
| 1-2259 | —CHMe— | C₂F₅ | SO₂Me | —N(Et)OMe | SCH₂C(O)OMe | |
| 1-2260 | —CHMe— | C₂F₅ | SO₂Me | —N(Et)OEt | SCH₂C(O)OMe | |
| 1-2261 | —CHMe— | C₂F₅ | SO₂Me | —N(Et)O(n-Pr) | SCH₂C(O)OMe | |
| 1-2262 | —CHMe— | CHF₂ | SO₂Me | —NH₂ | SCH₂C(O)OMe | |
| 1-2263 | —CHMe— | CHF₂ | SO₂Me | —NHMe | SCH₂C(O)OMe | |
| 1-2264 | —CHMe— | CHF₂ | SO₂Me | —NMe₂ | SCH₂C(O)OMe | |
| 1-2265 | —CHMe— | CHF₂ | SO₂Me | —NHEt | SCH₂C(O)OMe | |
| 1-2266 | —CHMe— | CHF₂ | SO₂Me | —NEt₂ | SCH₂C(O)OMe | |
| 1-2267 | —CHMe— | CHF₂ | SO₂Me | —NH(n-Pr) | SCH₂C(O)OMe | |
| 1-2268 | —CHMe— | CHF₂ | SO₂Me | —N(n-Pr)₂ | SCH₂C(O)OMe | |
| 1-2269 | —CHMe— | CHF₂ | SO₂Me | —NMeEt | SCH₂C(O)OMe | |
| 1-2270 | —CHMe— | CHF₂ | SO₂Me | —NMe(n-Pr) | SCH₂C(O)OMe | |
| 1-2271 | —CHMe— | CHF₂ | SO₂Me | —NEt(n-Pr) | SCH₂C(O)OMe | |
| 1-2272 | —CHMe— | CHF₂ | SO₂Me | —NH(i-Pr) | SCH₂C(O)OMe | |
| 1-2273 | —CHMe— | CHF₂ | SO₂Me | —NMe(i-Pr) | SCH₂C(O)OMe | |
| 1-2274 | —CHMe— | CHF₂ | SO₂Me | —NEt(i-Pr) | SCH₂C(O)OMe | |
| 1-2275 | —CHMe— | CHF₂ | SO₂Me | —N(Me)OMe | SCH₂C(O)OMe | |
| 1-2276 | —CHMe— | CHF₂ | SO₂Me | —N(Me)OEt | SCH₂C(O)OMe | |
| 1-2277 | —CHMe— | CHF₂ | SO₂Me | —N(Me)O(n-Pr) | SCH₂C(O)OMe | |
| 1-2278 | —CHMe— | CHF₂ | SO₂Me | —N(Et)OMe | SCH₂C(O)OMe | |
| 1-2279 | —CHMe— | CHF₂ | SO₂Me | —N(Et)OEt | SCH₂C(O)OMe | |
| 1-2280 | —CHMe— | CHF₂ | SO₂Me | —N(Et)O(n-Pr) | SCH₂C(O)OMe | |
| 1-2281 | —CH₂— | CF₃ | SO₂Et | —NH₂ | OH | |
| 1-2282 | —CH₂— | CF₃ | SO₂Et | —NHMe | OH | |
| 1-2283 | —CH₂— | CF₃ | SO₂Et | —NMe₂ | OH | CDCl₃: 16.33 (bs, 1H), 8.19 (d, 1H), 7.08 (d, 1H), 4.87-5.00 (m, 2H), 3.72 (q, 2H), 3.00 (s, 3H); 2.84 (s, 3H), 2.80 (t, 2H), 2.41 (t, 2H), 2.07 (quin, 2H), 1.22 (t, 3H) |
| 1-2284 | —CH₂— | CF₃ | SO₂Et | —NHEt | OH | |
| 1-2285 | —CH₂— | CF₃ | SO₂Et | —NEt₂ | OH | CDCl₃: 16.35 (bs, 1H), 8.20 (d, 1H), 7.07 (d, 1H), 4.88-4.98 (m, 2H), 3.73 (q, 2H), 3.45 (q, 2H), 3.13 (q, 2H), 2.80 (t, 2H), 2.41 (t, 2H), 2.06 (quin, 2H), 1.22 (t, 3H), 1.17 (t, 3H), 1.16 (t, 3H) |
| 1-2286 | —CH₂— | CF₃ | SO₂Et | —NH(n-Pr) | OH | |
| 1-2287 | —CH₂— | CF₃ | SO₂Et | —N(n-Pr)₂ | OH | |
| 1-2288 | —CH₂— | CF₃ | SO₂Et | —NMeEt | OH | CDCl₃: 16.33 (bs, 1H), 8.19 (d, 1H), 7.07 (d, 1H), 4.83-5.00 (m, 2H), 3.72 (q, 2H), 3.48 (q, 1H), 3.15 (q, 1H), 2.98 (s, 1H), 2.77-2.85 (m, 4H) 2.40 (t, 2H), 2.07 (quin, 2H), 1.11-1.20 (m, 3H), 1.20-1.25 (m, 3H) |
| 1-2289 | —CH₂— | CF₃ | SO₂Et | —NMe(n-Pr) | OH | |
| 1-2290 | —CH₂— | CF₃ | SO₂Et | —NEt(n-Pr) | OH | |
| 1-2291 | —CH₂— | CF₃ | SO₂Et | —NH(i-Pr) | OH | |
| 1-2292 | —CH₂— | CF₃ | SO₂Et | —NMe(i-Pr) | OH | |
| 1-2293 | —CH₂— | CF₃ | SO₂Et | —NEt(i-Pr) | OH | |
| 1-2294 | —CH₂— | CF₃ | SO₂Et | —N(Me)OMe | OH | CDCl₃: 16.32 (bs, 1H), 8.19 (d, 1H), |

TABLE 1-continued

| No. | X¹ | R¹ | R² | —NR³R⁴ | R⁵ | Physical data |
|---|---|---|---|---|---|---|
| | | | | | | 7.07 (d, 1H), 5.01-5.08 (m, 2H), 3.69 (q, 2H), 3.65 (s, 3H); 3.22 (s, 3H), 2.80 (t, 2H), 2.41 (t, 2H), 2.07 (quin, 2H), 1.22 (t, 3H) |
| 1-2295 | —CH₂— | CF₃ | SO₂Et | —N(Me)OEt | OH | |
| 1-2296 | —CH₂— | CF₃ | SO₂Et | —N(Me)O(n-Pr) | OH | |
| 1-2297 | —CH₂— | CF₃ | SO₂Et | —N(Et)OMe | OH | |
| 1-2298 | —CH₂— | CF₃ | SO₂Et | —N(Et)OEt | OH | |
| 1-2299 | —CH₂— | CF₃ | SO₂Et | —N(Et)O(n-Pr) | OH | |
| 1-2300 | —CH₂— | CCl₃ | SO₂Et | —NH₂ | OH | |
| 1-2301 | —CH₂— | CCl₃ | SO₂Et | —NHMe | OH | |
| 1-2302 | —CH₂— | CCl₃ | SO₂Et | —NMe₂ | OH | |
| 1-2303 | —CH₂— | CCl₃ | SO₂Et | —NHEt | OH | |
| 1-2304 | —CH₂— | CCl₃ | SO₂Et | —NEt₂ | OH | |
| 1-2305 | —CH₂— | CCl₃ | SO₂Et | —NH(n-Pr) | OH | |
| 1-2306 | —CH₂— | CCl₃ | SO₂Et | —N(n-Pr)₂ | OH | |
| 1-2307 | —CH₂— | CCl₃ | SO₂Et | —NMeEt | OH | |
| 1-2308 | —CH₂— | CCl₃ | SO₂Et | —NMe(n-Pr) | OH | |
| 1-2309 | —CH₂— | CCl₃ | SO₂Et | —NEt(n-Pr) | OH | |
| 1-2310 | —CH₂— | CCl₃ | SO₂Et | —NH(i-Pr) | OH | |
| 1-2311 | —CH₂— | CCl₃ | SO₂Et | —NMe(i-Pr) | OH | |
| 1-2312 | —CH₂— | CCl₃ | SO₂Et | —NEt(i-Pr) | OH | |
| 1-2313 | —CH₂— | CCl₃ | SO₂Et | —N(Me)OMe | OH | |
| 1-2314 | —CH₂— | CCl₃ | SO₂Et | —N(Me)OEt | OH | |
| 1-2315 | —CH₂— | CCl₃ | SO₂Et | —N(Me)O(n-Pr) | OH | |
| 1-2316 | —CH₂— | CCl₃ | SO₂Et | —N(Et)OMe | OH | |
| 1-2317 | —CH₂— | CCl₃ | SO₂Et | —N(Et)OEt | OH | |
| 1-2318 | —CH₂— | CCl₃ | SO₂Et | —N(Et)O(n-Pr) | OH | |
| 1-2319 | —CH₂— | C₂F₅ | SO₂Et | —NH₂ | OH | |
| 1-2320 | —CH₂— | C₂F₅ | SO₂Et | —NHMe | OH | |
| 1-2321 | —CH₂— | C₂F₅ | SO₂Et | —NMe₂ | OH | |
| 1-2322 | —CH₂— | C₂F₅ | SO₂Et | —NHEt | OH | |
| 1-2323 | —CH₂— | C₂F₅ | SO₂Et | —NEt₂ | OH | |
| 1-2324 | —CH₂— | C₂F₅ | SO₂Et | —NH(n-Pr) | OH | |
| 1-2325 | —CH₂— | C₂F₅ | SO₂Et | —N(n-Pr)₂ | OH | |
| 1-2326 | —CH₂— | C₂F₅ | SO₂Et | —NMeEt | OH | |
| 1-2327 | —CH₂— | C₂F₅ | SO₂Et | —NMe(n-Pr) | OH | |
| 1-2328 | —CH₂— | C₂F₅ | SO₂Et | —NEt(n-Pr) | OH | |
| 1-2329 | —CH₂— | C₂F₅ | SO₂Et | —NH(i-Pr) | OH | |
| 1-2330 | —CH₂— | C₂F₅ | SO₂Et | —NMe(i-Pr) | OH | |
| 1-2331 | —CH₂— | C₂F₅ | SO₂Et | —NEt(i-Pr) | OH | |
| 1-2332 | —CH₂— | C₂F₅ | SO₂Et | —N(Me)OMe | OH | |
| 1-2333 | —CH₂— | C₂F₅ | SO₂Et | —N(Me)OEt | OH | |
| 1-2334 | —CH₂— | C₂F₅ | SO₂Et | —N(Me)O(n-Pr) | OH | |
| 1-2335 | —CH₂— | C₂F₅ | SO₂Et | —N(Et)OMe | OH | |
| 1-2336 | —CH₂— | C₂F₅ | SO₂Et | —N(Et)OEt | OH | |
| 1-2337 | —CH₂— | C₂F₅ | SO₂Et | —N(Et)O(n-Pr) | OH | |
| 1-2338 | —CH₂— | CHF₂ | SO₂Et | —NH₂ | OH | |
| 1-2339 | —CH₂— | CHF₂ | SO₂Et | —NHMe | OH | |
| 1-2340 | —CH₂— | CHF₂ | SO₂Et | —NMe₂ | OH | |
| 1-2341 | —CH₂— | CHF₂ | SO₂Et | —NHEt | OH | |
| 1-2342 | —CH₂— | CHF₂ | SO₂Et | —NEt₂ | OH | |
| 1-2343 | —CH₂— | CHF₂ | SO₂Et | —NH(n-Pr) | OH | |
| 1-2344 | —CH₂— | CHF₂ | SO₂Et | —N(n-Pr)₂ | OH | |
| 1-2345 | —CH₂— | CHF₂ | SO₂Et | —NMeEt | OH | |
| 1-2346 | —CH₂— | CHF₂ | SO₂Et | —NMe(n-Pr) | OH | |
| 1-2347 | —CH₂— | CHF₂ | SO₂Et | —NEt(n-Pr) | OH | |
| 1-2348 | —CH₂— | CHF₂ | SO₂Et | —NH(i-Pr) | OH | |
| 1-2349 | —CH₂— | CHF₂ | SO₂Et | —NMe(i-Pr) | OH | |
| 1-2350 | —CH₂— | CHF₂ | SO₂Et | —NEt(i-Pr) | OH | |
| 1-2351 | —CH₂— | CHF₂ | SO₂Et | —N(Me)OMe | OH | |
| 1-2352 | —CH₂— | CHF₂ | SO₂Et | —N(Me)OEt | OH | |
| 1-2353 | —CH₂— | CHF₂ | SO₂Et | —N(Me)O(n-Pr) | OH | |
| 1-2354 | —CH₂— | CHF₂ | SO₂Et | —N(Et)OMe | OH | |
| 1-2355 | —CH₂— | CHF₂ | SO₂Et | —N(Et)OEt | OH | |
| 1-2356 | —CH₂— | CHF₂ | SO₂Et | —N(Et)O(n-Pr) | OH | |
| 1-2357 | —CH₂— | CF₃ | SO₂Et | —NH₂ | SCH₂C(O)OMe | |
| 1-2358 | —CH₂— | CF₃ | SO₂Et | —NHMe | SCH₂C(O)OMe | |
| 1-2359 | —CH₂— | CF₃ | SO₂Et | —NMe₂ | SCH₂C(O)OMe | CDCl₃: 8.12 (d, 1H), 7.06 (d, 1H), 4.90 (s, 2H), 3.80 (s, 3H), 3.73 (s, 2H), 3.70 (q, 2H), 3.01 (s, 3H); |

TABLE 1-continued

| No. | X$^1$ | R$^1$ | R$^2$ | —NR$^3$R$^4$ | R$^5$ | Physical data |
|---|---|---|---|---|---|---|
| | | | | | | 3.00 (t, 2H), 2.88 (s, 3H), 2.40-2.46 (m, 2H), 2.04-2.15 (m, 2H), 1.21 (t, 3H) |
| 1-2360 | —CH$_2$— | CF$_3$ | SO$_2$Et | —NHEt | SCH$_2$C(O)OMe | |
| 1-2361 | —CH$_2$— | CF$_3$ | SO$_2$Et | —NEt$_2$ | SCH$_2$C(O)OMe | |
| 1-2362 | —CH$_2$— | CF$_3$ | SO$_2$Et | —NH(n-Pr) | SCH$_2$C(O)OMe | |
| 1-2363 | —CH$_2$— | CF$_3$ | SO$_2$Et | —N(n-Pr)$_2$ | SCH$_2$C(O)OMe | |
| 1-2364 | —CH$_2$— | CF$_3$ | SO$_2$Et | —NMeEt | SCH$_2$C(O)OMe | |
| 1-2365 | —CH$_2$— | CF$_3$ | SO$_2$Et | —NMe(n-Pr) | SCH$_2$C(O)OMe | |
| 1-2366 | —CH$_2$— | CF$_3$ | SO$_2$Et | —NEt(n-Pr) | SCH$_2$C(O)OMe | |
| 1-2367 | —CH$_2$— | CF$_3$ | SO$_2$Et | —NH(i-Pr) | SCH$_2$C(O)OMe | |
| 1-2368 | —CH$_2$— | CF$_3$ | SO$_2$Et | —NMe(i-Pr) | SCH$_2$C(O)OMe | |
| 1-2369 | —CH$_2$— | CF$_3$ | SO$_2$Et | —NEt(i-Pr) | SCH$_2$C(O)OMe | |
| 1-2370 | —CH$_2$— | CF$_3$ | SO$_2$Et | —N(Me)OMe | SCH$_2$C(O)OMe | |
| 1-2371 | —CH$_2$— | CF$_3$ | SO$_2$Et | —N(Me)OEt | SCH$_2$C(O)OMe | |
| 1-2372 | —CH$_2$— | CF$_3$ | SO$_2$Et | —N(Me)O(n-Pr) | SCH$_2$C(O)OMe | |
| 1-2373 | —CH$_2$— | CF$_3$ | SO$_2$Et | —N(Et)OMe | SCH$_2$C(O)OMe | |
| 1-2374 | —CH$_2$— | CF$_3$ | SO$_2$Et | —N(Et)OEt | SCH$_2$C(O)OMe | |
| 1-2375 | —CH$_2$— | CF$_3$ | SO$_2$Et | —N(Et)O(n-Pr) | SCH$_2$C(O)OMe | |
| 1-2376 | —CH$_2$— | CCl$_3$ | SO$_2$Et | —NH$_2$ | SCH$_2$C(O)OMe | |
| 1-2377 | —CH$_2$— | CCl$_3$ | SO$_2$Et | —NHMe | SCH$_2$C(O)OMe | |
| 1-2378 | —CH$_2$— | CCl$_3$ | SO$_2$Et | —NMe$_2$ | SCH$_2$C(O)OMe | |
| 1-2379 | —CH$_2$— | CCl$_3$ | SO$_2$Et | —NHEt | SCH$_2$C(O)OMe | |
| 1-2380 | —CH$_2$— | CCl$_3$ | SO$_2$Et | —NEt$_2$ | SCH$_2$C(O)OMe | |
| 1-2381 | —CH$_2$— | CCl$_3$ | SO$_2$Et | —NH(n-Pr) | SCH$_2$C(O)OMe | |
| 1-2382 | —CH$_2$— | CCl$_3$ | SO$_2$Et | —N(n-Pr)$_2$ | SCH$_2$C(O)OMe | |
| 1-2383 | —CH$_2$— | CCl$_3$ | SO$_2$Et | —NMeEt | SCH$_2$C(O)OMe | |
| 1-2384 | —CH$_2$— | CCl$_3$ | SO$_2$Et | —NMe(n-Pr) | SCH$_2$C(O)OMe | |
| 1-2385 | —CH$_2$— | CCl$_3$ | SO$_2$Et | —NEt(n-Pr) | SCH$_2$C(O)OMe | |
| 1-2386 | —CH$_2$— | CCl$_3$ | SO$_2$Et | —NH(i-Pr) | SCH$_2$C(O)OMe | |
| 1-2387 | —CH$_2$— | CCl$_3$ | SO$_2$Et | —NMe(i-Pr) | SCH$_2$C(O)OMe | |
| 1-2388 | —CH$_2$— | CCl$_3$ | SO$_2$Et | —NEt(i-Pr) | SCH$_2$C(O)OMe | |
| 1-2389 | —CH$_2$— | CCl$_3$ | SO$_2$Et | —N(Me)OMe | SCH$_2$C(O)OMe | |
| 1-2390 | —CH$_2$— | CCl$_3$ | SO$_2$Et | —N(Me)OEt | SCH$_2$C(O)OMe | |
| 1-2391 | —CH$_2$— | CCl$_3$ | SO$_2$Et | —N(Me)O(n-Pr) | SCH$_2$C(O)OMe | |
| 1-2392 | —CH$_2$— | CCl$_3$ | SO$_2$Et | —N(Et)OMe | SCH$_2$C(O)OMe | |
| 1-2393 | —CH$_2$— | CCl$_3$ | SO$_2$Et | —N(Et)OEt | SCH$_2$C(O)OMe | |
| 1-2394 | —CH$_2$— | CCl$_3$ | SO$_2$Et | —N(Et)O(n-Pr) | SCH$_2$C(O)OMe | |
| 1-2395 | —CH$_2$— | C$_2$F$_5$ | SO$_2$Et | —NH$_2$ | SCH$_2$C(O)OMe | |
| 1-2396 | —CH$_2$— | C$_2$F$_5$ | SO$_2$Et | —NHMe | SCH$_2$C(O)OMe | |
| 1-2397 | —CH$_2$— | C$_2$F$_5$ | SO$_2$Et | —NMe$_2$ | SCH$_2$C(O)OMe | |
| 1-2398 | —CH$_2$— | C$_2$F$_5$ | SO$_2$Et | —NHEt | SCH$_2$C(O)OMe | |
| 1-2399 | —CH$_2$— | C$_2$F$_5$ | SO$_2$Et | —NEt$_2$ | SCH$_2$C(O)OMe | |
| 1-2400 | —CH$_2$— | C$_2$F$_5$ | SO$_2$Et | —NH(n-Pr) | SCH$_2$C(O)OMe | |
| 1-2401 | —CH$_2$— | C$_2$F$_5$ | SO$_2$Et | —N(n-Pr)$_2$ | SCH$_2$C(O)OMe | |
| 1-2402 | —CH$_2$— | C$_2$F$_5$ | SO$_2$Et | —NMeEt | SCH$_2$C(O)OMe | |
| 1-2403 | —CH$_2$— | C$_2$F$_5$ | SO$_2$Et | —NMe(n-Pr) | SCH$_2$C(O)OMe | |
| 1-2404 | —CH$_2$— | C$_2$F$_5$ | SO$_2$Et | —NEt(n-Pr) | SCH$_2$C(O)OMe | |
| 1-2405 | —CH$_2$— | C$_2$F$_5$ | SO$_2$Et | —NH(i-Pr) | SCH$_2$C(O)OMe | |
| 1-2406 | —CH$_2$— | C$_2$F$_5$ | SO$_2$Et | —NMe(i-Pr) | SCH$_2$C(O)OMe | |
| 1-2407 | —CH$_2$— | C$_2$F$_5$ | SO$_2$Et | —NEt(i-Pr) | SCH$_2$C(O)OMe | |
| 1-2408 | —CH$_2$— | C$_2$F$_5$ | SO$_2$Et | —N(Me)OMe | SCH$_2$C(O)OMe | |
| 1-2409 | —CH$_2$— | C$_2$F$_5$ | SO$_2$Et | —N(Me)OEt | SCH$_2$C(O)OMe | |
| 1-2410 | —CH$_2$— | C$_2$F$_5$ | SO$_2$Et | —N(Me)O(n-Pr) | SCH$_2$C(O)OMe | |
| 1-2411 | —CH$_2$— | C$_2$F$_5$ | SO$_2$Et | —N(Et)OMe | SCH$_2$C(O)OMe | |
| 1-2412 | —CH$_2$— | C$_2$F$_5$ | SO$_2$Et | —N(Et)OEt | SCH$_2$C(O)OMe | |
| 1-2413 | —CH$_2$— | C$_2$F$_5$ | SO$_2$Et | —N(Et)O(n-Pr) | SCH$_2$C(O)OMe | |
| 1-2414 | —CH$_2$— | CHF$_2$ | SO$_2$Et | —NH$_2$ | SCH$_2$C(O)OMe | |
| 1-2415 | —CH$_2$— | CHF$_2$ | SO$_2$Et | —NHMe | SCH$_2$C(O)OMe | |
| 1-2416 | —CH$_2$— | CHF$_2$ | SO$_2$Et | —NMe$_2$ | SCH$_2$C(O)OMe | |
| 1-2417 | —CH$_2$— | CHF$_2$ | SO$_2$Et | —NHEt | SCH$_2$C(O)OMe | |
| 1-2418 | —CH$_2$— | CHF$_2$ | SO$_2$Et | —NEt$_2$ | SCH$_2$C(O)OMe | |
| 1-2419 | —CH$_2$— | CHF$_2$ | SO$_2$Et | —NH(n-Pr) | SCH$_2$C(O)OMe | |
| 1-2420 | —CH$_2$— | CHF$_2$ | SO$_2$Et | —N(n-Pr)$_2$ | SCH$_2$C(O)OMe | |
| 1-2421 | —CH$_2$— | CHF$_2$ | SO$_2$Et | —NMeEt | SCH$_2$C(O)OMe | |
| 1-2422 | —CH$_2$— | CHF$_2$ | SO$_2$Et | —NMe(n-Pr) | SCH$_2$C(O)OMe | |
| 1-2423 | —CH$_2$— | CHF$_2$ | SO$_2$Et | —NEt(n-Pr) | SCH$_2$C(O)OMe | |
| 1-2424 | —CH$_2$— | CHF$_2$ | SO$_2$Et | —NH(i-Pr) | SCH$_2$C(O)OMe | |
| 1-2425 | —CH$_2$— | CHF$_2$ | SO$_2$Et | —NMe(i-Pr) | SCH$_2$C(O)OMe | |
| 1-2426 | —CH$_2$— | CHF$_2$ | SO$_2$Et | —NEt(i-Pr) | SCH$_2$C(O)OMe | |
| 1-2427 | —CH$_2$— | CHF$_2$ | SO$_2$Et | —N(Me)OMe | SCH$_2$C(O)OMe | |
| 1-2428 | —CH$_2$— | CHF$_2$ | SO$_2$Et | —N(Me)OEt | SCH$_2$C(O)OMe | |
| 1-2429 | —CH$_2$— | CHF$_2$ | SO$_2$Et | —N(Me)O(n-Pr) | SCH$_2$C(O)OMe | |
| 1-2430 | —CH$_2$— | CHF$_2$ | SO$_2$Et | —N(Et)OMe | SCH$_2$C(O)OMe | |
| 1-2431 | —CH$_2$— | CHF$_2$ | SO$_2$Et | —N(Et)OEt | SCH$_2$C(O)OMe | |
| 1-2432 | —CH$_2$— | CHF$_2$ | SO$_2$Et | —N(Et)O(n-Pr) | SCH$_2$C(O)OMe | |

TABLE 1-continued

| No. | X¹ | R¹ | R² | —NR³R⁴ | R⁵ | Physical data |
|---|---|---|---|---|---|---|
| 1-2433 | —(CH$_2$)$_2$— | CF$_3$ | SO$_2$Et | —NH$_2$ | OH | |
| 1-2434 | —(CH$_2$)$_2$— | CF$_3$ | SO$_2$Et | —NHMe | OH | |
| 1-2435 | —(CH$_2$)$_2$— | CF$_3$ | SO$_2$Et | —NMe$_2$ | OH | |
| 1-2436 | —(CH$_2$)$_2$— | CF$_3$ | SO$_2$Et | —NHEt | OH | |
| 1-2437 | —(CH$_2$)$_2$— | CF$_3$ | SO$_2$Et | —NEt$_2$ | OH | |
| 1-2438 | —(CH$_2$)$_2$— | CF$_3$ | SO$_2$Et | —NH(n-Pr) | OH | |
| 1-2439 | —(CH$_2$)$_2$— | CF$_3$ | SO$_2$Et | —N(n-Pr)$_2$ | OH | |
| 1-2440 | —(CH$_2$)$_2$— | CF$_3$ | SO$_2$Et | —NMeEt | OH | |
| 1-2441 | —(CH$_2$)$_2$— | CF$_3$ | SO$_2$Et | —NMe(n-Pr) | OH | |
| 1-2442 | —(CH$_2$)$_2$— | CF$_3$ | SO$_2$Et | —NEt(n-Pr) | OH | |
| 1-2443 | —(CH$_2$)$_2$— | CF$_3$ | SO$_2$Et | —NH(i-Pr) | OH | |
| 1-2444 | —(CH$_2$)$_2$— | CF$_3$ | SO$_2$Et | —NMe(i-Pr) | OH | |
| 1-2445 | —(CH$_2$)$_2$— | CF$_3$ | SO$_2$Et | —NEt(i-Pr) | OH | |
| 1-2446 | —(CH$_2$)$_2$— | CF$_3$ | SO$_2$Et | —N(Me)OMe | OH | |
| 1-2447 | —(CH$_2$)$_2$— | CF$_3$ | SO$_2$Et | —N(Me)OEt | OH | |
| 1-2448 | —(CH$_2$)$_2$— | CF$_3$ | SO$_2$Et | —N(Me)O(n-Pr) | OH | |
| 1-2449 | —(CH$_2$)$_2$— | CF$_3$ | SO$_2$Et | —N(Et)OMe | OH | |
| 1-2450 | —(CH$_2$)$_2$— | CF$_3$ | SO$_2$Et | —N(Et)OEt | OH | |
| 1-2451 | —(CH$_2$)$_2$— | CF$_3$ | SO$_2$Et | —N(Et)O(n-Pr) | OH | |
| 1-2452 | —(CH$_2$)$_2$— | CCl$_3$ | SO$_2$Et | —NH$_2$ | OH | |
| 1-2453 | —(CH$_2$)$_2$— | CCl$_3$ | SO$_2$Et | —NHMe | OH | |
| 1-2454 | —(CH$_2$)$_2$— | CCl$_3$ | SO$_2$Et | —NMe$_2$ | OH | |
| 1-2455 | —(CH$_2$)$_2$— | CCl$_3$ | SO$_2$Et | —NHEt | OH | |
| 1-2456 | —(CH$_2$)$_2$— | CCl$_3$ | SO$_2$Et | —NEt$_2$ | OH | |
| 1-2457 | —(CH$_2$)$_2$— | CCl$_3$ | SO$_2$Et | —NH(n-Pr) | OH | |
| 1-2458 | —(CH$_2$)$_2$— | CCl$_3$ | SO$_2$Et | —N(n-Pr)$_2$ | OH | |
| 1-2459 | —(CH$_2$)$_2$— | CCl$_3$ | SO$_2$Et | —NMeEt | OH | |
| 1-2460 | —(CH$_2$)$_2$— | CCl$_3$ | SO$_2$Et | —NMe(n-Pr) | OH | |
| 1-2461 | —(CH$_2$)$_2$— | CCl$_3$ | SO$_2$Et | —NEt(n-Pr) | OH | |
| 1-2462 | —(CH$_2$)$_2$— | CCl$_3$ | SO$_2$Et | —NH(i-Pr) | OH | |
| 1-2463 | —(CH$_2$)$_2$— | CCl$_3$ | SO$_2$Et | —NMe(i-Pr) | OH | |
| 1-2464 | —(CH$_2$)$_2$— | CCl$_3$ | SO$_2$Et | —NEt(i-Pr) | OH | |
| 1-2465 | —(CH$_2$)$_2$— | CCl$_3$ | SO$_2$Et | —N(Me)OMe | OH | |
| 1-2466 | —(CH$_2$)$_2$— | CCl$_3$ | SO$_2$Et | —N(Me)OEt | OH | |
| 1-2467 | —(CH$_2$)$_2$— | CCl$_3$ | SO$_2$Et | —N(Me)O(n-Pr) | OH | |
| 1-2468 | —(CH$_2$)$_2$— | CCl$_3$ | SO$_2$Et | —N(Et)OMe | OH | |
| 1-2469 | —(CH$_2$)$_2$— | CCl$_3$ | SO$_2$Et | —N(Et)OEt | OH | |
| 1-2470 | —(CH$_2$)$_2$— | CCl$_3$ | SO$_2$Et | —N(Et)O(n-Pr) | OH | |
| 1-2471 | —(CH$_2$)$_2$— | C$_2$F$_5$ | SO$_2$Et | —NH$_2$ | OH | |
| 1-2472 | —(CH$_2$)$_2$— | C$_2$F$_5$ | SO$_2$Et | —NHMe | OH | |
| 1-2473 | —(CH$_2$)$_2$— | C$_2$F$_5$ | SO$_2$Et | —NMe$_2$ | OH | |
| 1-2474 | —(CH$_2$)$_2$— | C$_2$F$_5$ | SO$_2$Et | —NHEt | OH | |
| 1-2475 | —(CH$_2$)$_2$— | C$_2$F$_5$ | SO$_2$Et | —NEt$_2$ | OH | |
| 1-2476 | —(CH$_2$)$_2$— | C$_2$F$_5$ | SO$_2$Et | —NH(n-Pr) | OH | |
| 1-2477 | —(CH$_2$)$_2$— | C$_2$F$_5$ | SO$_2$Et | —N(n-Pr)$_2$ | OH | |
| 1-2478 | —(CH$_2$)$_2$— | C$_2$F$_5$ | SO$_2$Et | —NMeEt | OH | |
| 1-2479 | —(CH$_2$)$_2$— | C$_2$F$_5$ | SO$_2$Et | —NMe(n-Pr) | OH | |
| 1-2480 | —(CH$_2$)$_2$— | C$_2$F$_5$ | SO$_2$Et | —NEt(n-Pr) | OH | |
| 1-2481 | —(CH$_2$)$_2$— | C$_2$F$_5$ | SO$_2$Et | —NH(i-Pr) | OH | |
| 1-2482 | —(CH$_2$)$_2$— | C$_2$F$_5$ | SO$_2$Et | —NMe(i-Pr) | OH | |
| 1-2483 | —(CH$_2$)$_2$— | C$_2$F$_5$ | SO$_2$Et | —NEt(i-Pr) | OH | |
| 1-2484 | —(CH$_2$)$_2$— | C$_2$F$_5$ | SO$_2$Et | —N(Me)OMe | OH | |
| 1-2485 | —(CH$_2$)$_2$— | C$_2$F$_5$ | SO$_2$Et | —N(Me)OEt | OH | |
| 1-2486 | —(CH$_2$)$_2$— | C$_2$F$_5$ | SO$_2$Et | —N(Me)O(n-Pr) | OH | |
| 1-2487 | —(CH$_2$)$_2$— | C$_2$F$_5$ | SO$_2$Et | —N(Et)OMe | OH | |
| 1-2488 | —(CH$_2$)$_2$— | C$_2$F$_5$ | SO$_2$Et | —N(Et)OEt | OH | |
| 1-2489 | —(CH$_2$)$_2$— | C$_2$F$_5$ | SO$_2$Et | —N(Et)O(n-Pr) | OH | |
| 1-2490 | —(CH$_2$)$_2$— | CHF$_2$ | SO$_2$Et | —NH$_2$ | OH | |
| 1-2491 | —(CH$_2$)$_2$— | CHF$_2$ | SO$_2$Et | —NHMe | OH | |
| 1-2492 | —(CH$_2$)$_2$— | CHF$_2$ | SO$_2$Et | —NMe$_2$ | OH | |
| 1-2493 | —(CH$_2$)$_2$— | CHF$_2$ | SO$_2$Et | —NHEt | OH | |
| 1-2494 | —(CH$_2$)$_2$— | CHF$_2$ | SO$_2$Et | —NEt$_2$ | OH | |
| 1-2495 | —(CH$_2$)$_2$— | CHF$_2$ | SO$_2$Et | —NH(n-Pr) | OH | |
| 1-2496 | —(CH$_2$)$_2$— | CHF$_2$ | SO$_2$Et | —N(n-Pr)$_2$ | OH | |
| 1-2497 | —(CH$_2$)$_2$— | CHF$_2$ | SO$_2$Et | —NMeEt | OH | |
| 1-2498 | —(CH$_2$)$_2$— | CHF$_2$ | SO$_2$Et | —NMe(n-Pr) | OH | |
| 1-2499 | —(CH$_2$)$_2$— | CHF$_2$ | SO$_2$Et | —NEt(n-Pr) | OH | |
| 1-2500 | —(CH$_2$)$_2$— | CHF$_2$ | SO$_2$Et | —NH(i-Pr) | OH | |
| 1-2501 | —(CH$_2$)$_2$— | CHF$_2$ | SO$_2$Et | —NMe(i-Pr) | OH | |
| 1-2502 | —(CH$_2$)$_2$— | CHF$_2$ | SO$_2$Et | —NEt(i-Pr) | OH | |
| 1-2503 | —(CH$_2$)$_2$— | CHF$_2$ | SO$_2$Et | —N(Me)OMe | OH | |
| 1-2504 | —(CH$_2$)$_2$— | CHF$_2$ | SO$_2$Et | —N(Me)OEt | OH | |
| 1-2505 | —(CH$_2$)$_2$— | CHF$_2$ | SO$_2$Et | —N(Me)O(n-Pr) | OH | |
| 1-2506 | —(CH$_2$)$_2$— | CHF$_2$ | SO$_2$Et | —N(Et)OMe | OH | |
| 1-2507 | —(CH$_2$)$_2$— | CHF$_2$ | SO$_2$Et | —N(Et)OEt | OH | |
| 1-2508 | —(CH$_2$)$_2$— | CHF$_2$ | SO$_2$Et | —N(Et)O(n-Pr) | OH | |
| 1-2509 | —(CH$_2$)$_2$— | CF$_3$ | SO$_2$Et | —NH$_2$ | SCH$_2$C(O)OMe | |

TABLE 1-continued

| No. | $X^1$ | $R^1$ | $R^2$ | —NR$^3$R$^4$ | $R^5$ | Physical data |
|---|---|---|---|---|---|---|
| 1-2510 | —(CH$_2$)$_2$— | CF$_3$ | SO$_2$Et | —NHMe | SCH$_2$C(O)OMe | |
| 1-2511 | —(CH$_2$)$_2$— | CF$_3$ | SO$_2$Et | —NMe$_2$ | SCH$_2$C(O)OMe | |
| 1-2512 | —(CH$_2$)$_2$— | CF$_3$ | SO$_2$Et | —NHEt | SCH$_2$C(O)OMe | |
| 1-2513 | —(CH$_2$)$_2$— | CF$_3$ | SO$_2$Et | —NEt$_2$ | SCH$_2$C(O)OMe | |
| 1-2514 | —(CH$_2$)$_2$— | CF$_3$ | SO$_2$Et | —NH(n-Pr) | SCH$_2$C(O)OMe | |
| 1-2515 | —(CH$_2$)$_2$— | CF$_3$ | SO$_2$Et | —N(n-Pr)$_2$ | SCH$_2$C(O)OMe | |
| 1-2516 | —(CH$_2$)$_2$— | CF$_3$ | SO$_2$Et | —NMeEt | SCH$_2$C(O)OMe | |
| 1-2517 | —(CH$_2$)$_2$— | CF$_3$ | SO$_2$Et | —NMe(n-Pr) | SCH$_2$C(O)OMe | |
| 1-2518 | —(CH$_2$)$_2$— | CF$_3$ | SO$_2$Et | —NEt(n-Pr) | SCH$_2$C(O)OMe | |
| 1-2519 | —(CH$_2$)$_2$— | CF$_3$ | SO$_2$Et | —NH(i-Pr) | SCH$_2$C(O)OMe | |
| 1-2520 | —(CH$_2$)$_2$— | CF$_3$ | SO$_2$Et | —NMe(i-Pr) | SCH$_2$C(O)OMe | |
| 1-2521 | —(CH$_2$)$_2$— | CF$_3$ | SO$_2$Et | —NEt(i-Pr) | SCH$_2$C(O)OMe | |
| 1-2522 | —(CH$_2$)$_2$— | CF$_3$ | SO$_2$Et | —N(Me)OMe | SCH$_2$C(O)OMe | |
| 1-2523 | —(CH$_2$)$_2$— | CF$_3$ | SO$_2$Et | —N(Me)OEt | SCH$_2$C(O)OMe | |
| 1-2524 | —(CH$_2$)$_2$— | CF$_3$ | SO$_2$Et | —N(Me)O(n-Pr) | SCH$_2$C(O)OMe | |
| 1-2525 | —(CH$_2$)$_2$— | CF$_3$ | SO$_2$Et | —N(Et)OMe | SCH$_2$C(O)OMe | |
| 1-2526 | —(CH$_2$)$_2$— | CF$_3$ | SO$_2$Et | —N(Et)OEt | SCH$_2$C(O)OMe | |
| 1-2527 | —(CH$_2$)$_2$— | CF$_3$ | SO$_2$Et | —N(Et)O(n-Pr) | SCH$_2$C(O)OMe | |
| 1-2528 | —(CH$_2$)$_2$— | CCl$_3$ | SO$_2$Et | —NH$_2$ | SCH$_2$C(O)OMe | |
| 1-2529 | —(CH$_2$)$_2$— | CCl$_3$ | SO$_2$Et | —NHMe | SCH$_2$C(O)OMe | |
| 1-2530 | —(CH$_2$)$_2$— | CCl$_3$ | SO$_2$Et | —NMe$_2$ | SCH$_2$C(O)OMe | |
| 1-2531 | —(CH$_2$)$_2$— | CCl$_3$ | SO$_2$Et | —NHEt | SCH$_2$C(O)OMe | |
| 1-2532 | —(CH$_2$)$_2$— | CCl$_3$ | SO$_2$Et | —NEt$_2$ | SCH$_2$C(O)OMe | |
| 1-2533 | —(CH$_2$)$_2$— | CCl$_3$ | SO$_2$Et | —NH(n-Pr) | SCH$_2$C(O)OMe | |
| 1-2534 | —(CH$_2$)$_2$— | CCl$_3$ | SO$_2$Et | —N(n-Pr)$_2$ | SCH$_2$C(O)OMe | |
| 1-2535 | —(CH$_2$)$_2$— | CCl$_3$ | SO$_2$Et | —NMeEt | SCH$_2$C(O)OMe | |
| 1-2536 | —(CH$_2$)$_2$— | CCl$_3$ | SO$_2$Et | —NMe(n-Pr) | SCH$_2$C(O)OMe | |
| 1-2537 | —(CH$_2$)$_2$— | CCl$_3$ | SO$_2$Et | —NEt(n-Pr) | SCH$_2$C(O)OMe | |
| 1-2538 | —(CH$_2$)$_2$— | CCl$_3$ | SO$_2$Et | —NH(i-Pr) | SCH$_2$C(O)OMe | |
| 1-2539 | —(CH$_2$)$_2$— | CCl$_3$ | SO$_2$Et | —NMe(i-Pr) | SCH$_2$C(O)OMe | |
| 1-2540 | —(CH$_2$)$_2$— | CCl$_3$ | SO$_2$Et | —NEt(i-Pr) | SCH$_2$C(O)OMe | |
| 1-2541 | —(CH$_2$)$_2$— | CCl$_3$ | SO$_2$Et | —N(Me)OMe | SCH$_2$C(O)OMe | |
| 1-2542 | —(CH$_2$)$_2$— | CCl$_3$ | SO$_2$Et | —N(Me)OEt | SCH$_2$C(O)OMe | |
| 1-2543 | —(CH$_2$)$_2$— | CCl$_3$ | SO$_2$Et | —N(Me)O(n-Pr) | SCH$_2$C(O)OMe | |
| 1-2544 | —(CH$_2$)$_2$— | CCl$_3$ | SO$_2$Et | —N(Et)OMe | SCH$_2$C(O)OMe | |
| 1-2545 | —(CH$_2$)$_2$— | CCl$_3$ | SO$_2$Et | —N(Et)OEt | SCH$_2$C(O)OMe | |
| 1-2546 | —(CH$_2$)$_2$— | CCl$_3$ | SO$_2$Et | —N(Et)O(n-Pr) | SCH$_2$C(O)OMe | |
| 1-2547 | —(CH$_2$)$_2$— | C$_2$F$_5$ | SO$_2$Et | —NH$_2$ | SCH$_2$C(O)OMe | |
| 1-2548 | —(CH$_2$)$_2$— | C$_2$F$_5$ | SO$_2$Et | —NHMe | SCH$_2$C(O)OMe | |
| 1-2549 | —(CH$_2$)$_2$— | C$_2$F$_5$ | SO$_2$Et | —NMe$_2$ | SCH$_2$C(O)OMe | |
| 1-2550 | —(CH$_2$)$_2$— | C$_2$F$_5$ | SO$_2$Et | —NHEt | SCH$_2$C(O)OMe | |
| 1-2551 | —(CH$_2$)$_2$— | C$_2$F$_5$ | SO$_2$Et | —NEt$_2$ | SCH$_2$C(O)OMe | |
| 1-2552 | —(CH$_2$)$_2$— | C$_2$F$_5$ | SO$_2$Et | —NH(n-Pr) | SCH$_2$C(O)OMe | |
| 1-2553 | —(CH$_2$)$_2$— | C$_2$F$_5$ | SO$_2$Et | —N(n-Pr)$_2$ | SCH$_2$C(O)OMe | |
| 1-2554 | —(CH$_2$)$_2$— | C$_2$F$_5$ | SO$_2$Et | —NMeEt | SCH$_2$C(O)OMe | |
| 1-2555 | —(CH$_2$)$_2$— | C$_2$F$_5$ | SO$_2$Et | —NMe(n-Pr) | SCH$_2$C(O)OMe | |
| 1-2556 | —(CH$_2$)$_2$— | C$_2$F$_5$ | SO$_2$Et | —NEt(n-Pr) | SCH$_2$C(O)OMe | |
| 1-2557 | —(CH$_2$)$_2$— | C$_2$F$_5$ | SO$_2$Et | —NH(i-Pr) | SCH$_2$C(O)OMe | |
| 1-2558 | —(CH$_2$)$_2$— | C$_2$F$_5$ | SO$_2$Et | —NMe(i-Pr) | SCH$_2$C(O)OMe | |
| 1-2559 | —(CH$_2$)$_2$— | C$_2$F$_5$ | SO$_2$Et | —NEt(i-Pr) | SCH$_2$C(O)OMe | |
| 1-2560 | —(CH$_2$)$_2$— | C$_2$F$_5$ | SO$_2$Et | —N(Me)OMe | SCH$_2$C(O)OMe | |
| 1-2561 | —(CH$_2$)$_2$— | C$_2$F$_5$ | SO$_2$Et | —N(Me)OEt | SCH$_2$C(O)OMe | |
| 1-2562 | —(CH$_2$)$_2$— | C$_2$F$_5$ | SO$_2$Et | —N(Me)O(n-Pr) | SCH$_2$C(O)OMe | |
| 1-2563 | —(CH$_2$)$_2$— | C$_2$F$_5$ | SO$_2$Et | —N(Et)OMe | SCH$_2$C(O)OMe | |
| 1-2564 | —(CH$_2$)$_2$— | C$_2$F$_5$ | SO$_2$Et | —N(Et)OEt | SCH$_2$C(O)OMe | |
| 1-2565 | —(CH$_2$)$_2$— | C$_2$F$_5$ | SO$_2$Et | —N(Et)O(n-Pr) | SCH$_2$C(O)OMe | |
| 1-2566 | —(CH$_2$)$_2$— | CHF$_2$ | SO$_2$Et | —NH$_2$ | SCH$_2$C(O)OMe | |
| 1-2567 | —(CH$_2$)$_2$— | CHF$_2$ | SO$_2$Et | —NHMe | SCH$_2$C(O)OMe | |
| 1-2568 | —(CH$_2$)$_2$— | CHF$_2$ | SO$_2$Et | —NMe$_2$ | SCH$_2$C(O)OMe | |
| 1-2569 | —(CH$_2$)$_2$— | CHF$_2$ | SO$_2$Et | —NHEt | SCH$_2$C(O)OMe | |
| 1-2570 | —(CH$_2$)$_2$— | CHF$_2$ | SO$_2$Et | —NEt$_2$ | SCH$_2$C(O)OMe | |
| 1-2571 | —(CH$_2$)$_2$— | CHF$_2$ | SO$_2$Et | —NH(n-Pr) | SCH$_2$C(O)OMe | |
| 1-2572 | —(CH$_2$)$_2$— | CHF$_2$ | SO$_2$Et | —N(n-Pr)$_2$ | SCH$_2$C(O)OMe | |
| 1-2573 | —(CH$_2$)$_2$— | CHF$_2$ | SO$_2$Et | —NMeEt | SCH$_2$C(O)OMe | |
| 1-2574 | —(CH$_2$)$_2$— | CHF$_2$ | SO$_2$Et | —NMe(n-Pr) | SCH$_2$C(O)OMe | |
| 1-2575 | —(CH$_2$)$_2$— | CHF$_2$ | SO$_2$Et | —NEt(n-Pr) | SCH$_2$C(O)OMe | |
| 1-2576 | —(CH$_2$)$_2$— | CHF$_2$ | SO$_2$Et | —NH(i-Pr) | SCH$_2$C(O)OMe | |
| 1-2577 | —(CH$_2$)$_2$— | CHF$_2$ | SO$_2$Et | —NMe(i-Pr) | SCH$_2$C(O)OMe | |
| 1-2578 | —(CH$_2$)$_2$— | CHF$_2$ | SO$_2$Et | —NEt(i-Pr) | SCH$_2$C(O)OMe | |
| 1-2579 | —(CH$_2$)$_2$— | CHF$_2$ | SO$_2$Et | —N(Me)OMe | SCH$_2$C(O)OMe | |
| 1-2580 | —(CH$_2$)$_2$— | CHF$_2$ | SO$_2$Et | —N(Me)OEt | SCH$_2$C(O)OMe | |
| 1-2581 | —(CH$_2$)$_2$— | CHF$_2$ | SO$_2$Et | —N(Me)O(n-Pr) | SCH$_2$C(O)OMe | |
| 1-2582 | —(CH$_2$)$_2$— | CHF$_2$ | SO$_2$Et | —N(Et)OMe | SCH$_2$C(O)OMe | |
| 1-2583 | —(CH$_2$)$_2$— | CHF$_2$ | SO$_2$Et | —N(Et)OEt | SCH$_2$C(O)OMe | |
| 1-2584 | —(CH$_2$)$_2$— | CHF$_2$ | SO$_2$Et | —N(Et)O(n-Pr) | SCH$_2$C(O)OMe | |
| 1-2585 | —CHMe— | CF$_3$ | SO$_2$Et | —NH$_2$ | OH | |
| 1-2586 | —CHMe— | CF$_3$ | SO$_2$Et | —NHMe | OH | |

TABLE 1-continued

| No. | X¹ | R¹ | R² | —NR³R⁴ | R⁵ | Physical data |
|---|---|---|---|---|---|---|
| 1-2587 | —CHMe— | CF₃ | SO₂Et | —NMe₂ | OH | |
| 1-2588 | —CHMe— | CF₃ | SO₂Et | —NHEt | OH | |
| 1-2589 | —CHMe— | CF₃ | SO₂Et | —NEt₂ | OH | |
| 1-2590 | —CHMe— | CF₃ | SO₂Et | —NH(n-Pr) | OH | |
| 1-2591 | —CHMe— | CF₃ | SO₂Et | —N(n-Pr)₂ | OH | |
| 1-2592 | —CHMe— | CF₃ | SO₂Et | —NMeEt | OH | |
| 1-2593 | —CHMe— | CF₃ | SO₂Et | —NMe(n-Pr) | OH | |
| 1-2594 | —CHMe— | CF₃ | SO₂Et | —NEt(n-Pr) | OH | |
| 1-2595 | —CHMe— | CF₃ | SO₂Et | —NH(i-Pr) | OH | |
| 1-2596 | —CHMe— | CF₃ | SO₂Et | —NMe(i-Pr) | OH | |
| 1-2597 | —CHMe— | CF₃ | SO₂Et | —NEt(i-Pr) | OH | |
| 1-2598 | —CHMe— | CF₃ | SO₂Et | —N(Me)OMe | OH | |
| 1-2599 | —CHMe— | CF₃ | SO₂Et | —N(Me)OEt | OH | |
| 1-2600 | —CHMe— | CF₃ | SO₂Et | —N(Me)O(n-Pr) | OH | |
| 1-2601 | —CHMe— | CF₃ | SO₂Et | —N(Et)OMe | OH | |
| 1-2602 | —CHMe— | CF₃ | SO₂Et | —N(Et)OEt | OH | |
| 1-2603 | —CHMe— | CF₃ | SO₂Et | —N(Et)O(n-Pr) | OH | |
| 1-2604 | —CHMe— | CCl₃ | SO₂Et | —NH₂ | OH | |
| 1-2605 | —CHMe— | CCl₃ | SO₂Et | —NHMe | OH | |
| 1-2606 | —CHMe— | CCl₃ | SO₂Et | —NMe₂ | OH | |
| 1-2607 | —CHMe— | CCl₃ | SO₂Et | —NHEt | OH | |
| 1-2608 | —CHMe— | CCl₃ | SO₂Et | —NEt₂ | OH | |
| 1-2609 | —CHMe— | CCl₃ | SO₂Et | —NH(n-Pr) | OH | |
| 1-2610 | —CHMe— | CCl₃ | SO₂Et | —N(n-Pr)₂ | OH | |
| 1-2611 | —CHMe— | CCl₃ | SO₂Et | —NMeEt | OH | |
| 1-2612 | —CHMe— | CCl₃ | SO₂Et | —NMe(n-Pr) | OH | |
| 1-2613 | —CHMe— | CCl₃ | SO₂Et | —NEt(n-Pr) | OH | |
| 1-2614 | —CHMe— | CCl₃ | SO₂Et | —NH(i-Pr) | OH | |
| 1-2615 | —CHMe— | CCl₃ | SO₂Et | —NMe(i-Pr) | OH | |
| 1-2616 | —CHMe— | CCl₃ | SO₂Et | —NEt(i-Pr) | OH | |
| 1-2617 | —CHMe— | CCl₃ | SO₂Et | —N(Me)OMe | OH | |
| 1-2618 | —CHMe— | CCl₃ | SO₂Et | —N(Me)OEt | OH | |
| 1-2619 | —CHMe— | CCl₃ | SO₂Et | —N(Me)O(n-Pr) | OH | |
| 1-2620 | —CHMe— | CCl₃ | SO₂Et | —N(Et)OMe | OH | |
| 1-2621 | —CHMe— | CCl₃ | SO₂Et | —N(Et)OEt | OH | |
| 1-2622 | —CHMe— | CCl₃ | SO₂Et | —N(Et)O(n-Pr) | OH | |
| 1-2623 | —CHMe— | C₂F₅ | SO₂Et | —NH₂ | OH | |
| 1-2624 | —CHMe— | C₂F₅ | SO₂Et | —NHMe | OH | |
| 1-2625 | —CHMe— | C₂F₅ | SO₂Et | —NMe₂ | OH | |
| 1-2626 | —CHMe— | C₂F₅ | SO₂Et | —NHEt | OH | |
| 1-2627 | —CHMe— | C₂F₅ | SO₂Et | —NEt₂ | OH | |
| 1-2628 | —CHMe— | C₂F₅ | SO₂Et | —NH(n-Pr) | OH | |
| 1-2629 | —CHMe— | C₂F₅ | SO₂Et | —N(n-Pr)₂ | OH | |
| 1-2630 | —CHMe— | C₂F₅ | SO₂Et | —NMeEt | OH | |
| 1-2631 | —CHMe— | C₂F₅ | SO₂Et | —NMe(n-Pr) | OH | |
| 1-2632 | —CHMe— | C₂F₅ | SO₂Et | —NEt(n-Pr) | OH | |
| 1-2633 | —CHMe— | C₂F₅ | SO₂Et | —NH(i-Pr) | OH | |
| 1-2634 | —CHMe— | C₂F₅ | SO₂Et | —NMe(i-Pr) | OH | |
| 1-2635 | —CHMe— | C₂F₅ | SO₂Et | —NEt(i-Pr) | OH | |
| 1-2636 | —CHMe— | C₂F₅ | SO₂Et | —N(Me)OMe | OH | |
| 1-2637 | —CHMe— | C₂F₅ | SO₂Et | —N(Me)OEt | OH | |
| 1-2638 | —CHMe— | C₂F₅ | SO₂Et | —N(Me)O(n-Pr) | OH | |
| 1-2639 | —CHMe— | C₂F₅ | SO₂Et | —N(Et)OMe | OH | |
| 1-2640 | —CHMe— | C₂F₅ | SO₂Et | —N(Et)OEt | OH | |
| 1-2641 | —CHMe— | C₂F₅ | SO₂Et | —N(Et)O(n-Pr) | OH | |
| 1-2642 | —CHMe— | CHF₂ | SO₂Et | —NH₂ | OH | |
| 1-2643 | —CHMe— | CHF₂ | SO₂Et | —NHMe | OH | |
| 1-2644 | —CHMe— | CHF₂ | SO₂Et | —NMe₂ | OH | |
| 1-2645 | —CHMe— | CHF₂ | SO₂Et | —NHEt | OH | |
| 1-2646 | —CHMe— | CHF₂ | SO₂Et | —NEt₂ | OH | |
| 1-2647 | —CHMe— | CHF₂ | SO₂Et | —NH(n-Pr) | OH | |
| 1-2648 | —CHMe— | CHF₂ | SO₂Et | —N(n-Pr)₂ | OH | |
| 1-2649 | —CHMe— | CHF₂ | SO₂Et | —NMeEt | OH | |
| 1-2650 | —CHMe— | CHF₂ | SO₂Et | —NMe(n-Pr) | OH | |
| 1-2651 | —CHMe— | CHF₂ | SO₂Et | —NEt(n-Pr) | OH | |
| 1-2652 | —CHMe— | CHF₂ | SO₂Et | —NH(i-Pr) | OH | |
| 1-2653 | —CHMe— | CHF₂ | SO₂Et | —NMe(i-Pr) | OH | |
| 1-2654 | —CHMe— | CHF₂ | SO₂Et | —NEt(i-Pr) | OH | |
| 1-2655 | —CHMe— | CHF₂ | SO₂Et | —N(Me)OMe | OH | |
| 1-2656 | —CHMe— | CHF₂ | SO₂Et | —N(Me)OEt | OH | |
| 1-2657 | —CHMe— | CHF₂ | SO₂Et | —N(Me)O(n-Pr) | OH | |
| 1-2658 | —CHMe— | CHF₂ | SO₂Et | —N(Et)OMe | OH | |
| 1-2659 | —CHMe— | CHF₂ | SO₂Et | —N(Et)OEt | OH | |
| 1-2660 | —CHMe— | CHF₂ | SO₂Et | —N(Et)O(n-Pr) | OH | |
| 1-2661 | —CHMe— | CF₃ | SO₂Et | —NH₂ | SCH₂C(O)OMe | |
| 1-2662 | —CHMe— | CF₃ | SO₂Et | —NHMe | SCH₂C(O)OMe | |
| 1-2663 | —CHMe— | CF₃ | SO₂Et | —NMe₂ | SCH₂C(O)OMe | |

TABLE 1-continued

| No. | X¹ | R¹ | R² | —NR³R⁴ | R⁵ | Physical data |
|---|---|---|---|---|---|---|
| 1-2664 | —CHMe— | CF₃ | SO₂Et | —NHEt | SCH₂C(O)OMe | |
| 1-2665 | —CHMe— | CF₃ | SO₂Et | —NEt₂ | SCH₂C(O)OMe | |
| 1-2666 | —CHMe— | CF₃ | SO₂Et | —NH(n-Pr) | SCH₂C(O)OMe | |
| 1-2667 | —CHMe— | CF₃ | SO₂Et | —N(n-Pr)₂ | SCH₂C(O)OMe | |
| 1-2668 | —CHMe— | CF₃ | SO₂Et | —NMeEt | SCH₂C(O)OMe | |
| 1-2669 | —CHMe— | CF₃ | SO₂Et | —NMe(n-Pr) | SCH₂C(O)OMe | |
| 1-2670 | —CHMe— | CF₃ | SO₂Et | —NEt(n-Pr) | SCH₂C(O)OMe | |
| 1-2671 | —CHMe— | CF₃ | SO₂Et | —NH(i-Pr) | SCH₂C(O)OMe | |
| 1-2672 | —CHMe— | CF₃ | SO₂Et | —NMe(i-Pr) | SCH₂C(O)OMe | |
| 1-2673 | —CHMe— | CF₃ | SO₂Et | —NEt(i-Pr) | SCH₂C(O)OMe | |
| 1-2674 | —CHMe— | CF₃ | SO₂Et | —N(Me)OMe | SCH₂C(O)OMe | |
| 1-2675 | —CHMe— | CF₃ | SO₂Et | —N(Me)OEt | SCH₂C(O)OMe | |
| 1-2676 | —CHMe— | CF₃ | SO₂Et | —N(Me)O(n-Pr) | SCH₂C(O)OMe | |
| 1-2677 | —CHMe— | CF₃ | SO₂Et | —N(Et)OMe | SCH₂C(O)OMe | |
| 1-2678 | —CHMe— | CF₃ | SO₂Et | —N(Et)OEt | SCH₂C(O)OMe | |
| 1-2679 | —CHMe— | CF₃ | SO₂Et | —N(Et)O(n-Pr) | SCH₂C(O)OMe | |
| 1-2680 | —CHMe— | CCl₃ | SO₂Et | —NH₂ | SCH₂C(O)OMe | |
| 1-2681 | —CHMe— | CCl₃ | SO₂Et | —NHMe | SCH₂C(O)OMe | |
| 1-2682 | —CHMe— | CCl₃ | SO₂Et | —NMe₂ | SCH₂C(O)OMe | |
| 1-2683 | —CHMe— | CCl₃ | SO₂Et | —NHEt | SCH₂C(O)OMe | |
| 1-2684 | —CHMe— | CCl₃ | SO₂Et | —NEt₂ | SCH₂C(O)OMe | |
| 1-2685 | —CHMe— | CCl₃ | SO₂Et | —NH(n-Pr) | SCH₂C(O)OMe | |
| 1-2686 | —CHMe— | CCl₃ | SO₂Et | —N(n-Pr)₂ | SCH₂C(O)OMe | |
| 1-2687 | —CHMe— | CCl₃ | SO₂Et | —NMeEt | SCH₂C(O)OMe | |
| 1-2688 | —CHMe— | CCl₃ | SO₂Et | —NMe(n-Pr) | SCH₂C(O)OMe | |
| 1-2689 | —CHMe— | CCl₃ | SO₂Et | —NEt(n-Pr) | SCH₂C(O)OMe | |
| 1-2690 | —CHMe— | CCl₃ | SO₂Et | —NH(i-Pr) | SCH₂C(O)OMe | |
| 1-2691 | —CHMe— | CCl₃ | SO₂Et | —NMe(i-Pr) | SCH₂C(O)OMe | |
| 1-2692 | —CHMe— | CCl₃ | SO₂Et | —NEt(i-Pr) | SCH₂C(O)OMe | |
| 1-2693 | —CHMe— | CCl₃ | SO₂Et | —N(Me)OMe | SCH₂C(O)OMe | |
| 1-2694 | —CHMe— | CCl₃ | SO₂Et | —N(Me)OEt | SCH₂C(O)OMe | |
| 1-2695 | —CHMe— | CCl₃ | SO₂Et | —N(Me)O(n-Pr) | SCH₂C(O)OMe | |
| 1-2696 | —CHMe— | CCl₃ | SO₂Et | —N(Et)OMe | SCH₂C(O)OMe | |
| 1-2697 | —CHMe— | CCl₃ | SO₂Et | —N(Et)OEt | SCH₂C(O)OMe | |
| 1-2698 | —CHMe— | CCl₃ | SO₂Et | —N(Et)O(n-Pr) | SCH₂C(O)OMe | |
| 1-2699 | —CHMe— | C₂F₅ | SO₂Et | —NH₂ | SCH₂C(O)OMe | |
| 1-2700 | —CHMe— | C₂F₅ | SO₂Et | —NHMe | SCH₂C(O)OMe | |
| 1-2701 | —CHMe— | C₂F₅ | SO₂Et | —NMe₂ | SCH₂C(O)OMe | |
| 1-2702 | —CHMe— | C₂F₅ | SO₂Et | —NHEt | SCH₂C(O)OMe | |
| 1-2703 | —CHMe— | C₂F₅ | SO₂Et | —NEt₂ | SCH₂C(O)OMe | |
| 1-2704 | —CHMe— | C₂F₅ | SO₂Et | —NH(n-Pr) | SCH₂C(O)OMe | |
| 1-2705 | —CHMe— | C₂F₅ | SO₂Et | —N(n-Pr)₂ | SCH₂C(O)OMe | |
| 1-2706 | —CHMe— | C₂F₅ | SO₂Et | —NMeEt | SCH₂C(O)OMe | |
| 1-2707 | —CHMe— | C₂F₅ | SO₂Et | —NMe(n-Pr) | SCH₂C(O)OMe | |
| 1-2708 | —CHMe— | C₂F₅ | SO₂Et | —NEt(n-Pr) | SCH₂C(O)OMe | |
| 1-2709 | —CHMe— | C₂F₅ | SO₂Et | —NH(i-Pr) | SCH₂C(O)OMe | |
| 1-2710 | —CHMe— | C₂F₅ | SO₂Et | —NMe(i-Pr) | SCH₂C(O)OMe | |
| 1-2711 | —CHMe— | C₂F₅ | SO₂Et | —NEt(i-Pr) | SCH₂C(O)OMe | |
| 1-2712 | —CHMe— | C₂F₅ | SO₂Et | —N(Me)OMe | SCH₂C(O)OMe | |
| 1-2713 | —CHMe— | C₂F₅ | SO₂Et | —N(Me)OEt | SCH₂C(O)OMe | |
| 1-2714 | —CHMe— | C₂F₅ | SO₂Et | —N(Me)O(n-Pr) | SCH₂C(O)OMe | |
| 1-2715 | —CHMe— | C₂F₅ | SO₂Et | —N(Et)OMe | SCH₂C(O)OMe | |
| 1-2716 | —CHMe— | C₂F₅ | SO₂Et | —N(Et)OEt | SCH₂C(O)OMe | |
| 1-2717 | —CHMe— | C₂F₅ | SO₂Et | —N(Et)O(n-Pr) | SCH₂C(O)OMe | |
| 1-2718 | —CHMe— | CHF₂ | SO₂Et | —NH₂ | SCH₂C(O)OMe | |
| 1-2719 | —CHMe— | CHF₂ | SO₂Et | —NHMe | SCH₂C(O)OMe | |
| 1-2720 | —CHMe— | CHF₂ | SO₂Et | —NMe₂ | SCH₂C(O)OMe | |
| 1-2721 | —CHMe— | CHF₂ | SO₂Et | —NHEt | SCH₂C(O)OMe | |
| 1-2722 | —CHMe— | CHF₂ | SO₂Et | —NEt₂ | SCH₂C(O)OMe | |
| 1-2723 | —CHMe— | CHF₂ | SO₂Et | —NH(n-Pr) | SCH₂C(O)OMe | |
| 1-2724 | —CHMe— | CHF₂ | SO₂Et | —N(n-Pr)₂ | SCH₂C(O)OMe | |
| 1-2725 | —CHMe— | CHF₂ | SO₂Et | —NMeEt | SCH₂C(O)OMe | |
| 1-2726 | —CHMe— | CHF₂ | SO₂Et | —NMe(n-Pr) | SCH₂C(O)OMe | |
| 1-2727 | —CHMe— | CHF₂ | SO₂Et | —NEt(n-Pr) | SCH₂C(O)OMe | |
| 1-2728 | —CHMe— | CHF₂ | SO₂Et | —NH(i-Pr) | SCH₂C(O)OMe | |
| 1-2729 | —CHMe— | CHF₂ | SO₂Et | —NMe(i-Pr) | SCH₂C(O)OMe | |
| 1-2730 | —CHMe— | CHF₂ | SO₂Et | —NEt(i-Pr) | SCH₂C(O)OMe | |
| 1-2731 | —CHMe— | CHF₂ | SO₂Et | —N(Me)OMe | SCH₂C(O)OMe | |
| 1-2732 | —CHMe— | CHF₂ | SO₂Et | —N(Me)OEt | SCH₂C(O)OMe | |
| 1-2733 | —CHMe— | CHF₂ | SO₂Et | —N(Me)O(n-Pr) | SCH₂C(O)OMe | |
| 1-2734 | —CHMe— | CHF₂ | SO₂Et | —N(Et)OMe | SCH₂C(O)OMe | |
| 1-2735 | —CHMe— | CHF₂ | SO₂Et | —N(Et)OEt | SCH₂C(O)OMe | |
| 1-2736 | —CHMe— | CHF₂ | SO₂Et | —N(Et)O(n-Pr) | SCH₂C(O)OMe | |

B. FORMULATION EXAMPLES a) A dust is obtained by mixing 10 parts by weight of a compound of the formula (I) and/or a salt thereof and 90 parts by weight of talc as inert substance and comminuting the mixture in a hammer mill.

b) A wettable powder which is readily dispersible in water is obtained by mixing 25 parts by weight of a compound of the formula (I) and/or a salt thereof, 64 parts by weight of kaolin-containing quartz as inert substance, 10 parts by weight of potassium lignosulfonate and 1 part by weight of sodium oleoylmethyltaurinate as wetting agent and dispersant, and grinding the mixture in a pinned-disk mill.

c) A readily water-dispersible dispersion concentrate is obtained by mixing 20 parts by weight of a compound of the formula (I) and/or a salt thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

d) An emulsifiable concentrate is obtained from 15 parts by weight of a compound of the formula (I) and/or a salt thereof, 75 parts by weight of cyclohexanone as solvent and 10 parts by weight of oxethylated nonylphenol as emulsifier.

e) Water-dispersible granules are obtained by mixing
  75 parts by weight of a compound of the formula (I) and/or a salt thereof,
  10 parts by weight of calcium lignosulfonate,
  5 parts by weight of sodium lauryl sulfate,
  3 parts by weight of polyvinyl alcohol and
  7 parts by weight of kaolin,
  grinding the mixture in a pinned-disk mill, and granulating the powder in a fluidized bed by spraying on water as granulating liquid.

f) Water-dispersible granules are also obtained by homogenizing and precomminuting, in a colloid mill,
  25 parts by weight of a compound of the formula (I) and/or a salt thereof,
  5 parts by weight of sodium 2,2'-dinaphthylmethane-6,6'-disulfonate,
  2 parts by weight of sodium oleoylmethyltaurinate,
  1 part by weight of polyvinyl alcohol,
  17 parts by weight of calcium carbonate and
  50 parts by weight of water,
  subsequently grinding the mixture in a bead mill and atomizing and drying the resulting suspension in a spray tower by means of a single-substance nozzle.

C. BIOLOGICAL COMPARATIVE EXAMPLES

The following compounds according to the invention and known from the closest prior art (WO 03/022810) were used for the biological comparative examples:

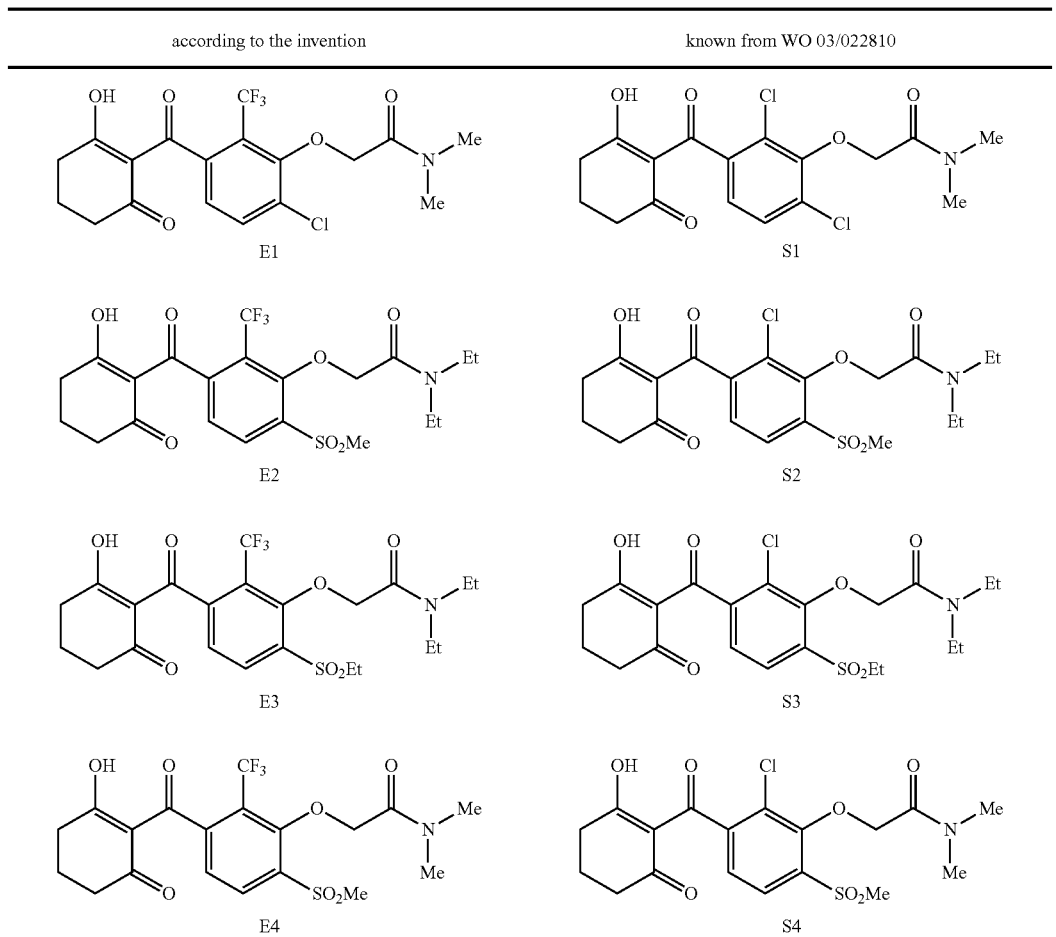

-continued

| according to the invention | known from WO 03/022810 |
|---|---|

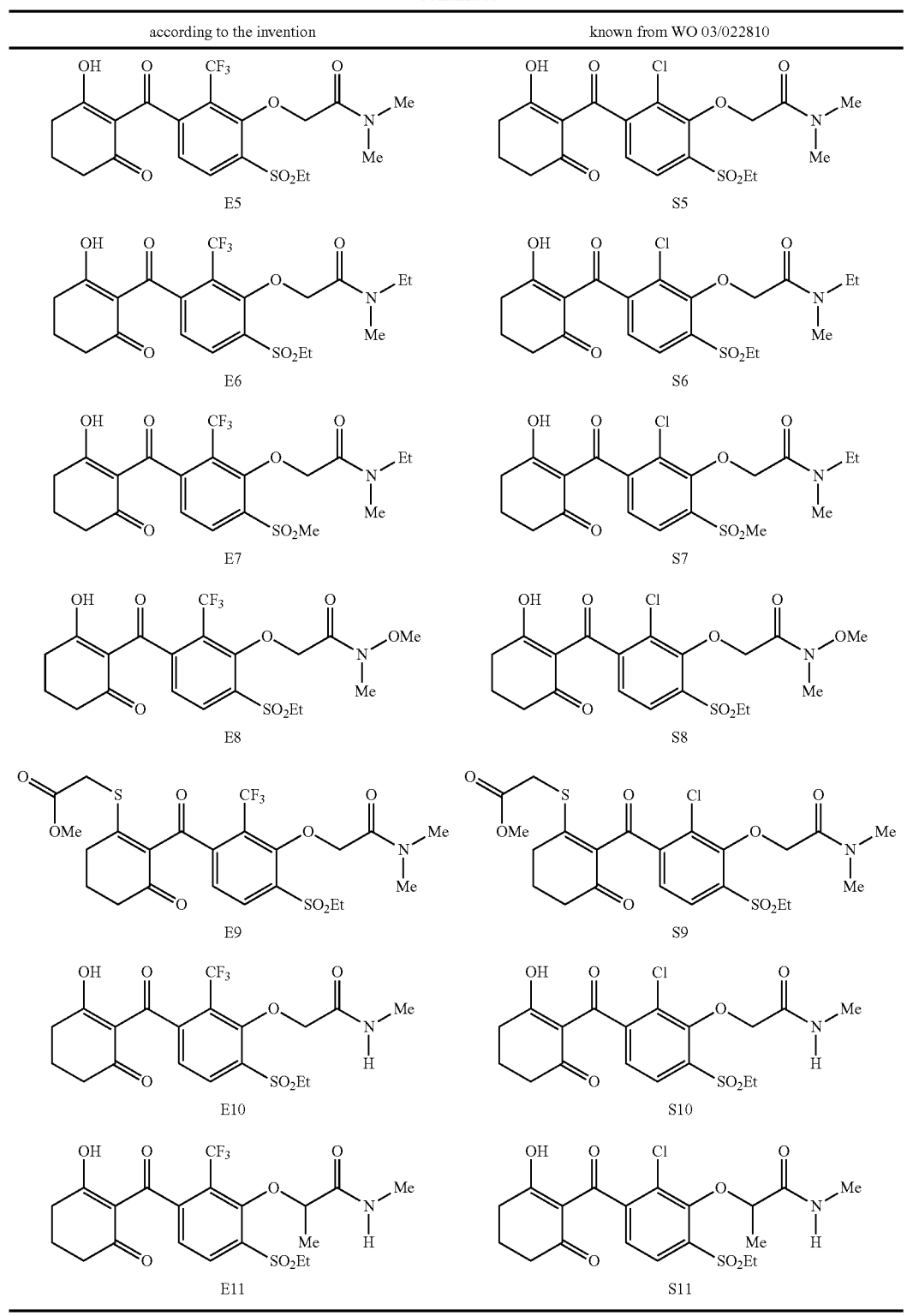

The abbreviations used in the tables below denote:
ABUTH Abutilon theophrasti
AMARE Amaranthus retroflexus
ECHCG Echinochloa crus galli
PHBPU Phartoitis purpureum
STEME Stellaria media ALOMY Alopecurus myosuroides
AVEFA Avena fatua
MATIN Matricaria inodora
POLCO Fallopia convolvulus
VERPE Veronica persica 1. Pre-emergence Herbicidal Action Against Harmful Plants Seeds of monocotyledonous and dicotyledonous weed plants and crop plants are placed in wood-fibre pots in sandy loam and covered with soil. The compounds according to the invention and the compounds known from the prior art, formulated in the form of wettable powders (WP) or as emulsion concentrates (EC), are then applied as aqueous suspension or emulsion at a water application rate of 600 to 800 l/ha (converted) with the addition of 0.2% of wetting agent to the surface of the covering soil. After the treatment, the pots are placed in a greenhouse and kept under good growth conditions for the test plants. The visual assessment of the damage to the test plants is carried out after a trial period of 3 weeks by comparison with untreated controls (herbicidal activity in percent (%): 100% activity=the plants have died, 0% activity=like control plants, —=not tested). The results of comparative table A show the compounds according to the invention have a higher herbicidal activity than the compounds of the greatest structural similarity known from the closest prior art.

2. Post-emergence Herbicidal Action Against Harmful Plants

Seeds of monocotyledonous and dicotyledonous weed and crop plants are placed in sandy loam in wood-fibre pots, covered with soil and cultivated in a greenhouse under good growth conditions. 2 to 3 weeks after sowing, the test plants are treated at the one-leaf stage. The compounds according to the invention, formulated in the form of wettable powders (WP) or as emulsion concentrates (EC), are then sprayed as aqueous suspension or emulsion at a water application rate of 600 to 800 l/ha (converted) with the addition of 0.2% of wetting agent onto the green parts of the plants. After the test plants have been kept in the greenhouse under optimum growth conditions for about 3 weeks, the activity of the preparations is rated visually in comparison to untreated controls (herbicidal activity in percent (%): 100% activity=the plants have died, 0% activity=control plants, —=not tested). The results of comparative table B show that the compounds according to the invention have a higher herbicidal activity than the compounds of the greatest structural similarity known from the closest prior art.

COMPARATIVE TABLE A pre-emergence, dosage 320 g/ha

Herbicidal action against

| Compound | ABUTH | ALOMY | AMARE | AVEFA | ECHCG | MATIN | PHBPU | STEME | VERPE |
|---|---|---|---|---|---|---|---|---|---|
| S1 | 90% | 40% | 60% | 20% | 30% | 100% | 40% | 80% | 70% |
| E1 | 100% | 100% | 100% | 90% | 100% | 100% | 80% | 90% | 100% |
| S2 | 40% | — | 100% | — | 70% | 60% | 70% | 20% | 100% |
| E2 | 100% | — | 100% | — | 100% | 100% | 80% | 90% | 100% |
| S3 | 70% | — | 80% | — | 50% | 80% | 40% | 50% | 100% |
| E3 | 100% | — | 100% | — | 100% | 100% | 90% | 100% | 100% |
| S4 | 50% | — | 100% | — | 40% | 80% | — | 90% | 100% |
| E4 | 100% | — | 100% | — | 100% | 100% | — | 90% | 100% |
| S5 | 90% | 0% | 100% | — | 100% | 90% | — | 90% | 100% |
| E5 | 100% | 100% | 100% | — | 100% | 100% | — | 90% | 100% |
| S6 | 100% | — | 100% | — | 90% | 80% | — | 80% | 90% |
| E6 | 100% | — | 100% | — | 100% | 100% | — | 100% | 100% |
| S7 | 80% | — | 100% | 0% | 80% | 100% | — | 90% | 100% |
| E7 | 100% | — | 100% | 80% | 100% | 100% | — | 100% | 100% |
| S6 | 100% | — | 100% | — | 90% | 80% | — | 80% | 90% |
| E8 | 100% | — | — | — | 100% | 100% | — | 100% | 100% |

COMPARATIVE TABLE B pre-emergence, dosage 80 g/ha

Herbicidal action against

| Compound | ABUTH | AMARE | STEME | VERPE | VIOTR |
|---|---|---|---|---|---|
| S9 | 20% | 40% | — | 20% | |
| E9 | 90% | 90% | — | 90% | |
| S11 | 70% | — | 30% | — | 40% |
| E11 | 90% | — | 70% | — | 90% |

COMPARATIVE TABLE C pre-emergence, dosage 320 g/ha

Herbicidal action against

| Compound | ABUTH | AMARE | ECHCG | MATIN | PHPBU | SETVI | VIOTR |
|---|---|---|---|---|---|---|---|
| S8 | 90% | 90% | 60% | 90% | 70% | 50% | 20% |
| E8 | 100% | 100% | 100% | 100% | 90% | 90% | 100% |

COMPARATIVE TABLE D post-emergence, dosage 80 g/ha

| Compound | Herbicidal action against | | | | | | | | |
|---|---|---|---|---|---|---|---|---|---|
| | ABUTH | AMARE | AVEFA | ECHCG | MATIN | PHBPU | POLCO | STEME | VERPE |
| S1 | — | 80% | 50% | 50% | 100% | 70% | 60% | 70% | 70% |
| E1 | — | 80% | 80% | 90% | 100% | 90% | 100% | 90% | 90% |
| S2 | 80% | 90% | — | 30% | 70% | 90% | — | 90% | 90% |
| E2 | 90% | 100% | — | 90% | 100% | 100% | — | 100% | 100% |
| S3 | 90% | 100% | — | 0% | 70% | 60% | 40% | 90% | 90% |
| E3 | 100% | 100% | — | 100% | 90% | 90% | 90% | 100% | 100% |
| S4 | 70% | 60% | — | — | 70% | — | 0% | 90% | 90% |
| E4 | 90% | 90% | — | — | 90% | — | 70% | 100% | 100% |
| S5 | 90% | 80% | — | 40% | — | 60% | 20% | 80% | 100% |
| E5 | 90% | 80% | — | 90% | — | 90% | 80% | 90% | 100% |
| S6 | 90% | 80% | — | 20% | 80% | 80% | 0% | 90% | 100% |
| E6 | 100% | 90% | — | 100% | 100% | 100% | 90% | 100% | 100% |
| S7 | 90% | 70% | — | 60% | 80% | 90% | 10% | 90% | 100% |
| E7 | 90% | 100% | — | 90% | 100% | 100% | 80% | 100% | 100% |

COMPARATIVE TABLE E post-emergence, dosage 80 g/ha

| Compound | Herbicidal action against | | | | | |
|---|---|---|---|---|---|---|
| | ABUTH | ECHCG | MATIN | PHPBU | POLCO | VIOTR |
| S8 | — | 80% | 60% | 80% | 80% | 80% |
| E8 | — | 90% | 90% | 80% | 90% | 90% |
| S10 | 90% | — | 70% | 90% | 80% | — |
| E10 | 100% | — | 90% | 100% | 100% | — |

COMPARATIVE TABLE F post-emergence, dosage 20 g/ha

| Compound | Herbicidal action against | | | | | | |
|---|---|---|---|---|---|---|---|
| | ABUTH | AMARE | ECHCG | MATIN | PHPBU | STEME | VERPE | VIOTR |
| S9 | 80% | — | 90% | — | 60% | 70% | 80% | 60% |
| E9 | 100% | — | 90% | — | 80% | 90% | 100% | 100% |
| S11 | — | 90% | — | 70% | 70% | 80% | 90% | 70% |
| E11 | — | 100% | — | 90% | 80% | 90% | 100% | 100% |

The invention claimed is:

1. A 3-aminocarbonyl-substituted benzoylcyclohexanedione of the formula (I) and/or a salt thereof

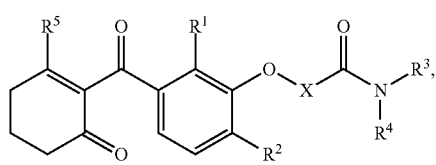

wherein
X is a straight-chain or branched $(C_1-C_6)$-alkylene chain;
$R^1$ is trifluoromethyl;
$R^2$ is halogen or $(C_1-C_6)$-alkyl-$S(O)_n$;
$R^3$ and $R^4$ independently of one another are hydrogen, $(C_1-C_6)$-alkyl or $(C_1-C_4)$-alkoxy;
$R^5$ is hydroxyl or (2-methoxy-2-oxoethyl)sulfanyl;
n is 0, 1 or 2.

2. The 3-aminocarbonyl-substituted benzoylcyclohexanedione and/or salt of claim 1 wherein X is methylene;
$R^2$ is $(C_1-C_6)$-alkyl-$S(O)_n$;
$R^3$ and $R^4$ independently of one another are hydrogen, methyl, ethyl, methoxy or ethoxy;
$R^5$ is hydroxyl;
n is 0, 1 or 2.

3. A herbicidal composition which comprises a herbicidally effective amount of at least one 3-aminocarbonyl-substituted benzoylcyclohexanedione of the formula (I) and/or salt as claimed in claim 1.

4. The herbicidal composition as claimed in claim 3 in a mixture with at least one formulation auxiliary.

5. The herbicidal composition as claimed in claim 3 which comprises at least one further pesticidally active compound selected from the group consisting of insecticides, acaricides, herbicides, fungicides, safeners and growth regulators.

6. The herbicidal composition as claimed in claim 5 which comprises at least one safener.

7. The herbicidal composition as claimed in claim 5 which comprises mefenpyr-diethyl, isoxadifen-ethyl or cyprosulfamide.

8. A method for controlling unwanted plants which comprises applying an effective amount of at least one compound of the formula (I) and/or salt as claimed in claim 1 to plants and/or to a site where vegetation is unwanted.

9. A method for controlling unwanted plants comprising applying an effective amount of a herbicidal composition of claim 3 to said plants and/or to a site where vegetation is unwanted.

10. The method as claimed in claim 8, wherein the compound of the formula (I) and/or salt is used for controlling unwanted plants in crops of useful plants.

11. The method as claimed in claim 10, wherein the useful plants are transgenic useful plants.

12. The 3-aminocarbonyl-substituted benzoylcyclohexanedione and/or salt of claim 1 wherein $R^5$ is (2-methoxy-2-oxoethyl)sulfanyl.

13. The 3-aminocarbonyl-substituted benzoylcyclohexanedione and/or salt of claim 1 wherein $R^2$ is halogen.

14. The 3-aminocarbonyl-substituted benzoylcyclohexanedione and/or salt of claim 1 wherein X is methylene.

15. The 3-aminocarbonyl-substituted benzoylcyclohexanedione and/or salt of claim 1 wherein $R^2$ is $SO_2Et$ or $SO_2Me$.

16. The 3-aminocarbonyl-substituted benzoylcyclohexanedione and/or salt of claim 1 wherein $R^2$ is $(C_1-C_6)$-alkyl-$S(O)_n$.

17. The 3-aminocarbonyl-substituted benzoylcyclohexanedione and/or salt of claim 1 wherein $R^3$ and $R^4$ are independent of each other Me, Et, H or OMe.

18. The 3-aminocarbonyl-substituted benzoylcyclohexanedione and/or salt of claim 1 wherein $R^5$ is OH.

19. The 3-aminocarbonyl-substituted benzoylcyclohexanedione and/or salt of claim 1 wherein $R^3$ and $R^4$ are independent of each other Me, Et, or OMe.

\* \* \* \* \*